(12) United States Patent
Robinson et al.

(10) Patent No.: US 8,292,954 B2
(45) Date of Patent: Oct. 23, 2012

(54) DISC-BASED ORTHOPEDIC DEVICES

(75) Inventors: Janine Robinson, Half Moon Bay, CA (US); Michael Hogendijk, Mountain View, CA (US)

(73) Assignee: Articulinx, Inc., Cupertino, CA (US)

( * ) Notice: Subject to any disclaimer, the term of this patent is extended or adjusted under 35 U.S.C. 154(b) by 161 days.

(21) Appl. No.: 12/879,963

(22) Filed: Sep. 10, 2010

(65) Prior Publication Data
US 2011/0224790 A1    Sep. 15, 2011

Related U.S. Application Data

(60) Provisional application No. 61/241,843, filed on Sep. 11, 2009.

(51) Int. Cl.
*A61F 2/08* (2006.01)

(52) U.S. Cl. .................................................. 623/14.12

(58) Field of Classification Search .... 623/17.11–17.16, 623/14.12, 18.11, 21.12, 21.15; 606/99, 606/246–249
See application file for complete search history.

(56) References Cited

U.S. PATENT DOCUMENTS

| | | | |
|---|---|---|---|
| 3,745,590 A | 7/1973 | Stubstad | |
| 3,879,767 A | 4/1975 | Stubstad | |
| 3,924,276 A | 12/1975 | Eaton | |
| 4,052,753 A | 10/1977 | Dedo | |
| 4,166,292 A | 9/1979 | Bokros | |
| 4,276,660 A | 7/1981 | Laure | |
| 4,344,193 A * | 8/1982 | Kenny | 623/14.12 |
| 4,385,404 A | 5/1983 | Sully et al. | |
| 4,446,578 A | 5/1984 | Perkins et al. | |
| 4,502,161 A | 3/1985 | Wall | |
| 4,781,190 A | 11/1988 | Lee | |
| 4,880,429 A * | 11/1989 | Stone | 623/14.12 |
| 4,919,667 A * | 4/1990 | Richmond | 623/14.12 |
| 4,932,969 A | 6/1990 | Frey et al. | |
| 4,936,854 A | 6/1990 | Swanson | |
| 4,955,915 A | 9/1990 | Swanson | |
| 4,955,916 A | 9/1990 | Carignan et al. | |
| 5,092,894 A * | 3/1992 | Kenny | 128/898 |
| 5,098,779 A | 3/1992 | Kranzler et al. | |
| 5,158,574 A | 10/1992 | Stone | |
| 5,171,280 A * | 12/1992 | Baumgartner | 623/17.12 |
| 5,326,364 A | 7/1994 | Clift, Jr. et al. | |
| 5,344,459 A | 9/1994 | Swartz | |
| 5,405,400 A | 4/1995 | Linscheid et al. | |

(Continued)

FOREIGN PATENT DOCUMENTS

WO    WO-2004/093767 A1    11/2004

(Continued)

OTHER PUBLICATIONS

Artimplant (Date Unknown). "Artelon® CMC Spacer Arthro," product insert, 2 pages.

(Continued)

*Primary Examiner* — Alvin J. Stewart
(74) *Attorney, Agent, or Firm* — Morrison & Foerster LLP

(57) ABSTRACT

Methods and apparatuses for treatment of various joint conditions include a device inserted into a joint space. During delivery, the profile of the device is constrained in at least one dimension to minimize invasive impact on tissue and/or bone. The device may be restrained for implantation by a thread or a rigid elongate member. After insertion, the device may expand at the implantation site.

25 Claims, 116 Drawing Sheets

U.S. PATENT DOCUMENTS

| | | |
|---|---|---|
| 5,505,735 A | 4/1996 | Li |
| 5,507,822 A | 4/1996 | Bouchon |
| 5,534,028 A * | 7/1996 | Bao et al. ................... 623/17.16 |
| 5,645,605 A | 7/1997 | Klawitter |
| 5,716,416 A | 2/1998 | Lin |
| 5,732,992 A | 3/1998 | Mauldin |
| 5,743,918 A | 4/1998 | Calandruccio |
| 5,782,926 A | 7/1998 | Lamprecht |
| 5,782,927 A | 7/1998 | Klawitter |
| 5,888,203 A | 3/1999 | Goldberg |
| 5,944,759 A | 8/1999 | Link |
| 6,007,580 A | 12/1999 | Lehto |
| 6,017,366 A | 1/2000 | Berman |
| 6,090,145 A | 7/2000 | Hassler |
| 6,132,468 A | 10/2000 | Mansmann |
| 6,159,247 A | 12/2000 | Klawitter |
| 6,206,927 B1 | 3/2001 | Fell |
| 6,264,695 B1 * | 7/2001 | Stoy ........................... 623/17.16 |
| 6,371,958 B1 | 4/2002 | Overaker |
| 6,425,920 B1 | 7/2002 | Hamada |
| 6,436,146 B1 | 8/2002 | Hassler |
| 6,558,421 B1 | 5/2003 | Fell |
| 6,652,587 B2 | 11/2003 | Felt |
| 6,656,178 B1 | 12/2003 | Veldhuizen |
| 6,679,914 B1 * | 1/2004 | Gabbay ....................... 623/14.12 |
| D490,900 S | 6/2004 | Ogilvie |
| 6,764,512 B2 | 7/2004 | Keller |
| 6,764,514 B1 * | 7/2004 | Li et al. ..................... 623/17.12 |
| 6,911,044 B2 * | 6/2005 | Fell et al. ................... 623/14.12 |
| 6,923,831 B2 * | 8/2005 | Fell et al. ................... 623/14.12 |
| 6,964,667 B2 | 11/2005 | Shaolian |
| 6,966,928 B2 * | 11/2005 | Fell et al. ................... 623/14.12 |
| 6,966,930 B2 | 11/2005 | Arnin |
| 6,997,958 B2 | 2/2006 | Hassler |
| 7,004,971 B2 * | 2/2006 | Serhan et al. ............... 623/17.16 |
| 7,037,342 B2 | 5/2006 | Nilsson |
| 7,052,516 B2 | 5/2006 | Cauthen, III |
| 7,124,762 B2 * | 10/2006 | Carter et al. ................... 128/898 |
| 7,172,628 B2 * | 2/2007 | Lamprich et al. ........... 623/17.16 |
| 7,182,787 B2 | 2/2007 | Hassler |
| 7,204,851 B2 * | 4/2007 | Trieu et al. ................. 623/17.11 |
| 7,204,897 B2 * | 4/2007 | Stoy et al. ......................... 156/61 |
| 7,291,169 B2 * | 11/2007 | Hodorek ..................... 623/14.12 |
| 7,291,171 B2 | 11/2007 | Ferree |
| 7,297,161 B2 | 11/2007 | Fell |
| 7,309,359 B2 * | 12/2007 | Trieu et al. ................. 623/17.16 |
| 7,320,709 B2 | 1/2008 | Felt |
| 7,338,524 B2 * | 3/2008 | Fell et al. ................... 623/14.12 |
| 7,491,235 B2 | 2/2009 | Fell et al. |
| 7,520,900 B2 * | 4/2009 | Trieu ........................... 623/17.16 |
| 7,601,174 B2 | 10/2009 | Kelly |
| 7,611,653 B1 | 11/2009 | Elsner |
| 7,618,461 B2 * | 11/2009 | Trieu ........................... 623/17.16 |
| 7,758,647 B2 * | 7/2010 | Arnin et al. ................. 623/17.16 |
| 7,758,649 B2 * | 7/2010 | Walsh et al. ................. 623/17.16 |
| 7,819,919 B2 | 10/2010 | Fell |
| 7,837,739 B2 | 11/2010 | Ogilvie |
| 7,857,856 B2 * | 12/2010 | Trieu ........................... 623/17.16 |
| 7,879,102 B2 * | 2/2011 | Slivka et al. ................ 623/17.16 |
| 7,901,430 B2 * | 3/2011 | Matsuura et al. ............... 606/213 |
| 7,901,460 B2 * | 3/2011 | Sherman ..................... 623/17.16 |
| 7,905,922 B2 * | 3/2011 | Bergeron ..................... 623/17.16 |
| 7,938,860 B2 * | 5/2011 | Trieu ........................... 623/17.16 |
| 7,947,080 B2 * | 5/2011 | Ferree ......................... 623/17.16 |
| RE42,480 E * | 6/2011 | Bryan et al. ................ 623/17.16 |
| 7,991,599 B2 | 8/2011 | Linder-Ganz |
| 8,016,884 B2 | 9/2011 | Shterling |
| RE42,837 E * | 10/2011 | Stoy et al. ................... 623/17.16 |
| 8,043,381 B2 * | 10/2011 | Hestad et al. ............... 623/17.16 |
| 2001/0027343 A1 | 10/2001 | Keller |
| 2002/0022884 A1 | 2/2002 | Mansmann |
| 2002/0026244 A1 | 2/2002 | Trieu |
| 2002/0035400 A1 | 3/2002 | Bryan et al. |
| 2002/0161114 A1 | 10/2002 | Gunatillake et al. |
| 2002/0183848 A1 * | 12/2002 | Ray et al. .................... 623/17.12 |
| 2002/0189622 A1 | 12/2002 | Cauthen, III et al. |
| 2003/0009224 A1 | 1/2003 | Kuras |
| 2003/0023311 A1 * | 1/2003 | Trieu ........................... 623/17.16 |
| 2003/0125748 A1 | 7/2003 | Li et al. |
| 2004/0006393 A1 | 1/2004 | Burkinshaw |
| 2004/0044410 A1 | 3/2004 | Ferree et al. |
| 2004/0059318 A1 | 3/2004 | Zhang et al. |
| 2004/0097943 A1 | 5/2004 | Hart |
| 2004/0193279 A1 | 9/2004 | Roger |
| 2004/0195727 A1 | 10/2004 | Stoy |
| 2004/0199249 A1 | 10/2004 | Fell |
| 2004/0220296 A1 | 11/2004 | Lowman et al. |
| 2004/0228901 A1 | 11/2004 | Trieu et al. |
| 2004/0267277 A1 | 12/2004 | Zannis et al. |
| 2005/0043808 A1 | 2/2005 | Felt et al. |
| 2005/0049705 A1 | 3/2005 | Hale et al. |
| 2005/0107879 A1 | 5/2005 | Christensen et al. |
| 2005/0131540 A1 | 6/2005 | Trieu |
| 2005/0131541 A1 | 6/2005 | Trieu |
| 2005/0154463 A1 | 7/2005 | Trieu |
| 2005/0177240 A1 | 8/2005 | Blain |
| 2005/0197711 A1 | 9/2005 | Cachia |
| 2005/0240269 A1 | 10/2005 | Lambrecht et al. |
| 2005/0283159 A1 | 12/2005 | Amara |
| 2006/0004378 A1 | 1/2006 | Raines, Jr. et al. |
| 2006/0084983 A1 | 4/2006 | Kim |
| 2006/0085068 A1 | 4/2006 | Barry |
| 2006/0129240 A1 | 6/2006 | Lessar et al. |
| 2006/0149259 A1 | 7/2006 | May et al. |
| 2006/0149261 A1 | 7/2006 | Nilsson et al. |
| 2006/0212110 A1 | 9/2006 | Osborne et al. |
| 2006/0235517 A1 | 10/2006 | Hodorek |
| 2006/0241778 A1 | 10/2006 | Ogilvie |
| 2006/0247787 A1 | 11/2006 | Rydell et al. |
| 2006/0265077 A1 | 11/2006 | Zwirkoski |
| 2006/0283159 A1 | 12/2006 | Scherrer |
| 2007/0016196 A1 | 1/2007 | Winslow et al. |
| 2007/0050038 A1 | 3/2007 | Snell et al. |
| 2007/0118218 A1 | 5/2007 | Hooper |
| 2007/0123993 A1 | 5/2007 | Hassler et al. |
| 2007/0233245 A1 | 10/2007 | Trieu |
| 2007/0288014 A1 | 12/2007 | Shadduck et al. |
| 2007/0293947 A1 | 12/2007 | Mansmann |
| 2008/0027560 A1 | 1/2008 | Jackson et al. |
| 2008/0058933 A1 | 3/2008 | Garner et al. |
| 2008/0086210 A1 | 4/2008 | Fox |
| 2008/0097606 A1 | 4/2008 | Cragg et al. |
| 2008/0208346 A1 | 8/2008 | Schwartz |
| 2008/0255501 A1 | 10/2008 | Hogendijk et al. |
| 2008/0255664 A1 | 10/2008 | Hogendijk et al. |
| 2008/0269908 A1 | 10/2008 | Warburton |
| 2009/0005871 A1 | 1/2009 | White et al. |
| 2009/0012612 A1 | 1/2009 | White et al. |
| 2009/0012617 A1 | 1/2009 | White et al. |
| 2009/0118830 A1 | 5/2009 | Fell |
| 2009/0259311 A1 | 10/2009 | Shterling et al. |
| 2009/0259313 A1 | 10/2009 | Elsner et al. |
| 2009/0259314 A1 | 10/2009 | Linder-Ganz et al. |
| 2010/0168864 A1 | 7/2010 | White et al. |
| 2011/0029094 A1 | 2/2011 | Hogendijk et al. |
| 2011/0112647 A1 | 5/2011 | Hogendijk et al. |
| 2012/0022649 A1 | 1/2012 | Robinson et al. |

FOREIGN PATENT DOCUMENTS

| | | |
|---|---|---|
| WO | WO-2005/070309 A1 | 8/2005 |
| WO | WO-2008/124737 A2 | 10/2008 |
| WO | WO-2008/124737 A3 | 10/2008 |
| WO | WO-2008/124739 A1 | 10/2008 |
| WO | WO-2009/052208 A2 | 4/2009 |
| WO | WO-2009/052208 A3 | 4/2009 |
| WO | WO-2010/030933 A1 | 3/2010 |
| WO | WO-2011/032043 A1 | 3/2011 |

OTHER PUBLICATIONS

Ascension Orthopedics (2005). "Ascension® PyroDisk® Surgical Technique," 2 pages.

Ascension Orthopedics (2009). "Ascension® PyroDisk® Surgical Technique," located at <http://www.ascensionortho.com/Assets/PDF/PyroDisk/PyroDisk_SurgTech-revC.pdf>, last visited on Nov. 10, 2011, 2 pages.

Berger, R.A. (1989). "A Brief History of Finger Anthroplasty," *Iowa Orhtop. J.* 9:77-82.

Bioprofile (Date Unknown). "STPI Scaphoid Trapezium Pyrocarbon Implant," Brochure, 4 pages.

Bioprofile (Date Unknown). "STPI X-Rays Templates," located at <http://www.orthopaedicsolutions.com/images/uploaded/docs/STPITemplate.pdf>, last visited on Nov. 10, 2011, 1 page.

Blair, W.F. (Mar. 1984). "Metacarpophalangeal Joint Implant Arthroplasty with a Silastic Spacer," *The Journal of Bone and Joint Surgery* 66-A(3):365-370.

Bouwer, S. (1972). "Silicone Implants in the Hand," *Acta Orthopaedica Belgica* 38(1):27-32.

Christenson, E.M. et al. (2004, e-pub. Jun. 2, 2004). "Oxidative Mechanisms of Poly(Carbonate Urethane) and Poly(Ether Urethane) Biodegration: in vivo and in vitro Correlations," *J. Biomed. Mater. Res.* 70A:245-255.

Cobey, M.C. (Sep.-Oct. 1967). "Arthroplasties Using Compressed Ivalon Sponge ("Intra-medic Sponge"). Long-Term Follow-up Studies in 109 Cases," Chapter 14 in *Clinical Orthopaedics and Related Research*, Marhsall R. Urist ed., J.B. Lippincott Company: Philadelphia, PA, 54:139-144.

Croog, A.S. et al. (2007). "Newest Advances in the Operative Treatment of Basal Joint Arthritis," *Bulletin of the NYU Hospital for Joint Diseases* 65(1):78-86.

Dumontier, C. (Date Unknown). "History of PIP and MCP Joints Replacement," located at <http://www.docstoc.com/docs/2197225/History-of-PIP-and-MCP-joints-replacement>, last visited on Nov. 10, 2011, 44 pages.

Final Rejection mailed on Mar. 1, 2010, for U.S. Appl. No. 11/862,095, filed Sep. 26, 2007, 14 pages.

Final Rejection mailed on Jan. 4, 2011, for U.S. Appl. No. 12/099,296, filed Apr. 8, 2008, 10 pages.

Final Rejection mailed on Jul. 6, 2011, U.S. Appl. No. 12/212,587, filed Sep. 17, 2008, 14 pages.

Final Rejection mailed on Jul. 18, 2011, for U.S. Appl. No. 12/694,178, filed Jan. 26, 2010, 15 pages.

Final Rejection mailed on Jul. 19, 2011, for U.S. Appl. No. 12/210,101, filed Sep. 12, 2008, 15 pages.

Final Rejection mailed on Oct. 19, 2011, for U.S. Appl. No. 12/694,056, filed Jan. 26, 2010, 13 pages.

Final Rejection mailed on Nov. 3, 2011, for U.S. Appl. No. 12/210,099, filed Sep. 12, 2008, 16 pages.

Gomez, P.F. et al. (2005). "Early Attempts at Hip Arthroplasty—1700s to 1950s," *Iowa Orthop. J.* 25:25-29.

International Preliminary Report on Patentability mailed on Oct. 22, 2009, for PCT Patent Application No. PCT/US2008/059682, filed on Apr. 8, 2008, 6 pages.

International Preliminary Report on Patentability mailed on Oct. 29, 2009, for PCT Patent Application No. PCT/US2008/059679, filed on Apr. 8, 2008, 7 pages.

International Search Report mailed on Sep. 3, 2008, for PCT Application No. PCT/US08/59682, filed on Apr. 8, 2008, 1 page.

International Search Report mailed on Jun. 8, 2009, for PCT Application No. PCT/US08/59679, filed on Apr. 8, 2008, 1 page.

International Search Report mailed on Jan. 11, 2010 for PCT Patent Application No. PCT/US2009/056724, filed on Sep. 11, 2009, 1 page.

International Search Report mailed on Dec. 30, 2010, for PCT Patent Application No. PCT/US2010/048529, filed on Sep. 10, 2010, 3 pages.

Kessler, I. et al. (Mar. 1971). "Arthroplasty of the First Carpometacarpal Joint with a Silicone Implant," *Plastic & Reconstructive Surgery* 47(3):252-257.

Linder-Ganz, et al. (Feb. 2009). "Can a Polycarbonate-Urethane Meniscal Implant Protect Articular Cartilage?" Poster No. 1200, presented at 55th Annual Meeting of the Orthopaedic Research Society, Las Vegas, NV, Feb. 22-25, 2009, 1 page.

Linder-Ganz, et al. (Mar. 2010). "Chondroprotective Effects of a Polycarbonate-Urethane Meniscal Implant in a Sheep Model," Paper No. 65, presented at 56th Annual Meeting of the Orthopaedic Research Society, New Orelans, LA, Mar. 6-9, 2010, 1 page.

Matullo, K.S. (2007, e-pub. Aug. 7, 2007). "CMC Arthroplasty of the Thumb: A Review," *HAND* 2:232-239.

Nelson, D. (May 20, 2000). "Arnold-Peter Weiss, MD," located at <http://www.davidlnelson.md/Weiss_talk.htm>, last visited on Nov. 10, 2011, 2 pages.

Non-Final Office Action mailed on Jul. 6, 2009, for U.S. Appl. No. 11/562,095, filed Sep. 26, 2007, 9 pages.

Non-Final Office Action mailed on Jun. 1, 2010, for U.S. Appl. No. 12/099,296, filed Apr. 8, 2008, 6 pages.

Non-Final Office Action mailed on Oct. 12, 2010, for U.S. Appl. No. 12/210,099, filed Sep. 12, 2008, 14 pages.

Non-Final Office Action mailed on Oct. 18, 2010, for U.S. Appl. No. 12/212,587, filed Sep. 17, 2008, 13 pages.

Non-Final Office Action mailed on Oct. 27, 2010, for U.S. Appl. No. 12/694,178, filed Jan. 26, 2010, 12 pages.

Non-Final Office Action mailed on Nov. 9, 2010, for U.S. Appl. No. 12/210,101, filed Sep. 12, 2008, 11 pages.

Non-Final Office Action mailed on Mar. 2, 2011, for U.S. Appl. No. 12/694,056, filed Jan. 26, 2010, 11 pages.

Non-Final Office Action mailed on Jun. 22, 2011, for U.S. Appl. No. 12/210,099, filed Sep. 12, 2008, 12 pages.

Non-Final Office Action mailed on Nov. 14, 2011, for U.S. Appl. No. 12/694,004, filed Jan. 26, 2000, 10 pages.

Non-Final Office action mailed on Nov. 22, 2022, for U.S. Appl. No. 13/245,736, filed Sep. 26, 2011, 13 pages.

Pramanik, S. et al. (2005). "Chronology of Total Hip Joint Replacement and Materials Development," *Trends Biomater. Artif. Organs* 19(1):15-26.

Ritt, M.J.P.F. et al. (Dec. 1994). "The Early History of Arthroplasty of the Wrist. From Amputation to Total Wrist Implant," *Journal of Hand Surgery* 19B(6):778-782.

Stark, H.H. (Dec. 1981). "Use of a Hand-Carved Silicone-Rubber Spacer for Advances Kienböck's Disease," *The Journal of Bone and Joint Surgery* 63-A(9):1359-1370.

Steinberg, D.R. et al. (May 2000). "The Early History of Arthroplasty in the United States," *Clinical Orthopaedics and Related Research* 374:55-89.

Swigart, C.R. (2008, e-pub. Feb. 24, 2008). "Arthritis of the Base on the Thumb," *Curr. Rev. Musculoskelet Med.* 1:142-146.

Waris, E. (2008). *Bioabsorbable Materials for Oesteosynthesis and Small Joint Arthroplasty in the Hand*, Academic Dissertation, University of Helsinki, pp. 1-83.

Written Opinion of the International Searching Authority, mailed on Sep. 2, 2004, for PCT Patent Application No. PCT/US04/11995, filed on Apr. 16, 2004, 4 pages.

Written Opinion of the International Searching Authority mailed on Sep. 3, 2008, for PCT Application No. PCT/US08/59682, filed on Apr. 8, 2008, 4 pages.

Written Opinion of the International Searching Authority mailed on Jun. 8, 2009, for PCT Application No. PCT/US08/59679, filed on Apr. 8, 2008, 3 pages.

Written Opinion of the International Searching Authority mailed on Jan. 11, 2010 for PCT Patent Application No. PCT/US2009/056724, filed on Sep. 11, 2009, 12 pages.

Written Opinion of the International Searching Authority mailed on Dec. 30, 2010, for PCT Patent Application No. PCT/US2010/048529, filed on Sep. 10, 2010, 12 pages.

Yoshinori, O. et al. (2000). "Silastic Interposition Arthroplasty for Osteoarthrosis of the Carpometacarpal Joint of the Thumb," *Tokai J. Exp. Clin. Med.* 25(1):15-21.

Zimmer, Inc. (Oct. 14, 2008). "UniSpacer® Knee replacement. An Alternative Treatment for Patients with Arthritis," located at <http://www.zimmer.com/z/ctl/op/global/action/1/id/9272/template/PC/navid/1879>, last visited on Nov. 10, 2011, 3 pages.

* cited by examiner

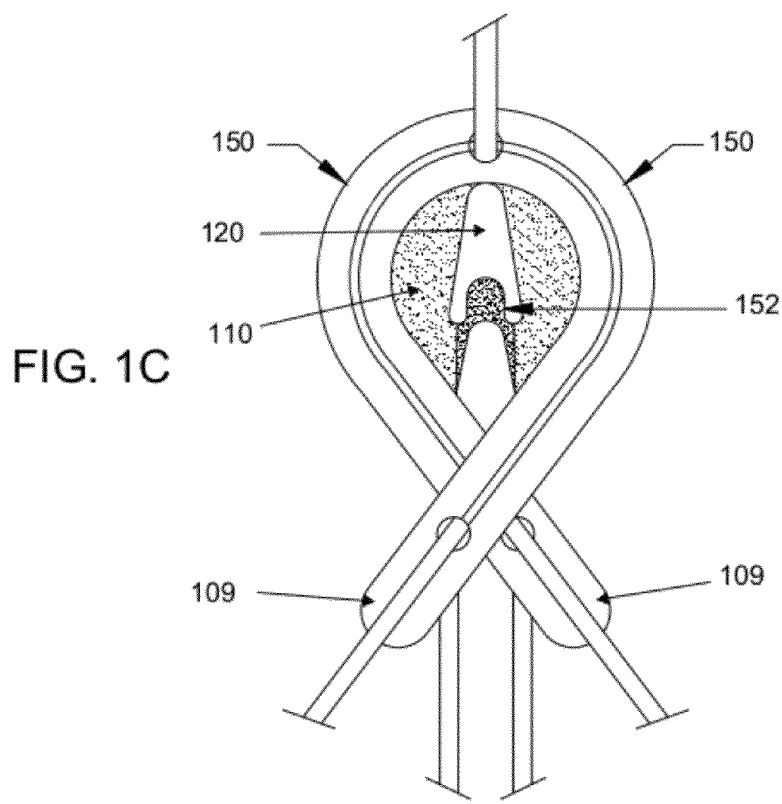

FIG. 4C
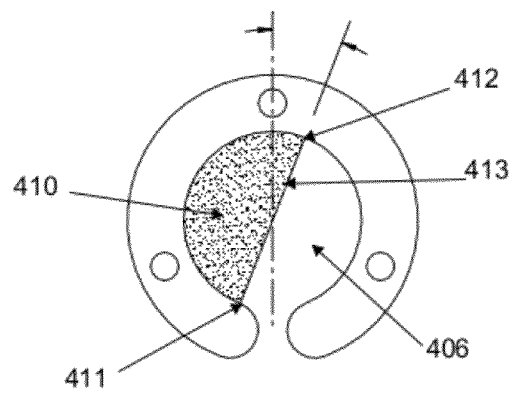
FIG. 4D
FIG. 4E
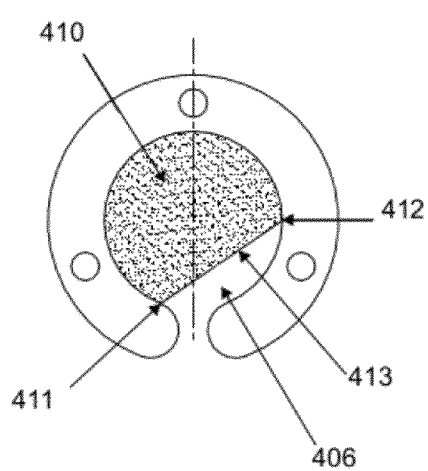
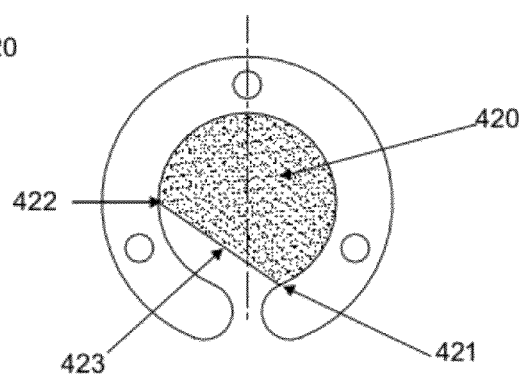
FIG. 4F

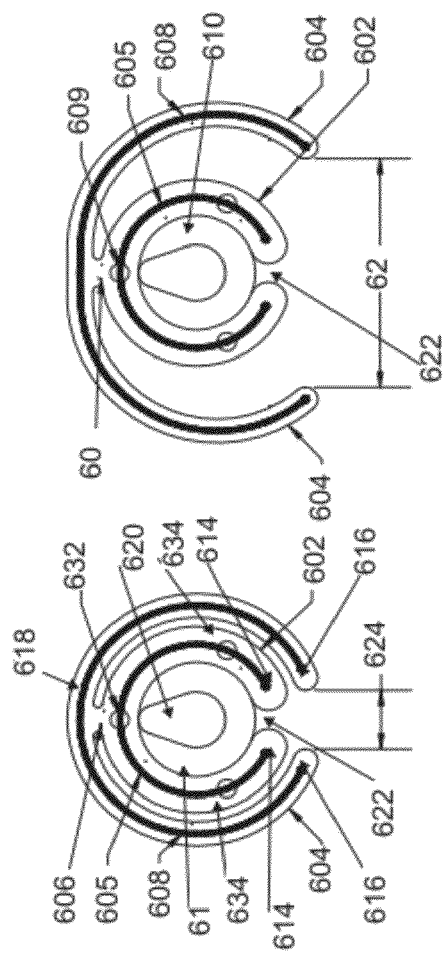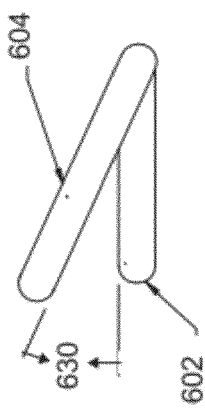

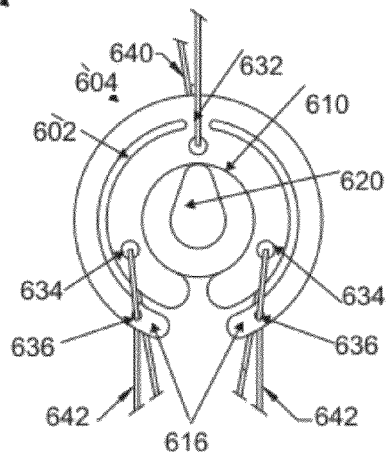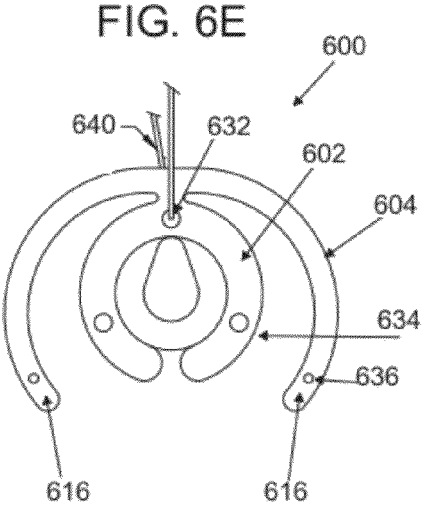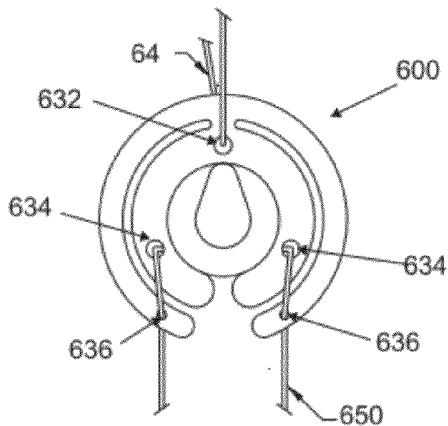

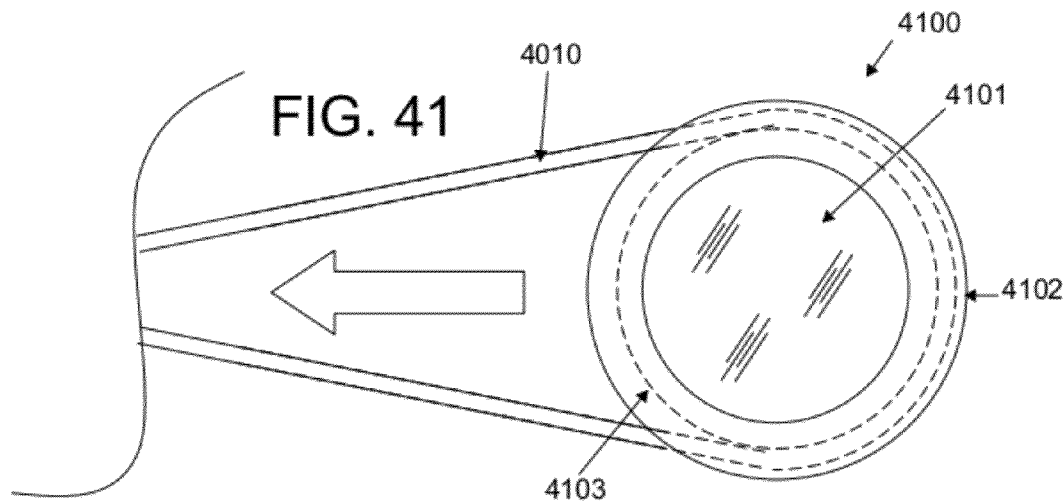
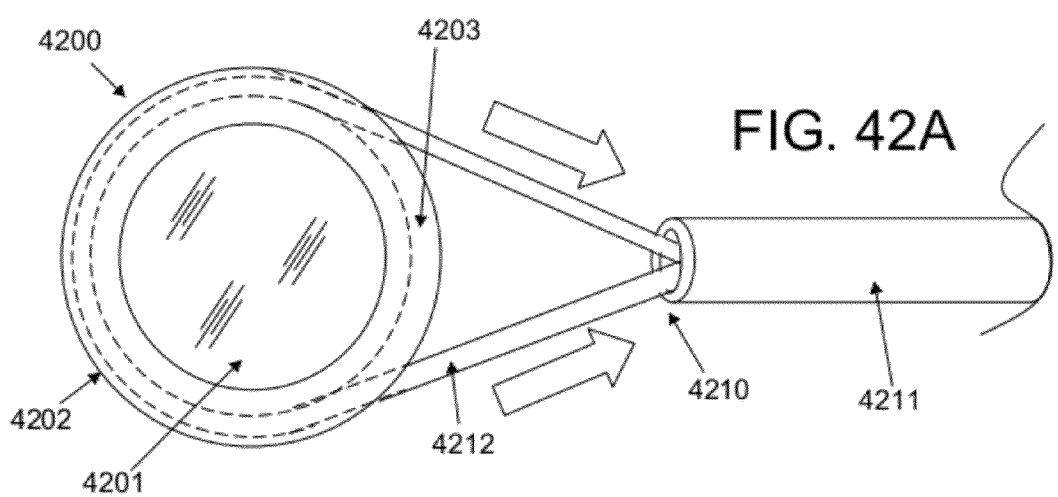
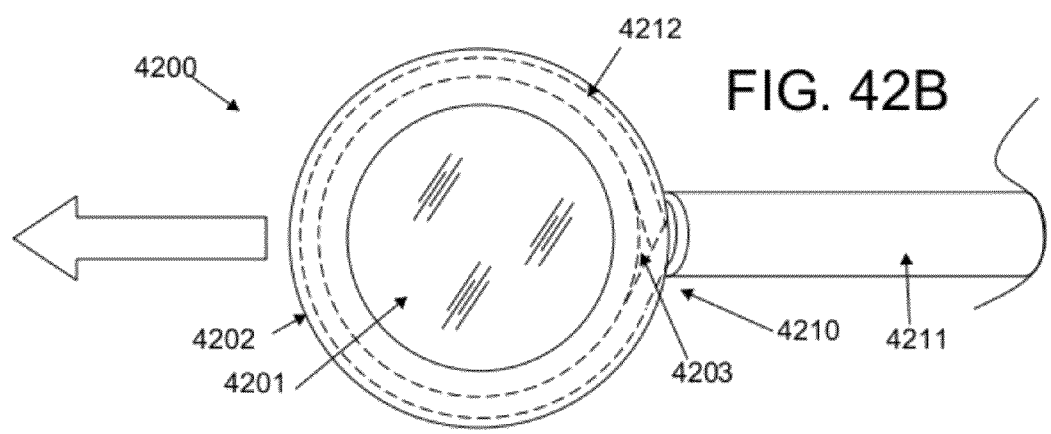

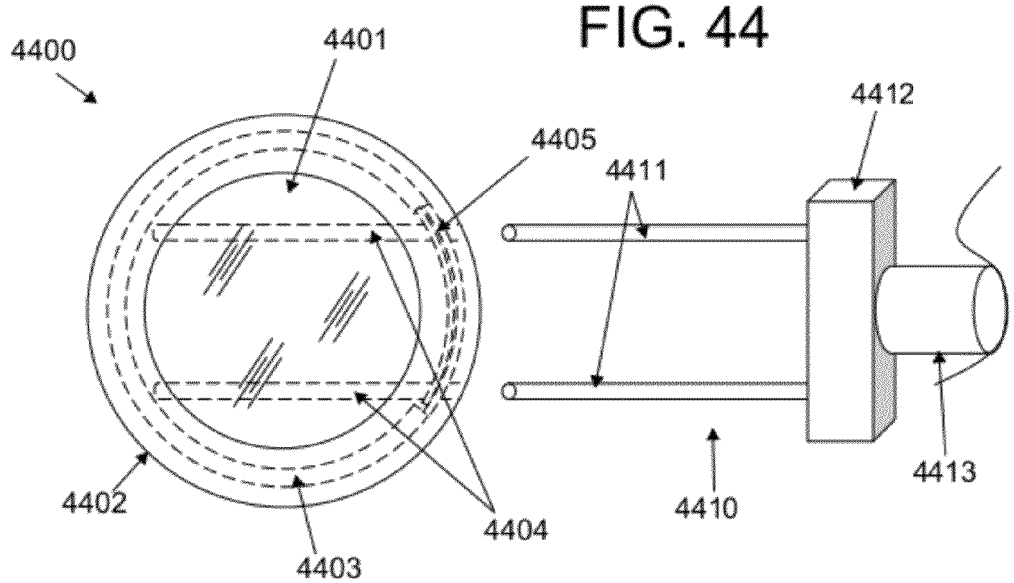
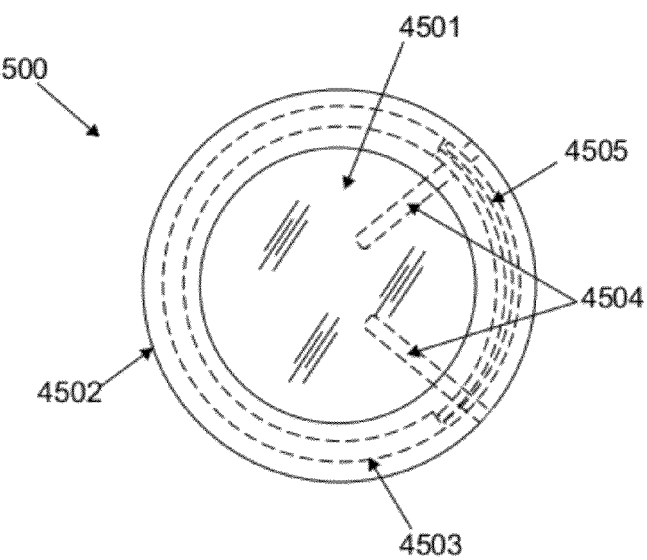
FIG. 44
FIG. 45

DISC-BASED ORTHOPEDIC DEVICES

CROSS-REFERENCE TO RELATED APPLICATION

This application claims priority under 35 U.S.C. §119(e) to U.S. Provisional Ser. No. 61/241,843, filed Sep. 11, 2009, which is hereby incorporated by reference in its entirety.

BACKGROUND

Osteoarthritis is by far the most common type of arthritis, with an estimated 12.1 percent of the U.S. population (nearly 21 million Americans) age 25 and older have osteoarthritis of one form or another. Although more common in older people, it usually is the result of a joint injury, a joint malformation, or a genetic defect in joint cartilage. The incidence and prevalence of osteoarthritis differs among various demographic groups: osteoarthritis tends to start for men before the age of 45, and after the age of 45 it is more common in women. It is also more likely to occur in people who are obese or overweight and is related to those jobs that stress particular joints.

Arthritis is a degenerative process that affects the musculoskeletal system and specifically the diarthrodal or synovial joints—where two or more bones meet and form a joint cavity surrounded by a synovial joint capsule. It often occurs in the joints of the hands and wrists (particularly in the fingers and thumbs, between the phalanges, the metacarpals and/or the carpals), feet (in the toes, between phalanges, metatarsals and/or tarsals), ankles, elbows, shoulders, knees, hips, and the spine (particularly at the neck and lower back). Joint problems can include inflammation and damage to joint cartilage (the tough, smooth tissue that covers the ends of the bones, enabling them to glide against one another) and surrounding structures. Such damage can lead to joint stiffness, weakness, instability and visible deformities that, depending on the location of joint involvement, can interfere with the basic daily activities such as walking, climbing stairs, using a computer keyboard, cutting food and brushing teeth. This ultimately results in moderate to severe pain. Drug regimes can provide temporary relief from the pain, but do not slow down the crippling affects. Drugs may also subject patients to serious side effects and risks, such as the increased cardiovascular risks associated with osteoarthritis drugs Vioxx and Bextra, which were withdrawn from the market. Drugs used to treat other forms of arthritis, such as corticosteroids, are associated with osteoporosis and hyperglycemia and can lead to increased risks of bone fracture and diabetes, for example. When pharmacologic therapy and physical therapy no longer provide adequate relief, only surgical options remain.

The treatment of severe arthritis may involve joint fusion, an open surgical procedure to implant a spacer, or to total joint replacement with a prosthetic device. Many of the current surgical treatments are not reversible. Current joint replacement therapies (spacers or a total prosthesis) require the joint capsule to be surgically opened and the bone surfaces to be partially or totally removed. Both modalities present various drawbacks. For example, U.S. Pat. No. 6,007,580 to Lehto et al. describes an implantable spacer that must be fixed at one or both ends to the bone of either end of the knuckle (e.g. the metacarpal-phalangeal (MCP) joint). The spacer must be implanted by opening of the joint capsule and be affixed at one or both ends to the corresponding bone surfaces.

Various spacers in the art can cause inflammation, while total joint replacement can limit the range of motion and also compromise the strength and stability of the joint. These surgeries are highly invasive and require the joint capsule to be surgically opened, and the incision itself can result in inflammation and infection. Due to the invasiveness of the procedure, prolonged healing times are required. Furthermore, the invasive nature of these surgeries sometimes precludes a second joint replacement or spacer when the first joint device wears out or fails.

It would be desirable as well as beneficial if there were an intermediary step or alternative treatment before subjecting patients to drastic joint replacement and/or long-term drug therapy.

BRIEF SUMMARY

Methods and apparatuses for treatment of various joint conditions include a device inserted into a joint space. During delivery, the profile of the device is constrained in at least one dimension to minimize invasive impact on tissue and/or bone. The device may be restrained for implantation by a thread or a rigid elongate member. After insertion, the device may expand at the implantation site.

In one example, an orthopedic implant configured to be inserted into a patient's joint comprises a main body with a generally planar configuration, a first dimension orthogonal to the planar configuration, a second coplanar dimension orthogonal to the direction of insertion of the implant, an inner region at least partially surrounded by the main body, and at least one transition region configured to gradually reduce the height of the main body in the first dimension to the height of the inner region in the first dimension, wherein the main body has a distal edge configured to be first inserted into the patient's joint, wherein the implant is configured to resiliently decrease in size in the second dimension, wherein the inner region comprises a span member at least partially spanning the inner region, wherein the span member comprises an inward proximal edge, wherein an inward proximal edge comprises at least one region that is closer to the distal edge of the device in the first dimension than the widest points of the distal edge in the second dimension and wherein the transition region comprises a slope selected from the group consisting of: a constant and a linear function of the distance of the transition region from the perimeter. In some further examples, the inward proximal edge comprises an arc of radius between 5-25% of the width of the orthopedic implant in the second dimension. In other examples, the inner region comprises a central opening and wherein the central opening comprises an inward distal edge of the span member, and wherein the inward distal edge comprises at least one region that is further from the distal edge of the device in the first dimension than the widest points of the distal edge in the second dimension. In some examples, the central opening comprises a diameter in the second dimension between 30-50% of the width of the orthopedic implant in the second dimension. In some other examples, the height of the inner region in the first dimension is between 15-35% of the height of the orthopedic implant in the first dimension. In yet further examples, the transition region comprises a proximal transition region configured to ease overlapping of the main body. In some further examples, the proximal region transition region further comprises an acute angle. In other examples, the inner region further comprises a distal outward edge and the transition region comprises a distal transition region configured to gradually reduce the distal height of the main body in the first dimension to the height of the inner region in the first dimension. In some further examples, the distal edge comprises a lead surface configured to ease insertion of the orthopedic implant through an incision, wherein the lead surface comprises at least one of an arc with a radius different from the radius of the main body and an arc eccentric to the main body, and a tapered region joining the distal edge to the main body. In some examples, the tapered region comprises a surface with a slope that is a linear function of distance from the distal edge. In other examples, a distal edge comprises a transition region which linearly increases the height of the distal edge to the height of the main body. In yet further examples, the main body further comprises at least one resilient core configured to resist deformation. In some examples, the main body further comprises two resilient cores. In further examples, at least one resilient core comprises at least one coupling member configured to resist movement of the at least one resilient core relative to the orthopedic implant. In some other examples, the main body comprises at least one radiopaque core or material. In yet other examples, the main body further comprises at least one hole configured for releasably coupling to a delivery member. In some examples, the at least one hole comprises at least one angle configured to reduce slippage of the delivery member. In some further examples, the at least one hole comprises a grommet configured to resist fracture of the implant during delivery, wherein the grommet has a tensile strength greater than the tensile strength of the orthopedic implant. In some implants, the wear protection mechanism further comprises a coupling member configured to resist movement of the wear protection mechanism relative to the orthopedic implant. In other implants, the coupling member further comprises at least one protrusion. In some examples, the at least one protrusion comprises a continuous perimeter. In further examples, the at least one protrusion comprises a series of flanges. Some implants comprise a main body with at least one resilient core configured to resist deformation, wherein at least one hole corresponds to attachment points of the at least one core during a manufacturing process. In some further examples, the inner region height in the first dimension is between 2-12% of the width of the orthopedic implant in the second dimension. In other examples, the main body comprises two leg tips. In some examples, leg tips are separated by a width in the second dimension between 10-30% of the width of the orthopedic implant in the second dimension. In some further examples, the perimeter comprises an arcuate shape. In yet further examples, the width of the orthopedic implant in the second dimension is sized to fit in a patient's carpometacarpal joint.

In another example, a carpo-metacarpal orthopedic system comprises a carpo-metacarpal implant and a delivery member configured to releasably couple to the implant and to substantially resist relative motion with the implant when coupled to the implant. In some further examples, the implant comprises at least one recess along a perimeter of the implant and the delivery member further comprises a loop. In other examples, the implant is generally disc-shaped and further comprises at least one perimeter, the at least one perimeter comprising a first receiving groove and a second receiving groove, and the delivery member further comprises a first opposing member configured to releasably couple to the first receiving groove and a second opposing member configured to releasably couple to the second receiving groove. In other systems, the implant comprises at least one substantially linear channel and the delivery member comprises at least one rigid elongated member.

In yet another example, an orthopedic joint device comprises an implant with at least one recess along a perimeter of the implant, a delivery member comprising a coupling portion comprising a loop and configured to releasably couple to the at least one recess to substantially resist relative motion between the implant and the delivery device. In some devices, the at least one recess is a contiguous recess. In some further examples, the contiguous recess is located along at least 50% of the perimeter of the implant. In yet further examples, the contiguous recess is located along at least 75% of the perimeter of the implant. In still further examples, the contiguous recess is located along at least 90% of the perimeter of the implant. In at least one example, the coupling portion of the delivery member further comprises a recessed coupling portion configured to releasably engage a non-recessed portion of the implant. In some further examples, the loop is a flexible loop. In yet further examples, the delivery member further comprises a securing member configured to increase the percentage of the at least one recess coupled to the coupling portion.

In yet another example, an orthopedic joint device comprises a generally disc-shaped implant comprising at least one perimeter and a delivery member comprising a first opposing member configured to releasably couple to the first receiving groove and a second opposing member configured to releasably couple to the second receiving groove, wherein the at least one perimeter comprises a first receiving groove and a second receiving groove, and wherein the first opposing member and the second opposing member are configured to substantially resist relative motion between the implant and the delivery member when the first opposing member is coupled to the first receiving groove and the second opposing member is coupled to the second receiving groove. In some further examples, the implant comprises at least one articulation comprising at least one axis of rotation about which the implant articulates. In yet further examples, the implant comprises at least one flex region about which the implant articulates. In some examples, the implant further comprises an inner membrane configured to resist splaying of the device in use. In some devices, at least one of the first and second grooves comprise side walls configured to resist relative motion between the opposing members and the implant. In some further devices, the implant comprises a resilient non-linear inner core. In some devices, the implant comprises a radiopaque core or material. In at least one device, the center of the implant, the first receiving groove, and the second receiving groove are co-linear.

In yet another example, an orthopedic implant system comprises an implant comprising at least one substantially linear channel and a delivery member comprising at least one rigid elongated member configured to insert into the at least one channel to substantially resist relative motion between the implant and the delivery member. In some further examples, the at least one channel comprises a longitudinal axis and non-circular cross-sectional shape perpendicular to the longitudinal axis. Yet further examples comprise at least two channels. In some examples, at least two channels are not parallel. Some implants are configured to deform by repositioning the at least two channels after the insertion of the at least one rigid elongated member. In yet further examples, the implant comprises a resilient non-linear inner core. In some examples, the implant comprises a channel entrance, wherein the resilient non-linear inner core comprises two ends, and wherein the channel entrance is positioned between the two ends. In some examples, the implant comprises a radiopaque non-linear core.

In yet another example, an orthopedic system comprises an orthopedic device comprising a resilient non-linear elongate body with two ends separated by a gap, an inner region surrounded by the elongate body, a flexible polymeric jacket covering at least a portion of the resilient non-linear elongate body, and a first sheet member partially spanning the inner region of the non-linear elongate body. In some further examples, the first sheet member comprises a contiguous layer. In yet further examples, the first sheet member is semipermeable. In other examples, the first sheet member comprises a closed perimeter opening. In some examples, the closed perimeter opening has a narrow end and a broad end. Some systems have a closed perimeter opening comprising a teardrop configuration. Some other systems have a closed perimeter opening located symmetrically about a midline of the device. Some examples include a free edge of the first sheet member intersecting the geometric center of the inner region of the device. Some further examples comprise a second sheet member at least partially spanning the inner region of the non-linear elongate body. In some other examples, a free edge of the second sheet member intersects the center of the inner region. In further examples, the first sheet member and the second sheet member form an enclosed cavity. In some further examples, the second sheet member is semipermeable. Some systems include a therapeutic agent configured for placement in the enclosed cavity. In some further systems, the therapeutic agent is a disease-modifying anti-rheumatic drug or a viscosupplement. In yet further systems, the drug is selected from a group consisting of cyclophosphamide, prednisone, methotrexate, azathioprine, gold, D-penicillamine, hydroxychloroquine, and a non-steroidal anti-inflammatory agent. In some further examples, a valve is included and configured to permit selective filling of the enclosed cavity. In yet further examples, the orthopedic device comprises a wedge member located on a leading surface of the resilient non-linear elongate body. In some examples, the orthopedic device further comprises at least one tab member located about an end of the resilient non-linear elongate body. In some further examples, the first sheet member comprises an inward edge in the region of the two ends. In other examples, a gradual transition region is located between the resilient elongate body and the inner region, wherein the gradual transition region comprises a slope selected form the group containing a constant and a linear function of the distance of the transition region from the perimeter. In some systems, a lead surface is configured to ease insertion of the orthopedic device through an incision, wherein the lead surface comprises at least one of an arc with a radius different from the radius of the elongate body and an arc eccentric to the elongate body, and a tapered region joining the lead surface to the elongate body.

In yet another example, a method of using an orthopedic device is disclosed, the method comprising constraining an arcuate joint implant to overlap its free ends and passing the joint implant into the joint space while its free ends are overlapped. Some further examples also include wedging a tapered structure of an arcuate joint implant into a joint space. Yet further examples include overlapping two separate membrane structures attached to the arcuate joint implant. Other examples include accessing a cavity located between two layer structures located across the arcuate joint implant, and filling the cavity with a material. Some methods further employ a material that is a viscosupplement or a disease-modifying anti-rheumatic drug. In some further examples, filling the cavity with the material comprises filling the cavity using a valve located in a cavity wall.

In yet another example, an orthopedic system comprises an orthopedic device comprising a closed perimeter with a generally planar configuration and a first dimension orthogonal to the planar configuration, the device configured to resiliently decrease in size along a second in-plane dimension, and wherein the device is further configured to be implanted within a joint cavity without attachment to surrounding tissue. In some further examples, the orthopedic device is configured to increase in size along a third in-plane dimension that is perpendicular to the second in-plane dimension. Some further examples comprise at least one articulation comprising at least one axis of rotation about which the implant articulates, wherein the at least one axis of rotation is orthogonal to the planar configuration. Further examples comprise a resilient inner core and at least one articulation including a first section of the resilient inner core coupled to a second section of the resilient inner core by at least one bearing. In yet further examples, the bearing is integrally formed with the first section of the resilient inner core. In further examples, the system comprises a radiopaque inner core or material. Some systems further comprise a resilient inner core and at least one articulation including a reduced profile section of the resilient inner core. In some further examples, the device is configured to increase in size along the first dimension by no more than three times when the second in-plane dimension is maximally decreased in size. In yet other examples, the device comprises a generally circular configuration. In some examples, the orthopedic device comprises a circular disk configuration. In some further examples, the orthopedic device comprises a ring configuration. In yet further examples, the ring configuration comprises a central opening. Some further examples include a ring configuration comprising an inner membrane. In some further devices, the inner membrane is biconcave. In some other examples, the inner membrane protrudes above the top surface of the closed perimeter. In some further examples, the inner membrane comprises at least one peak and at least one trough. In yet other examples, the at least one peak and the at least one trough are arranged linearly. In some further examples, the at least one peak and the at least one trough are arranged radially. In other examples, the inner membrane comprises at least one opening. In yet further examples, the at least one opening has a smaller dimension along the second in-plane dimension of the device and a greater dimension along a third in-plane dimension that is perpendicular to the second in-plane dimension. In some systems, the orthopedic device comprises a hyperbolic paraboloid saddle shape that is configured to be implanted within a joint capsule of a joint cavity. In other systems, an orthopedic device comprises a curved planar shape that is configured to be implanted within a joint capsule of a joint cavity without attachment to surrounding tissue.

In yet another example, an orthopedic implant has a first dimension, a second dimension and a third dimension, wherein the first dimension is less than the second and third dimensions, and wherein at least one of the second and third dimensions is a maximum dimension of the orthopedic implant, the implant configured with a base configuration and a resiliently strained configuration that has a decreased size along the second dimension compared to the base configuration and wherein a first region and a second region of the orthopedic implant are closer to each other than in the base configuration. In some further examples, the resiliently strained configuration has an increased size along the third dimension compared to the base configuration. In yet further examples, the implant is configured so that the first dimension increases in size by no more than three times when transitioned from the base configuration to the strained configuration. Some implants are configured for implantation within a joint capsule of a diarthrodal joint. In some further examples, the orthopedic implant is configured for implantation in the joint without attachment to the surrounding tissue. In some examples, the orthopedic implant comprises a perimeter thickness and a central thickness that is less than the perimeter thickness. In yet further examples, the central thickness is greater than zero. Some implants comprise a circular configuration. Other implants comprise a ring configuration. Yet other implants comprise a biconcave disk configuration. Yet other implants comprise a convex/concave disc configuration. Some implants are configured for implantation in a carpal-metacarpal joint. Some further implants are configured for implantation in a carpal-metacarpal joint of a thumb.

In another example, a method of implanting an orthopedic implant is disclosed, the method comprising deforming an orthopedic implant by displacing a first region and a second region of an implant toward each other within a plane, and displacing a third region and a fourth region of an implant away from each other within the plane. Some methods further comprise deforming the orthopedic implant without out-of-plane displacement of any other region of the implant. Yet further methods comprise inserting the deformed implant into a diarthrodal joint. Some methods comprise inserting the deformed implant into a carpo-metacarpal joint. Other methods comprise inserting the deformed implant into a first carpo-metacarpal joint of a hand. Yet other methods comprise inserting the deformed implant into a first carpo-metacarpal joint of a cadaver hand.

BRIEF DESCRIPTION OF THE DRAWINGS

FIG. 1C depicts the embodiment in FIG. 1A during delivery into a joint space.

FIGS. 4C to 4F are schematic superior views of an orthopedic device comprising various embodiments of leaflets.

FIGS. 6A and 6B are schematic superior cross-sectional views of another embodiment of an orthopedic device comprising a passive anchoring element in its delivery and deployed configurations, respectively; FIG. 6C is a schematic side elevational view of the embodiment in FIGS. 6A and 6B; FIG. 6D is a schematic superior elevational view of the device in FIG. 6A with attached delivery tethers; FIG. 6E depicts the device of FIG. 6D with the delivery tethers removed; FIG. 6F is an alternate embodiment of an orthopedic device with a delivery tether.

FIG. 41 is a schematic superior view of an orthopedic joint device coupled to a delivery member.

FIG. 42A is a schematic superior view of an orthopedic joint device coupled to a delivery member having a lumen. FIG. 42B is a schematic superior view of the orthopedic joint device in FIG. 42A fully coupled to the delivery member.

FIG. 44 is a schematic superior view of an orthopedic joint device comprising two channels and a delivery member.

FIG. 45 is a schematic superior view of an orthopedic joint device comprising two non-linear channels.

DETAILED DESCRIPTION

As should be understood in view of the following detailed description, the exemplary embodiments are generally directed to systems and methods for minimally-invasive treatment of joints, in both medical and veterinary settings (including both small and large animal veterinary medicine). Joints contemplated for various embodiments of the orthopedic systems and methods include, but are not limited to, hands (fingers and thumbs, between phalanges, metacarpals and/or carpals), feet (in the toes, between phalanges, metatarsals and/or tarsals), wrists, elbows, shoulders, knees, hips, and the spine (particularly at the neck and lower back). In some embodiments, an orthopedic device comprises a shape memory body that is inserted into the joint space, which may restore proper joint alignment and joint mobility affected by degenerative processes. In some embodiments, the orthopedic device has a generally arcuate or rectilinear configuration, which may enhance self-centering or self-positioning of the orthopedic device when deployed.

Figure 1A:
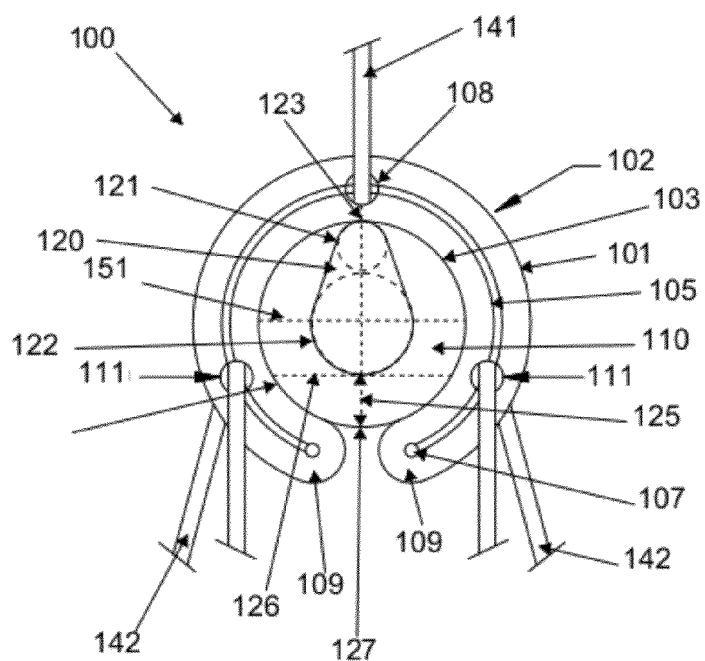
FIG. 1A is a schematic superior view of one embodiment of an orthopedic device comprising an inner membrane with an opening with a closed perimeter.
Figure 1B:
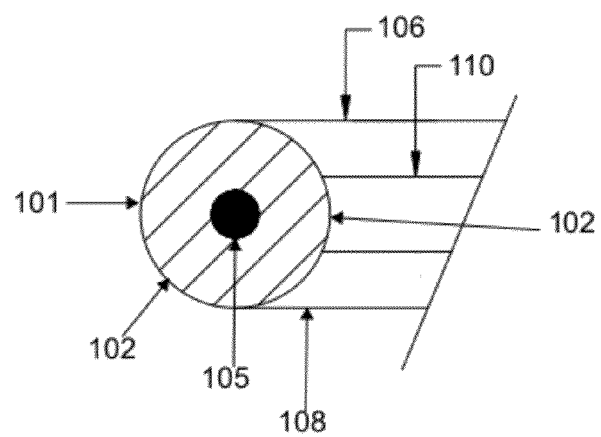
FIG. 1B is an axial cross-sectional view of the embodiment in FIG. 1A.

Referring to FIGS. 1A to 1C, in one embodiment, an orthopedic joint device 100 comprises a resilient or flexible non-linear outer body 102 with one or more inner membrane or sheet structures 110. The non-linear shape of the outer body 102 may comprise an open loop arcuate configuration (e.g., a "C"-shape) with two free loop ends 109, but in other embodiments, the outer body may comprise other shapes, including but not limited to oval or polygonal shapes, may include both open and closed configurations. Examples of orthopedic devices of various open configurations are described in greater detail in U.S. patent application Ser. No. 12/210,101, filed on Sep. 12, 2008, and titled "Suture-Based Orthopedic Joint Devices", which is hereby incorporated by reference in its entirety. In some variations, the open loop configuration may impart greater flexibility by distributing of the loading, shearing, and/or compressive forces applied to the articulation and/or loading of the joint, which may reduce resistance to shape change. However, orthopedic devices with a closed configuration may also be used in some embodiments.

The outer body 102 of the orthopedic device 100 has a circular cross-sectional profile as shown in FIG. 1B. However, it may have any of a variety of cross-sectional profiles in other embodiments, including but not limited to square, ellipse, triangle or any other shape. The outer body 102 of the orthopedic device 100 may further comprise a removable internal support or core element 105. In the embodiment shown in FIG. 1A, the core element 105 also comprises an open loop arcuate configuration. In other embodiments, the core element may or may not comprise the same or similar configuration as the outer body 102. For example, a removable inner core may be embedded in the outer body as a plurality of segments. The removable core 105 may be located anywhere between the outer surface 101 and the inner surface 103 of the outer body 102 or its superior or inferior surfaces, or even partially or completely on the surface of the outer body 102. In some embodiments, the orthopedic device 100 may be initially implanted into a joint with the core 105 in place, but the core 105 may later be removed. In some instances, temporary use of a core 105 in the articular structure or layer may facilitate the implantation of the orthopedic device 100, while the removal of the core may augment the floating characteristics and/or the flexibility of the orthopedic device 100 during use. Various embodiments of removable cores in orthopedic joint devices are described in greater detail in U.S. Pat. Appl. No. 61/171,408, filed on Apr. 21, 2009 and titled "Orthopedic Joint Device with Removable Core", which is hereby incorporated by reference in its entirety. As illustrated in FIG. 1A, the core 105 may have one or more enlarged or bulbous ends 107. The enlarged end 107 of the core component 105 may reduce the risk that the ends 105 may penetrate or protrude from the outer body 102. In some embodiments, the core element 105 may be made from a shape memory material such as nickel-titanium. In some embodiments, the core element may be radiopaque.

The outer body 102 of the orthopedic device 100 may comprise one or more openings configured for attachment of a tether. In FIG. 1A, a delivery tether 141 is used to pull or otherwise delivery the orthopedic device 100 to a joint space. The delivery tether 141 may be attached to the device 100 using an opening, or hole, 108 located on the outer body 102. The opening 108 may be located midway between the two ends 109 of the outer body 102, but in other embodiments, the opening 108 may be anywhere along the outer body 102. The orthopedic device 100 may optionally further comprise additional openings 111 to further facilitate delivery or manipulation of the device 100. Additional tethers 142 may be removably attached at locations closer to loop ends 109. In some embodiments, the additional tethers may also be used to facilitate device 100 removal. As depicted in FIG. 1A, the tethers 141 and 142 may be located between the core element 105 and the inner surface 103 of the outer body 102. By wrapping around the core element 105 as the tether 141 and 142 passes through the openings 108 and 111, damage to the outer body 102 of the device 100 may be reduced by redistributing forces to the core element 105. In other variations, the tether openings may be offset from the core element 105 either closer to the outer surface 101 or the inner surface 103 of the outer body 102. In addition to the openings in the outer body, sutures may be coupled to the outer body 102 by other suitable mechanisms. Various examples of suture coupling mechanisms have been described in greater detail in U.S. patent application Ser. No. 12/210,101, filed on Sep. 12, 2008, and titled "Suture-Based Orthopedic Joint Devices", which was incorporated by reference previously.

In some variations, the outer body 102 of the orthopedic device 100 may comprise any of a variety of rigid, semi-rigid, flexible, gel or liquid materials, which may be metallic or non-metallic, polymeric or non-polymeric, bioresorbable or non-bioresorbable, permeable or semi-permeable, lipophilic, hydrophilic or hydrophobic, for example. These materials may include but are not limited to stainless steel, cobalt-chromium, titanium, and the like. In some embodiments, the outer body 102 of the orthopedic device 100 comprises a shape memory material, such as Nitinol, or a shape memory plastic, polymeric, or synthetic material, such as polycarbonate urethane. pyrolytic carbon, any of a variety of ceramic or hydroxyapatite-based materials, polymers such as PTFE, silicone, nylon, polyethylene, polypropylene, polycarbonate, polyimide, polycarbonate, polyurethane, polyurethane carbonate, PEEK, PEKK and PEBAX, any of a variety of bioresorbable materials such as PGA, PLA, PLGA, PDS and the like, as well as chitosan, collagen, wax and alginate-based materials, animal-derived materials such as small intestine submucosa (SIS), and combinations of the above. In some embodiments, one or more therapeutic agents may be coated on the surface of the orthopedic device 100 or be embedded in one or more reservoirs, depots, cavities, wells, pockets, porous materials, bubbles or capsules for drug delivery. Various examples of therapeutic agents that may be used in conjunction with an orthopedic joint device and the associated drug-releasing mechanisms have been described in greater detail in U.S. patent application Ser. No. 12/210,101, filed on Sep. 12, 2008 and titled "Suture-Based Orthopedic Joint Devices", which was incorporated by reference previously.

The core element 105 may comprise any of the above materials, and may have the same or different composition as the outer body 102. In some variations, the core element 105 comprises a shape memory material. The shape memory material may be made from a heat set/shaped shape-memory material, such as Nitinol, or a shape memory plastic, polymeric, synthetic material. In one embodiment, the core element 105 comprises a metal "open" ring such as Nitinol encapsulated by an outer body 102, or outer blanket, comprising silicone or polycarbonate urethane. In one embodiment the core element 105 comprises a hardened polymer, while in other embodiments, the core material may comprise a gel or liquid within a cavity of the outer body 102, which may or may not be radiopaque. In one embodiment, the core element 105 comprises a polymer and a radiopaque material. In one embodiment, the core element 105 is configured such that a heat set Nitinol with an arcuate configuration, such as an open ring configuration, a horseshoe configuration, or a spiral configuration, can be straightened for delivery through cooling or plastic deformation, then recovered to its original heat-set shape once released from a delivery system, such as one embodiment using a properly sized hypodermic needle. In one embodiment the core element 105 comprises a non-shape memory material which can be bent or deformed. In one embodiment the core element 105 comprises a plurality of structures comprising one or more of the above listed materials that are braided, weaved, or joined. In still other embodiments, the core element 105 may comprise a plurality of non-connected structures, e.g. beads, rods, rings, cubes, etc.

The inner sheet structure or membrane 110, may span at least a portion of the inner region 104 of the outer body 102, may be used to limit expansion of the device 100 and/or to constrain the movement of the two ends 109 of the outer body 102. These and other structural features may facilitate a reduced delivery profile while restricting excessive distortion of the delivery configuration. The inner membrane may provide additional articulating surface for the implanted device. Although the membrane 110 may have a generally flat or planar configuration, in other examples, the membrane 110 may have redundant material in its native configuration that may permit increased stretching of the outer body 102. The reduced thickness may be uniform or non-uniform. In some examples, the thickness may decrease or increase from the outer region of the membrane 110 to the central region, or from the end 109 to the midline of the membrane 110. In the embodiment shown in FIG. 1B, the inner membrane 110 is of a generally uniform thickness 112 and a generally planar configuration that is located midway between the superior surface 106 and the inferior surface 108 of the orthopedic device 100. In other embodiments, the membrane 110 may have a variable thickness, including one or more depressions or grooves along one or more surfaces of the membrane 110. In addition to planar configurations, the membrane 110 may have one or more regions with a non-planer configuration, including corrugated, concave, convex, or tapered regions, for example. In some embodiments, the inner membrane 110 may be located at a position closer to either the superior surface 106 or the inferior surface 108 of the orthopedic device 100. In some variations, the average location of the membrane 110 or the location of the a region of the membrane 110 may be characterized as a percentage of the distance from the inferior surface 108 to the superior surface 106 of the device, and may be anywhere from about 0% to 100%, and may sometimes be about 0%, 5%, 10%, 15%, 20%, 25%, 30%, 35%, 40%, 45%, 50%, 55%, 60%, 65% 70%, 75%, 80%, 85%, 90%, 95, or 100%. In some further variations, the membrane may have a non-planar configuration, e.g. a convex/concave/corrugated configuration, which may protrude beyond the inferior surface 108 and/or the superior surface 106, and may be described either as a negative percentage or a percentage greater than about 100%, for example. The thickness 112 of the inner membrane 110 may be less than that of the outer body 102, as shown in FIG. 1B, or may be about the same as that of the outer body 102. The membrane 110 may be integrally formed with the outer body 102 using common manufacturing techniques such as injection molding or compression molding. The membrane 110 may also be attached or embedded to the outer body 102 directly or with reinforced structures, such as wires, struts, or meshes. The inner membrane 110 may be coupled to the outer body 102 along its entire perimeter where it has contact with the outer body 102. In some embodiments, the membrane 110 may be coupled to the outer body 102 only along a distal portion of the membrane's perimeter, therefore enhancing the mobility of the ends 109 of outer body 102. In some embodiments, the distance between the ends 109 is about 0.1 mm to about 5 mm, sometimes about 0.5 to about 3 mm, and other times about 1 to about 3 mm. In some embodiments, the inner membrane 110 comprises the same material as the outer body 102. In some embodiments, the inner membrane 110 comprises a different material from the outer body 102. In some embodiments, a percentage of the inner membrane 110 (by weight or volume) that comprises the same material as the outer body 102 and may be, for example, 5%, 10%, 15%, 20%, 25%, 30% 35%, 40%, 45%, 50%, 55%, 60%, 65%, 70%, 75%, 80%, 85%, 90%, or 95%. For example, the inner membrane 110 may comprise a similar material as the outer body 102, but also further comprising a polymeric or metallic strands that may be of uniform or nonuniform size or length, and have a random or random organization and orientation, e.g. weave or screen configuration. This additional inner membrane structure may be internal, external or both, to the inner membrane 110, and may comprise a single layer or multiple layers.

The inner membrane 110 may further comprise an opening 120 that is centrally located with respect to the central axis or delivery axis of the orthopedic device 100. In some variations, an inner membrane with an opening may provide greater deformation or folding, which may permit a greater reduction in the delivery profile of the device 100, while also reducing the out-of-plane displacement of the membrane 110. As will be discussed in greater detail below, the inner membrane 110 with an opening 120 may also provide a transition surface for deformed ends 109 to enter the joint space with reduced resistance or reduce strain.

The opening may have any of a variety of shapes, but in the depicted example, the opening comprises a generally teardrop-shape with a narrow end and a broad end. In some further examples, the ends may have a generally arcuate shape that may be characterized as circles 121 and 122 or portions thereof. In other examples, however, the perimeter of the opening may be non-arcuate or may comprise a non-elongate configuration, e.g. lacking any ends. The distal circle 121 with a smaller diameter 121' and the proximal circle 122 with a larger diameter 122' may be externally tangential to one another with both circles aligned along the central axis of the device 100. The distal circle 121 may contact the inner border 104 of outer body 102 (or outer perimeter of the membrane 110), or may be centrally offset from the inner border 104 of the outer body 102. The distal circle 121 may also be further configured or oriented so that its distalmost point 123 is located along the length of the outer body 102. The center of the proximal circle 122 may be aligned with the center of the membrane 110, with a distance 125 between the most proximal point 126 of the opening 120 (e.g., the proximal-most point of the proximal circle 122 in this particular embodiment) and the most proximal point 127 of the inner membrane 110. In some embodiments, the distance 125 between the proximal-most point 126 of the proximal circle 122 and the proximal-most point 127 of the inner membrane 110 is about 0.1 mm to about 5 mm or more, sometimes about 0.5 mm to about 3 mm and other times about 1 mm to about 2 mm.

In other variations, the lateral edges of the opening may not comprise tangential lines connecting the perimeters of the proximal circle and distal circles. The circles may be overlapped or may be spaced apart, either along the central axis of the device or with one or both circles offset to one side of the central axis of the device. In other variations, the diameter of the distal circle may be about the same as the diameter of the proximal circle, thereby forming a rectangular opening with rounded ends. In still other variations, the diameter of the distal circle may be larger than the diameter of the proximal circle. In still other embodiments, the proximal circle may not be concentric with the inner circle of the outer body. The center point of the proximal circle may be located either above or below the transverse center line of the orthopedic device. All these parameters (e.g., the relative positions of two circles to each other and/or to the inner region of the outer body, the relative size of the two circles, etc.) may be independently varied to form an opening with different configurations. Examples of alternative configurations of the opening may include, but are not limited to circular, triangular, rounded rectangle, trapezoidal, oval, elliptical, reverse teardrop (e.g. reversed circle positions) and figure-8 shapes. In some examples, the opening may have a regular or irregular curvilinear or polygonal shape.

In some embodiments, the ratio of the diameter 121' of the distal circle 121 to the diameter 122' of the proximal circle 122 may be about 1:5, sometimes about 1:3, sometimes about 1:1, and other times about 2:1. In some embodiments, the center-to-center spacing between the center points of two circles is about 0.01 mm to about 10 mm, sometimes about 0.1 mm to about 5 mm, and other times about 1 mm to about 3 mm.

When the orthopedic device 100 is pulled by the delivery tether 141 and/or otherwise inserted into a joint through an arthrotomy, the shoulder regions 150 (e.g., the leading edges of the device 100 when the device 100 first enters the arthrotomy, depicted best in FIG. 1C) may begin to deform or compress the portion of the opening 120 occupied by the distal circle 121. In some embodiments where the orthopedic device does not comprise one or more central openings, the inner membrane may fold when the orthopedic device 100 is pulled by the delivery tether 141. As the device 100 is pulled further into the joint, the compression force translates along the arcuate outer body 102 toward the two ends 109, causing the two ends to deform both inwardly and vertically. As a result, the two ends 109 of the device 100 may move out of the plane of the device 100 and cross to one another, forming an alpha shape, as illustrated in FIG. 1C. As the device 100 is further delivered into the joint space, the compression force translated from the outer body 102 to the inner membrane 110 and/or the crossing of the two ends 109 may cause the inner membrane to deform and/or fold. In some examples, the proximal portion 152 of the inner membrane 110 may bulge and fold distally, forming a wedge-like transition surface for the crossed two ends 109 of the orthopedic device 100 to enter the arthrotomy with little resistance. The folding may occur along a line proximally tangent to the proximal circle 122. In other embodiments, the folding may occur at any point along the central axis of the two circles. (e.g., any point between the distal-most point 128 of the distal circle 121 and the proximal-most point 126 of the proximal circle 122).

Once the orthopedic device 100 is pulled into the joint space and the crossed loop ends 109 pass through the incision of the joint, the device 100 may revert or expand toward its base or pre-deployment configuration, which may be the original or base open loop arcuate configuration with two loop ends 109 uncrossed and generally placed within the same plane. In other examples, anatomical and/or mechanical constraints may limit the reversion of the device 100 back to an unconstrained state. In some embodiments, the additional tethers(s) 142 may be used to facilitate repositioning of device 100 after its initial insertion and/or adjusting the positions of the two ends 109 after insertion to help the device revert to its original configuration.

Figure 2A:
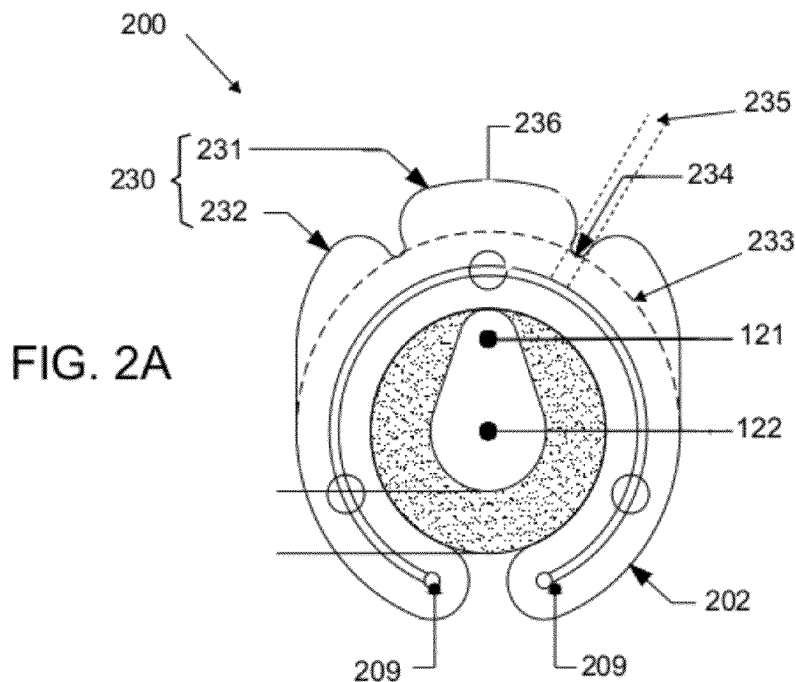
FIG. 2A is a schematic superior view of another embodiment of an orthopedic device comprising multiple distal wedge elements.

FIG. 2A depicts another embodiment of an orthopedic joint device 200 comprising an outer body 202 with an open loop arcuate configuration and an inner membrane 210 with a teardrop-shaped opening 220. The device 200 further comprises a tapered or wedge-shaped insertion structure 230 configured to facilitate insertion or access to tight joints, where the bone-on-bone contact has reduced spacing. An orthopedic device with a tapered insertion configuration may gradually separate a joint as the device is pulled through the joint space, thereby facilitating entry of the orthopedic device through the arthrotomy. The tapered or wedge elements may also provide additional articulating elements or surfaces around the periphery of the outer body. In other variations, the peripheral articulating elements need to have tapered or wedge configurations.

The tapered insertion structure may comprise a single element along the distal region of the outer body 202 and spanning a portion of or the entire distal half of the outer curvature 201 of the outer body 202. The insertion structure 230 may or may not generally lie in the same plane and may have a uniform or non-uniform cross-sectional shape or size along its length. The material comprising the insertion structure 230 may be the same or different as the material of the outer body 202. In other examples, the tapered insertion structure 230 may be segmented or comprise a plurality of insertion structures (e.g., insertion elements 231 to 233 in FIG. 2A). A segmented or plural insertion structure may comprise multiple insertion elements, each with a similar or a different taper configuration, including but not limited to structural characteristics, e.g. cross sectional shape, length, material or durometer. Further, a plural insertion structure may augment the device's overall flexibility by allowing independent bending or deforming. Adjacent insertion elements may be separated by one or more gaps. The gaps may be characterized as an absolute length or a relative length with respect to the length of the outer body 102, the total length of the tapered insertion structure 230, or the length of a single insertion element 231, 232 or 233. The gaps may also vertically separate the insertion elements, e.g. one or more insertion elements may be located at different heights with respect to the superior and inferior surfaces of the outer body. In some examples, adjacent insertion elements may have overlapping lengths but are spaced or separated with respect to their relative heights or vertical positions.

Figures 2B, 2C:
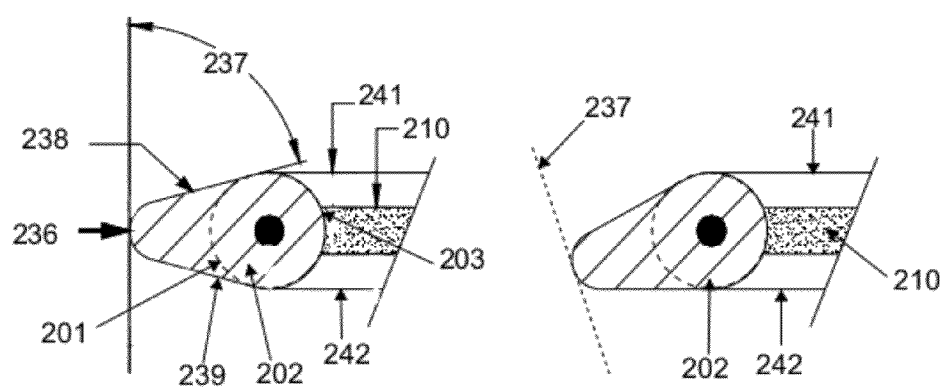
FIGS. 2B and 2C are schematic axial cross-sectional views of two embodiments of the wedge elements.

The embodiment of FIG. 2A comprises a center insertion element 231 and two shoulder insertion elements 232 and 233. In other variations, the elements may be fewer or greater in number, e.g. one, two, four, five or more. The insertion elements may be symmetrically or asymmetrically located with respect to the outer body. As illustrated in FIG. 2B, the center insertion element 231 may have a tapered configuration from the outer body 202 to its distal edge 236. In some embodiments, the taper length may be characterized as the distance between the distal edge 236 of the insertion element 231 and the midpoint between where the tapered surfaces meet the outer body. As illustrated in FIG. 2B, the superior surface 238 and the inferior surface 239 of the insertion element 231 taper from the uppermost surface 241 and lowermost surface 242 of the outer body 102, but in other variations, may taper from any location therebetween. The relative taper angle 237 of a taper surface may be characterized by the angle between the distal tangent line of the distal edge 236 of the insertion element 231 (or other line intersecting the distal edge of the insertion element and orthogonal to the weighted center of the outer body) and tapered upper surface 238 or lower surface 239 of the insertion element 231. The taper angle of each surface may be the same or different, and may be anywhere in the range of about 1 degree to about 90 degrees, sometimes about 25 degrees to about 85 degrees, and other times about 45 degrees to about 80 degrees. The taper profile of an insertion element may or may not be centered with respect to the mid-plane of the device 200. The vertical location of the distal edge 236 of the insertion element 231 may be located anywhere from the superior surface 241 to the inferior surface 242 of the device 200, or above or below the superior surface 241 to the inferior surface 242. FIG. 2C depicts a variant of the device wherein the inferior surface 239 of the device 200, as illustrated in FIG. 2C. An insertion element may or may not have a linear taper profile as illustrated in FIGS. 2B and 2C. For example, the upper surface 238 of an insertion element 231 may comprise a curved or an undulating configuration. For examples, center insertion element 231 in the shown embodiment has a rounded rectangular-like shape; but in other embodiments, it may have recessed shoulders to have an arc-like shape.

The shoulder insertion elements 232 and 233 may or may not have the same shape and/or taper profile as the center insertion element 231. Various aspects of an insertion element (e.g., the shape and/or material of a segment, the taper profile) may be independently altered to form various embodiments of insertion elements. Such flexibility permits each insertion elements to be independently designed. For example, in some applications, shoulder insertion elements may comprise a smaller taper angle than the center insertion element to enhance the device's capacity to cut the peripheral connective tissues that sound the joint space.

In some embodiments, the insertion elements may comprise a smooth or blunt distal edge, which may facilitate an atraumatic entry into a joint space. In other embodiments, some or all of the insertion elements may comprise blade-like edges configured to cut through tissue. The insertion elements may or may not be made from the same material as the outer body of the orthopedic device, and may have a higher or lower durometer than the outer body material. In some embodiments, an insertion element may be made of more than one material so that the segment may comprise variable stiffness.

Figure 3A:
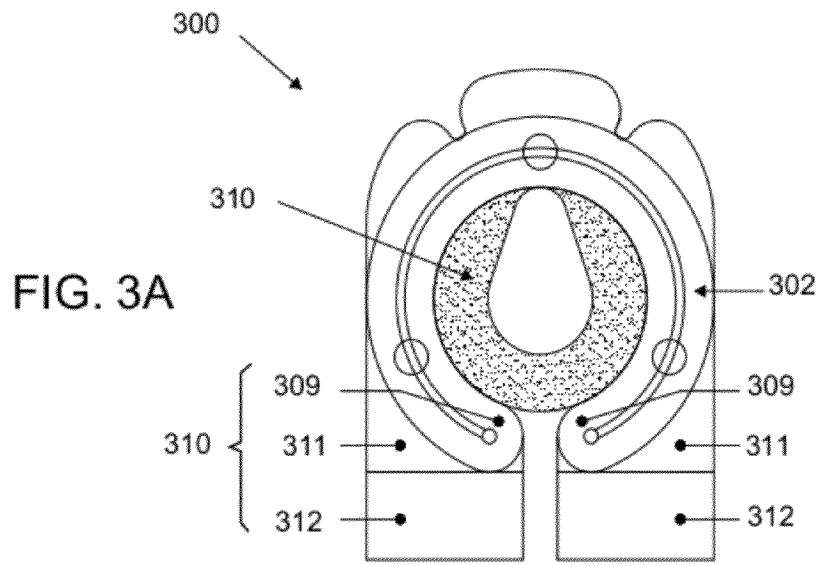
FIGS. 3A to 3C are schematic superior views of various embodiments of an orthopedic device comprising proximal tabs.

In some embodiments, an orthopedic joint device may further comprise proximal wings or tabs located about its open loop ends. The wings or tabs may facilitate manipulation and/or maintaining the orientation of the device during implantation. In FIG. 3A, the orthopedic device 300 comprises proximal wings 310 extending proximally from the outer body 302. The wings 310 may comprise two zones 311 and 312. The taper profile of each zone may be the same or different. For example, the distal zone 311 may comprise a thickness that is about the same as the outer body 302 of the orthopedic device 300 whereas the proximal zone 312 of wing 310 may comprise a tapered configuration tapering from its intersection with the distal zone 311 towards its proximal end. The wing 310 may be integrally formed with the outer body 302 or may be attached or embedded to the outer body 302 in a similar way to how the insertion elements are attached to the device body 302. In some embodiments, length of the wing 310 proximal to the ends 309 of the outer body 302 may be in the range of about 0 mm to about 10 mm or more, sometimes about 1 mm to about 5 mm, and other times about 2 mm to about 4 mm. The wings 310 in FIG. 3A do not extend laterally beyond the most lateral region of the outer body 302, but may or may not do so in other variations.

Figure 3B:
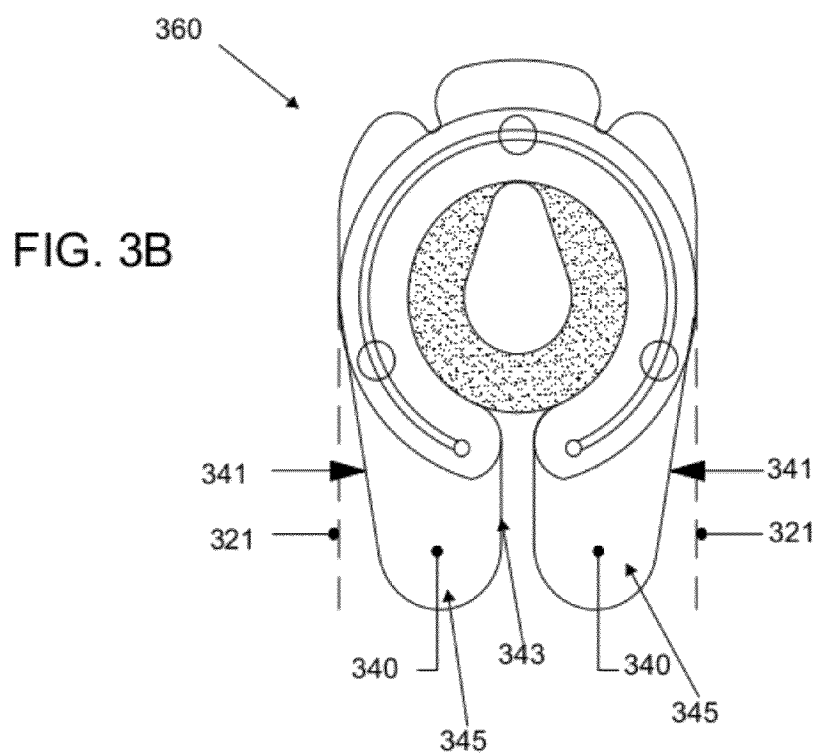
Figure 3C:
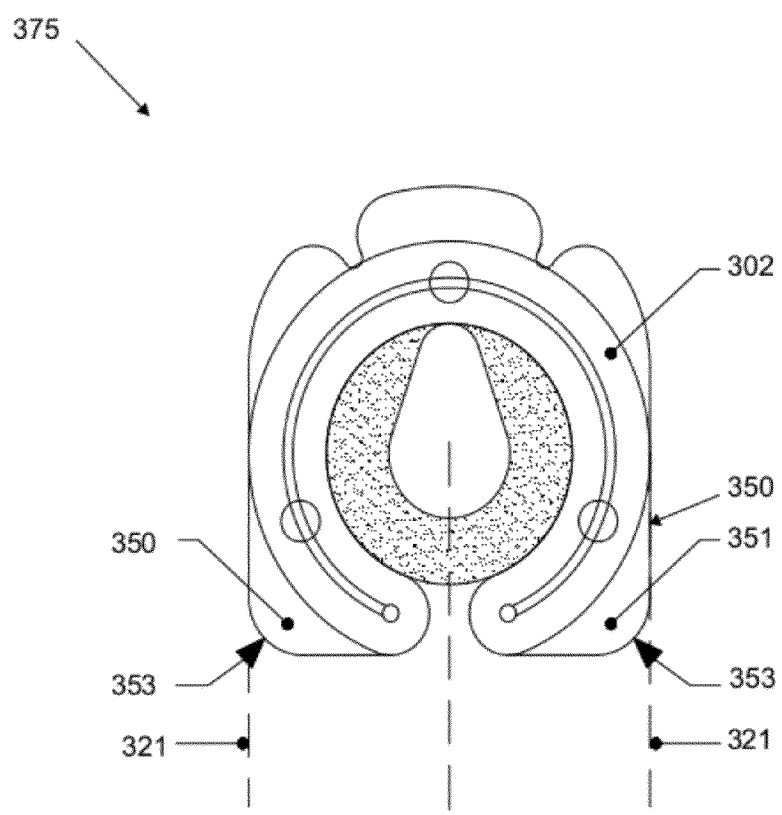

FIG. 3B illustrates a variation of the orthopedic device 360 with a proximal tab or wing 340 comprising a tapered lateral edge 341, a rounded proximal edge 345 and a straight inner edge 343. In other variations, the lateral edge may be straight or flared and the inner edge may be tapered or flared, while the proximal edge may be squared or sharply tapered, for example. FIG. 3C depicts another variation of the orthopedic device 375 with a distal wing 350 with rounded corners 353 but does not extend beyond the lateral or proximal profile of the outer body 302. The lateral edges 351 of the wings 350 comprise a generally parallel configuration with respect to each other or to the central axis of the device 375, but may also have a tapered or flared profile, and may also have profiles that are different from each other. In other variations, the insertion elements on the leading edge of the devices illustrated in FIGS. 3A to 3C may be omitted while retaining their particular wing elements.

Figure 4A:
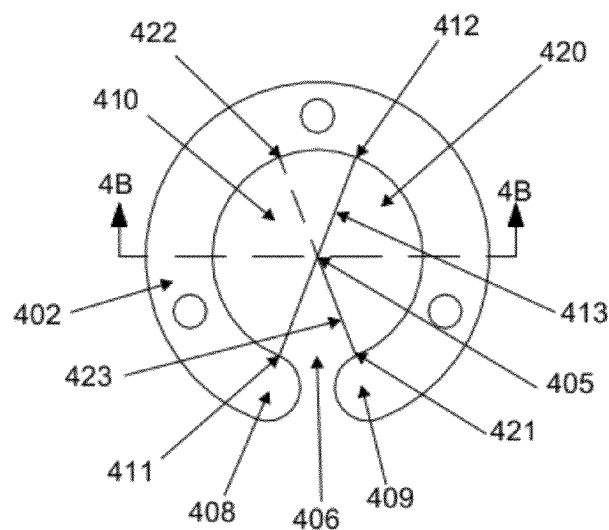
FIG. 4A is a schematic superior view of another embodiment of an orthopedic device comprising multiple inner leaflets.
Figure 4B:
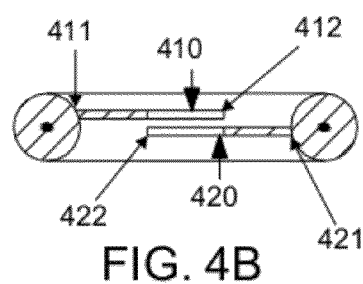
FIG. 4B is a schematic axial cross-sectional view of the device in FIG. 4A.

In some embodiments, an orthopedic joint device may comprise a central articulating surface comprising two or more overlapping leaflets, each of which spans at least a portion of the inner region of the outer body of the device. The overlapping leaflets may be configured to limit the travel of the free loop ends of the outer body while providing for additional articulating surfaces. FIGS. 4A and 4B depict one embodiment of an orthopedic joint device 400 comprising two overlapping leaflets 410 and 420, each of which spans about half of the region 404 bordered by the outer body 402. The two leaflets 410, 420 may or may not be disposed symmetrically with respect to the mid-plane 431 of the device 400. In some embodiments, both leaflets 410, 420 are located above the mid-plane 431; but in other embodiments, they may be both located below the mid-plane 431 of the device 400. In some embodiments, the vertical distance between leaflets 410 and 412 may be about 0.1 mm to about 5 mm or more, sometimes about 0.5 mm to about 3 mm, and other times about 1 mm to about 2 mm. In some embodiments, an orthopedic device may comprise more than two leaflets. The leaflet 410 may attach to the outer body 402 between a proximal base point 411 and a distal apex point 412. A leaflet edge 413 between the base point 411 and the apex point 412 may or may not cross the center point 405 of the inner region 406 of the outer body 402, as illustrated in FIG. 4C and FIG. 4D, respectively. As illustrated in FIGS. 4E and 4F, in some variations, the apex point 412 and 422 of a leaflet 410 and 420, respectively may be located at or proximal to the center point 405 of the inner region 406 of the device 402. In these examples, the leaflets 410, 412 may provide a relatively greater constraining force on the ends 408, 409 of the device 400 as well as a larger articulating surface. In some embodiments, the angle between the leaflet edges 413, 423 and the central axis of the device 400 may be in the range of about 0 degree to about 90 degrees, sometimes about 20 degrees to about 70 degrees, and other times about 40 degrees to about 60 degrees. The leaflet edges may have the same or different thickness as the rest of the leaflet, and in some examples may be reinforced with a wire, chord or other element. The two leaflets 410 and 420 may comprise the same material or may comprise different materials. Also, the leaflets 410 and 420 may have the same thickness or may have different thicknesses.

Referring back to FIGS. 4A to 4D, when the device 400 is inserted into a joint space, and the lateral regions of the outer body 402 are constrained toward the central axis of the device 400, the flexibility of the leaflets 410 and 420 may permit inward or overlapping movements of the two ends 408 and 409. Where the two ends 408 and 409 are crossed, the leaflets 410 and 420 may be elevated by the out-of-plane movements of the ends 408 and 409, thereby providing a wedged or angled transition surface to facilitate insertion of the two crossed ends 408 and 409.

In some variations, the space or potential space between the leaflets 410 and 420 may contain a drug-releasing structure or a one or more biodegradable materials. The leaflets 410 and 420 may comprise a porous material or other rate controlling layer that controls the release and/or degradation of substances therein. In some further variations, one or more portions of the overlapping leaflets may be sealed or integrally formed to facilitate retention of liquids, suspensions or other materials. In one specific example the membrane may comprise a layer structure folded over onto itself and sealed along its exposed edges to the inner border 104 of outer body 102. A valve element may be provided to facilitate access to the space between the folded layer structure, while resisting exit of any substances through the valve.

Figure 5A:
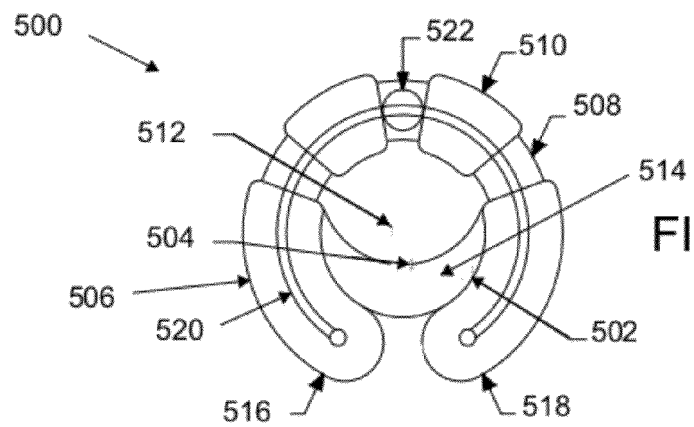
FIGS. 5A and 5B are schematic superior views of two embodiments of an orthopedic device comprising multiple articulation zones.
Figure 5B:
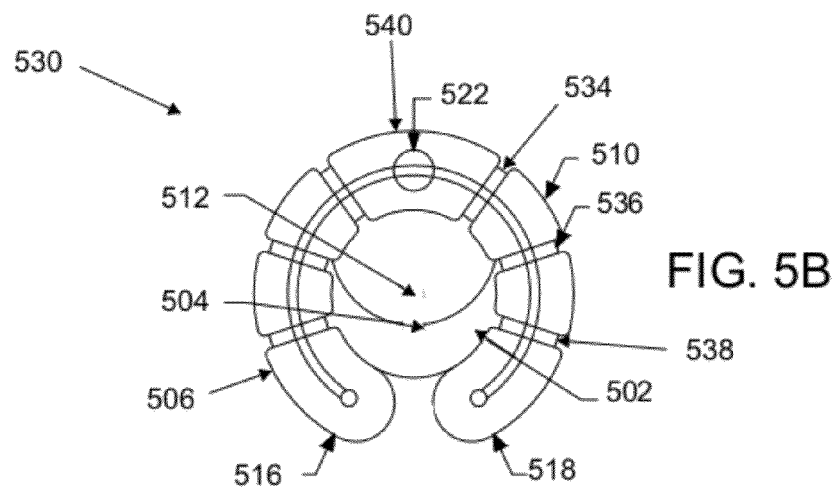

FIG. 5A depicts another embodiment of an orthopedic joint device 500 comprising an inner membrane 502 with an arcuate or crescent shaped slit or edge 504 and a segmented outer body 506 that further comprises multiple articulation zones 508 comprising a smaller cross-sectional area, which are located between support zones 510. Slit 504 separates membrane 502 into a distal membrane section 512 and a proximal membrane section 514. Outer body 506 may further comprise ends 516, 518 and an optional core 520 and a delivery opening 522. FIG. 5B illustrates another embodiment of an orthopedic joint device 530 wherein the segmented outer body 532 comprises a greater number of articulation zones 534, 536, 538. As stated previously, for the articulation zones 508 of device 500, articulation zones 534, 536, 538 of device 530 may comprise regions of reduced diameter or cross-sectional area that may facilitate greater flexion of the outer body 506, which may further reduce the delivery profile of the device 530. In some embodiments, the axial cross-sectional area of the articulation zones 534, 536, 538 may be in the range of about 1% to about 99% of the axial cross-sectional area of the rest of the outer body 502, sometimes about 25% to about 90%, and other times about 50% to about 80%. The articulation zones may or may not be made from the same material as the non-articulation zones. In some embodiments, articulation zones may be made from a more elastic material than non-articulation zones to provide even greater flexibility or deformability. Although the depicted articulation zones 534, 536, 538 are generally symmetrically located with respect to the outer body 506 and the core element 520, in other examples, one or more articulation zones may have an offset position. Each articulation zone may have the same or different configuration, e.g. material, length, axial cross-sectional area.

Figure 5C:
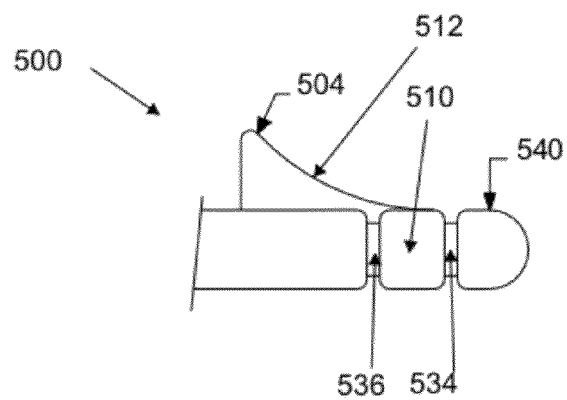
FIG. 5C depicts the deformation of the device in FIG. 5B during delivery into a joint space.

FIGS. 5B and 5C illustrate one exemplary deformation of the orthopedic device comprising articulation zones 534, 536, 538 and inner membrane 502 during delivery. When the device 530 is pulled through an incision of a joint, the distal end 540 of the device 530 first enters the arthrotomy as device 530 is pulled or inserted with respect to the delivery opening 522. The compression force exerted upon the distal end 540 may translate circumferentially through articulation zones 534, 536, 538, causing the ends 516, 518 of the device 530 to cross and form an alpha shape. During the delivery of the device 530, the proximal membrane 512 with a arcuate or partial circular configuration may also be compressed. As illustrated in FIG. 5C, the proximal membrane 512 may be compressed and fold upwardly with its proximal edge 504 assuming a tapered configuration, which may facilitate the further insertion of the crossed ends 516, 518 of the device 530 into the joint space. Although in the embodiments shown in FIGS. 5A and 5B, articulation zones with an inner membrane comprising a arcuate-shaped opening are used to enhance the device's flexibility during device's delivery, a membrane with a opening of other shapes (e.g., teardrop as discussed above) or a membrane comprised of multiple leaflets may also be used.

Figure 8:
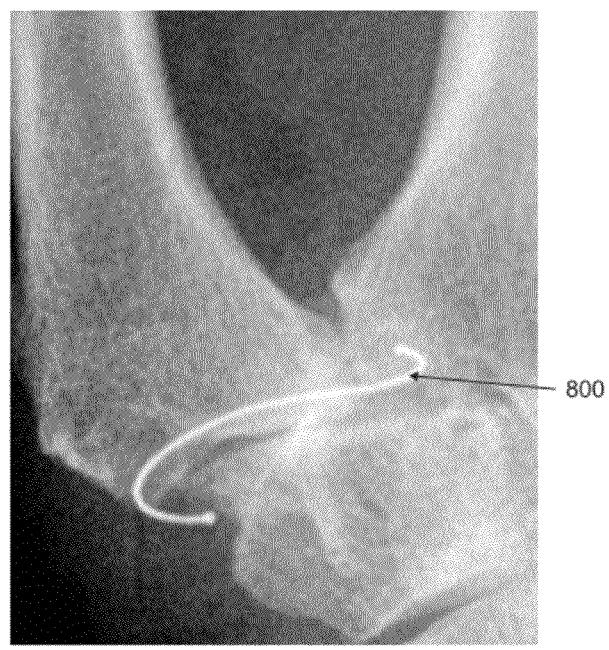
FIG. 8 is a fluoroscopic image depicting the device in FIG. 6B deployed in a trapezio-metacarpal joint.

As depicted in some prior examples, the implanted orthopedic device may be deformed out of plane, depending upon the shape of the joint capsule and/or the relative locations and condition of the articulation surfaces of the joint. In FIG. 8, for example, a C-shaped orthopedic device 800 inserted into a carpo-metacarpal joint of the hand may be deformed into a corkscrew or spiral configuration. In some examples, the out-of-plane configuration may involve passive engagement of the bony prominences of the joint space, and in some further examples, may facilitate anchoring or orientation of the device without requiring penetration of the bony and/or soft tissue. In some examples, mechanical features may be added to one or more outer surfaces of orthopedic joint device to positively engage the device with the surrounding bone and/or tissue. Such mechanical features may include micro-surface features, such as ridges, grooves, velcro hooks, one or more glues, or any equivalent mechanism that mates the surface of the orthopedic device to the surrounding bone and/or tissue.

In some variations, the orthopedic device may comprise passive anchoring elements configured, in use, to passively wrap around or otherwise engage one or more structures of the joint space. In FIG. 6A, for example, the orthopedic device 600 comprises an outer body 602 with a superelastic core 605 (e.g. nickel-titanium alloy) with both the outer body 602 and the core 605 in a ring or C-shaped configuration. In some embodiments, core 605 may be radiopaque. The device 600 may also comprise an inner membrane 610 and membrane opening 620. The device further comprises an anchoring body 604 attached to on the greater surface 618 of the outer body 602 at a coupling site or bridge 606. In some variations, multiple bridges may be provided between the outer body and inner body. In some further examples, additional anchoring bodies may be provided, and may be attached to the inner body or the outer body at either the same or different bridge structure. The outer body 604 may also comprise a superelastic core 608. The cores 605 and 608 may or may not be connected using an interconnecting core through the bridge 606, and may or may not comprise the same configuration, e.g. cross-sectional size, shape and material. In FIG. 6A, the cores 605 and 608 are not interconnected by a core, which may or may not provide additional flexibility at the bridge 606. The inner body, 602, outer body 604 and bridge 606 may or may not comprise the same configuration, e.g. cross-sectional size, shape and material. In this example, the superelastic cores 605 and 608 both comprise nickel-titanium alloy and both the outer body 602 and the anchoring body 606 comprise polycarbonate urethane, but the anchoring body 606 has a reduced cross-sectional area compared to the outer body 602, which may provide greater flexibility to the anchor body 604. In this example, both the inner body 602 and the anchor body 604 also comprise gaps 622 and 624 located between their ends 614 and 616, respectively.

FIG. 6B depicts the device 600 in a deployed configuration, where the gap 622 between the ends 616 of the outer body 604 are splayed or otherwise further separated, which may facilitate engagement of structures in the joint space, which in turn may facilitate anchoring and positioning of the outer body 602. The gap 622 between the ends 614 of the outer body 602 may generally remain the same, with separation restricted by the membrane 110

The outer body and the anchoring body may or may not lie in the same plane when in its deployed configuration or native configuration. FIG. 6C is a side elevational view of the device 600 in FIGS. 6A and 6B depicting the outer body 602 and the relative out-of-plane orientation of the anchor body 604. The relative angle 630 between the outer and anchor bodies may be in the range of about 0 degrees to about 180 degrees or more, sometimes about 0 degrees to about 45 degrees, and sometimes about 10 degrees to about 25 degrees.

It is noted that various features of an orthopedic joint device, such as inner membranes with openings, distal penetrating sections, proximal wings and/or articulation zones have been discussed throughout this specification. In any embodiment, they may be present individually or in any combination with any of the combinations of other aspects of the device, such as the configuration of the outer body, the material of the outer body, and/or the suture attaching mechanism to the outer body.

Figure 7:
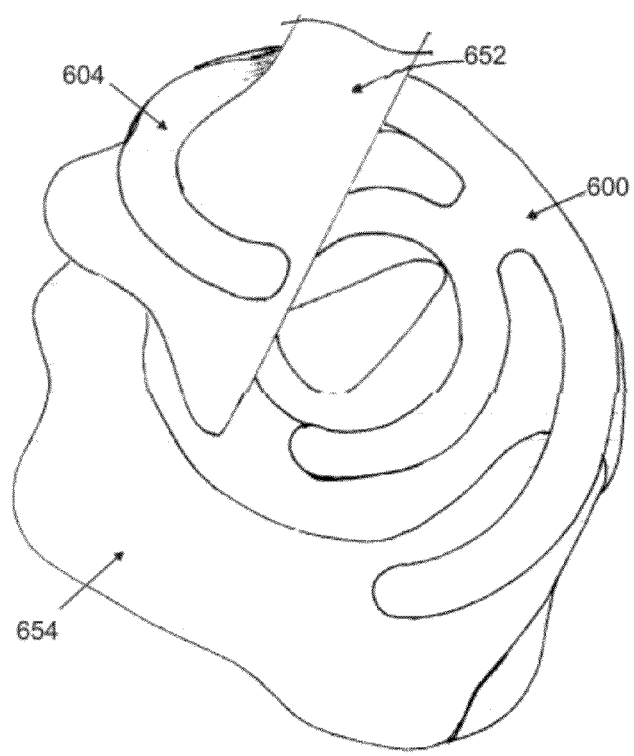
FIG. 7 is a schematic perspective view of the device in FIG. 6B deployed in a trapezio-metacarpal joint.

As depicted in FIG. 6A, the device 600 may also comprise one or more tether openings 632, 634 and 636 on the outer body 602 and/or the anchor body 604 to facilitate manipulation and delivery of the device. FIGS. 6D and 6E depict one example of the use of tethers 640 and 642 with the device in FIGS. 6A to 6C. A first tether 640 may be removably coupled to a tether opening 632 located in the outer body 602 along the delivery axis of the device 600. Lateral tethers 642 are slidably coupled to both the lateral tether openings 634 and 636, one tether 642 to each lateral set of openings 634 and 636. The use of two lateral tethers 642 may permit separate manipulation of different regions of the device 600. Tensioning of the lateral tethers 624 may facilitate further reduction of the delivery profile of the device 600. Upon positioning of the device 600 in the joint space, the lateral tethers 642 may be separated from the device 600 to release the anchor body 604 from a restrained state and permit displacement or separation of the anchor body ends 616. FIG. 7 schematically depicts the passive engagement of the anchor body 604 of the device 600 around the proximal end 652 of a metacarpal articulating with the trapezium 654 in a wrist. In other variations, additional tethers and tether openings may be provided, or different tether locations may be used. In an alternate embodiment depicted in FIG. 6F, rather than two lateral tethers 642, a single posterior tether 650 may be passed through one lateral tether opening 636 of the anchor body 604, into the ipsilateral lateral tether opening on the outer body 602, then to the contralateral lateral tether opening, through the contralateral lateral tether opening 636 of the anchor body 604.

Figure 9A:
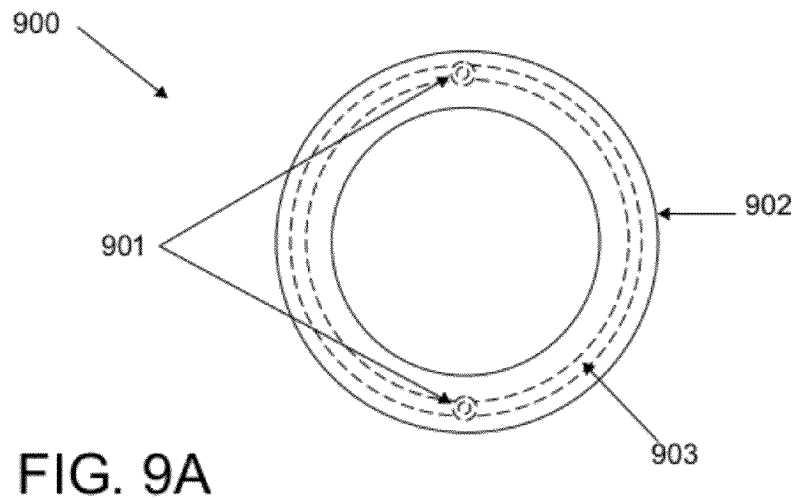
FIGS. 9A and 9B are schematic superior views of a base and a strained configuration, respectively, of an embodiment of an orthopedic joint device comprising a resilient inner core comprising articulations.
Figure 9B:
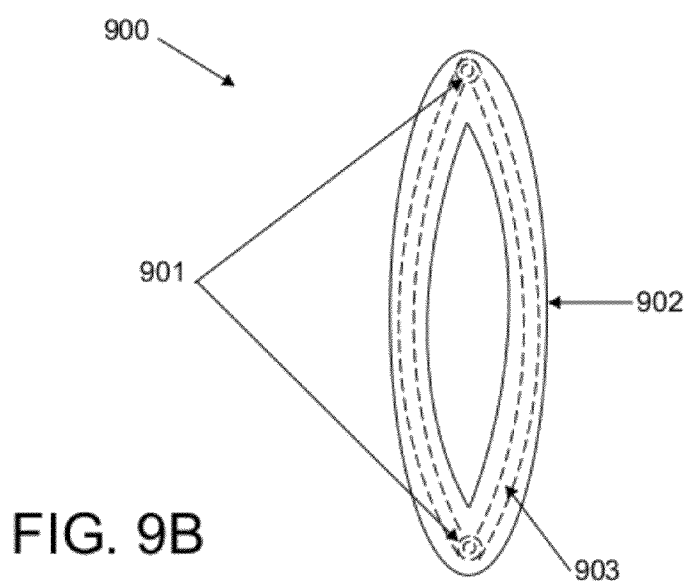

FIGS. 9A and 9B illustrate, respectively, a base and a strained configuration of another embodiment of an orthopedic joint device 900. The orthopedic joint device 900 may comprise one or more articulations 901 along a core 903, and surrounded by an outer body 902. The articulations 901 provide hinge points which control the deformation of orthopedic joint device 900. In some variations, the articulations may be configured to facilitate deformation of the device 900 within a particular plane, e.g. the plane in which the articulations are located, or in a particular direction that may be in or out of plane. In some variations, the orthopedic joint device 900 in the strained configuration may be inserted into a joint of a patient's body, for example the first carpal-metacarpal joint, although the device could be inserted into any joint of a human or animal body. The strained configuration may be the result of a constraining delivery force exerted by the user or a delivery instrument and/or forces exerted by the surrounding anatomy, e.g. a small incision opening that deforms the device into a strained configuration. The reduced width of the first dimension in the strained configuration may reduce the size of the incision used to insert the orthopedic joint device 900 into the joint. Once the orthopedic joint device 900 is inserted into the joint in the strained configuration and the constraining force is substantially removed, the orthopedic joint device 900 may return toward the base configuration depicted in FIG. 9A, subject to static and dynamic constraining forces from the surrounding anatomical structures, if any. In some variations, the constraining delivery force may be imparted by the dimensions of the joint incision as the joint device is pulled or pushed into the joint. Various examples of articulations that may be used with an orthopedic joint device are described in more detail below.

In FIGS. 9A and 9B, the orthopedic joint device 900 comprises two articulations 901 at opposing ends of the outer body 902, but some embodiments may have any number of articulations, including a single articulation. The number of articulations may be configured, for example, to achieve a desired range of motion, a desired collapsed configuration, or to provide a desired restoration force. A single articulation may provide a large restoration force, i.e., a large resistance to deformation, but a limited reduction of width in the first dimension when the orthopedic joint device is in the strained configuration. Conversely, a large number of articulations may provide a large reduction of width, but result in a reduced magnitude of the restoration force. In some embodiments, the width of the orthopedic joint device in the collapsed configuration may be up to or equal to about twice the diameter of the outer body 902, i.e., the sides of the outer body 902 are in contact, or almost in contact, and the inner diameter of the outer body 902 is reduced to approximately 0. In other embodiments, the reduction in the width of the orthopedic joint device may be characterized as a percentage from 0% to 100% of the inner diameter of the outer body 902, and may sometimes be about 0%, 5%, 10%, 15%, 20%, 25%, 30%, 35%, 40%, 45%, 50%, 55%, 60%, 65%, 70%, 75%, 80%, 85%, 90%, 95%, or 100%. In other embodiments, the reduction in width is greater than 100% of the inner diameter, i.e., the sides of the outer body contact and are further contracted. Although the magnitudes of width reduction and restoration force may be controlled by the number of articulations of the orthopedic joint device, other mechanisms could also be employed to control those parameters. These additional mechanisms include, but are not limited to, the placement of the articulations, the core material, and any combination of such mechanisms. Accordingly, the reduced restoring force magnitude of a multi-articulation orthopedic joint device may be compensated with, for example, a core of increased resistance to deformation. In addition to the magnitudes of the restoration force and the width of deformation, multiple articulations may allow for deformation of an orthopedic joint device in multiple planes. In some variations comprising hinge joints where the movement range may limited to a particular plane transverse to the pivot or movement axis of the hinge joint, multiple articulations allow for deformations in multiple planes. In other variations, one or more polyaxial joints, e.g. ball-and-socket joints, may be provides, which may be configured to provide multi-planar deformation of the device. The orthopedic joint device may thereby be configured to conform to particular joint or incision geometries. Further, the articulations 901 may be located anywhere with respect to the core 903 and/or the outer body 902 and the location may be configured to realize a desired base or strained configuration. The articulations may be equally or unequally spaced and the articulation mechanisms may be similar or different.

The embodiments of FIGS. 9A and 9B schematically depict articulations 901 as having a circular cross-sectional profile (as viewed in a plane transverse to the rotational axis of the articulations 901), but some embodiments may use articulations of non-circular profile. In some variations, the circular profile permits rotational movement of the articulation within outer body 902. A circular profile may comprise a hinge pin assembly joining separate segments of the core, similar to a traditional hinge, for example. The pin may protrude from the core or a counter-bore may reduce the protrusion of the articulation. An articulation may be configured to promote deformation and/or augment a restoration force. For example, an articulation may include a locking mechanism in the strained configuration to facilitate insertion of the orthopedic joint device into a patient's joint. In addition, an articulation may include a locking mechanism in the base configuration to prevent deformation after insertion of the orthopedic joint device into a patient's joint. An articulation may also be configured to resist deformation to the strained configuration, thereby increasing the restoration force that facilitates return of the orthopedic joint device to the base configuration. In some embodiments, the function of the articulation 901 are provided by alternative mechanisms, such as configuring a profile change of the core's cross section or reducing the core material's density, for example. In such embodiments, no secondary equipment, such as a pin and cap, may be needed for the articulation because the deformation is facilitated at the articulations by the core's natural tendency to deform at regions of reduced strength, i.e., a reduced profile of the core's cross section. The profile change may be adjusted according to the desired properties of the orthopedic joint device.

FIG. 9A illustrates a base configuration of the orthopedic joint device 900 having a closed, circular shape, but in other embodiments the outer body may comprise other shapes, including but not limited to oval or polygonal shapes. The outer body 902 and core 903 may be similar to the bodies and cores of embodiments described with reference to the other figures, but are not limited to those embodiments. In the embodiments shown in FIGS. 9A and 9B, the core 903 comprises the same shape as the outer body 902, but the core may take the same or a different shape from outer body 902. In some embodiments, the core comprises a radiopaque material. The articulations 901, outer body 902, and the core 903 may or may not comprise any variety of the materials described herein.

FIG. 9B depicts an embodiment of the orthopedic joint device 900 in a strained configuration wherein the width of a first dimension of the orthopedic joint device 900 is less than the width of the first dimension when the orthopedic joint device 900 is in the base configuration. The orthopedic joint device 900 in the strained configuration may be inserted into a joint by any of the mechanisms described herein, but implantation is not limited to those devices and any suitable mechanism could be employed for implantation. When inserted into the joint, the orthopedic joint device 900 may or may not be attached to the surrounding tissue.

As shown in the embodiment of FIG. 9B, the width of a second dimension is increased in the strained configuration, but the strained configuration may or may not result in an increase in the width of either of the two dimensions orthogonal to the first dimension. In some embodiments, the size of the orthopedic joint device 900 may increase in a third dimension perpendicular to the plane shown in FIG. 9B. In some further embodiments, the increase of the third dimension may be limited by a multiple of three when the first dimension is maximally reduced in size.

Although not depicted in FIGS. 9A and 9B, some embodiments may include an inner membrane in the interior space of orthopedic joint device 900. The inner membrane may take any of the forms described herein, including but not limited to a generally planar shape, a hyperbolic paraboloid saddle shape, or a hemi-spherical shape, for example.

Figure 10A:
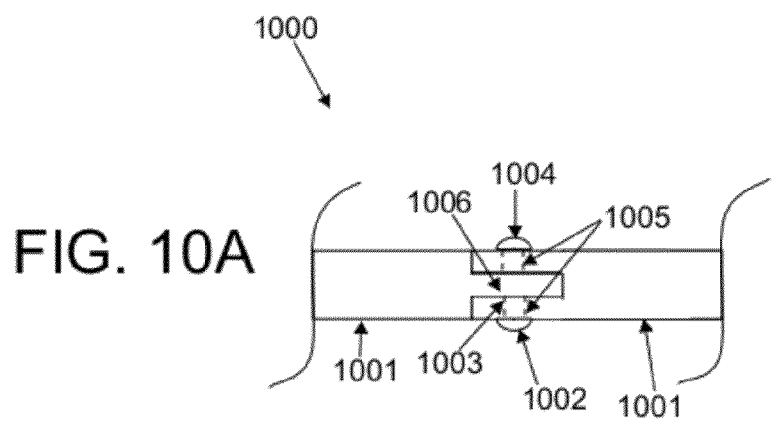
FIGS. 10A-10C are schematic side views of three embodiments of articulations comprising a pin.
Figure 10B:
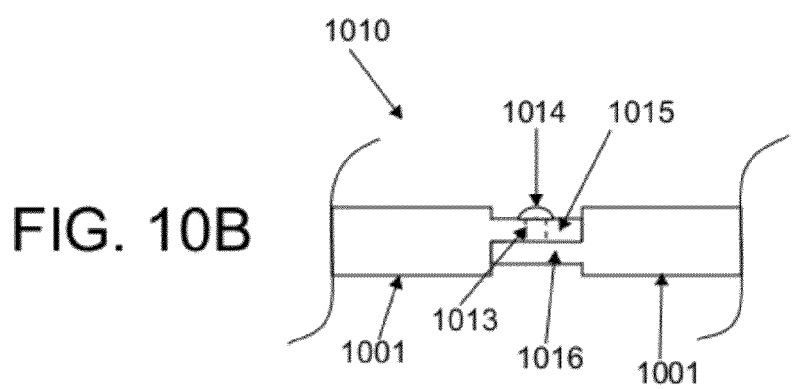
Figure 10C:
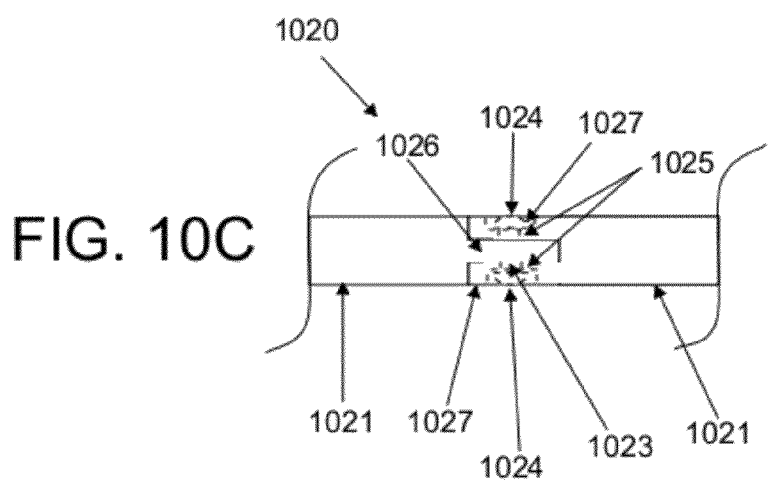

FIGS. 10A-10C depict various embodiments of articulations for connecting two regions of a core and/or outer body. FIGS. 10A-10C depict variations of an articulation and a core, but it should be appreciated that the features described may also refer to an articulation and outer body. Although not depicted, a coupled articulation and core may be surrounded by an outer body, which may or may not include additional features, such as recesses, for example, to accommodate the articulations and/or core. Further, FIGS. 10A-10C depict the cores as symmetrically surrounding the articulations, but the cores need not symmetrically surround the articulations. FIGS. 10A-10C also depict the cores as having constant diameter, but some embodiments may comprise a core with a variable diameter, such as a core tapered toward or away from an articulation.

FIG. 10A depicts an articulation 1000 connecting two regions of a core 1001, one region comprising a male component 1006 and the other region comprising a female component 1005. Articulation 1000 further comprises a pin 1003 passing through the core 1001 which provides an axis of rotation for an orthopedic joint device. Articulation 1000 may facilitate deformation of the orthopedic joint device in at least one dimension, thereby enabling insertion of the orthopedic joint device into a joint of a patient, as described above in more detail. Pin 1003 may be held in position by the outer body, may comprise securing mechanisms integral to the pin that couple to complementary receiving mechanisms in the core 1001, or may be held in place with caps secured tot the ends of the pin that are added after the pin is inserted, such as caps 1002 and 1004 depicted in FIG. 10A. The securing mechanism may comprise a mechanical snapfit, adhesives, welding, melting, or other mechanisms known in the art. The embodiment of FIG. 10A shows articulation 1000 as comprising a pin and cap configuration, but any equivalent mechanism may be used for providing a bearing to facilitate an axis of rotation. Such mechanisms include, but are not limited to, the embodiments described below with respect to FIGS. 10B and 10C.

FIG. 10B depicts an articulation 1010 connecting two regions of a core 1011, each region including a tongue 1015 and 1016. Articulation 1010 further comprises a pin 1013 passing through at least one region of the core 1011, with a cap 1014 securing the pin 1013 in position. Pin 1013 may be integrally formed with tongue 1016 and tongue 1015 may comprise a corresponding aperture for receiving the pin. As such, articulation 1010 may be considered as comprising two components—a first and second tongue. Articulation 1010 also provides an axis of rotation for an orthopedic joint device when pin 1013 is inserted into tongue 1015. Articulation 1010 may facilitate deformation of the orthopedic joint device in at least one dimension, thereby enabling insertion of the orthopedic joint device into a joint of a patient, as described above in more detail. In some embodiments, the aperture may not protrude through tongue 1015, as is depicted in articulation 1010, but may reach only a portion of the depth of the tongue. The corresponding pin may also be shorter than the depth of the tongue. In those embodiments, articulation 1010 may be secured when the outer body surrounds the core. In further embodiments, the pin and recess may be configured to secure articulation 1010 through a locking mechanism. Such mechanisms for securing the pin when it is fully inserted into the aperture include, but are not limited to, a releasable ball-bearing in the pin that couples to a corresponding depression in the aperture. In an alternate embodiment, the articulation may comprise a core segments with interlocking apertures or eyelets, or interconnecting hooks, or an eyelet and a hook, for example. In one specific example, the pin may further comprise an extension at the distal end of the pin in a direction away from the axis of the pin, that protrudes above the surface of the other tongue, and couples the two tongues together.

FIG. 10C depicts an articulation 1020 connecting two regions of a core 1021, one region comprising a male component 1026 and the other region comprising a female component 1025. Articulation 1020 further comprises a pin 1023 passing through the core 1021, with caps 1022 and 1024 securing the pin 1023 in position. Articulation 1020, however, includes counterbores 1027 which are added to permit the caps 1022 and 1024 of articulation 1020 to be secured in a position below the surface of the core 1021. Counterbores 1027 can be replaced by any recess which reduces the profile of the caps 1022 and 1024 above the superior surface of core 1021. Further, the caps 1022 and 1024 may or may not be flush with the surface of the core, and some embodiments may include a partially reduced profile of the caps 1022 and 1024 above the surface of the core. The counterbores 1027 of articulation 1020 may be provided with other articulation configurations described herein, including but not limited the articulation 1010 depicted in FIG. 10B.

Figure 11A:
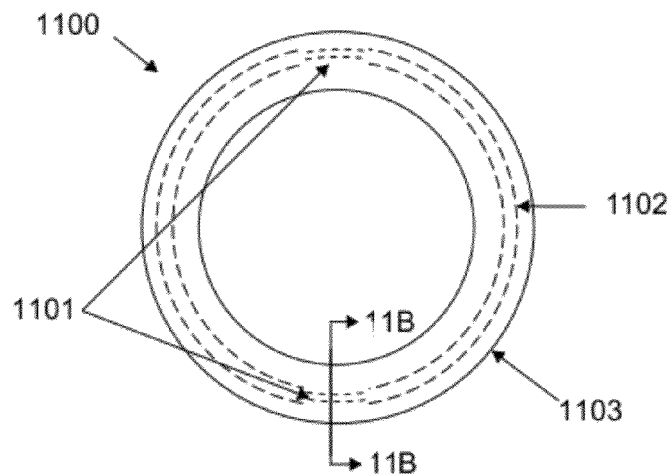
FIG. 11A is a schematic superior view of an embodiment of an orthopedic joint device comprising a living hinge.
Figure 11B:
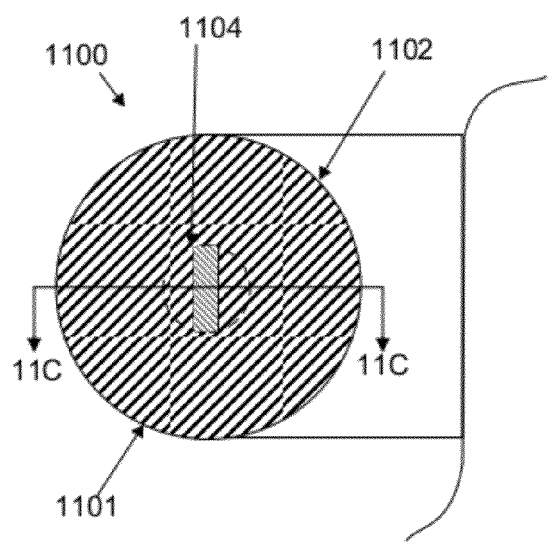
FIG. 11B is a schematic axial cross-sectional view of the orthopedic joint device in FIG. 11A.
Figure 11C:
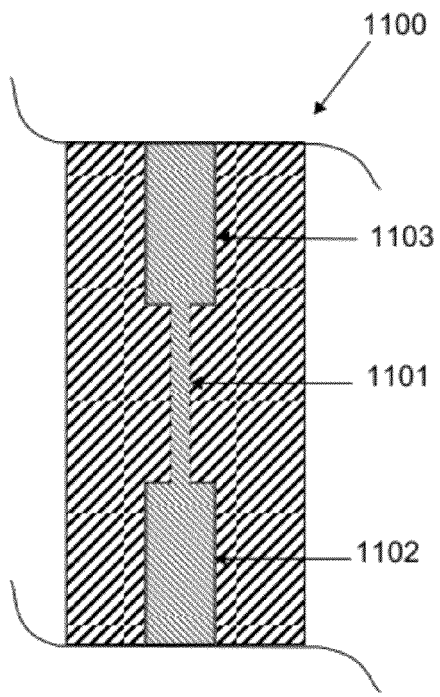
FIG. 11C is a superior schematic cross-sectional view of the orthopedic joint device in FIG. 11A.

FIGS. 11A-11C depict an orthopedic joint device 1100, comprising one or more flex regions 1101 and a core 1103 surrounded by an outer body 1102. As used herein, the term "flex region" can be understood to describe any section of a core joining two segments of the core and configured to yield elastically when relative forces are applied to the two segments. Flex regions 1101 comprise a region of the core 1103 with a reduced cross-sectional profile and facilitate deformation of the orthopedic joint device through the tendency of the core 1103 to bend at thinner regions when forces are applied to two regions of the core 1103, thereby permitting insertion of the orthopedic joint device into a joint of a patient, as described above in more detail. The rectangular profile of flex regions 1101 facilitates bending of the orthopedic joint device about one axis only because the non-reduced dimension will not yield to the same degree when relative forces are applied to the two segments. In the embodiment of orthopedic joint device 1100, a flex region may be achieved by reducing the core's cross sectional profile in one dimension. In other embodiments, the cross-section of flex region 1101 may not be rectangular, as depicted in FIGS. 11A-11C, and may not be continuous. In some embodiments, the flex region is achieved by reducing the stiffness of the core material. In some other embodiments, the flex region is achieved by configuring a living hinge in the core. The profile change may be adjusted according to the desired properties of the orthopedic joint device. For example, the ratio/length of the cross-sectional profile reduction can be altered to provide a desired resistance to deformation.

In FIGS. 11A-11C, the orthopedic joint device 1100 comprises two flex regions 1101 at opposing ends of the outer body 1102, but some embodiments may have any number of flex regions, including a single flex region. Further, the flex regions 1101 may be located anywhere with respect to the core 1103 and/or the outer body 1102. The flex regions may be equally or unequally spaced and the flex mechanisms may be similar or different.

FIG. 11A depicts orthopedic joint device 1100 in the base configuration. The reduced cross-sectional profile of the core 1103 at the flex regions 1101 is illustrated therein. In some embodiments, a flex region may be characterized as a percentage from 0% to 50% of the circumference of orthopedic joint device 1100, and may sometimes be about 0%, 2%, 4%, 6%, 8%, 10%, 12%, 14%, 16%, 18%, 20%, 22%, 24%, 28%, 30%, 32%, 34%, 36%, 38%, 40%, 42%, 44%, 46%, 48%, or 50%. In orthopedic joint device 1100, flex region 1101 is approximately 4-8% of the circumference of orthopedic joint device 1100. FIG. 11B depicts a cross-section of orthopedic joint device 1100 taken through the plane shown in FIG. 11A. The non-reduced cross-sectional profile of core 1102 is depicted in FIG. 11B as circle 1104.

FIG. 11C depicts a cross-section of orthopedic joint device 1100 taken through the plane shown in FIG. 11B. The cross-section of orthopedic joint device 1100 illustrated in FIG. 11C encompasses both flex region 1101 and the surrounding regions of core 1103. Although flex region 1101 comprises a rectangular cross-sectional profile, any geometry could be equivalently used without deviating from the scope of the invention. Further, the cross-sectional profile need not be constant over flex region 1101, nor need there be discontinuities of the cross-sectional profile at the transition regions between the core and the flex regions. In some embodiments, the reduction in width of a flex region may be characterized as a percentage from 0% to 99% of the diameter of the core, and may sometimes be about 0%, 5%, 10%, 15%, 20%, 25%, 30%, 35%, 40%, 45%, 50%, 55%, 60%, 65%, 70%, 75%, 80%, 85%, 90%, 95%, or 99%. In orthopedic joint device 1101, the reduction in width of flex region 1101 is approximately 70-80% of the diameter of core 1103.

Figure 12:
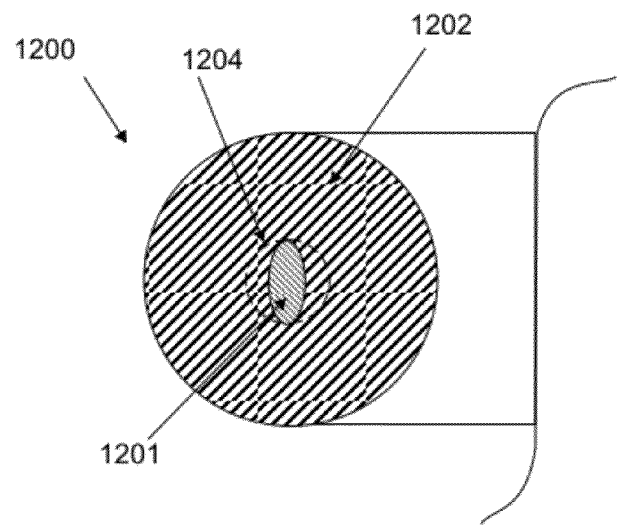
FIG. 12 is a schematic axial cross-sectional view of another embodiment of an orthopedic joint device comprising a resilient core comprising a living hinge.
Figure 13:
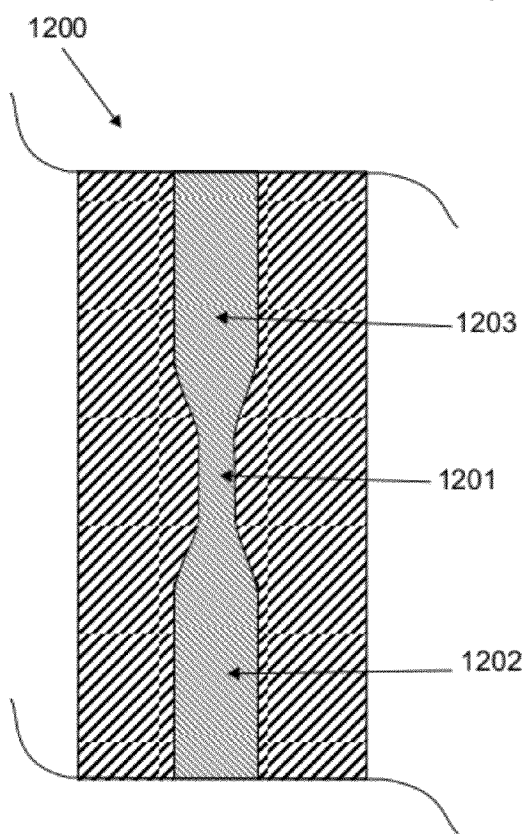
FIG. 13 is a schematic superior cross-sectional view of the orthopedic joint device in FIG. 12.

FIGS. 12 and 13 depict an orthopedic joint device 1200 comprising one or more flex regions 1201 and a core 1203 surrounded by an outer body 1202. Flex regions 1201 comprise a region of the core 1203 with a reduced cross-sectional profile relative to the rest of the core 1203. The flex regions 1201 of orthopedic joint device 1200 also comprise regions of reduced cross-sectional profile, but flex regions 1201 include an oval cross-sectional profile. The non-reduced cross-sectional profile of core 1202 is depicted in FIG. 12 as circle 1204. FIG. 13 depicts a cross-section of the orthopedic joint device 1200 in a plane parallel to central axis of the core. The cross-section of orthopedic joint device 1200 illustrated in FIG. 13 encompasses flex region 1201 and the surrounding regions of core 1203. As seen in FIG. 13, the cross-sectional profile is not constant over flex region 1201, nor are there discontinuities of the cross-sectional profile at the transition regions between the core and the articulations.

Figure 14A:
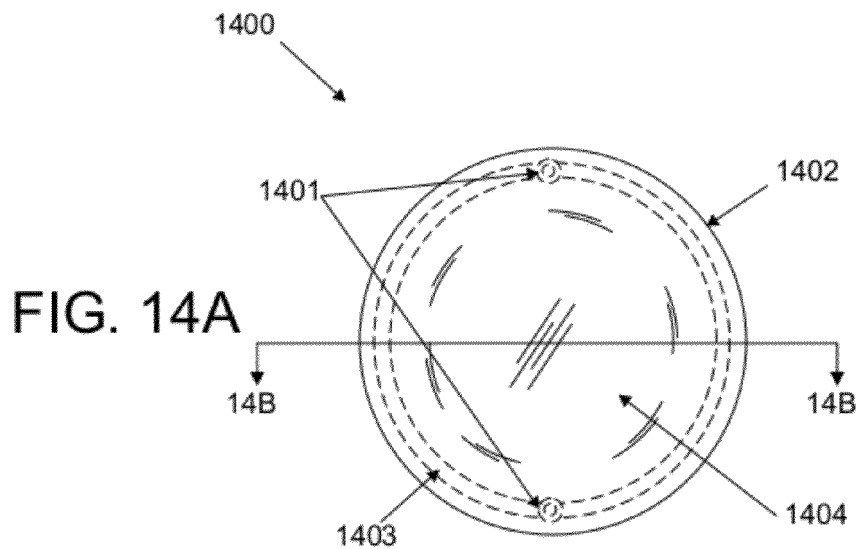
FIG. 14A is a schematic superior view of an embodiment of an orthopedic joint device comprising a resilient core with articulations and an inner membrane.
Figure 14B:
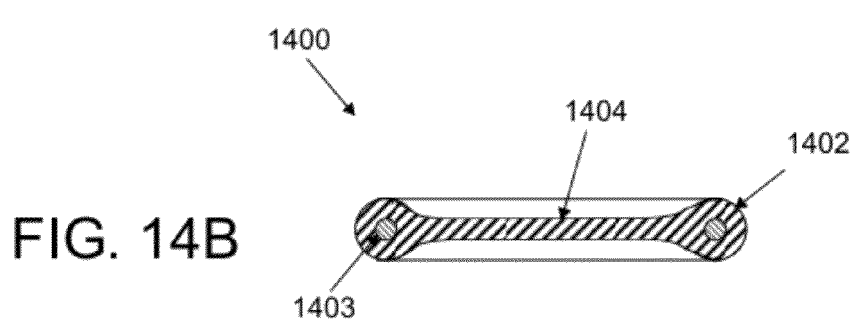
FIG. 14B is a schematic axial cross-sectional view of the orthopedic joint device in FIG. 14A.

FIGS. 14A and 14B depict another embodiment of an orthopedic joint device 1400 which may comprise an outer body 1402, surrounding a core 1403 with one or more articulations 1401, and an inner membrane 1404. Inner membrane 1404 may be configured to limit expansion of the orthopedic joint device 1400 and/or to provide a restorative force after insertion of the orthopedic joint device 1400. For example, inner membrane 1404 may resist or limit deformation of the orthopedic joint device 1404 in a direction away from the center of the orthopedic joint device, thereby ensuring that the device realizes a desired configuration upon implantation and continues to maintain that configuration upon use. Thus, inner membrane 1404 may be used with an orthopedic joint device wherein the core and/or outer body exhibit elastic properties that, although necessary for deformation, may be undesirable when the device is used. In this way, inner membrane 1404 may reduce the interaction between orthopedic joint device 1400 and the surrounding membranes and/or tissues. Inner membrane 1404 may also be configured, for example, to provide a restorative force for returning the orthopedic joint device 1400 to the base or implanted configuration. In such embodiments, the inner membrane 1404 may comprise a material which resists deformation. These and other structural features may facilitate a reduced delivery profile while restricting excessive distortion of the delivery configuration. Various examples of inner membranes that may be used with an orthopedic joint device are described in more detail below.

The embodiment of FIGS. 14A and 14B depicted the inner membrane 1404 as spanning the entire interior of orthopedic joint device 1400, but the membrane may span only a portion of the device's interior. For example, if a certain region or plurality of regions of the device is prone to splaying, those regions may be targeted and an inner membrane strategically connected to the body. The inner membranes of FIGS. 14A and B depict a uniform material composition throughout, but the inner membrane need not comprise a single material and may comprise other materials, such as, for example, a strengthened core for providing restorative forces or radiopacity. Inner membrane 1404 may be integrally formed with outer body 1402 using common manufacturing techniques such as injection molding or compression molding. Inner membrane 1404 may also be attached or embedded to outer body 1402 directly or with reinforced structures, such as wires, struts, or meshes. In addition to the planar configuration of FIGS. 14A and B, inner membrane 1404 may have one or more regions with a non-planer configuration, including corrugated, concave, convex, or tapered regions, for example. These and other geometries may configure the orthopedic joint device 1400 to better suit a specific joint or patient, or may be configured to enhance the deformability.

FIGS. 14A and 14B illustrate the orthopedic joint device 1400 in superior and cross-sectional views, respectively. As can be seen in FIG. 14B, the inner membrane 1404 comprises a cross-sectional shape with substantially linear upper and lower surfaces. However, any cross-sectional geometry may be equivalently used, including, but not limited to, the embodiments described below. The embodiment of FIGS. 14A and 14B also depict the inner membrane gradually transitioning from the perimeter of the orthopedic joint device 1400, but the transition may not be gradual, and may even be discontinuous in some embodiments. In some embodiments, the width of the membrane may be characterized as a percentage reduction from 0% to 99% of the radius of the outer body, and may sometimes be about 0%, 5%, 10%, 15%, 20%, 25%, 30%, 35%, 40%, 45%, 50%, 55%, 60%, 65%, 70%, 75%, 80%, 85%, 90%, 95%, or 99%. In orthopedic joint device 1400, the width of inner membrane 1404 is approximately 30-40% of the diameter of outer body 1402.

Figure 15A:
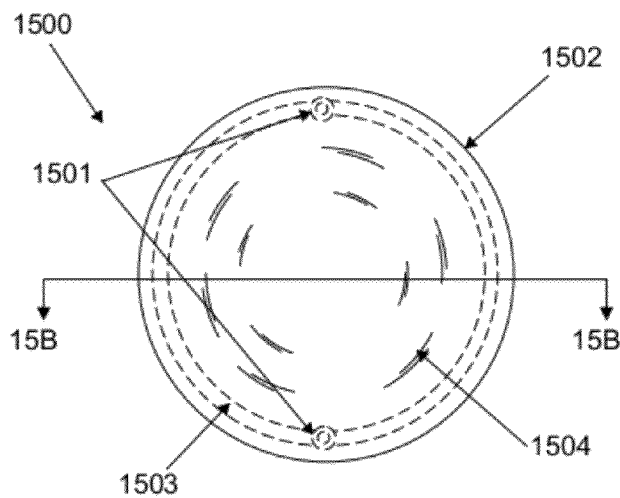
FIG. 15A is a schematic superior view of another embodiment of an orthopedic joint device comprising a resilient core with articulations and an inner membrane.
Figure 15B:
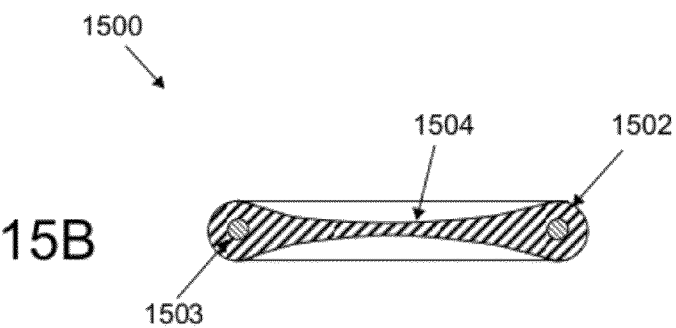
FIG. 15B is a schematic axial cross-sectional view of the orthopedic joint device in FIG. 15A.

FIGS. 15A and 15B illustrate another embodiment of orthopedic joint device 1500 in, respectively, superior and cross-sectional views. As depicted therein, the orthopedic joint device 1500 may comprise an outer body 1502, surrounding a core 1503 with one or more articulations 1501, and a non-linear inner membrane 1504. In the cross-sectional view of FIG. 15B, the inner membrane has a substantially concave shape on both the inferior and superior surface of the inner membrane 1504. However, the cross-sectional profile of the inner membrane of other embodiments of an orthopedic joint device may take the same or different shapes on the inferior and superior surfaces. In addition, the embodiment of FIG. 15B depicts the inner membrane 1504 as being substantially symmetrical on the superior and inferior sides of the orthopedic joint device, but other embodiments may comprise an asymmetrical membrane over all, or some, of the membrane's span. In other embodiments, a cross-sectional view of inner membrane taken through articulations may be substantially convex along a single axis, which may give the inner membrane a substantially U-shape or saddle-like shape on cross section. In some embodiments, the geometry of the cross-sectional curve of the inner membrane may be characterized by the shape of the curve and the position of minima or maxima of the curve. In some embodiments, the curve may be shaped as a circular or a parabolic arc, for example. In orthopedic joint device 1500, the concave arc of inner membrane 1504 comprises a circular arc of radius approximately 2.5 times the width of the orthopedic joint device 1500. In some embodiments, the minima of a concave curve may be positioned anywhere from 0% to 99% of the radius of the outer body below the surface of the outer body, and may sometimes be about 0%, 5%, 10%, 15%, 20%, 25%, 30%, 35%, 40%, 45%, 50%, 55%, 60%, 65%, 70%, 75%, 80%, 85%, 90%, 95%, or 99%. In some embodiments, the maxima of a convex curve could be positioned anywhere from 0 to 100% of the width of the outer body above the surface of the outer body, and may sometimes be about 0%, 5%, 10%, 15%, 20%, 25%, 30%, 35%, 40%, 45%, 50%, 55%, 60%, 65%, 70%, 75%, 80%, 85%, 90%, 95%, or 100%. In orthopedic joint device 1500, the concave arc of inner membrane is positioned approximately 55-65% of the diameter of outer body 1502 below the surface of outer body 1502. In other embodiments, different shapes may be used at various locations.

Figure 16A:
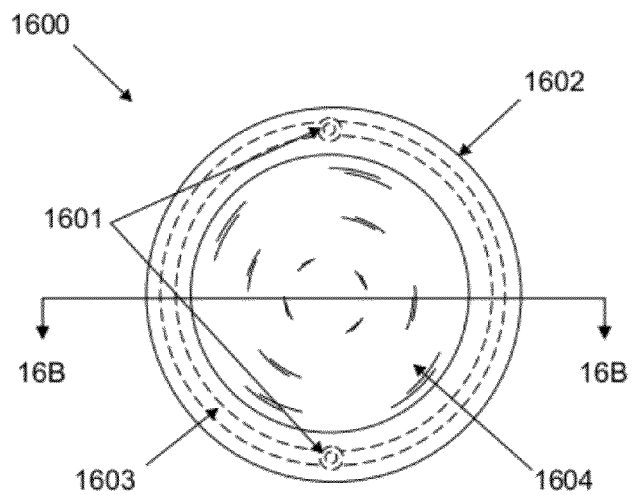
FIG. 16A is a schematic superior view of another embodiment of an orthopedic joint device comprising a resilient core with articulations and an inner membrane.
Figure 16B:
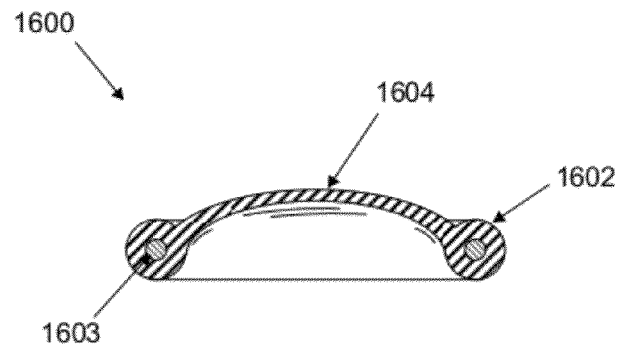
FIG. 16B is a schematic axial cross-sectional view of the orthopedic joint device in FIG. 16A.

FIGS. 16A and 16B illustrate another embodiment of orthopedic joint device 1600 in, respectively, superior and cross-sectional views. As depicted therein, the orthopedic joint device 1600 may comprise an outer body 1602, surrounding a core 1603 with one or more articulations 1601, and a protruding inner membrane 1604. The inner membrane of FIGS. 16A and 16B is depicted as protruding from the superior side of orthopedic joint device 1600, but the inner membrane 1604 may protrude from the inferior surface, which, in some embodiments, may be achieved by rotating the device 180 degrees about an axis comprising both articulations, for example. Further, inner membrane 1604 need not protrude over the surface of the orthopedic joint device 1600 and may be aligned with the superior surface of the orthopedic joint device. In some embodiments, the protruding inner membrane is below the superior surface of the perimeter of the orthopedic joint device 1600. Protruding inner membrane 1604 may have substantially constant thickness, or the thickness may vary. The superior and inferior surfaces of protruding inner membrane 1604 may be inversely shaped, or they may be dissimilar.

In the embodiments of FIGS. 14A-16B above, reducing the profile of the orthopedic joint device in the deformed configuration may cause the profile of the inner membrane to increase along a transverse axis to the generally planar configuration of the device. Such "tenting", "puckering" or perpendicular displacement of the inner membrane may necessitate a larger incision in the patient, greater traction on the joint, or may generate increased resistance to implantation as a result of the increased dimension of the implant along an axis transverse to its general planar configuration. In other embodiments, the inner membrane is configured to reduce deformation by, for example, providing a sinusoidal inner membrane and/or strategically positioned apertures in the membrane. In this way, the orthopedic joint device may enjoy the benefits of an inner membrane described above, such as controlled deformation in the base configuration and restorative forces, while reducing, or eliminating, the need for a larger incision. Various examples of inner membranes configured to reduce puckering are described in more detail below.

Figure 17A:
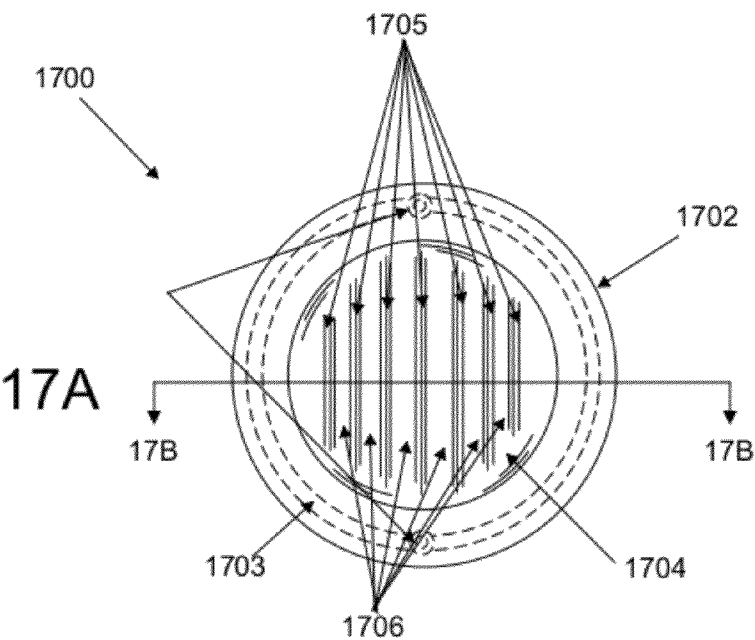
FIG. 17A is a schematic superior view of another embodiment of an orthopedic joint device comprising a resilient core with articulations and an inner membrane.
Figure 17B:
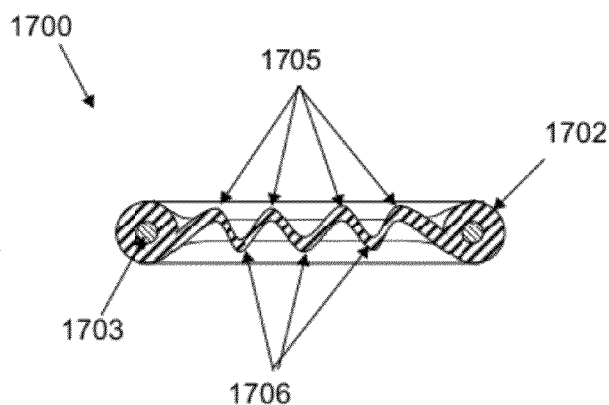
FIG. 17B is a schematic axial cross-sectional view of the orthopedic joint device in FIG. 17A.

FIGS. 17A and 17B depict an embodiment of an orthopedic joint device 1700 in superior and cross-sectional views, respectively. The orthopedic joint device 1700 may comprise an outer body 1702, surrounding a core 1703 with one or more articulations 1701, and an oscillating or sinusoidal inner membrane 1704. Sinusoidal inner membrane 1704 comprises a series of crests 1705 and troughs 1706, configured to collapse the inner membrane when the orthopedic joint device 1700 is in the deformed configuration. The series of crests and troughs of inner membrane 1704 cycle linearly. Thus, any cross-section of the device, taken in a plane parallel to the view of FIG. 17B may reveal the same sinusoid profile truncated at the points of connection of the inner membrane 1704 and the outer body 1702. In other embodiments, the sinusoid may cycle non-linearly, with a packet of troughs expanding as it extends from one end of the device to the other, for example. In some further embodiments, the non-linear sinusoidal pattern is configured to conform to the deformation profile of the device. The series of crests and troughs may have the same or different amplitudes and each crest or trough may have constant or varying amplitude. Sinusoidal inner membrane 1704 may comprise an identifiable wave, such as a sine or cosine wave, or may comprise a random pattern of crests and troughs with no apparent or actual ordered structure. Sinusoidal inner membrane 1704 may or may not be sinusoidal over the entire span of inner membrane 1704. In some embodiments, sinusoidal inner membrane 1704 may contain crests and troughs on one surface only, wherein that surface is configured to control deformation of the inner membrane. In further embodiments, the opposite surface may be configured to fit a geometry of a specific joint or patient, or may be configured to achieve any number of the functions described above, such as controlling deformation of the orthopedic device in the base configuration, for example. Further, there may be any number of crests and troughs, and there may or may not be an equal number of crests and troughs. In some embodiments, the crests and troughs may be configured bi-axially, with the same or a different pattern along each axis.

Figure 18A:
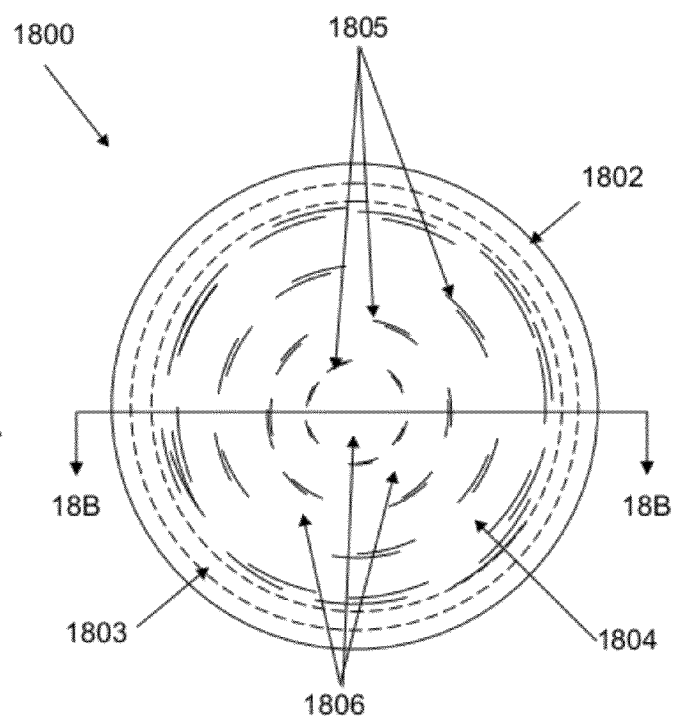
FIG. 18A is a schematic superior view of another embodiment of an orthopedic joint device comprising a resilient core and an inner membrane.
Figure 18B:
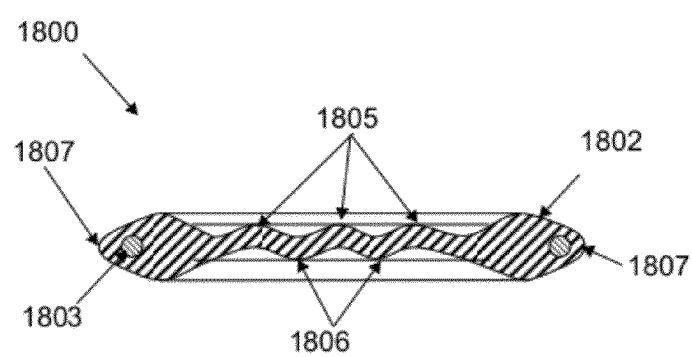
FIG. 18B is a schematic axial cross-sectional view of the orthopedic joint device in FIG. 18A.

FIGS. 18A and 18B depict another embodiment of an orthopedic joint device 1800 in superior and cross-sectional views, respectively. As depicted therein, the orthopedic joint device 1800 may comprise an outer body 1802, surrounding a core 1803, and a sinusoidal inner membrane 1804. Sinusoidal inner membrane 1804 comprises a series of crests 1805 and troughs 1806, configured to collapse the inner membrane when the orthopedic joint device 1800 is in a deformed configuration. The series of crests and troughs of inner membrane 1804 is oriented radially, with no angular variation, resulting in identical wave patterns for all profiles taken through a straight line incorporating the center of the orthopedic joint device 1800. In other embodiments, identical wave patterns may result from straight lines incorporating a point other than the center of the device. In some embodiments, the series of crest and troughs of inner membrane 1804 may have the same or different amplitudes and may or may not cycle linearly. Some embodiments may comprise a concentric series of crests and troughs, with angular variation, similar to a series of contour lines on a topographic map, for example. The series of crests and troughs may have the same or different amplitudes and each crest or trough may have constant or varying amplitude in an angular direction. The embodiment of FIGS. 18A and 18B do not contain articulations to assist deformation, but other embodiments may include a radial sinusoidal inner membrane with one or multiple articulations. The embodiment of FIGS. 18A and 18B also contain a protruding outer edge 1807 of outer core 1802, which may be configured to assist with entry of the device through the incision or may be configured to conform to the geometry of a particular joint or patient.

Figure 19:
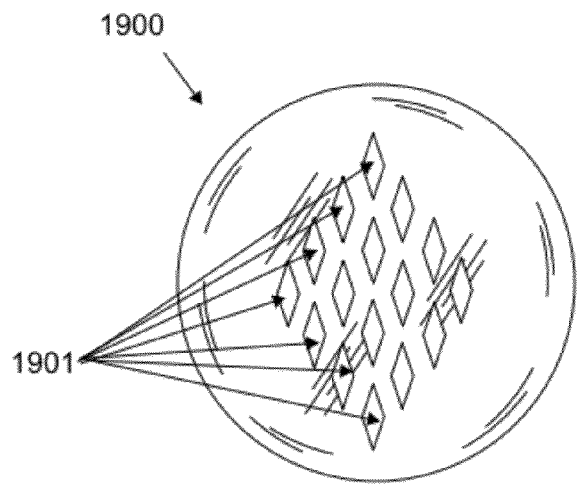
FIG. 19 is a schematic superior view of an embodiment of an orthopedic joint device comprising an inner membrane with apertures.

FIG. 19 depicts an embodiment of an inner membrane 1900 containing apertures 1901 configured to reduce puckering of the inner membrane when an associated orthopedic joint device (not shown) is in a deformation configuration. The apertures provide the inner membrane with relief areas to fill when the membrane is compressed, reducing or eliminating bulging of the inner membrane in a direction orthogonal to the device's contraction dimension. Any number of apertures may be used, including a single aperture. Any geometry or size of aperture may also be used, and the apertures may not be of equal size or shape. Geometries for an aperture include, but are not limited to, polygons, curves, and combinations of polygons and curves. In some embodiments, smaller apertures are placed closer to the outer body wherein less puckering may be expected. The apertures may be used in conjunction with a sinusoidal inner membrane, described above, and the apertures may be placed at some or all of the crests and troughs of the sinusoidal inner membrane.

Figure 20:
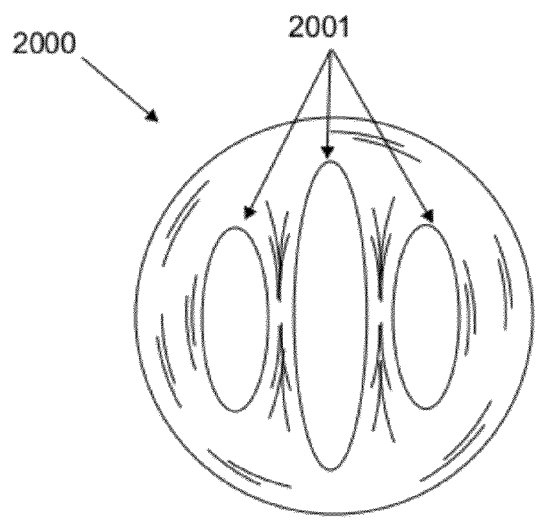
FIG. 20 is a schematic superior view of another embodiment of an orthopedic joint device comprising an inner membrane with apertures.

FIG. 20 depicts an embodiment of an inner membrane 2000 containing apertures 2001. In this embodiment, the apertures are fewer in number but larger in size. As an associated orthopedic joint device is deformed, the inner membrane will fill the open spaces thereby reducing or eliminating bulging of the inner membrane in a direction orthogonal to the device's contraction dimension.

Figure 21A:
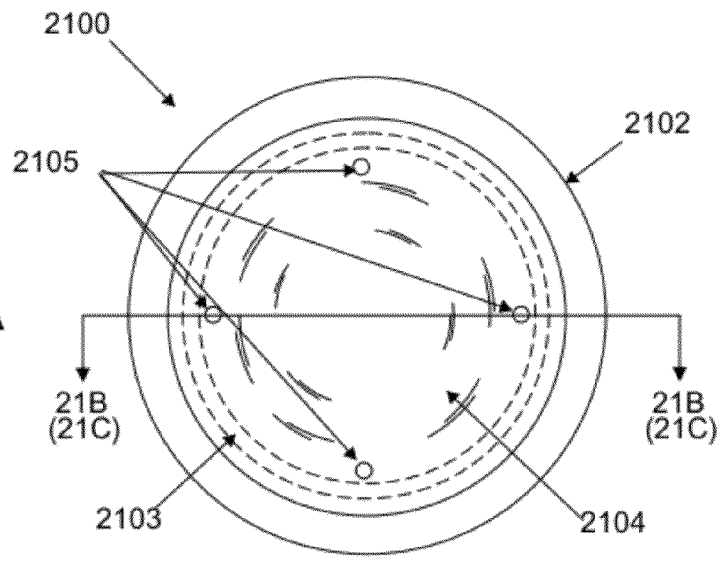
FIG. 21A is a schematic superior view of an embodiment of an orthopedic joint device comprising a resilient core and an inner membrane with apertures.

FIG. 21A depicts a superior view of an embodiment of an orthopedic joint device 2100. As depicted therein, the orthopedic joint device 2100 may comprise an outer body 2102, surrounding a core 2103, an inner membrane 2104, and holes 2105 through various points of the core and membrane transition region. Although not depicted in FIG. 21A, orthopedic joint device 2100 may include articulations to assist deformation and/or apertures or sinusoidal membranes to reduce puckering of the inner membrane. The holes 2105 are configured to permit entry of a thread or similar restraining device to deform the orthopedic joint device. All of the holes 2105 may be used to constrain the joint device or some holes may be used to constrain and others to stretch the orthopedic joint device 2100. For example, one pair of opposing holes may stretch the orthopedic joint device while another pair of opposing holes assists the deformation process by constraining the device. In this way, the profile of orthopedic joint device 2100 can be further deformed in the desired dimension than may be possible if the device had only one pair of opposing holes.

Figure 21B:
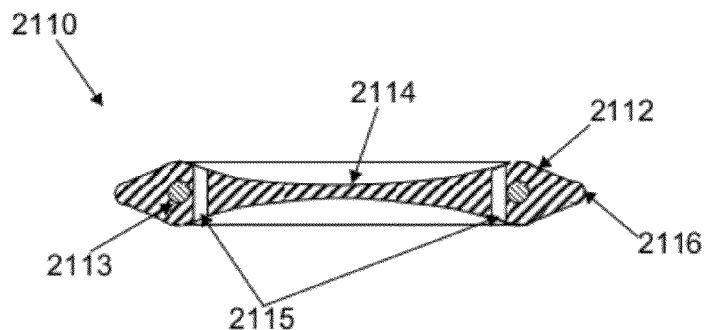
FIGS. 21B and 21C are schematic axial cross-sectional views of two embodiments of an orthopedic joint device with protruding outer edges.
Figure 21C:
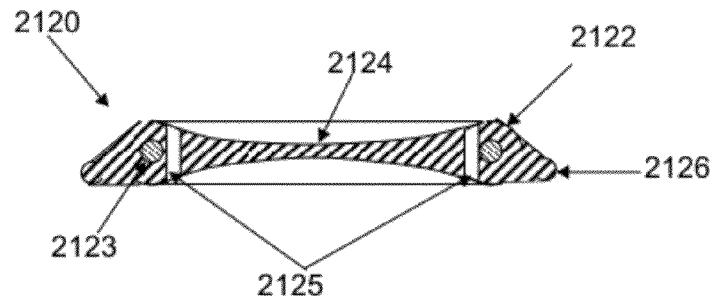

FIGS. 21B and 21C depict cross-sectional views of an orthopedic joint device 2110 and 2120, respectively. As depicted therein, each orthopedic joint device 2100 may comprise an outer body 2112 and 2122, surrounding a core 2113 and 2123, an inner membrane 2114 and 2124, and holes 2115 and 2125 through the core and membrane transition regions. The embodiments of FIGS. 21B and C may represent cross-sectional views of the embodiment of orthopedic joint device 2100 taken through the plane shown in FIG. 21A. Each outer body 2112 and 2122 comprise protruding outer edges 2116 and 2126. Protruding outer edges 2116 and 2126 may be configured to facilitate entry of an orthopedic joint device into an incision or may be configured to conform to the geometries of a particular joint or patient. The protruding edges comprise rounded tips to facilitate initial entry of the edge into an incision and a linear transition from the tips to widest portion of the outer body. This geometry of the protruding tips then minimizes the extent of mechanical interference relative on the tissue of the membrane by the orthopedic joint device.

Figure 22A:
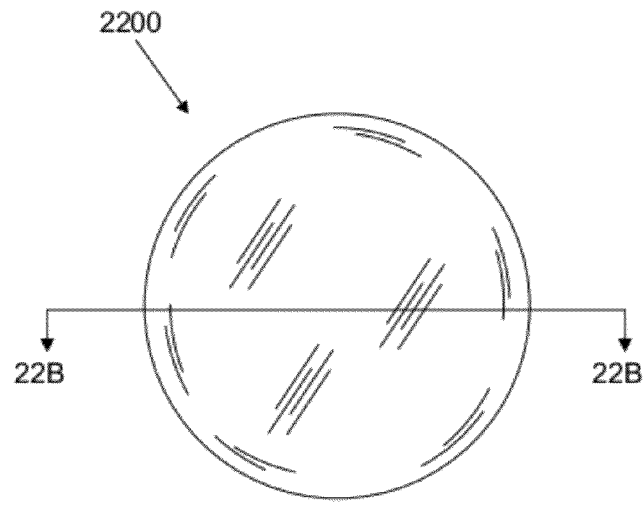
FIGS. 22A and 22B are schematic superior and cross-sectional views, respectively, of an embodiment of a flat-disc orthopedic joint device.
Figure 22B:
Figure 23:
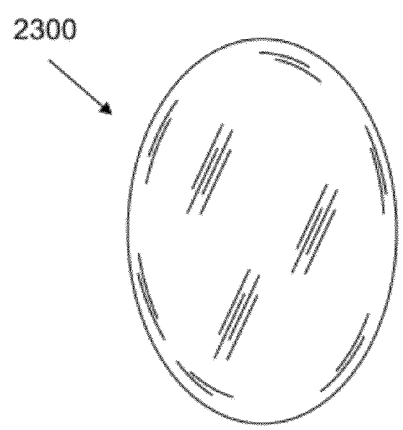
FIG. 23 is a schematic superior view of an embodiment of an oval orthopedic joint device.
Figure 24A:
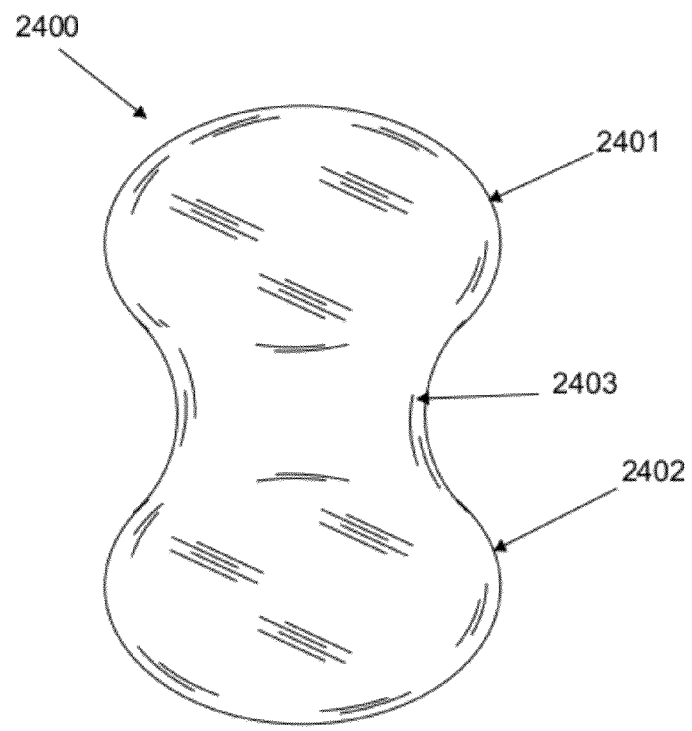
FIGS. 24A and 24B are schematic superior views of two embodiments of an orthopedic joint device comprising two oval regions joined by a connecting region.
Figure 24B:
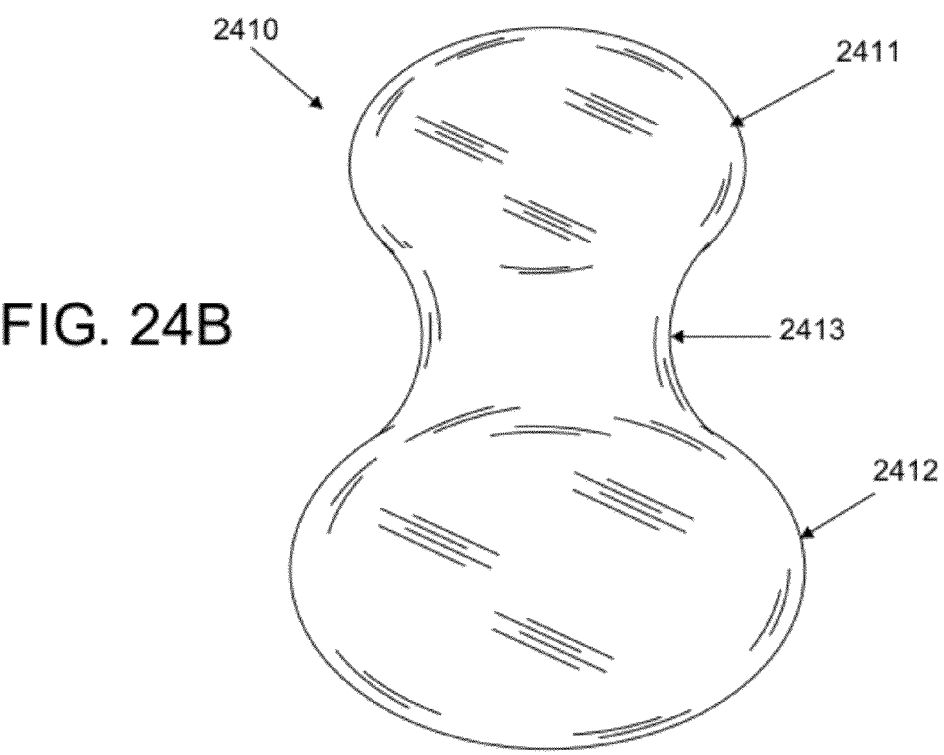

FIGS. 22A and 22B depict another embodiment of an orthopedic joint device 2200 in, respectively, superior and cross-sectional views. Orthopedic joint device 2200 comprises a flat disc which may be inserted directly into a joint of a patient, such as carpal-metacarpal joint, for example. Any of the structural features described herein may be added to orthopedic joint device 2200 to achieve any of the corresponding functions. Orthopedic joint 2200 device need not be disk shape, however, and may by oval when observed from a superior view, as depicted in FIG. 23. Further, the orthopedic joint device may combine a number of shapes. For example, FIG. 24A depicts an orthopedic joint device 2400 wherein two oval regions 2401 and 2402 are joined by a connecting region 2403. The size and shape of the ovals may be varied to achieve different configurations, as with orthopedic joint device 2410 depicted in FIG. 24B. Orthopedic joint device 2410 comprises two ovals 2411 and 2412 of different sizes joined by a connecting region 2413. In some embodiments, the ovals may comprise holes, cores, membranes, and/or any of the other structural features described in other variations herein.

Figure 25A:
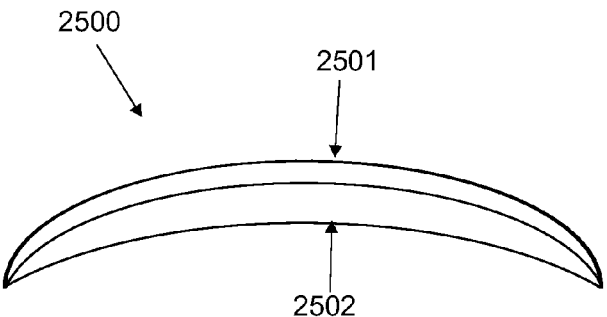
FIGS. 25A and 25B are cross sectional views of two embodiments of non-planar orthopedic joint devices.
Figure 25B:
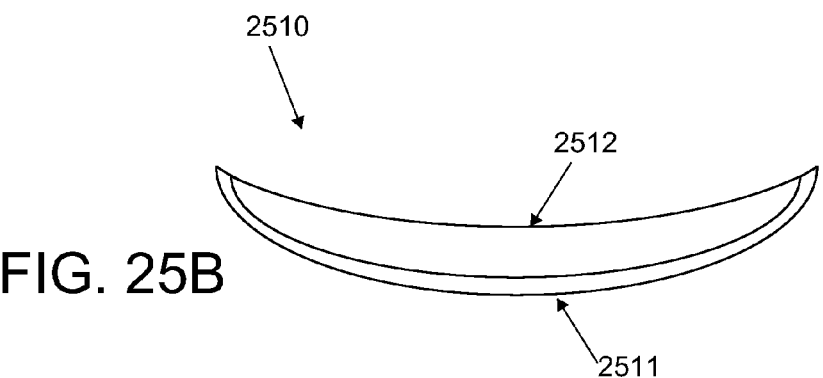

FIGS. 25A and 25B depict a non-planar orthopedic joint device 2500 in a cross-sectional view. Orthopedic joint device 2500 may be strategically shaped to facilitate insertion of the device through an incision, to fit a geometry of a specific joint or patient, or to achieve other functional aspects. In the cross-sectional view of FIG. 25A, the profile 2501 of orthopedic joint device is concave. The superior surface 2502 of the perimeter of orthopedic joint device 2501 can be seen to be non-uniform, with a valley existing at the point furthest away from the viewer in FIG. 25A. FIG. 25B depicts orthopedic joint device 2500 inverted.

Figure 26A:
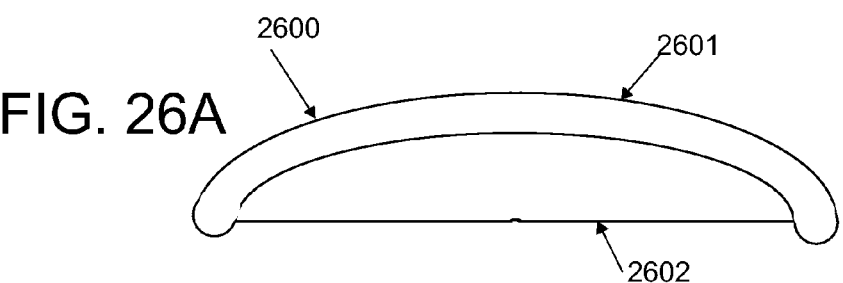
FIGS. 26A and 26B are cross-sectional views of two embodiments of non-planar orthopedic joint devices.
Figure 26B:
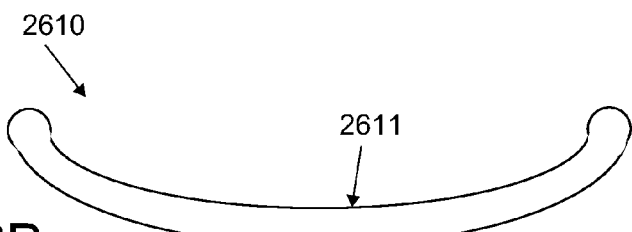

FIG. 26A depicts another embodiment of an orthopedic joint device 2600 in a cross-sectional view. Orthopedic joint device 2600 includes a concave body 2601 with a constant cross-sectional profile in planes parallel to the view of FIG. 26A and a membrane 2601 for controlling deformation, as discussed above. The device need not include a membrane, however, as depicted in orthopedic joint device 2610 in FIG. 26B.

FIGS. 27A-27G depict another embodiment of an orthopedic joint device 2700. As depicted therein, the orthopedic joint device 2700 may comprise a main body 2702, transition region 2720, and an interior region 2710. The profile of orthopedic joint device 2700 may be configured to reduce in a direction orthogonal to the direction of insertion of the device into an incision. The profile of orthopedic joint device 2700 may be reduced by, for example, stretching the device in the direction of insertion, overlapping the ends of the device, or a combination of both.

In the embodiment of FIGS. 27A-27G, main body 2702 comprises a generally arcuate shape, but other embodiments may take other shapes, including open and closed curves and/or polygons. Main body 2702 may include one or more cores to provide radiopacity, resist deformation, or both. A radiopaque core may provide practitioners with a non-invasive mechanism by which to monitor the device after insertion. Such radiopaque cores may take any form that prevents passage of electromagnetic radiation, including, but not limited to, a radiopaque wire, radiopaque particles, or radiopaque liquid. Such radiopaque liquid may comprise a radiolucent liquid infused with a radiopaque dye and may be encased in one or more tubes. In some embodiments the radiopaque core may be continuous. In some embodiments, the radiopaque core may be fragmented. In some variations, a liquid or gel core, or a combination of particles suspended in a liquid or gel, may be provided to facilitate detection of device fracture or rupture, when evidence of liquid dispersion or dissipation is seen radiographically. When taking an arcuate shape, main body 2702 may include rounded leg tips 2704, but the leg tips may take other configurations. The leg tips may be overlapped to reduce the profile of the orthopedic joint device prior for delivery or may impinge on one another as the device is stretched. In some embodiments, the leg tips may be configured to ease overlapping of the ends of the main body of the device or to maximize contraction of the device. For example, the surfaces of leg tips 2704 may be sloped to ease mutual-sliding of the leg tips when the ends of the main body are overlapped. In other embodiments, the surfaces of leg tips 2704 may be sloped to maximize the contact area between the ends when the device is fully stretched, i.e., when the orthopedic joint device is stretched and the leg tips impinge on one another, the leg tips may be sloped away from each other so that more of the leg tips' surfaces are in contact as the device is further contracted. Some embodiments may include both configurations. Further, the distance between the leg tips and their relative angle may be varied. In this way, the increase in height of the orthopedic joint device in the deformation configuration can be initially reduced or eliminated entirely, when the device is overlapped for delivery, or the degree of puckering at the proximal region may be reduced when the device is stretched for delivery. Main body 2702 includes three holes 2708, but any number of holes may be included in an orthopedic joint device, including one hole. Some embodiments may have no holes. In embodiments comprising no holes, the devices may be inserted using forceps or the surgeon's fingers, for example. In some variations, holes 2708 may result from a manufacturing process and may correlate to the points at which a core or cores are secured as an outer body is added to the device. In some embodiments, holes 2708 may provide attachment points with which to control deformation of the device during delivery. Some embodiments may have only one hole for attachment. In some further embodiments, one attachment hole is located at the distal end of the device and in yet further embodiments, the hole is on a line that includes the center of the device and the midpoint between the leg tips. Some further embodiments may also comprise one or more small suture holes located near one of the legs, which may be used to attach a suture for device retrieval. Some or all of the holes may be configured to reduce slippage of a thread or other mechanism used to control deformation of the orthopedic joint device during delivery. Such configurations include, for example, a "D" configuration, wherein the vertical line of the D is the surface of the hole that engages the thread, and a "V" configuration, wherein the "angle" of the V is the surface of the hole that engages the thread. Some or all of the holes may also include grommets at the surface of the hole that engages the thread. These grommets may include, for example, a strengthened tubular member inserted through the entirety of the hole, or a strengthened plane configured to be coupled to the surface of the hole that engages the thread. The grommets may further include a flange coupled to the grommet and configured to prevent motion of the grommet in a direction along an axis of the grommet. Such a flange may include, for example, a washer, a series of protrusions, or any mechanism configured to prevent relative motion between the grommet and the main body. Main body 2702 may also include a lead surface 2706, which may be configured to ease insertion of the orthopedic joint device into an incision. As described herein, the term "lead surface" can be understood to refer to the region of the orthopedic joint device which is configured to first enter an incision, which may also be referred to herein as the "distal" end of the device. In the embodiment of FIGS. 27A-27G, lead surface 2706 may protrude from the predominate shape of main body 2702. In other embodiments, the lead surface of the orthopedic joint device does not protrude from the predominate shape of the main body 2702, a configuration which may lead to undesired stretching of the incision when the force of a broad lead surface impacts the patient's tissue. A protruding surface may reduce the mechanical interference relative to a patient's tissue as the orthopedic joint device 2700 is inserted through an incision, where the protruding surface is configured to gradually increases in width as the device enters the incision, e.g. a reduced entry angle. Thus, the incision area may not be subjected to an abrupt change in the entry angle, resulting in a substantial increase in insertion resistance, but may instead experience a gradual increase in insertion resistance. The protrusion of the lead surface may take different shapes and protrude to different depths. In some embodiments, the protrusion is shaped as an arc with a radius of curvature larger than the radius of the main body. The arc and main body need not share the same center point. The arc and main body are joined by a tapered region, which may take a linear or non-linear cross-sectional shape. In some embodiments, the shape of the tapered region is determined by the depth of protrusion and the radius of curvature of the arc. In some embodiments, the lead surface comprises a reduced angle distal superior and inferior surfaces for further reducing the entry angle of the device relative to the incision or delivery opening. The reduced angle distal surfaces comprise a smaller initial height at the lead surface with a gradual increase to the height of the main body where the angle between the lead surface and the maximum height of the main body is less than about 45 degrees, sometimes less than about 30 degrees, and other times less than about 20 degrees or less than about 10 degrees. Such surfaces may also comprise an arc with a radius different from the radius of the main body or an arc eccentric to the main body, for example, with a tapered region joining the distal arc to the height main body.

Transition region 2720 provides a gradual reduction of height from main body 2702 to interior region 2710. Accordingly, the transition region can be understood to comprise a surface with a different shape and/or orientation to both the main body and interior regions, which begins at the highest point of the main body and continues to the highest point of the interior region. In some embodiments, the transition region may be equivalently considered to comprise a portion of the main body and/or interior region, without deviating from the scope of the invention. The gradual reduction of height may facilitate minimal puckering of orthopedic joint device 2700 when in the deformed configuration. As the profile of the device is reduced for delivery by stretching or overlapping the ends, the material in the transition regions and the interior region (see below) will expand in a direction perpendicular to deformation. This lateral expansion of the material may lead to puckering. The internal forces may be greater where the transition region is wider because a larger volume of material is being compressed, leading to greater expansion forces. With a gradual reduction of height, less expansion resistance will be felt at the narrower widths. Thus, these regions will be less prone to puckering. Thicker transition regions, however, may result in less deformation of the device. Accordingly, the slope of the transition regions may be configured to permit a desired degree of deformation and maintain a desired degree of puckering. The slope of the transition region may also be varied to accommodate different materials and/or orthopedic device configurations, and may take any value, including a constant and a function of the distance from the main body, which may be a linear or non-linear function, including a piecewise function. A gradual transition region may connect the entire main body to the interior region, or may connect only a section or sections of the main body and/or the interior region. Different sections of the transition region may take the same or different shapes. Transition region 2720 may also comprise proximal transition regions 2722, which may be configured to reduce puckering, promote overlapping of the ends, or both, near the proximal region of the orthopedic device. Some embodiments of an orthopedic joint device may include a distal transition region configured to relieve increased puckering of the device in the distal end of the transition region.

As used herein with respect to the embodiments of FIGS. 27A-37I, the term "interior region" can be understood to refer to the central region of the main body, including the volume between the leg tips and the center of the device, but excluding the transition regions. In the embodiment of FIGS. 27A-27G, interior region 2710 has a central opening, which may reduce the puckering of the device in the deformed configuration. In some embodiments, the interior region is not open and may comprise one or more span members covering the central region of the device. In orthopedic device 2700, a span member 2712 is added in the region of the leg tips to prevent splaying of the device in the deformed configuration, as has been discussed in more detail above. The location of span member 2712 at the proximal region of the interior region may cause increased puckering. Accordingly, an inward edge 2714 may be added to the proximal region of the span member. Although inward edge 2714 is concave in the embodiment of FIGS. 27A-27G, the edge need not be concave and may take any inward shape configured to reduce puckering of the proximal region of the span member, including an arc, a parabola, a conic section, a curve with one or more local maxima and/or minima, and a piecewise function. Further, the edge 2714 need not be smooth and may contain one or more first derivative step discontinuities. Orthopedic joint device 2700 also includes proximal transition regions 2722, which may be shaped differently from the remainder of the transition region 2720. The proximal transition regions may be configured to reduce puckering at the proximal region, ease overlapping of the ends, or both.

Figure 27A:
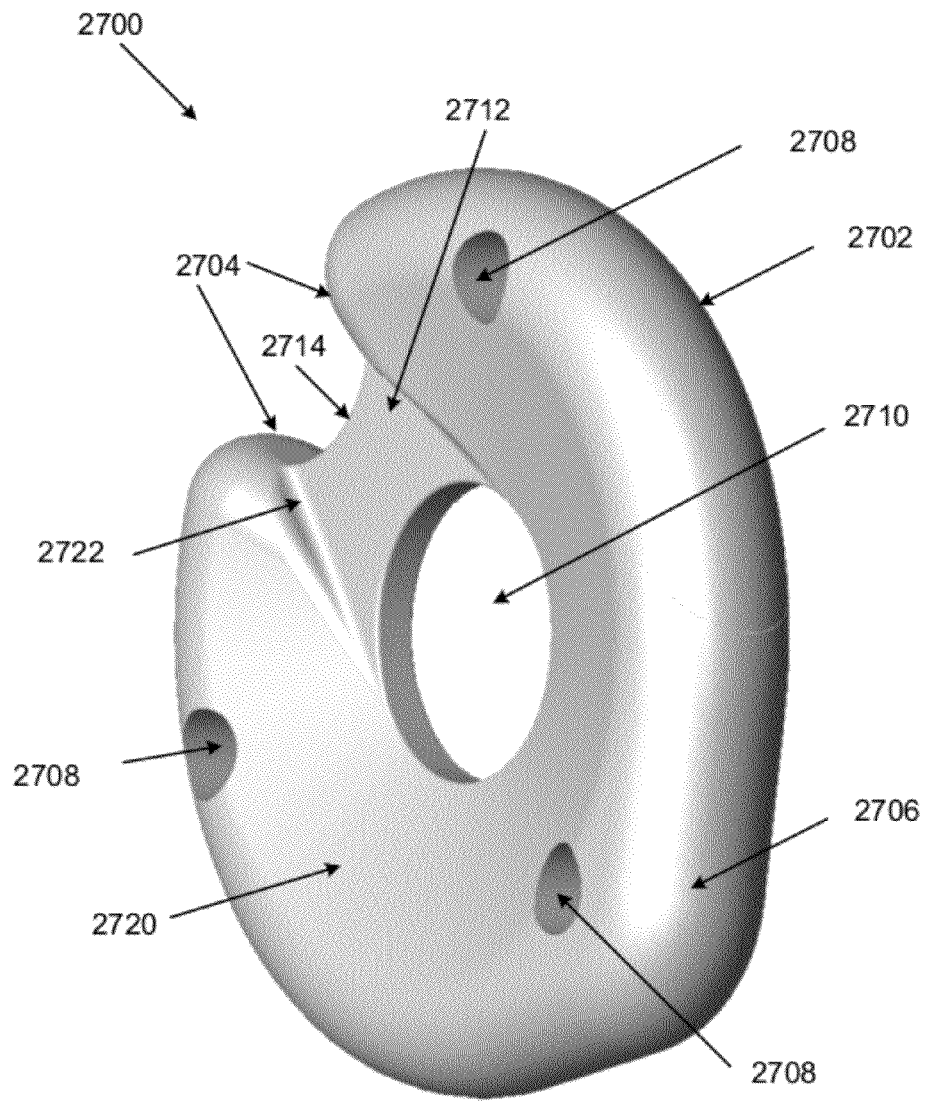
FIG. 27A is a solid isometric view of an embodiment of an orthopedic joint device comprising a transition region and a central cutout.

FIG. 27A depicts a solid isometric view of orthopedic joint device 2700. As depicted therein, orthopedic joint device 2700 may comprise a main body 2702, transition region 2720, and an interior region 2710. Main body 2702 may comprise leg tips 2704, lead surface 2706, and holes 2708. Transition region 2720 may comprise proximal transition regions 2722. Interior region 2710 may comprise span member 2712 and an inward proximal edge 2714 on span member 2712.

Figure 27B:
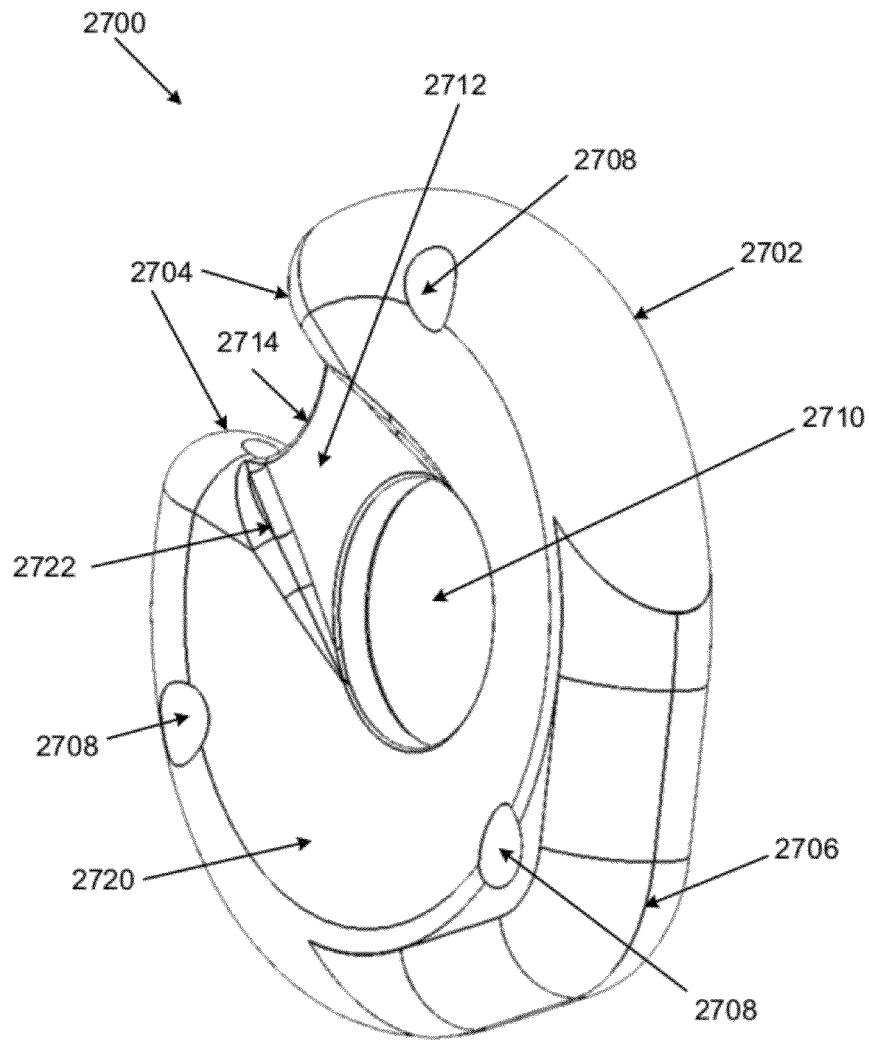
FIG. 27B is a line-drawing isometric view of the orthopedic joint device in FIG. 27A.
Figure 27C:
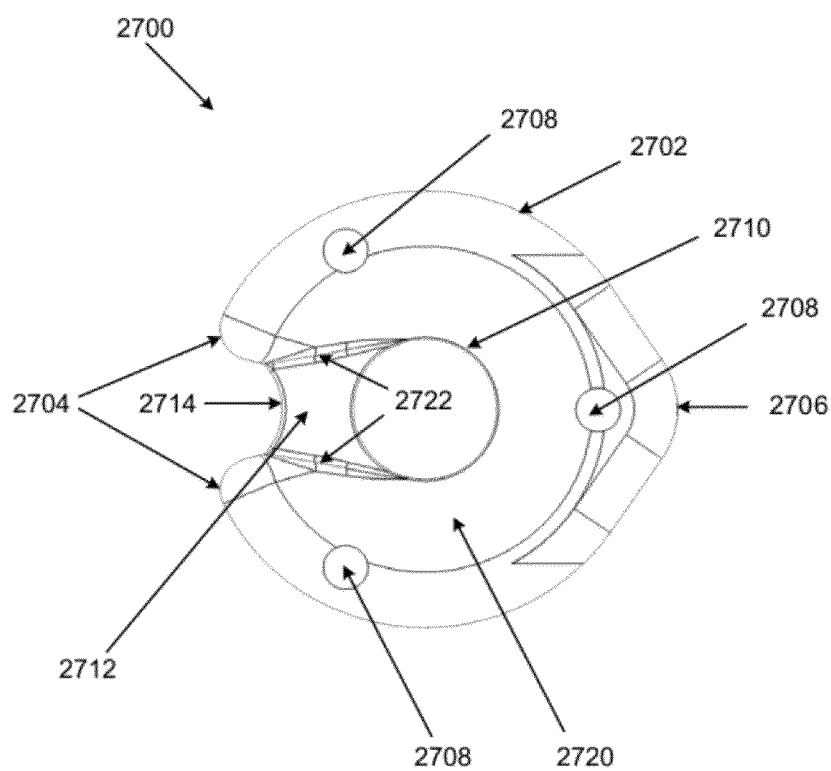
FIG. 27C is a line-drawing superior view of the orthopedic joint device in FIG. 27A.
Figure 27D:
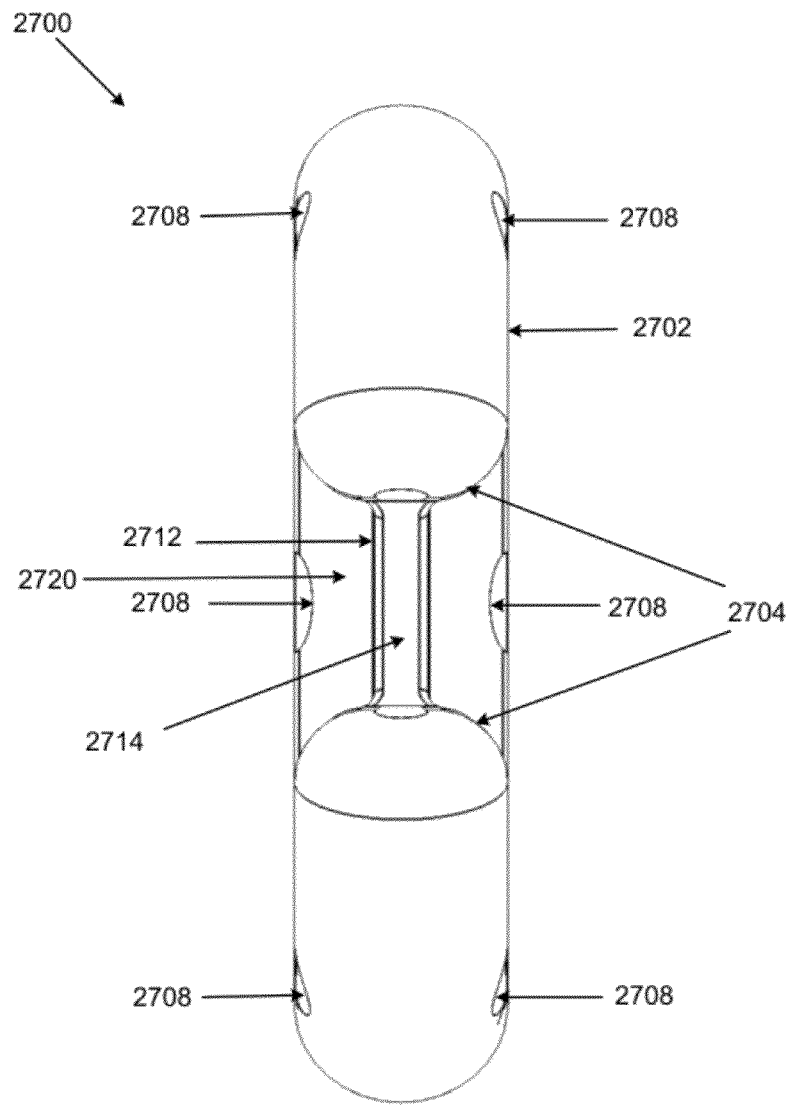
FIG. 27D is a line-drawing rear view of the orthopedic joint device in FIG. 27A.
Figure 27E:
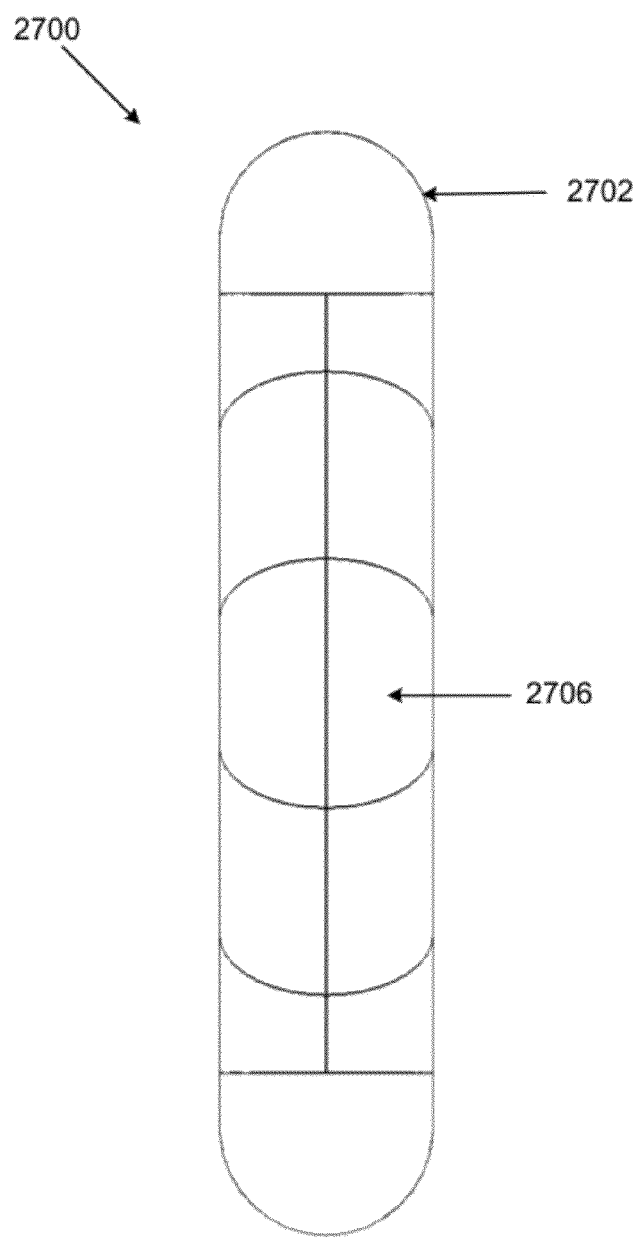
FIG. 27E is a line-drawing front view of the orthopedic joint device in FIG. 27A.
Figure 27F:
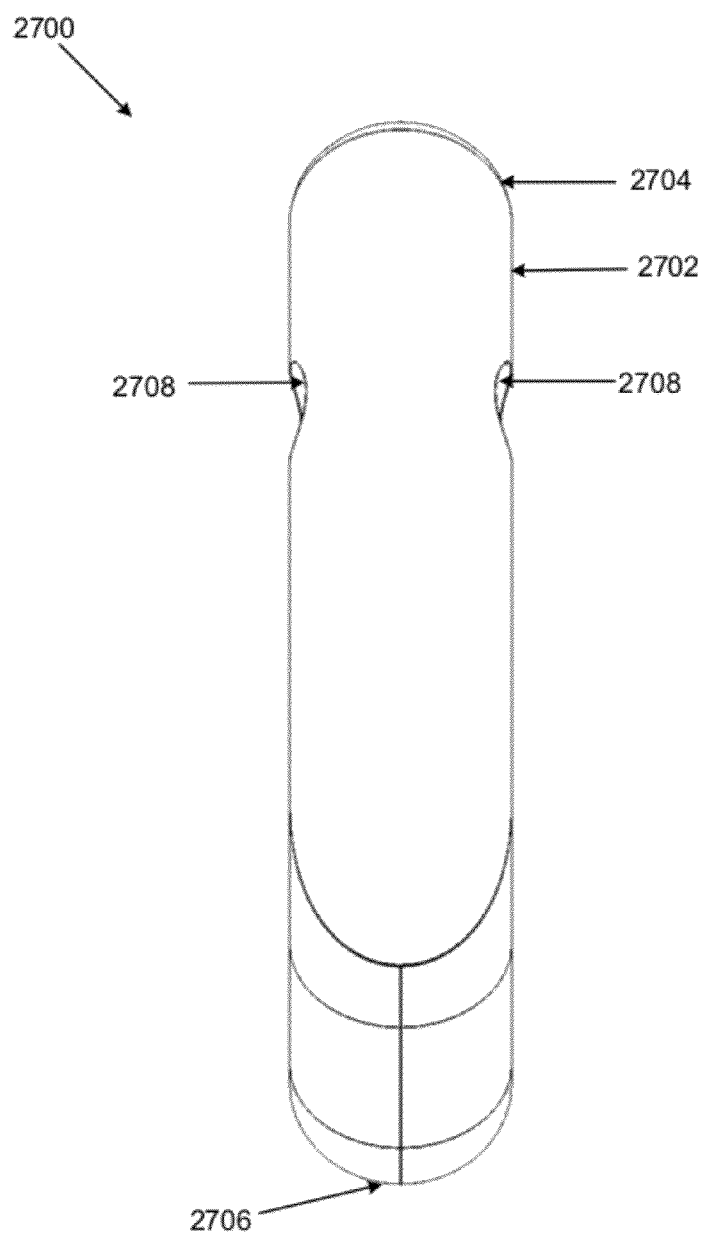
FIG. 27F is a line-drawing side view of the orthopedic joint device in FIG.
Figure 27G:
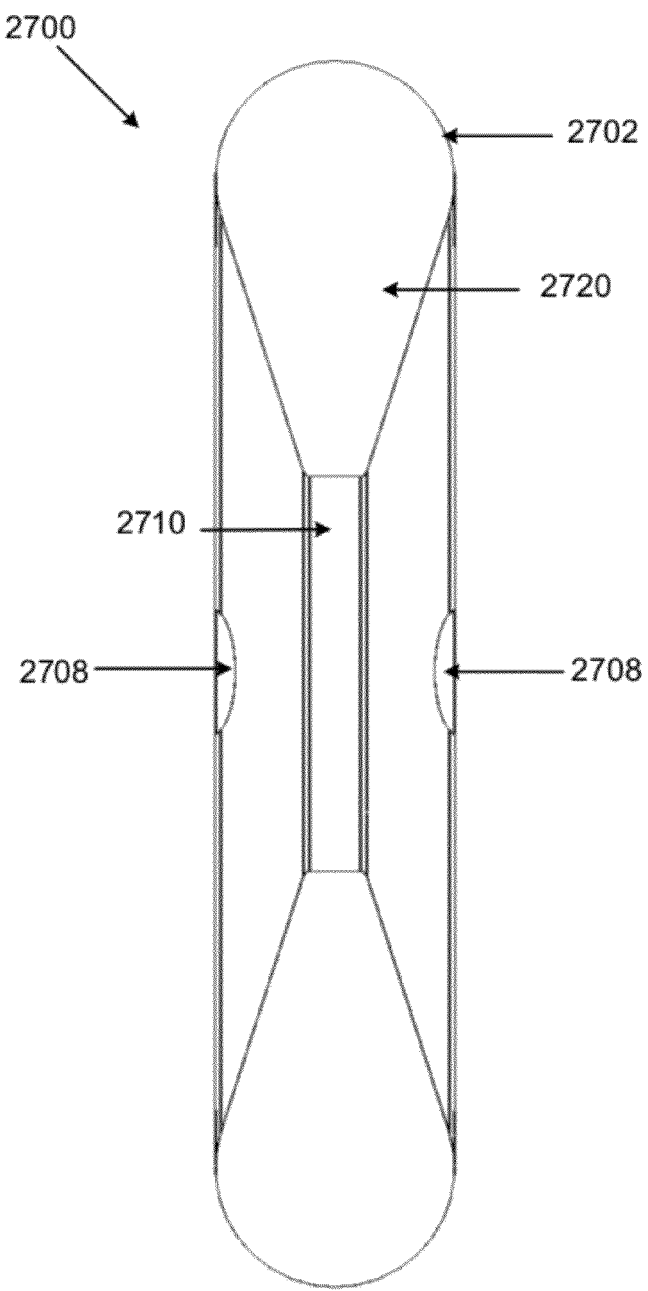
FIG. 27G is a line-drawing cross-sectional view of the orthopedic joint device in FIG. 27A, taken through a plane at the mid-point of the device, looking toward the distal end of the device.

FIG. 27B depicts a line-drawing isometric view of orthopedic joint device 2700. FIG. 27C depicts a line-drawing superior view of orthopedic joint device 2700. As depicted therein, lead surface 2706 comprises an arc with a radius of curvature larger than the radius of the main body 2702, and a linear tapering region from the protrusion to the predominate shape of the main body. In orthopedic joint device 2700, the radius of the protrusion arc is approximately equal to $11/10$ of the radius of main body 2702, but other ratios could be used without deviating from the scope of the invention. Proximal transition regions 2722 are configured to reduce puckering of the span member 2712. In orthopedic device 2700, the leg tips 2704 are spaced a distance apart equal to approximately $1/5$ the overall width of the orthopedic joint device 2700. Inward edge 2714 comprises an arc of radius approximately equal to $9/20$ the width of the orthopedic joint device 2700 in the base configuration. The central region of interior region 2710 comprises a diameter equal to approximately $1/3$ the width of the device. FIG. 27D depicts a line-drawing rear view of orthopedic joint device 2700. As depicted therein, the leg tips 2704 are rounded, but the leg tips could take a variety of configurations, as discussed in more detail above. FIG. 27E depicts a line-drawing front view of orthopedic joint device 2700. Lead edge 2706 is illustrated therein as being symmetrical about a centerline of the orthopedic joint device 2700, but other embodiments might favor one or more surfaces of the device. FIG. 27F depicts a line-drawing side view of orthopedic joint device 2700. As shown therein, holes 2708 are located at approximately $3/4$ of the distance from the lead surface to the leg tips. FIG. 27G depicts a line-drawing cross-sectional view of orthopedic joint device 2700, taken through a plane at the mid-point of the device, looking toward the distal end of the device. Main body 2702 has a height equal to approximately $1/5$ the width of the orthopedic joint device 2700, interior region 2710 has a height equal to between 2-12% the width of the device, and transition region 2720 has a width of approximately $2/5$ the width of the device. The outer surfaces of transition region 2720 comprise planes sloped at approximately 30-400. In some embodiments, interior region 2710 has a height equal to between 15-35% of the height of the orthopedic implant.

Figure 28A:
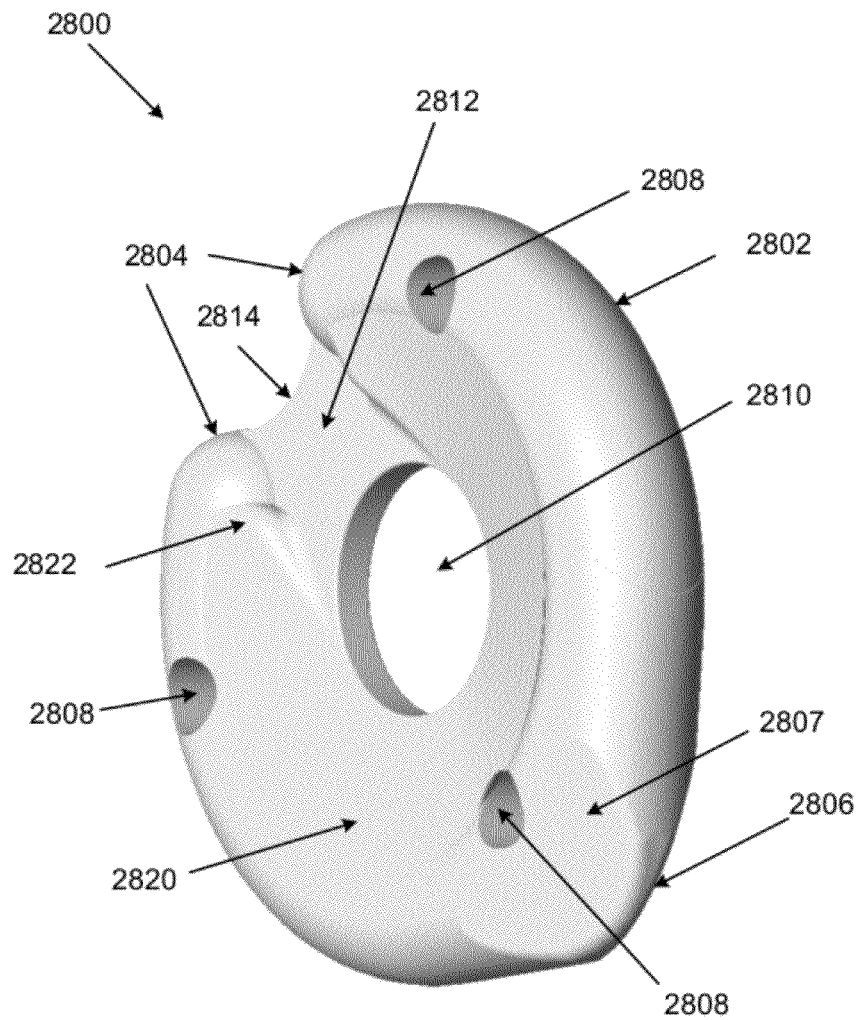
FIG. 28A is a solid isometric view of an embodiment of an orthopedic joint device comprising a transition region, a central cutout, and a pinched lead surface.

FIGS. 28A-28G depict another embodiment of an orthopedic joint device 2800. FIG. 28A depicts a solid isometric view of orthopedic joint device 2800. As depicted therein, the orthopedic joint device 2800 may comprise a main body 2802, transition region 2820, and an interior region 2810. Orthopedic joint device 2800 may share structural features similar to those of orthopedic joint device 2700, discussed above. Main body 2802 may comprise leg tips 2804, lead surface 2806, and one or more optional holes 2808 located symmetrically at approximately the 12 o'clock, 4 o'clock and 8 o'clock positions. In other variations, one or more holes, if any, may be located at any other clock position, and need not be symmetrically positioned circumferentially or axially, and may have different sizes or shapes. Leg tips 2804 may be closer to one another than the embodiment of orthopedic joint device 2700, thereby reducing the amount of movement between the leg tips during use. Lead surface 2806 is protruded, similar to lead surface 2706 described above, but may also comprise a reduced angle or sloped surfaces 2807, to further ease entry of the orthopedic joint device 2800 into an incision. The sloped surfaces 2807 gradually increase the height of the orthopedic joint device 2800 from the distal edge of the lead surface 2806 to the height of the main body 2802. Sloped surfaces 2807 may be configured to increase in width as they approach the height of the main body. This increase in width may further ease entry of the device into an incision by distributing the force exerted on the incision across a wider surface area, thereby reducing the pressure, or force per unit area, exerted on the incision. Transition region 2820 may include proximal transition regions 2822. Interior region 2810 may comprise span member 2812 and an inward proximal edge 2814 on span member 2812. In comparison to span member 2712, span member 2812 occupies more of the volume between the leg tips 2804, thereby reducing the leg tips' freedom to splay during use.

Figure 28B:
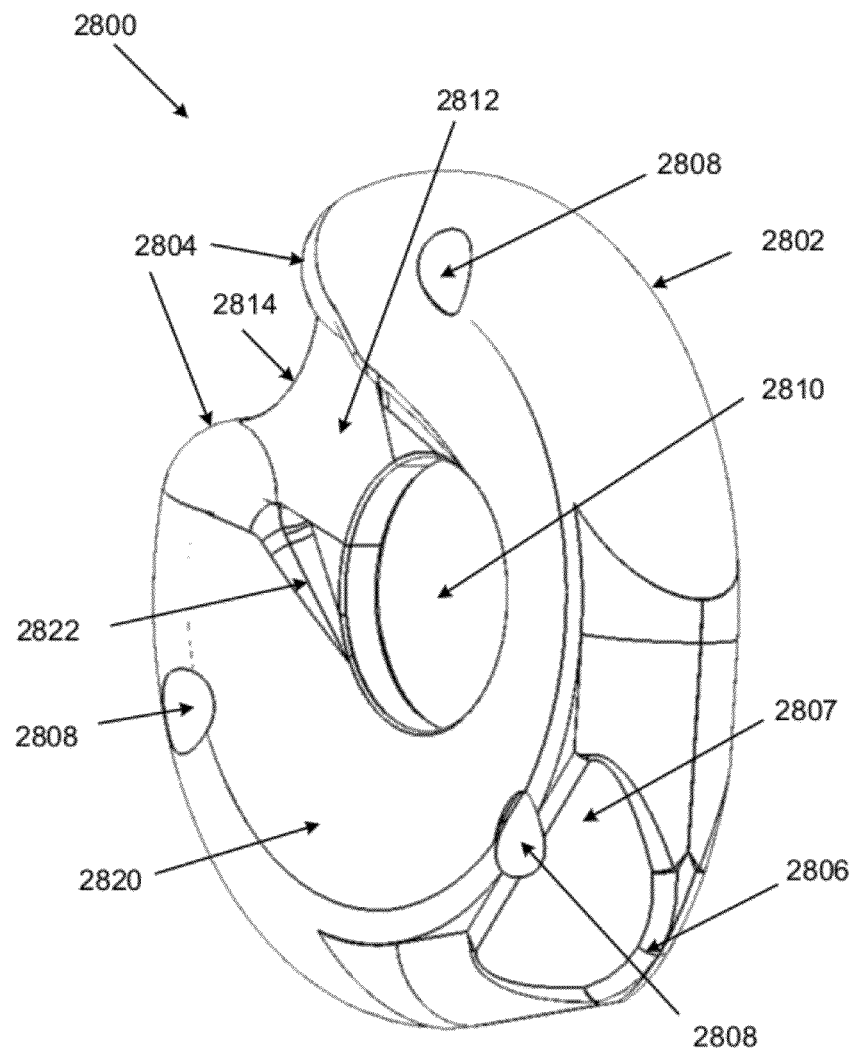
FIG. 28B is a line-drawing isometric view of the orthopedic joint device in FIG. 28A.
Figure 28C:
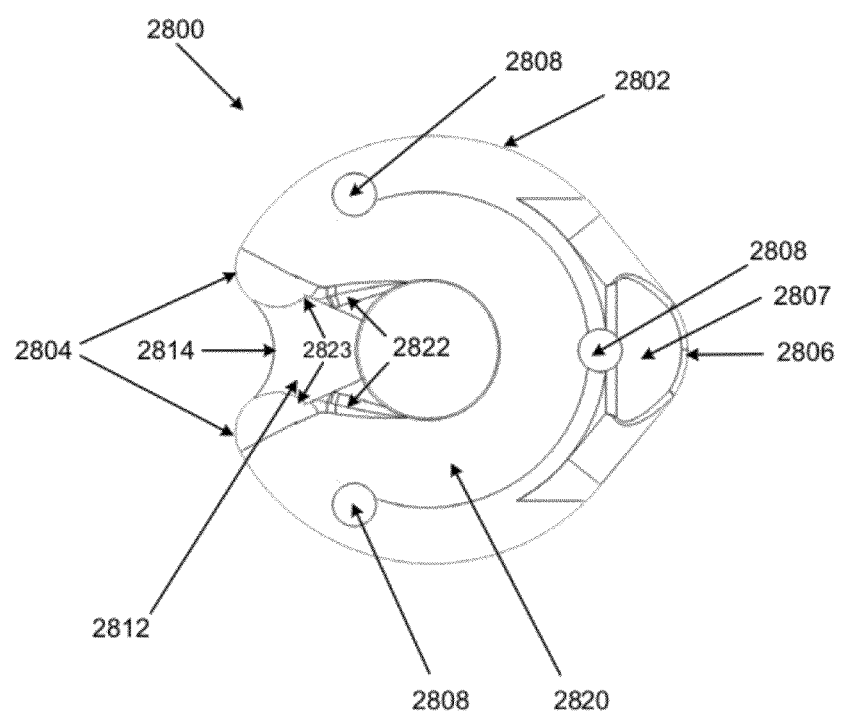
FIG. 28C is a line-drawing superior view of the orthopedic joint device in FIG. 28A.
Figure 28D:
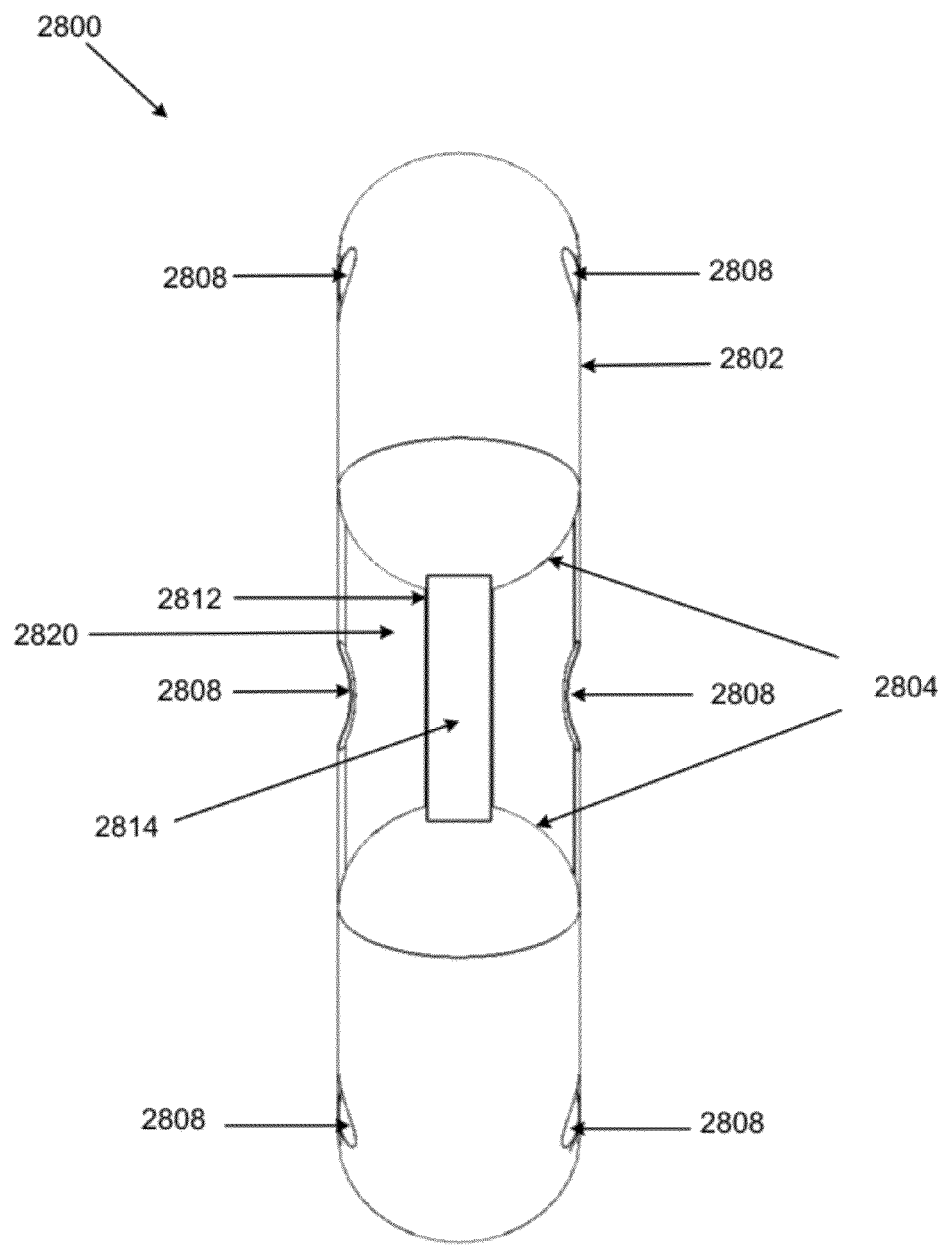
FIG. 28D is a line-drawing rear view of the orthopedic joint device in FIG. 28A.
Figure 28E:
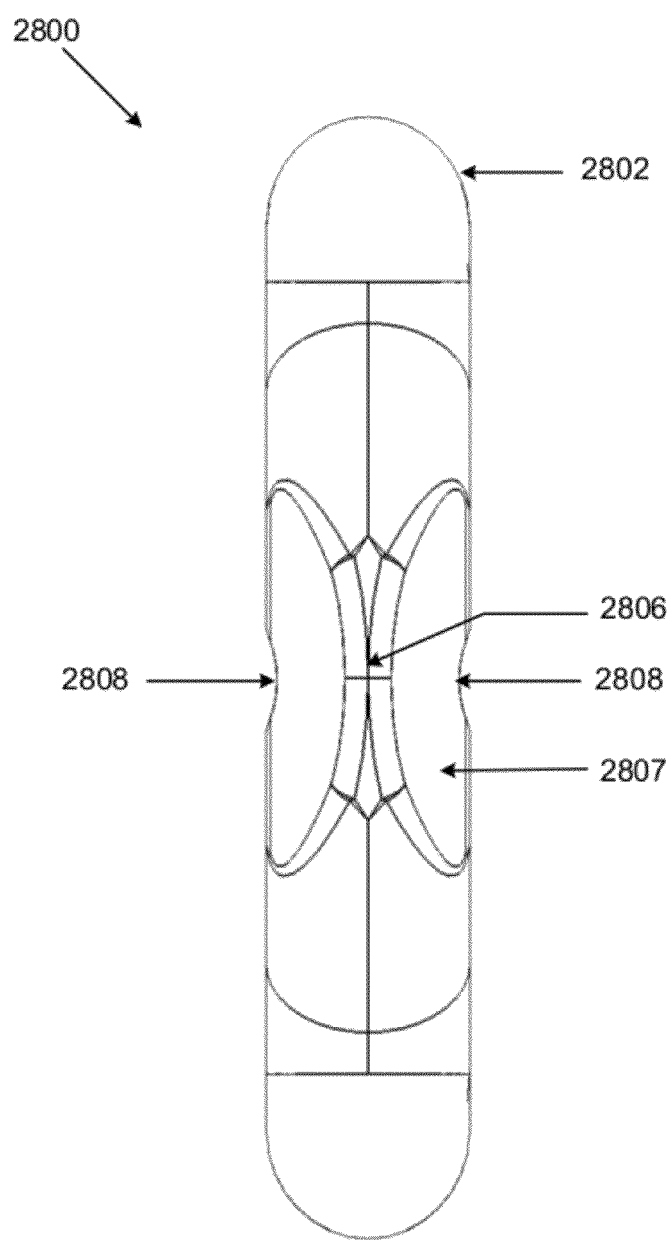
FIG. 28E is a line-drawing front view of the orthopedic joint device in FIG. 28A.
Figure 28F:
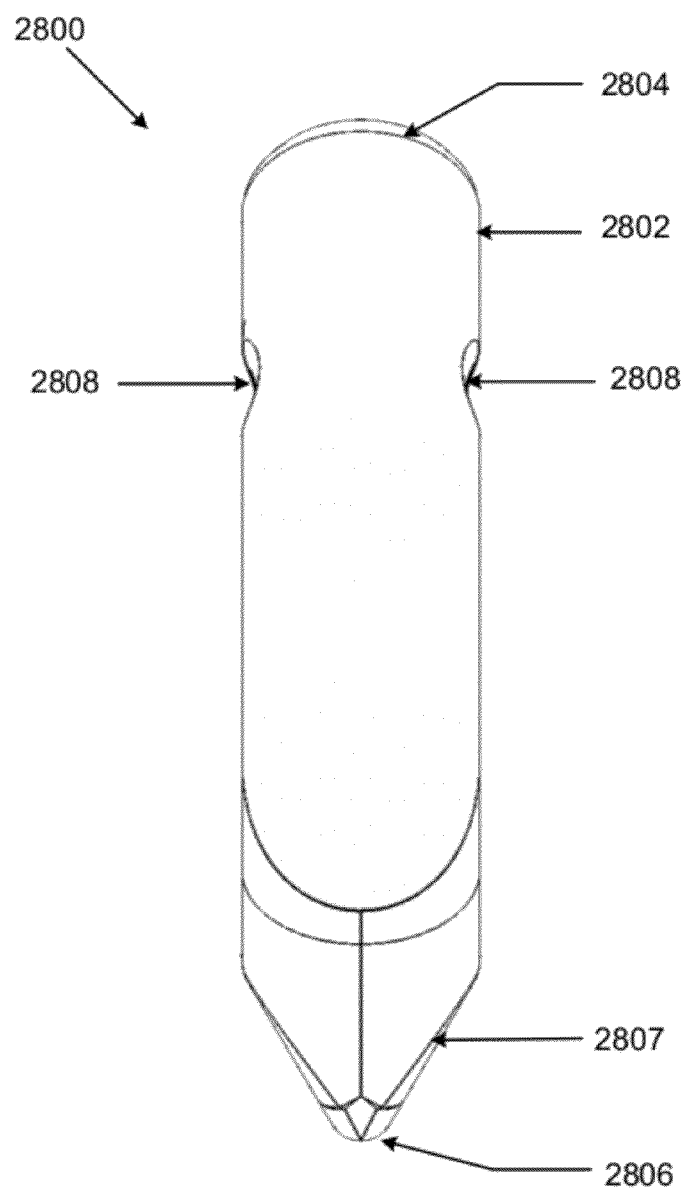
FIG. 28F is a line-drawing side view of the orthopedic joint device in FIG. 28A.
Figure 28G:
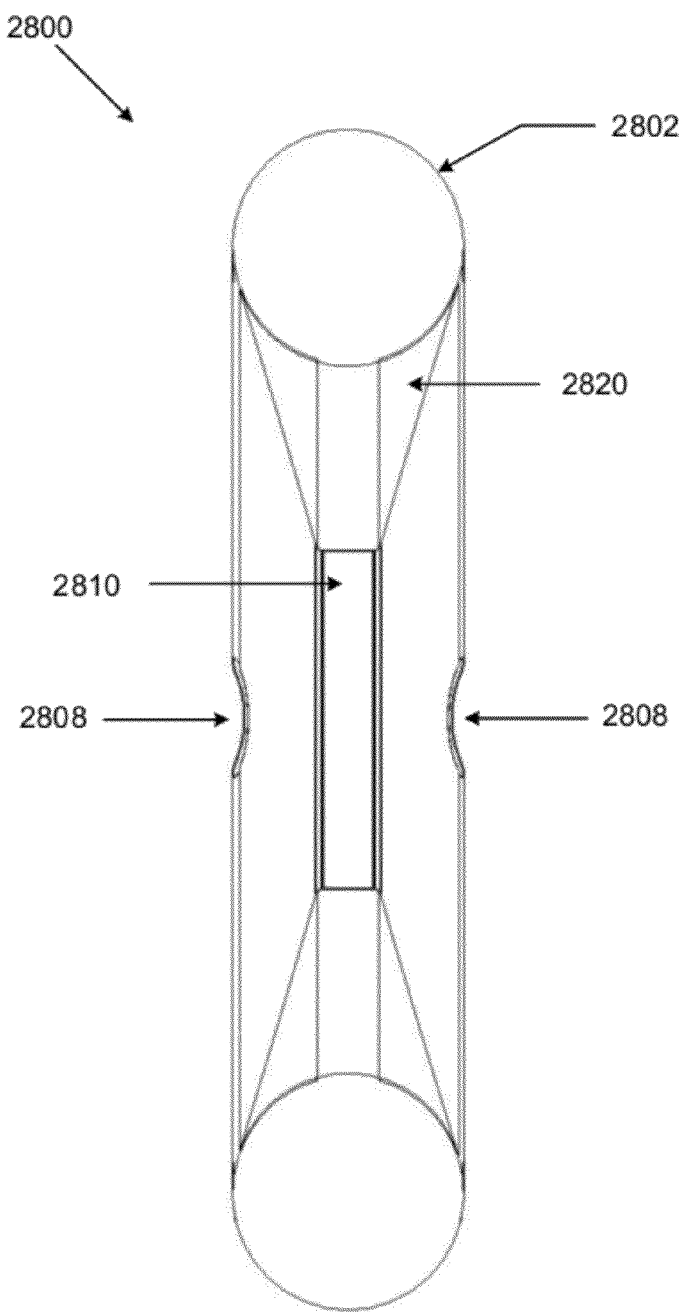
FIG. 28G is a line-drawing cross-sectional view of the orthopedic joint device in FIG. 28A, taken through a plane at the mid-point of the device, looking toward the distal end of the device.

FIG. 28B depicts a line-drawing isometric view of orthopedic joint device 2800. FIG. 28C depicts a line-drawing superior view of orthopedic joint device 2800. Proximal transition regions 2822 are configured to reduce puckering of the span member 2812. Unlike proximal transition regions 2722, proximal transition regions 2822 include angles 2823 configured to distribute the height of the puckering over the width of the span member 2812, thereby reducing the highest point of the span member 2812 in the deformed configuration. The degree of the angle 2823 can be varied to vary the height of the span member 2812 in the deformed configuration The inward proximal edge 2814 of the span member 2812 comprises an arc of radius approximately equal to the radius of the central region of the interior region. FIG. 28D depicts a line-drawing rear view of orthopedic joint device 2800. FIG. 28E depicts a line-drawing front view of orthopedic joint device 2800. FIG. 28F depicts a line-drawing side view of orthopedic joint device 2800. Leading surface 2806 comprises a small arc which then tapers out to the predominate shape of main body 2802. Leading surface 2806 need not comprise an arc, however, and may, for example, comprise an angle. FIG. 28G depicts a line-drawing cross-sectional view of orthopedic joint device 2800, taken through a plane at the mid-point of the device, looking toward the distal end of the device.

Figure 29A:
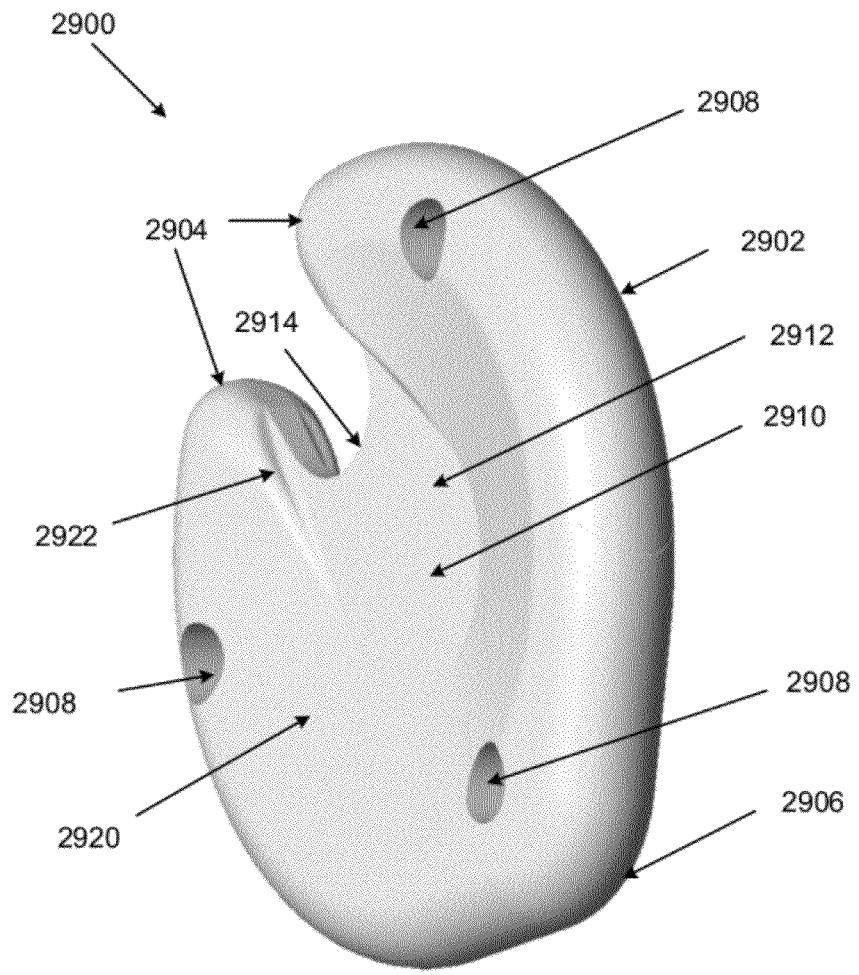
FIG. 29A is a solid isometric view of an embodiment of an orthopedic joint device comprising a transition region and a span member covering a central region.

FIGS. 29A-29G depict another embodiment of an orthopedic joint device 2900 wherein a span member 2912 covers the central region of an interior region 2912. The span member may be configured to prevent splaying of the leg tips after insertion, which may reduce the necessity for a proximal span member discussed above in more detail. Accordingly, an inward proximal edge 2914 of span member 2912 may comprise a larger radius than embodiments without a span member covering the central region. FIG. 29A depicts a solid isometric view of orthopedic joint device 2900. As depicted therein, the orthopedic joint device 2900 may comprise a main body 2902, transition region 2920, and an interior region 2910. Main body 2902 may comprise leg tips 2904, lead surface 2906, and one or more optional holes 2908, as generally described with regards to device 2800 in FIGS. 28A-28G. Transition region 2920 may include proximal transition regions 2922. Interior region 2910 may comprise span member 2912 and inward proximal edge 2914 on span member 2912. Unlike the span members of the orthopedic joint devices 2700 and 2800, span member 2912 covers the central region of interior region 2912. Although span member 2912 covers the entire central region of the interior region, other embodiments may partially cover the central region. Because span member 2912 provides a resistance to splaying of the leg tips during use, some embodiments may not include a span member at the proximal region of the interior region, as with orthopedic joint devices 2700 and 2800. Because the anti-splaying function of span members 2712 and 2812 may be performed by the span member 2912, the inward proximal edge 2914 of span member 2912 may be set deeper into the central region, thereby reducing puckering at the proximal end of the device.

Figure 29B:
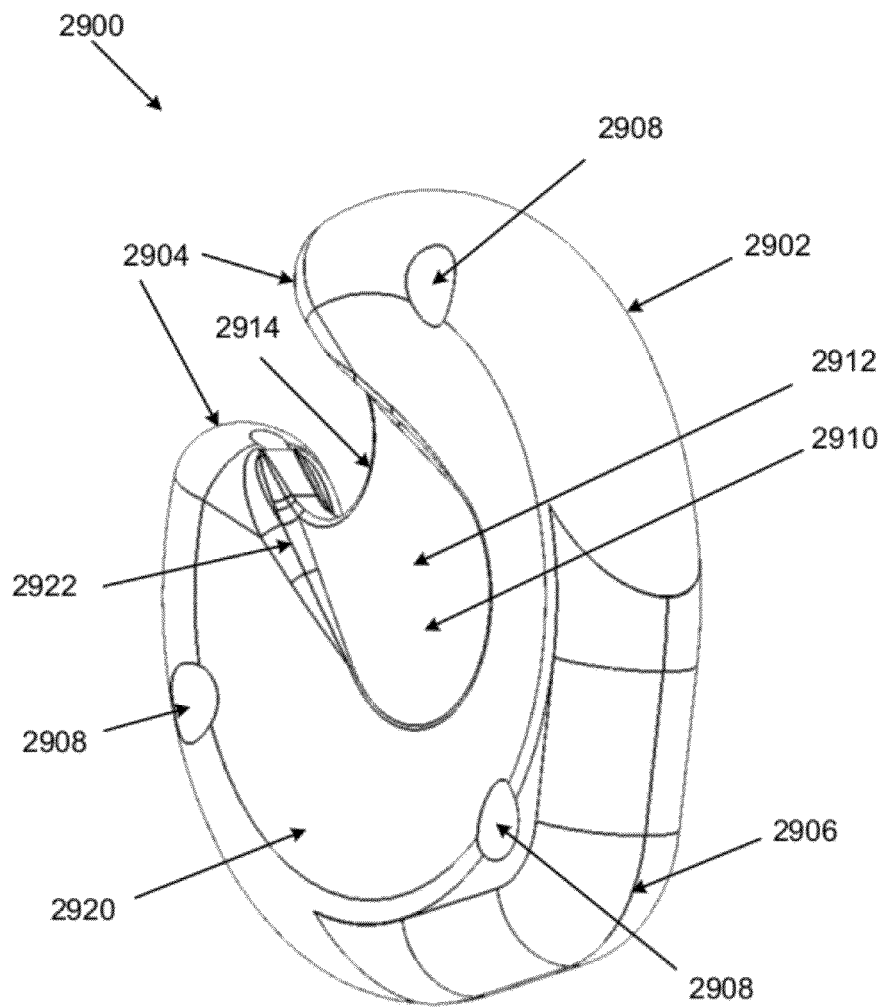
FIG. 29B is a line-drawing isometric view of the orthopedic joint device in FIG. 29A.
Figure 29C:
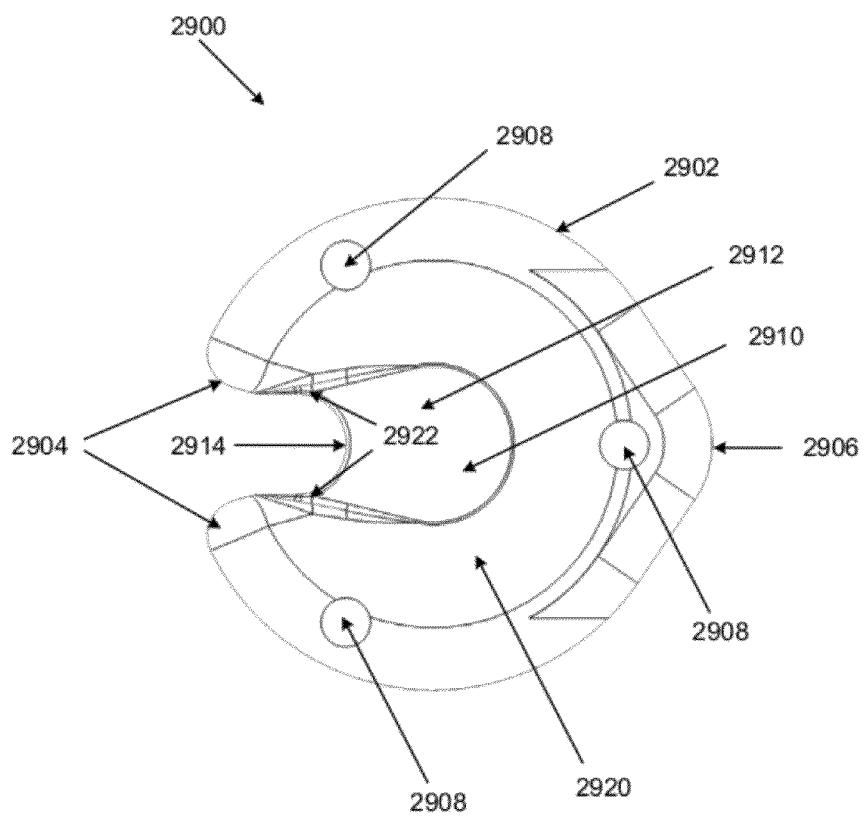
FIG. 29C is a line-drawing superior view of the orthopedic joint device in FIG. 29A.
Figure 29D:
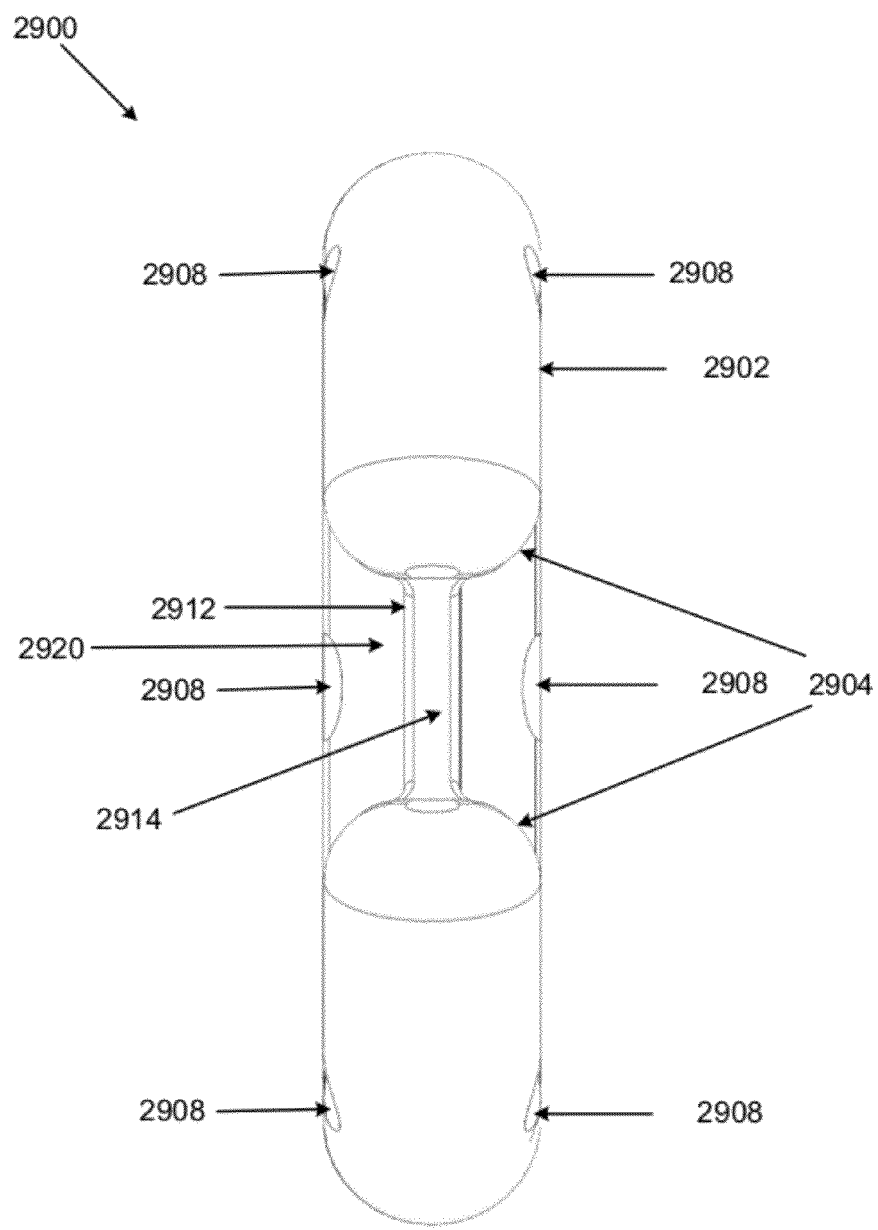
FIG. 29D is a line-drawing rear view of the orthopedic joint device in FIG. 29A.
Figure 29E:
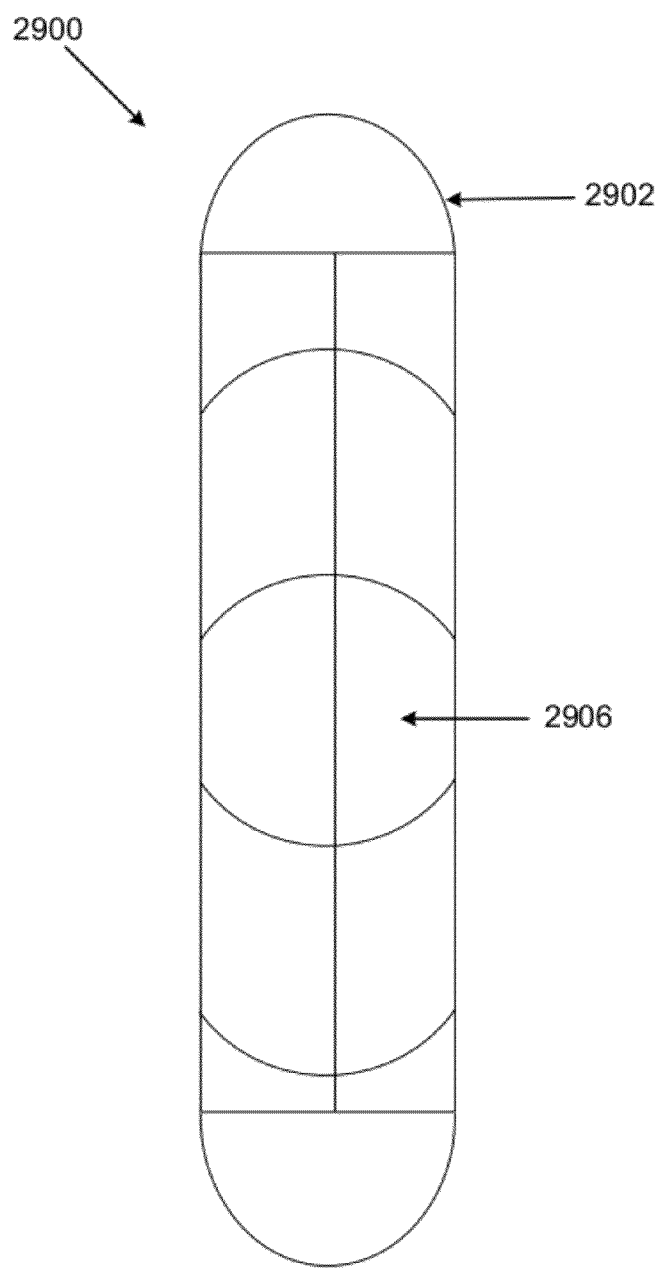
FIG. 29E is a line-drawing front view of the orthopedic joint device in FIG. 29A.
Figure 29F:
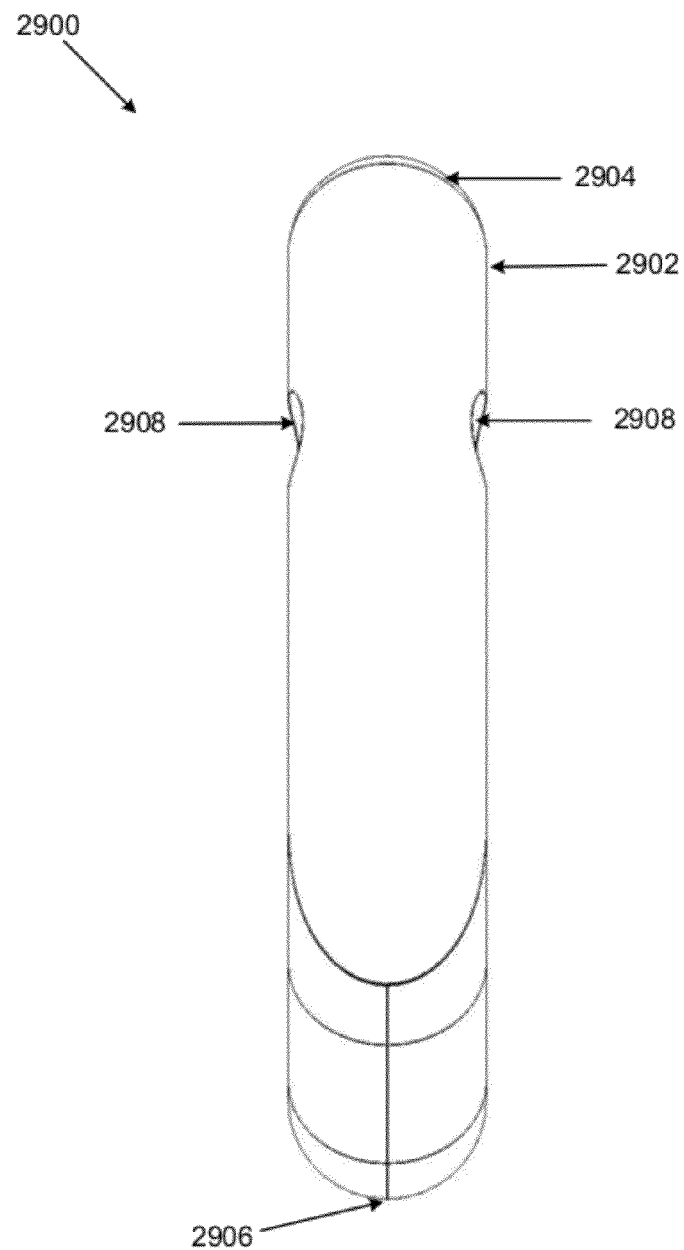
FIG. 29F is a line-drawing side view of the orthopedic joint device in FIG. 29A.
Figure 29G:
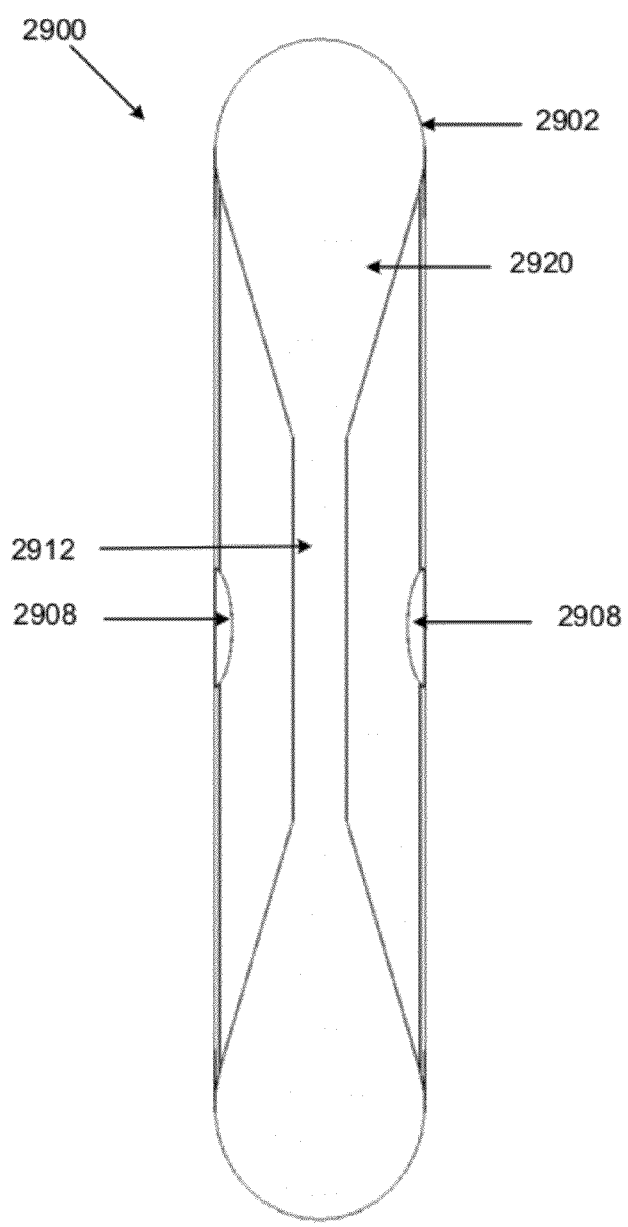
FIG. 29G is a line-drawing cross-sectional view of the orthopedic joint device in FIG. 29A, taken through a plane at the mid-point of the device, looking toward the distal end of the device.

FIG. 29B depicts a line-drawing isometric view of orthopedic joint device 2900. FIG. 29C depicts a line-drawing superior view of orthopedic joint device 2900. Inward edge 2714 comprises an arc of radius approximately equal to ⅕ the width of the orthopedic joint device 2900 in the base configuration. In some embodiments, the radius of the arc of the inward edge may be characterized as a percentage of the width of the leg tips, and may comprise 20%, 25%, 30%, 35%, 40%, 45%, 50%, 55%, 60%, 65%, 70%, 75%, 80%, 85%, 90%, 95%, and 100%. In some embodiments the radius of the arc of the inward edge may be characterized as a percentage of the radius of the central region of the interior region, and may comprise 20%, 25%, 30%, 35%, 40%, 45%, 50%, 55%, 60%, 65%, 70%, 75%, 80%, 85%, 90%, 95%, and 100%. In some embodiments, the radius of the arc of the inward edge may be characterized as a percentage of the width between the leg tips, the radius of the central region of the interior region, and the width of the orthopedic joint device, or any combination thereof. FIG. 29D depicts a line-drawing rear view of orthopedic joint device 2900. FIG. 29E depicts a line-drawing front view of orthopedic joint device 2900. FIG. 29F depicts a line-drawing side view of orthopedic joint device 2900. FIG. 29G depicts a line-drawing cross-sectional view of orthopedic joint device 2900, taken through a plane at the mid-point of the device, looking toward the distal end of the device.

Figure 30A:
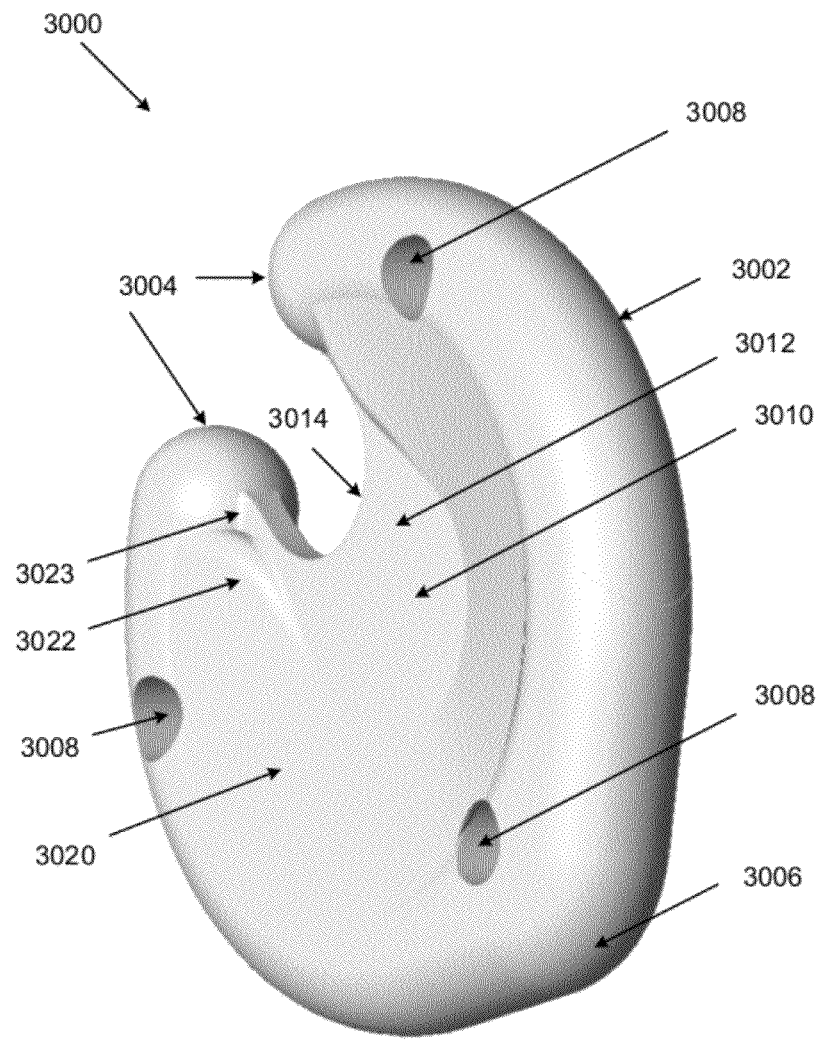
FIG. 30A is a solid isometric view of another embodiment of an orthopedic joint device comprising a transition region and a span member covering a central region.

FIGS. 30A-30G depict another embodiment of an orthopedic joint device 3000 wherein the distance between leg tips 3004 is greater than the corresponding leg tips in orthopedic joint device 2900, which may reduce the increase in height of the device during overlapping, or eliminate the height increase entirely. FIG. 30A depicts a solid isometric view of orthopedic joint device 3000. As depicted therein, the orthopedic joint device 3000 may comprise a main body 3002, transition region 3020, and an interior region 3010. Main body 3002 may comprise leg tips 3004, lead surface 3206, and one or more optional holes 3008, as generally described with regards to holes 2808 of device 2800 in FIGS. 28A-28G. Transition region 3020 may include proximal transition regions 3022. Interior region 3010 may comprise span member 3012 and an inward proximal edge 3014 on span member 3012. The interior region 3010 of orthopedic joint device 3000 may be larger than the interior region of the orthopedic joint device 2900.

Figure 30B:
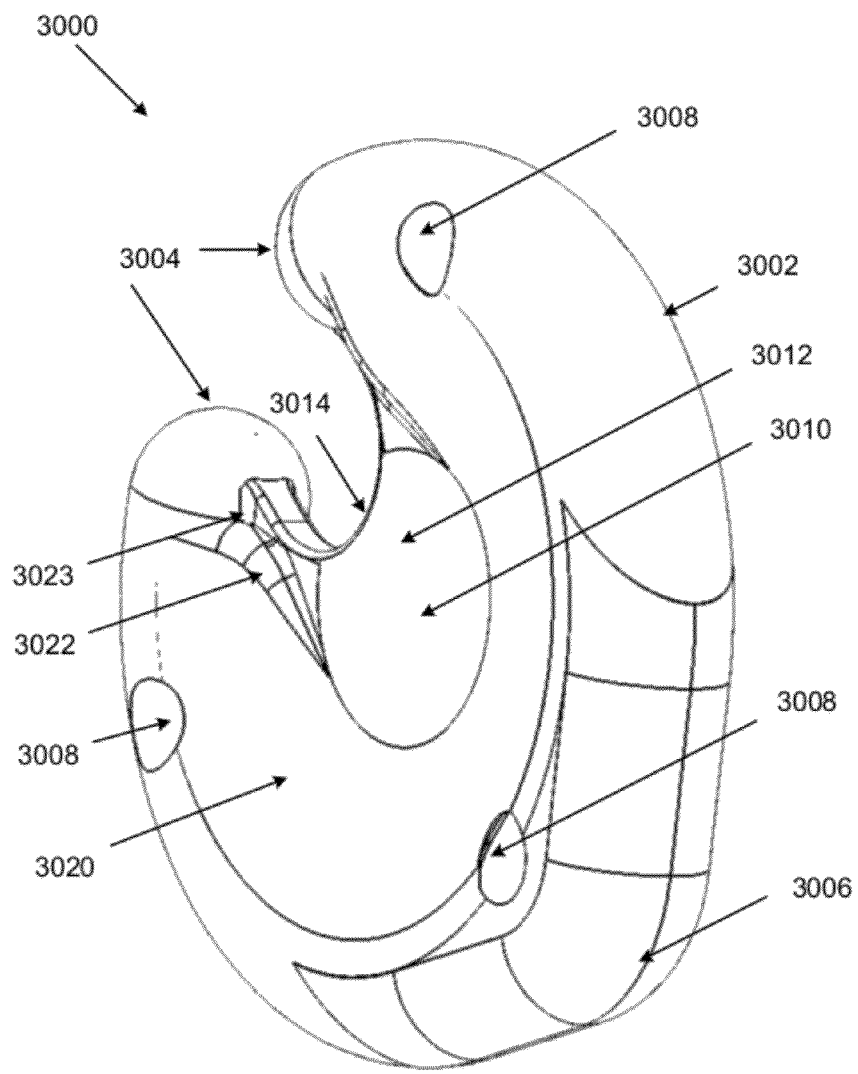
FIG. 30B is a line-drawing isometric view of the orthopedic joint device in FIG. 30A.
Figure 30C:
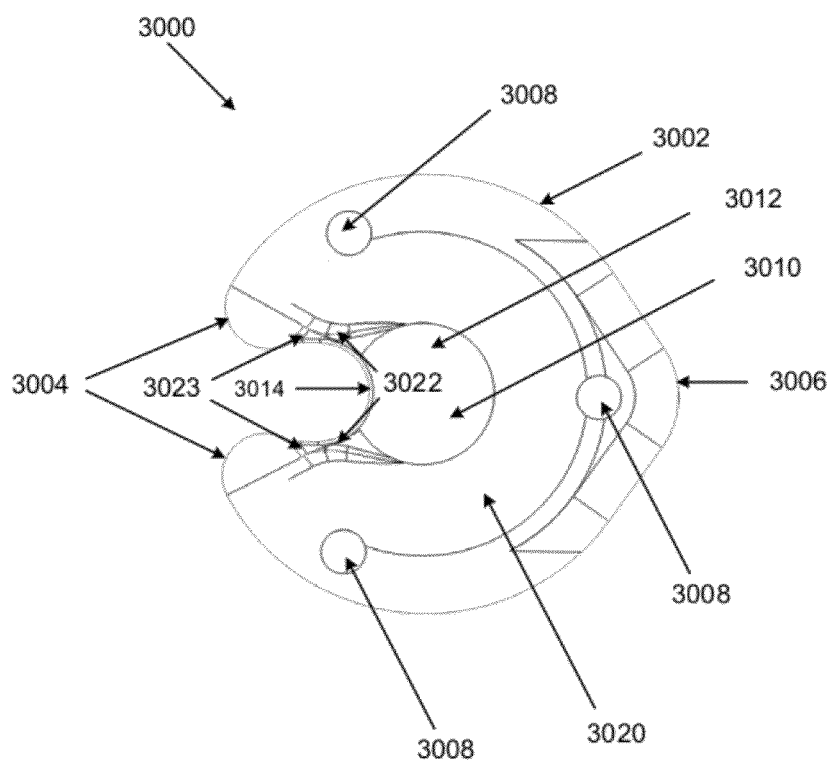
FIG. 30C is a line-drawing superior view of the orthopedic joint device in FIG. 30A.
Figure 30D:
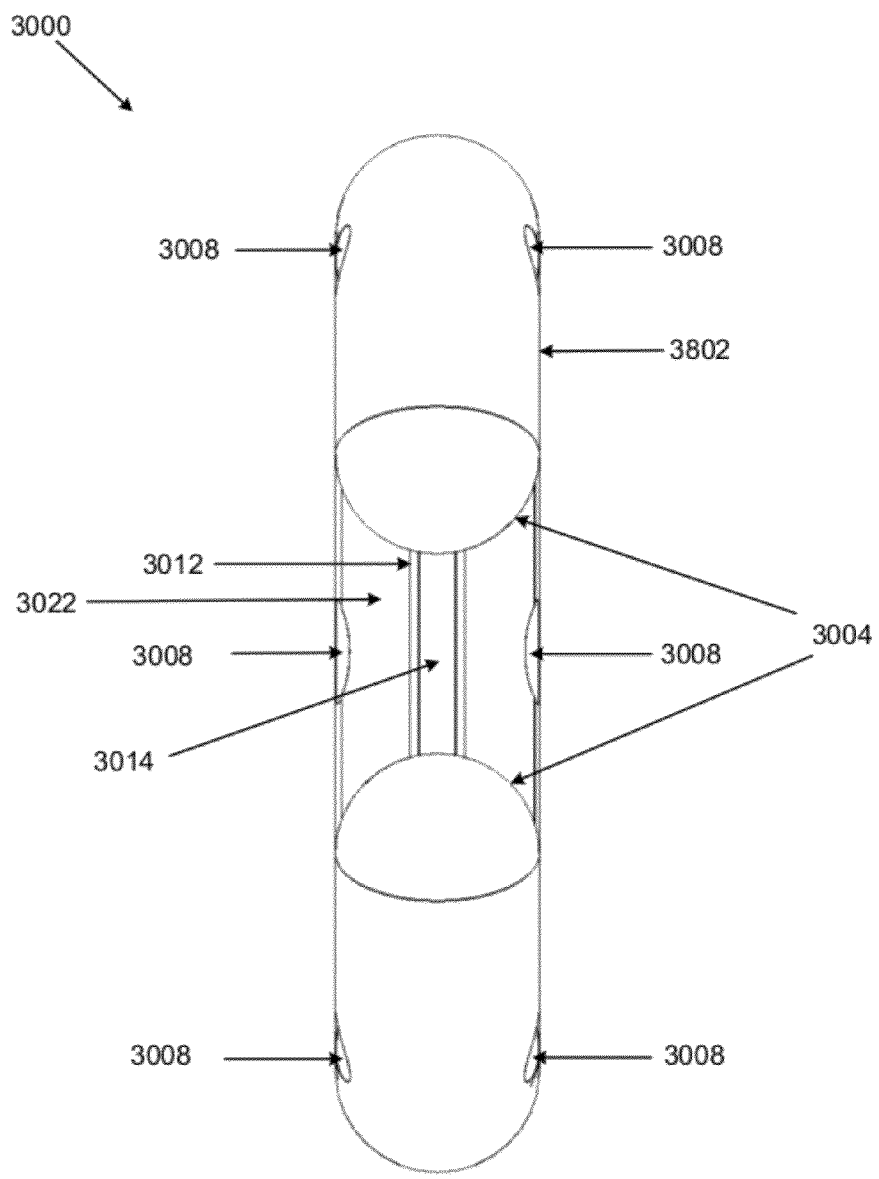
FIG. 30D is a line-drawing rear view of the orthopedic joint device in FIG. 30A.
Figure 30E:
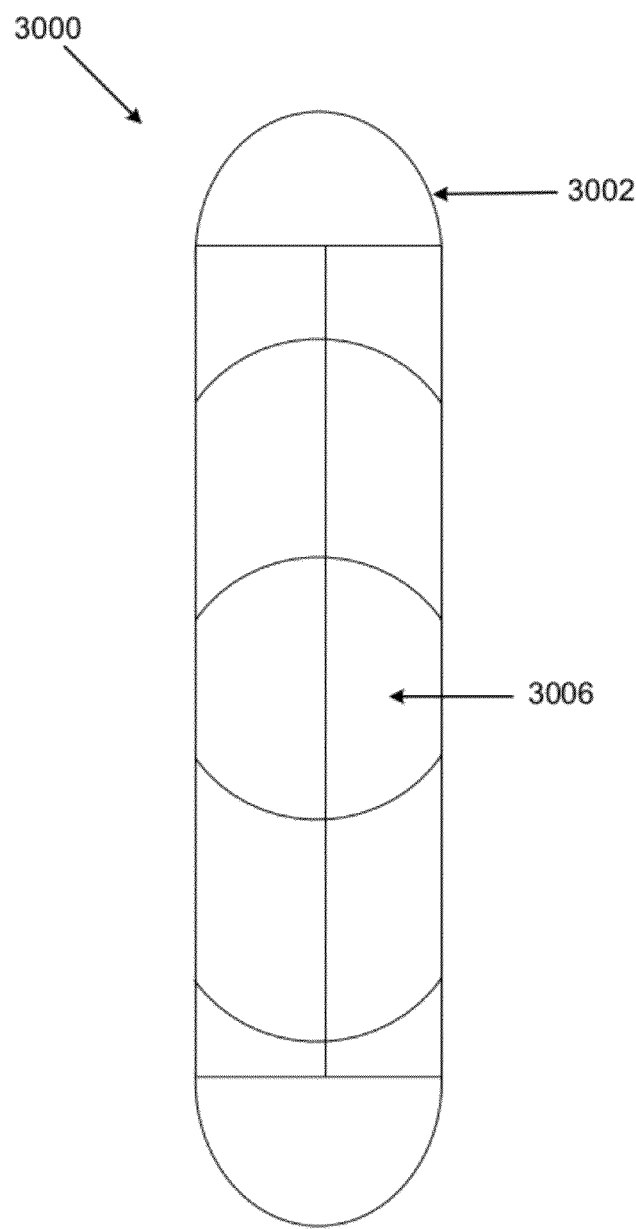
FIG. 30E is a line-drawing front view of the orthopedic joint device in FIG. 30A.
Figure 30F:
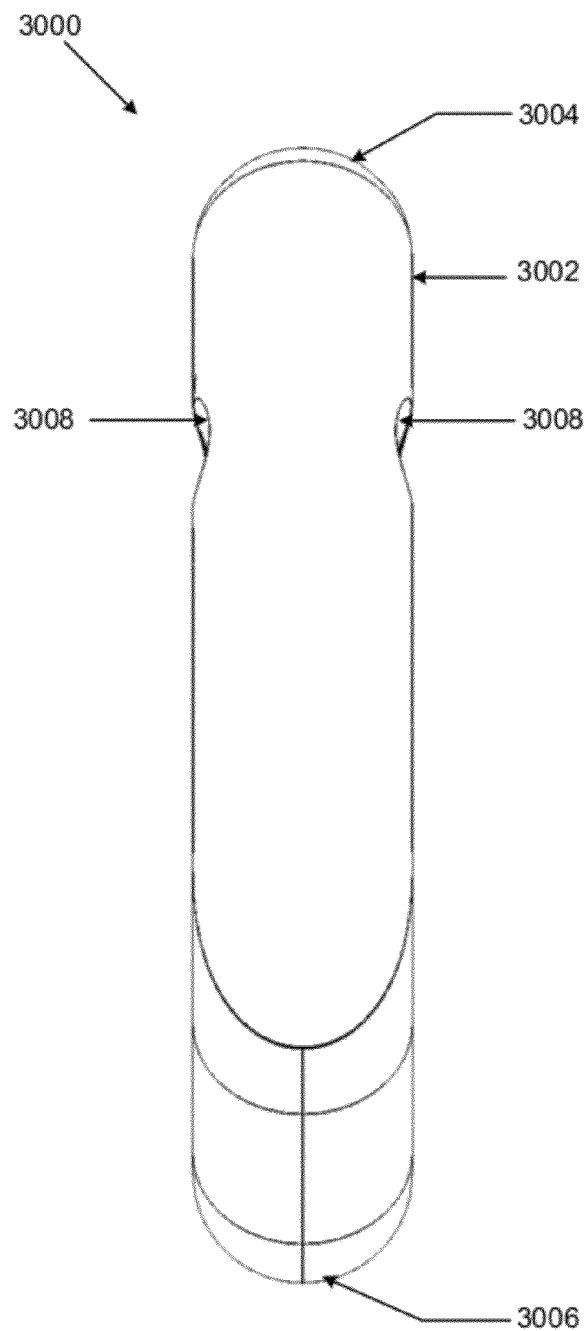
FIG. 30F is a line-drawing side view of the orthopedic joint device in FIG. 30A.
Figure 30G:
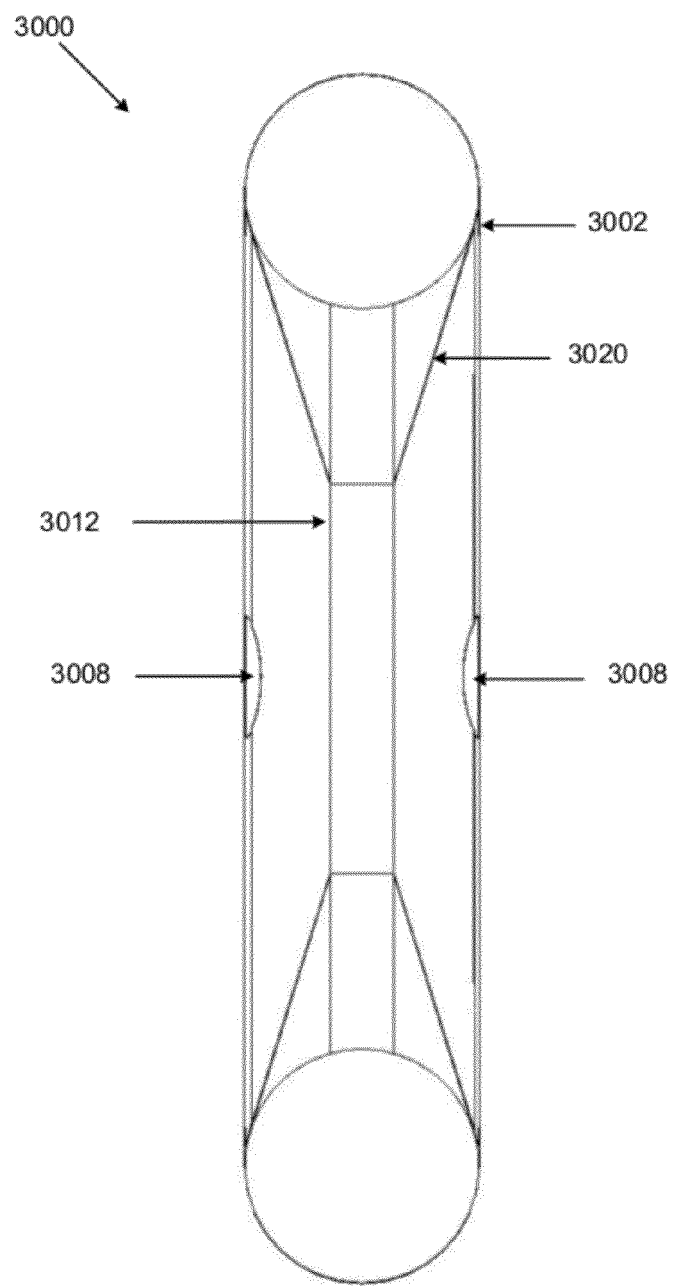
FIG. 30G is a line-drawing cross-sectional view of the orthopedic joint device in FIG. 30A, taken through a plane at the mid-point of the device, looking toward the distal end of the device.

FIG. 30B depicts a line-drawing isometric view of orthopedic joint device 3000. FIG. 30C depicts a line-drawing superior view of orthopedic joint device 3000. FIG. 30D depicts a line-drawing rear view of orthopedic joint device 3000. FIG. 30E depicts a line-drawing front view of orthopedic joint device 3000. FIG. 30F depicts a line-drawing side view of orthopedic joint device 3000. FIG. 30G depicts a line-drawing cross-sectional view of orthopedic joint device 3000, taken through a plane at the mid-point of the device, looking toward the distal end of the device.

Figure 31A:
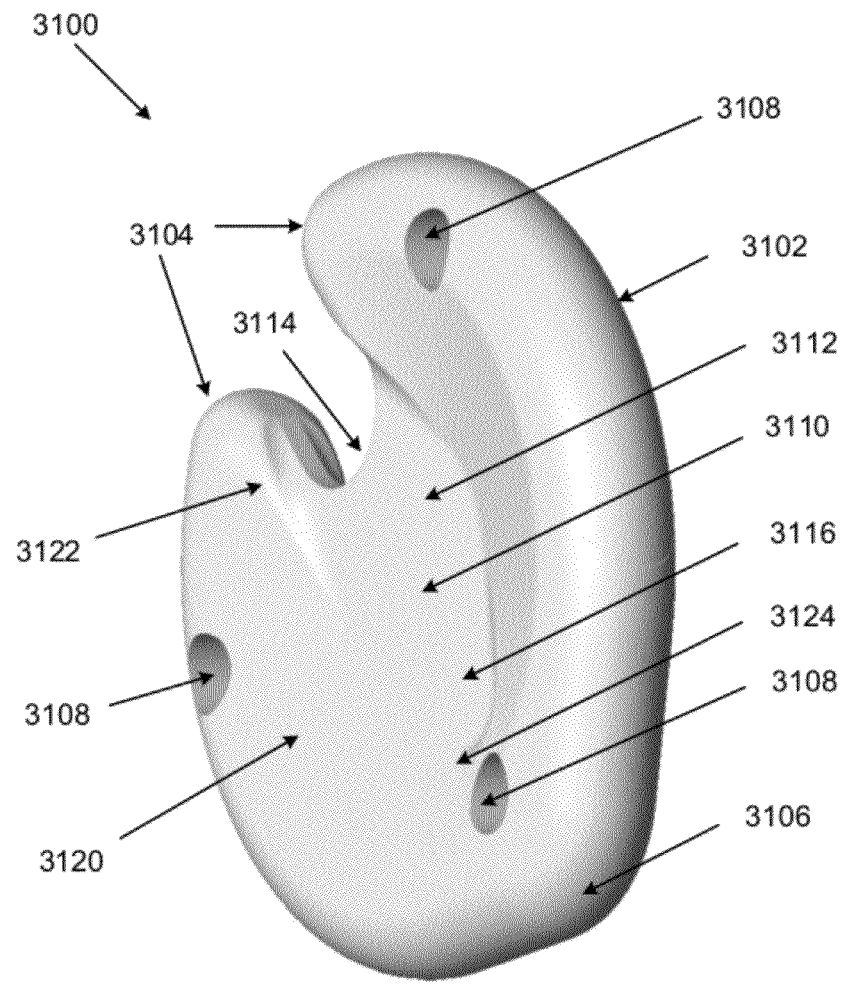
FIG. 31A is a solid isometric view of an embodiment of an orthopedic joint device comprising a transition region and a span member covering a central region, wherein the span member comprises an outward distal edge.

FIGS. 31A-31G depict another embodiment of an orthopedic joint device 3100 wherein an interior region 3110 may comprise a span member 3112 with an outward distal edge 3116. Distal edge 3116 may enhance the ability of the orthopedic joint device 3100 to deform by reducing resistance to deformation resulting from the high volume of material contracted in the relatively small space at the distal end 3124 of the interior region. To accommodate the outward distal edge 3116 of the span member 3112, the distal transition region 3124 may have a steeper face than the other sections of the transition region 3120. This steeper face also reduces resistance to deformation because a steeper face equates to less material contracted in the same volume. FIG. 31A depicts a solid isometric view of orthopedic joint device 3100. As depicted therein, the orthopedic joint device 3100 may comprise a main body 3102, transition region 3120, and an interior region 3110. Main body 3102 may comprise leg tips 3104, lead surface 3106, and one or more optional holes 3108, as generally described with regards to holes 2808 of device 2800 in FIGS. 28A-28G. Transition region 3220 may include proximal transition regions 3122 and distal transition regions 3124. Interior 3110 may comprise span member 3112, an inward proximal edge 3114 on span member 3112, and outward distal edge 3116.

Figure 31B:
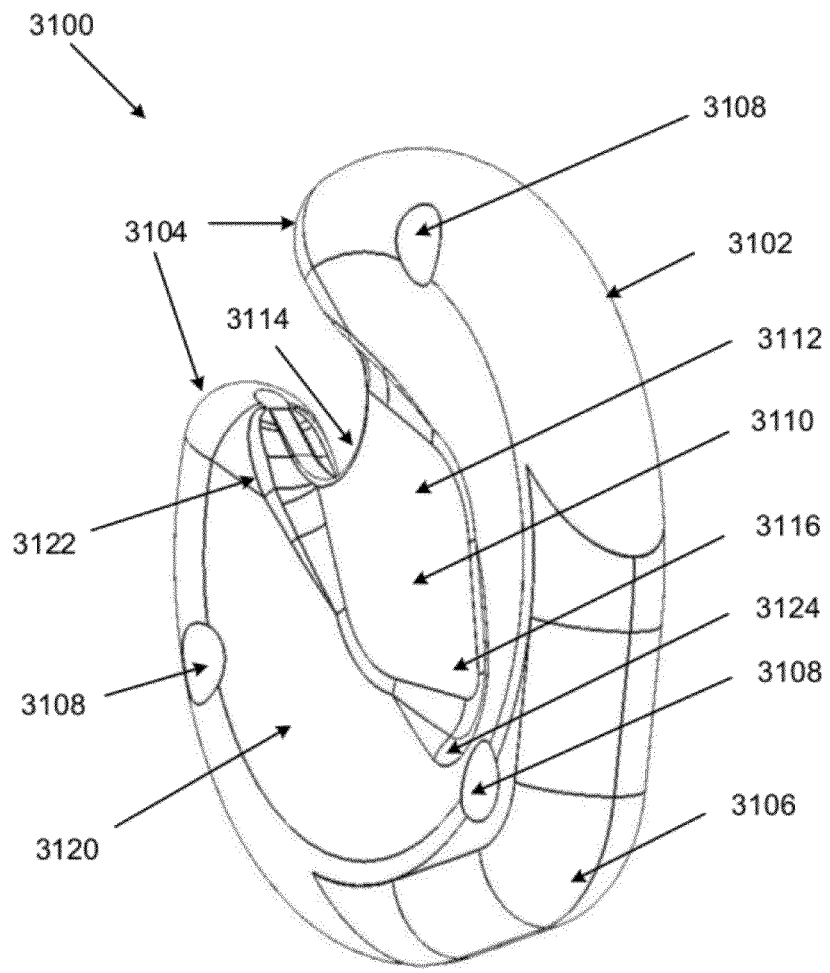
FIG. 31B is a line-drawing isometric view of the orthopedic joint device in FIG. 31A.
Figure 31C:
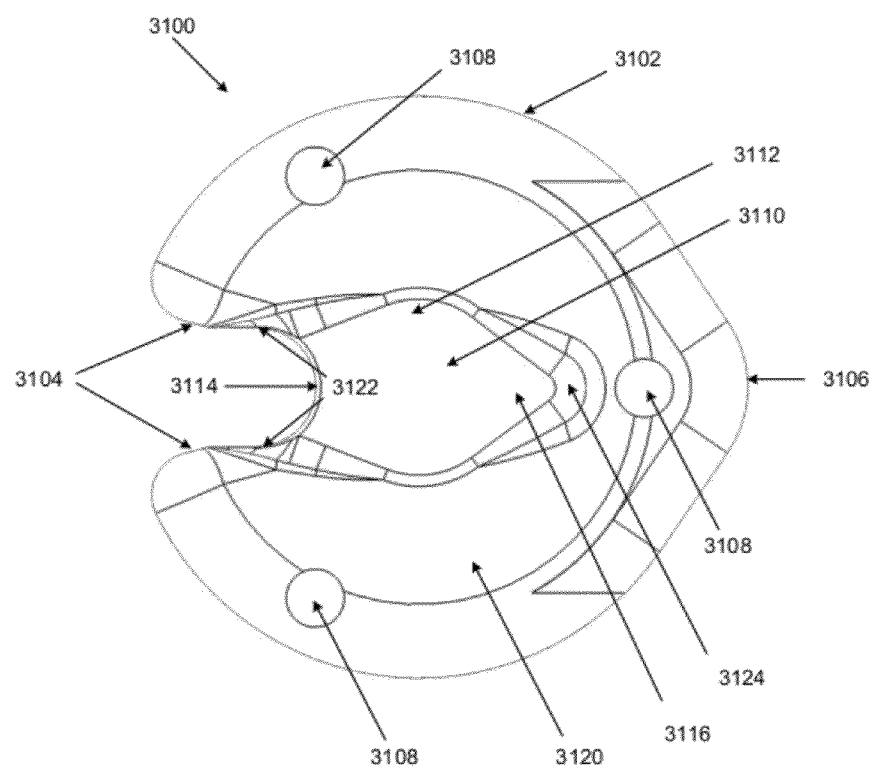
FIG. 31C is a line-drawing superior view of the orthopedic joint device in FIG. 31A.
Figure 31D:
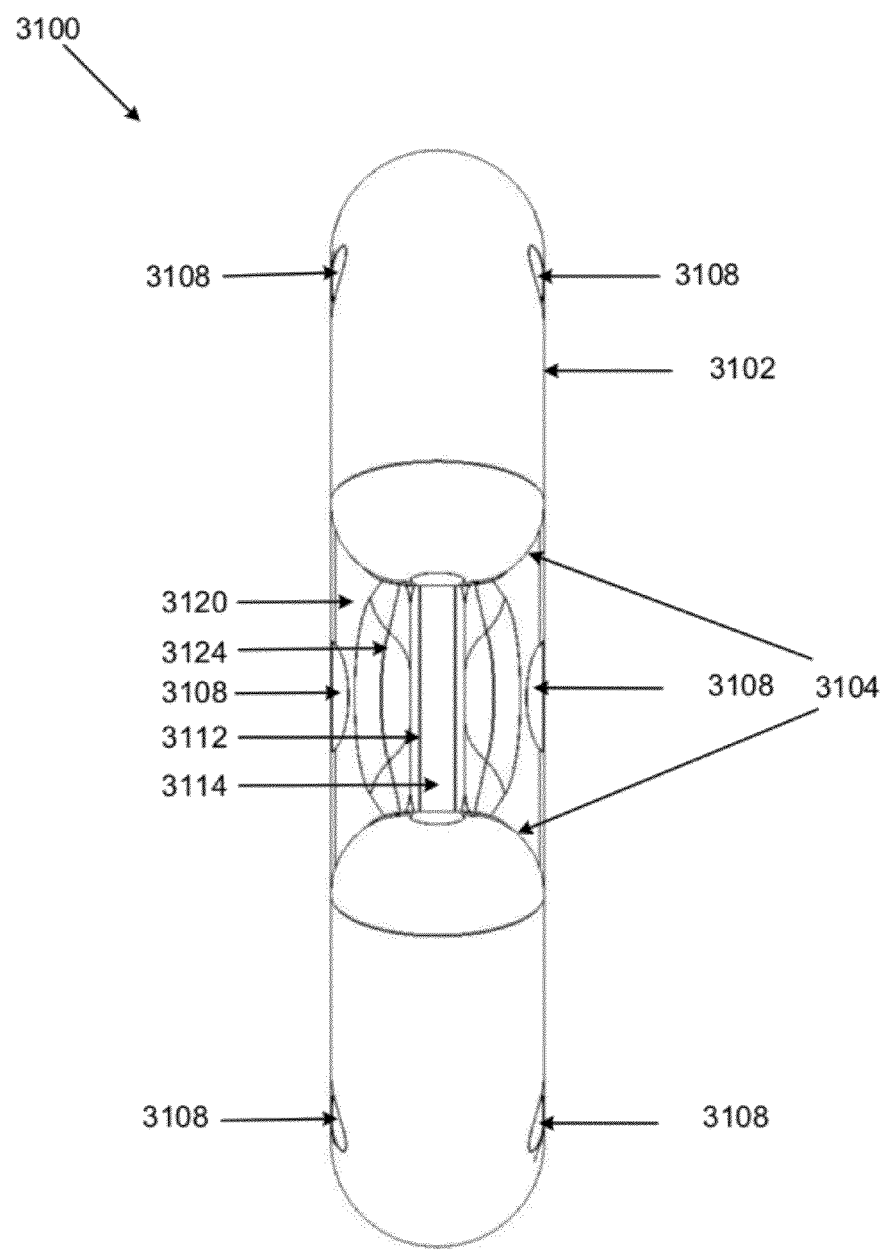
FIG. 31D is a line-drawing rear view of the orthopedic joint device in FIG. 31A.
Figure 31E:
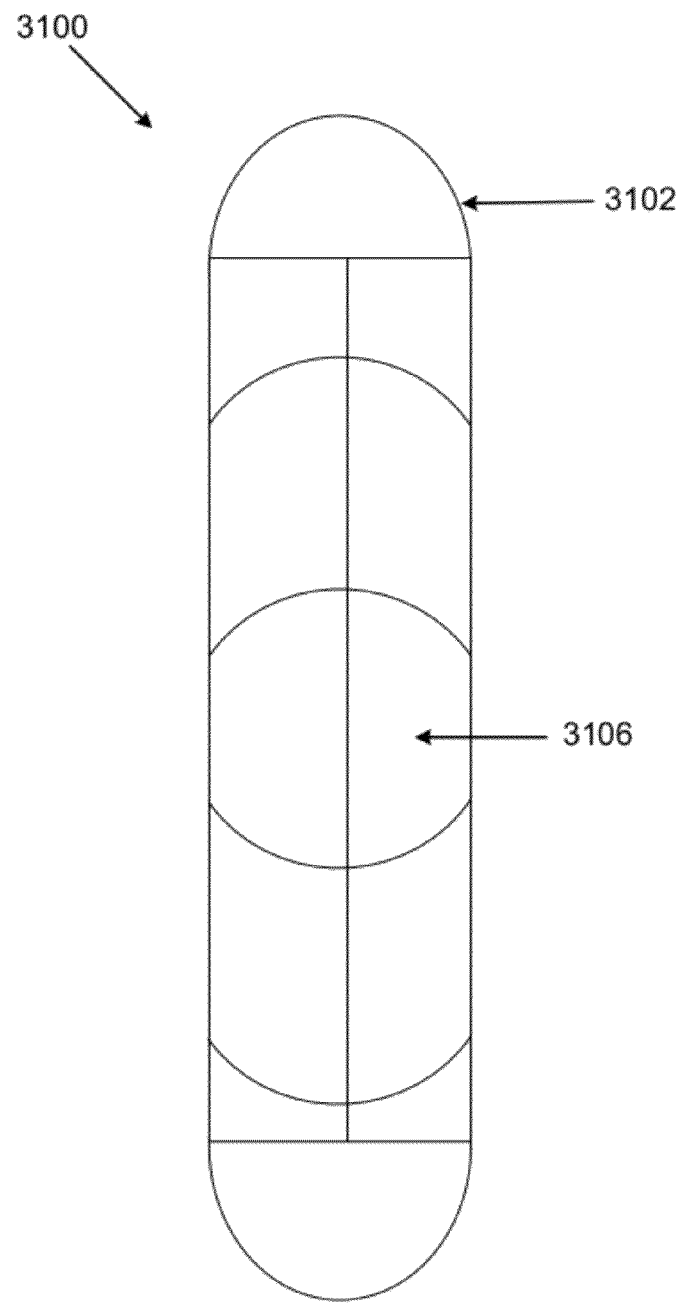
FIG. 31E is a line-drawing front view of the orthopedic joint device in FIG. 31A.
Figure 31F:
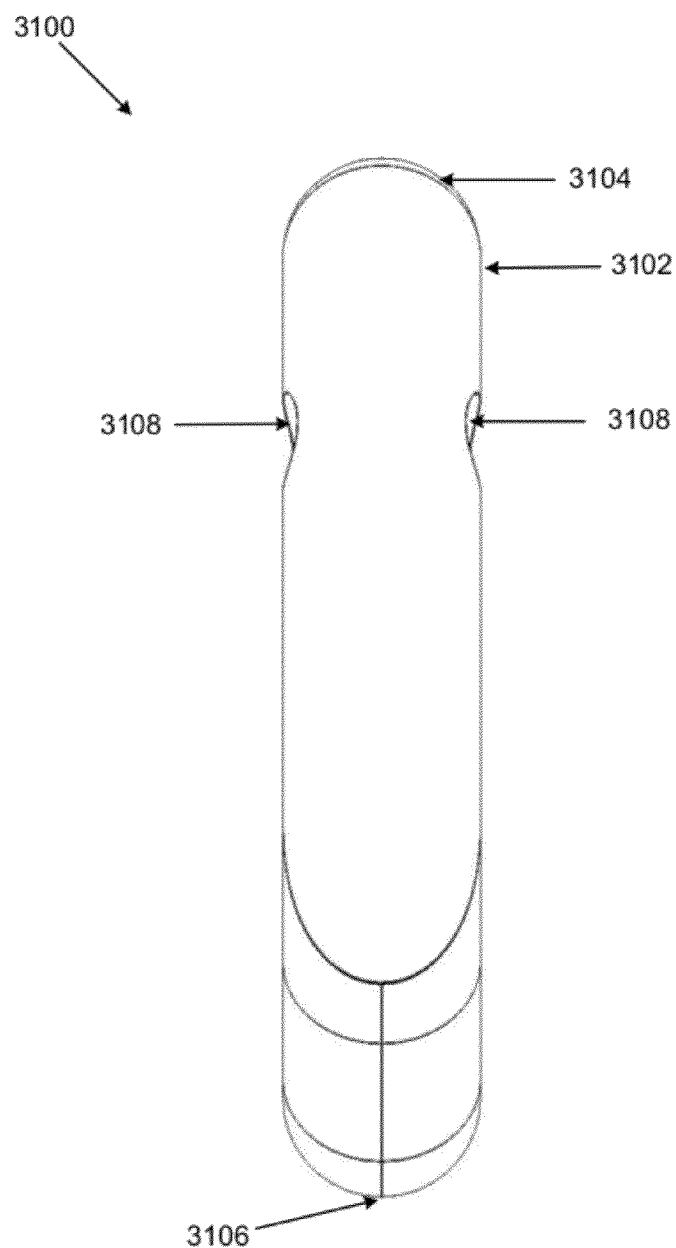
FIG. 31F is a line-drawing side view of the orthopedic joint device in FIG. 31A.
Figure 31G:
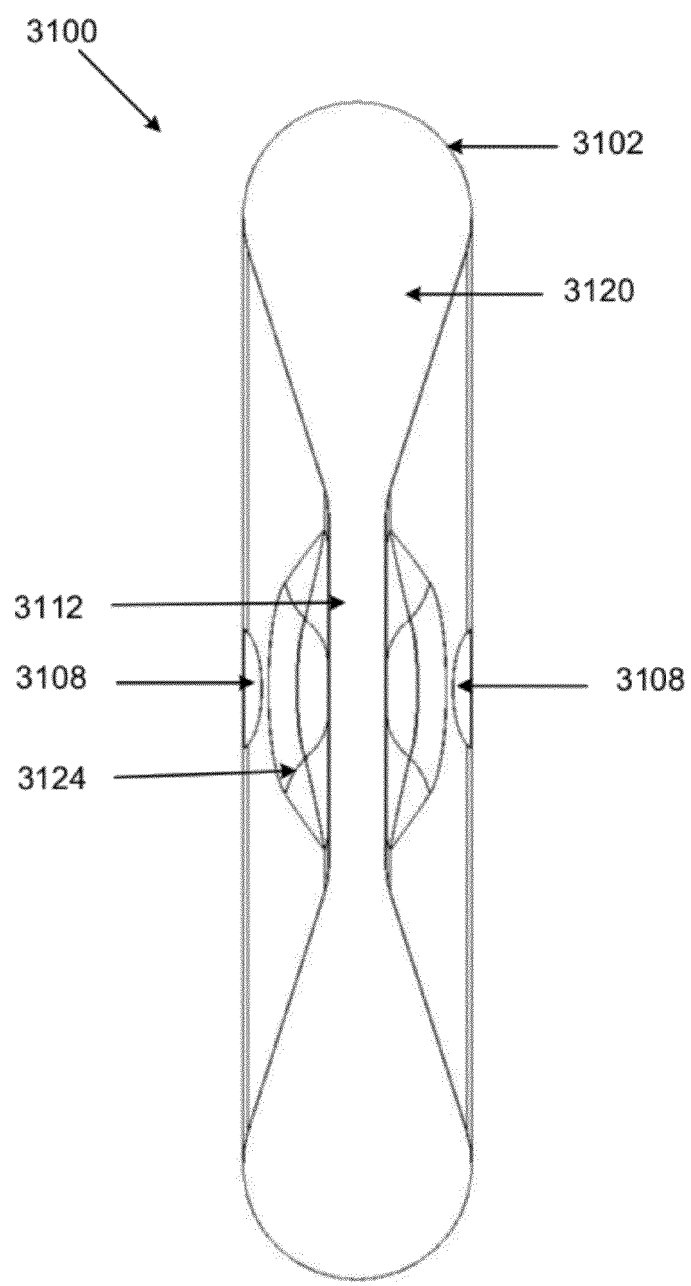
FIG. 31G is a line-drawing cross-sectional view of the orthopedic joint device in FIG. 31A, taken through a plane at the mid-point of the device, looking toward the distal end of the device.

FIG. 31B depicts a line-drawing isometric view of orthopedic joint device 3100. FIG. 31C depicts a line-drawing superior view of orthopedic joint device 3100. Outward edge 3116 comprises a small arc centered at approximately ¼ the distance from the distal end of the device to the proximal end, which then tapers out to the perimeter of the central region of the interior region. FIG. 31D depicts a line-drawing rear view of orthopedic joint device 3100. FIG. 31E depicts a line-drawing front view of orthopedic joint device 3100. FIG. 31F depicts a line-drawing side view of orthopedic joint device 3100. FIG. 31G depicts a line-drawing cross-sectional view of orthopedic joint device 3100, taken through a plane at the mid-point of the device, looking toward the distal end of the device.

FIGS. 32A-32G depict another embodiment of an orthopedic joint device 3200 wherein an outward distal edge 3216 on a span member 3212 is configured to extend further from an interior region 3210, which thereby results in a steeper distal transition region 3224, which may cause less resistance to deformation at the distal end of the device. In addition, orthopedic joint device 3200 comprises proximal transition regions 3222 which discontinues prior to reaching the leg tips

Figure 32A:
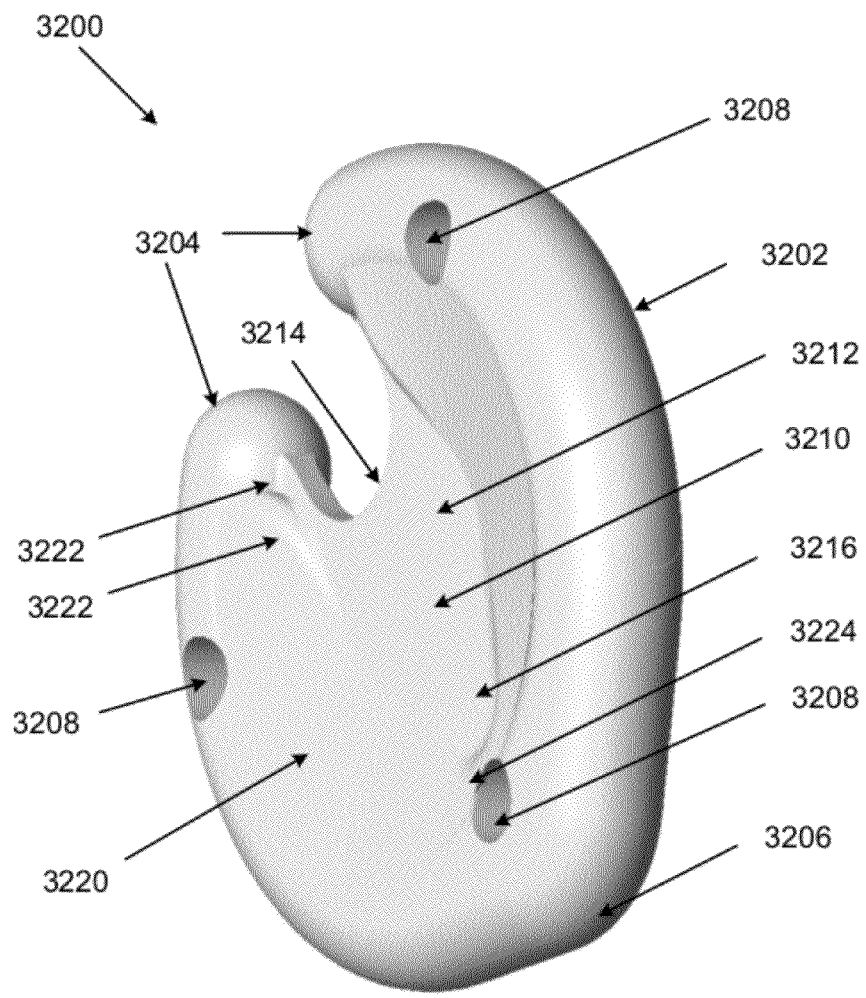
FIG. 32A is a solid isometric view of another embodiment of an orthopedic joint device comprising a transition region and a span member covering a central region, wherein the span member comprises an outward distal edge.

3204. This configuration may reduce puckering or ease overlapping of the device in the insertion configuration. FIG. 32A depicts a solid isometric view of orthopedic joint device 3200. As depicted therein, the orthopedic joint device 3200 may comprise a main body 3202, transition region 3220, and the interior region 3210. Main body 3202 may comprise the leg tips 3204, lead surface 3206, and one or more optional holes 3208, as generally described with regards to holes 2808 of device 2800 in FIGS. 28A-28G. Transition region 3220 may include the proximal transition regions 3222 and distal transition region 3224. Distal transition region 3224 is larger than distal transition region 3124. Interior region 3210 may comprise span member 3212, an inward proximal edge 3214 on span member 3212, and the outward distal edge 3216.

Figure 32B:
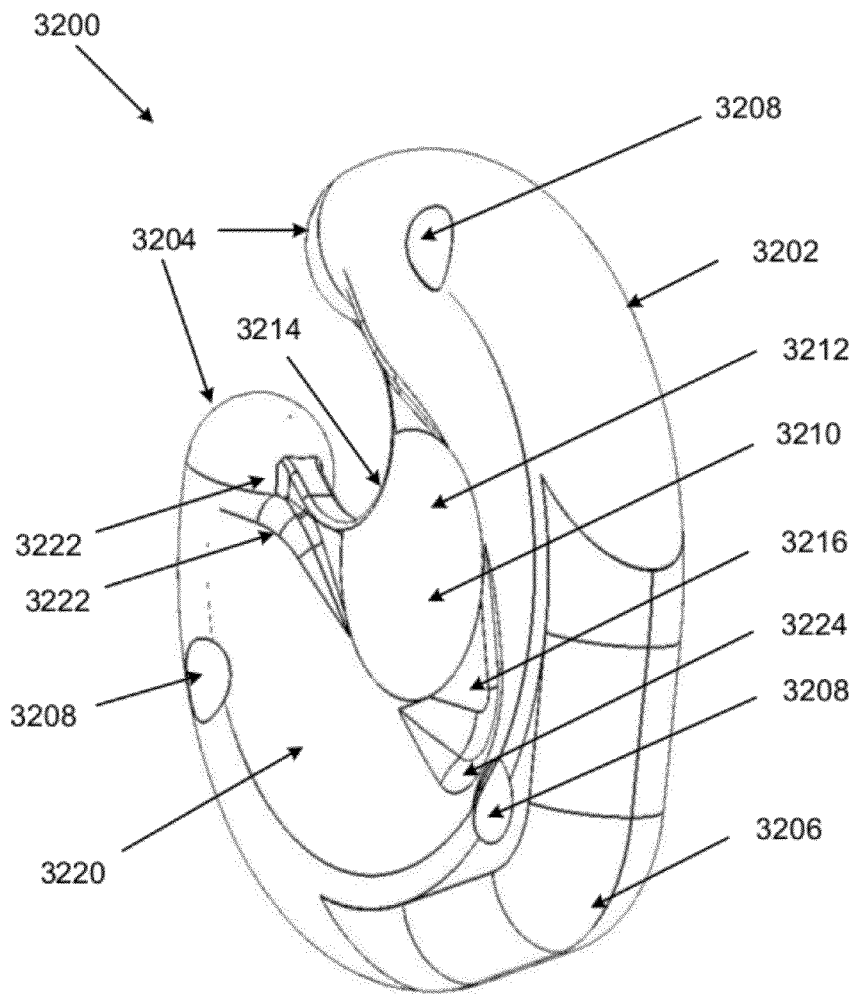
FIG. 32B is a line-drawing isometric view of the orthopedic joint device in FIG. 32A.
Figure 32C:
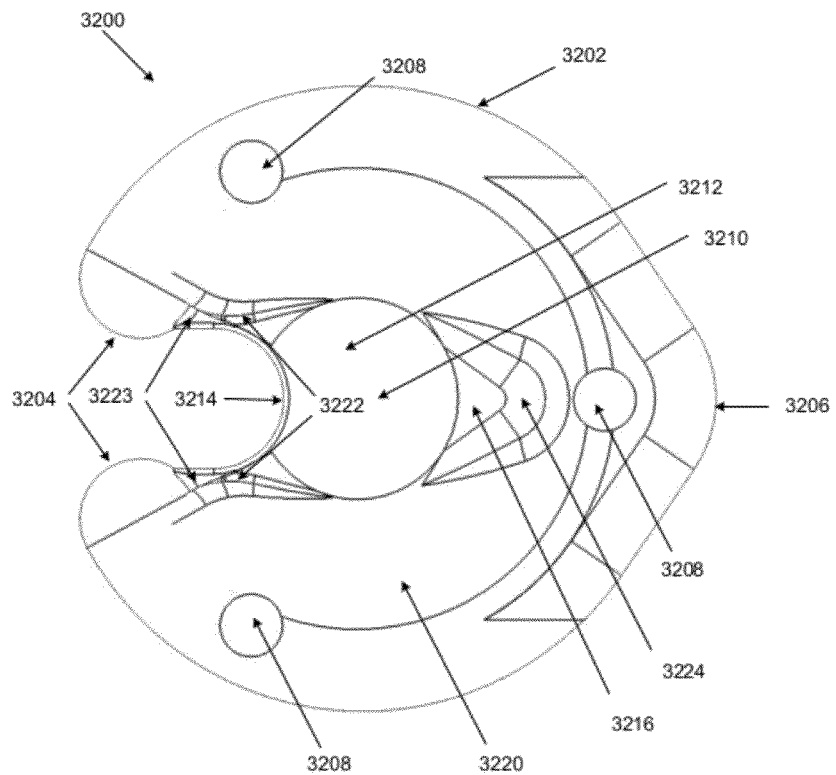
FIG. 32C is a line-drawing superior view of the orthopedic joint device in FIG. 32A.
Figure 32D:
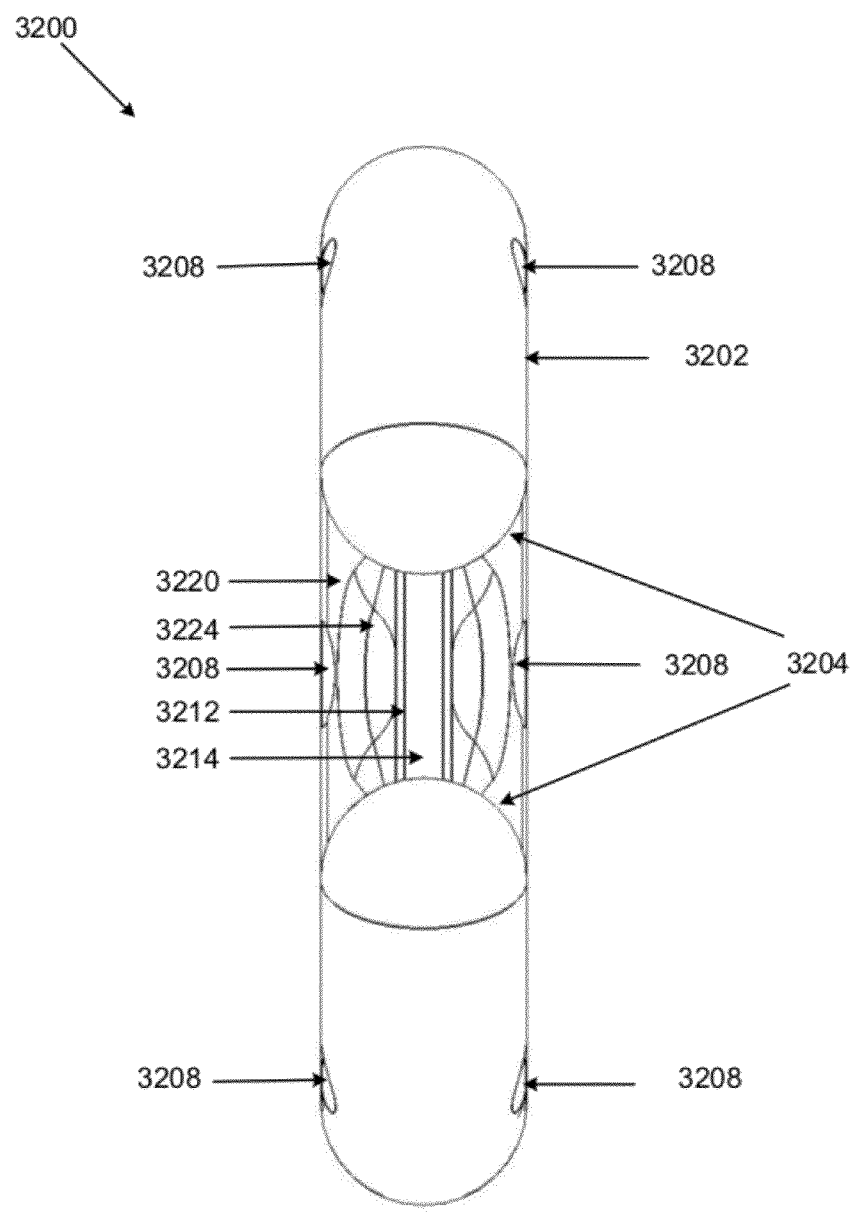
FIG. 32D is a line-drawing rear view of the orthopedic joint device in FIG. 32A.
Figure 32E:
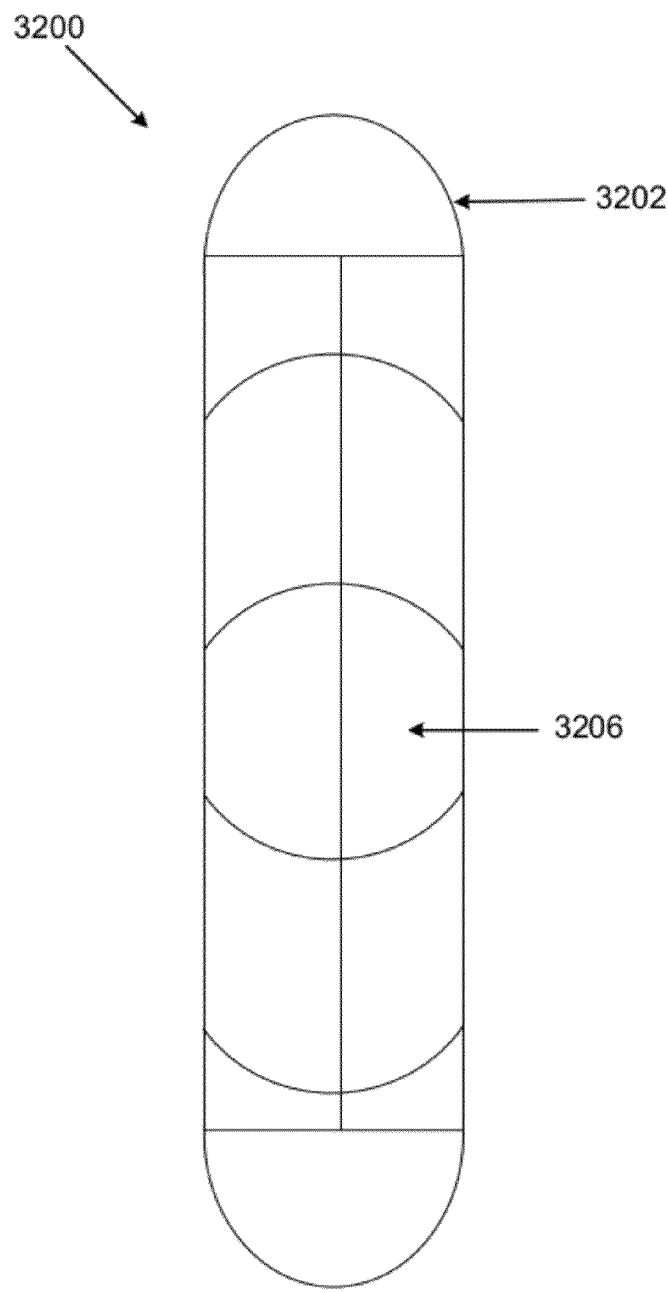
FIG. 32E is a line-drawing front view of the orthopedic joint device in FIG. 32A.
Figure 32F:
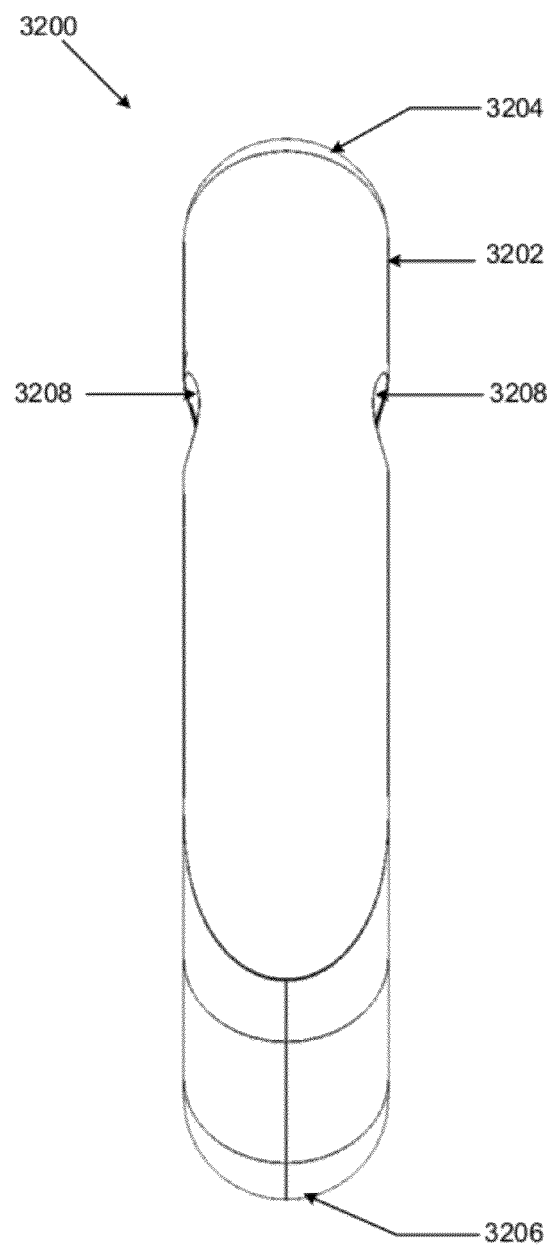
FIG. 32F is a line-drawing side view of the orthopedic joint device in FIG. 32A.
Figure 32G:
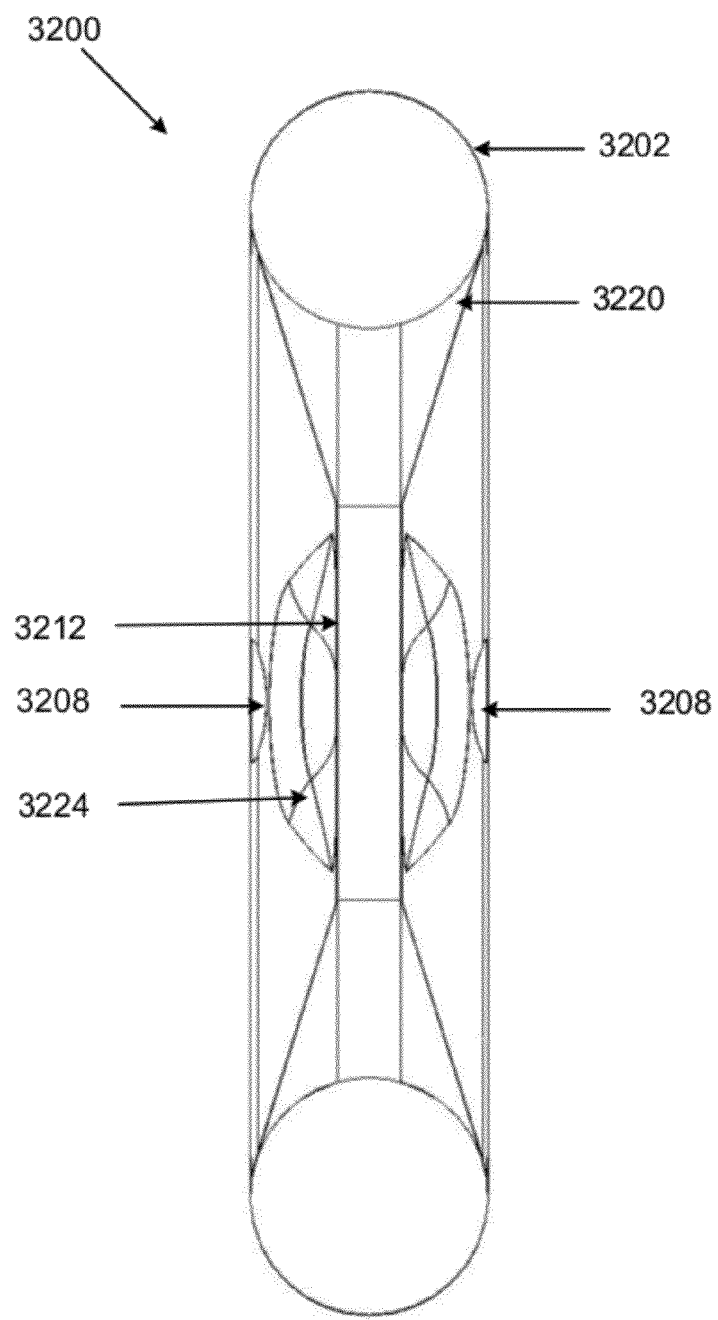
FIG. 32G is a line-drawing cross-sectional view of the orthopedic joint device in FIG. 32A, taken through a plane at the mid-point of the device, looking toward the distal end of the device.

FIG. 32B depicts a line-drawing isometric view of orthopedic joint device 3200. FIG. 32C depicts a line-drawing superior view of orthopedic joint device 3200. FIG. 32D depicts a line-drawing rear view of orthopedic joint device 3200. FIG. 32E depicts a line-drawing front view of orthopedic joint device 3200. FIG. 32F depicts a line-drawing side view of orthopedic joint device 3200. FIG. 32G depicts a line-drawing cross-sectional view of orthopedic joint device 3200, taken through a plane at the mid-point of the device, looking toward the distal end of the device.

Figure 33A:
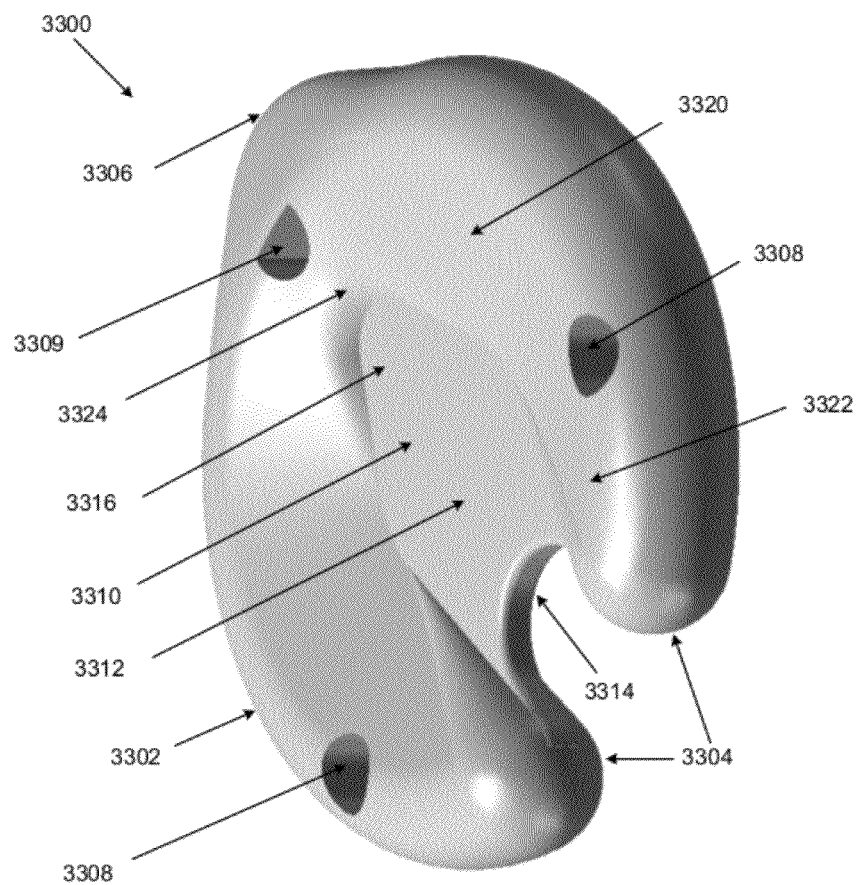
FIG. 33A is a solid isometric view of an embodiment of an orthopedic joint device comprising a transition region, a span member covering a central region, and a distal aperture configured to limit the freedom of movement of a suture coupled to the device.

FIGS. 33A-33G depict another embodiment of an orthopedic joint device 3300 wherein an optional distal hole 3309 contains a distal edge configured to limit the freedom of movement of a suture threaded through the hole when the orthopedic joint device 3300 is being inserted into an incision, thus preventing device slippage. The distal edge may be configured to provide one or more acute angles which may limit the lateral movement of a suture during insertion of the device. FIG. 33A depicts a solid isometric view of orthopedic joint device 3300. As depicted therein, the orthopedic joint device 3300 may comprise a main body 3302, transition region 3320, and an interior region 3310. Main body 3302 may comprise leg tips 3304, lead surface 3306, optional proximal holes 3308, and distal hole 3309. Transition region 3320 may include proximal transition regions 3322 and distal transition region 3324. Interior region 3310 may comprise span member 3312, an inward proximal edge 3314 on span member 3312, and an outward distal edge 3316.

Figure 33B:
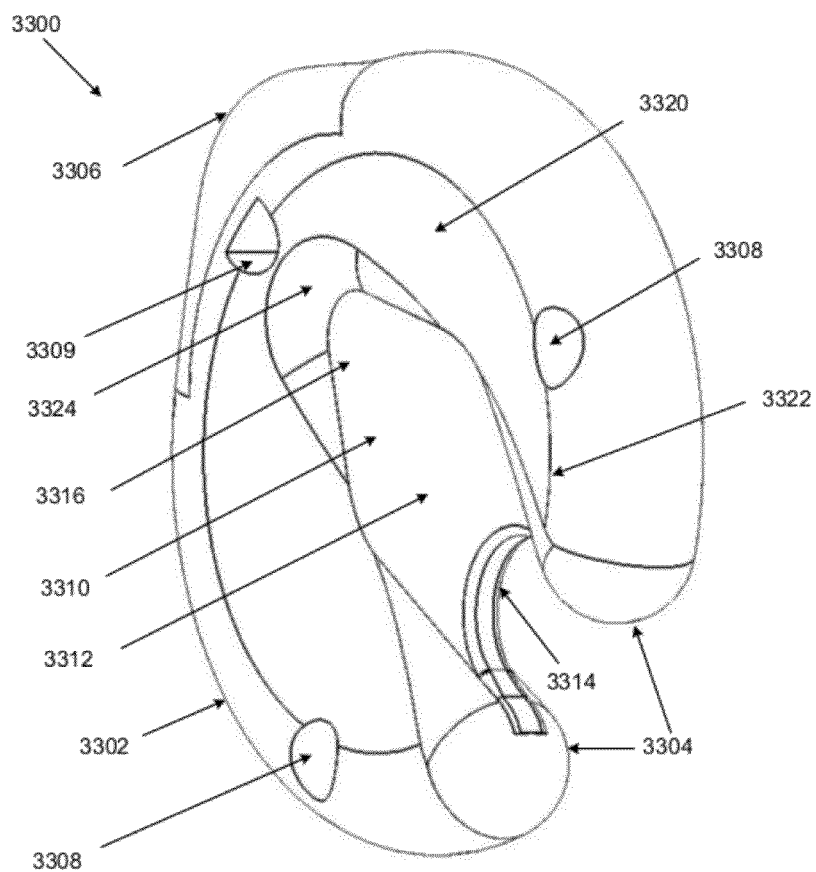
FIG. 33B is a line-drawing isometric view of the orthopedic joint device in FIG. 33A.
Figure 33C:
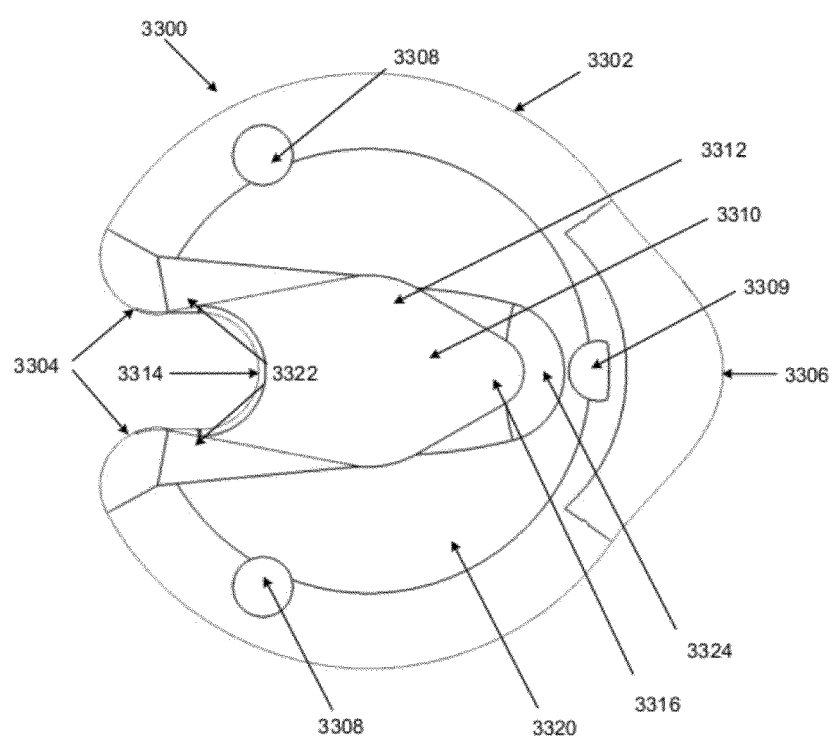
FIG. 33C is a line-drawing superior view of the orthopedic joint device in FIG. 33A.
Figure 33D:
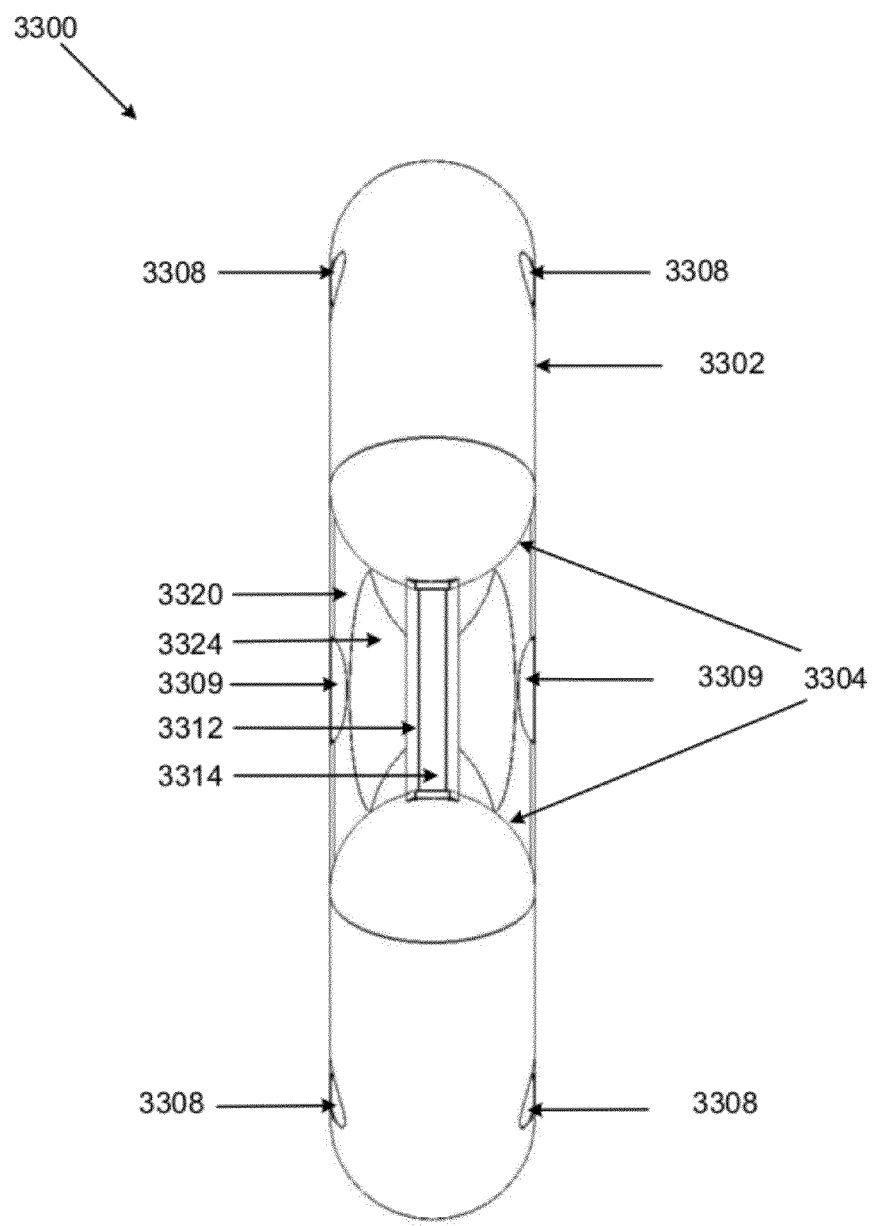
FIG. 33D is a line-drawing rear view of the orthopedic joint device in FIG. 33A.
Figure 33E:
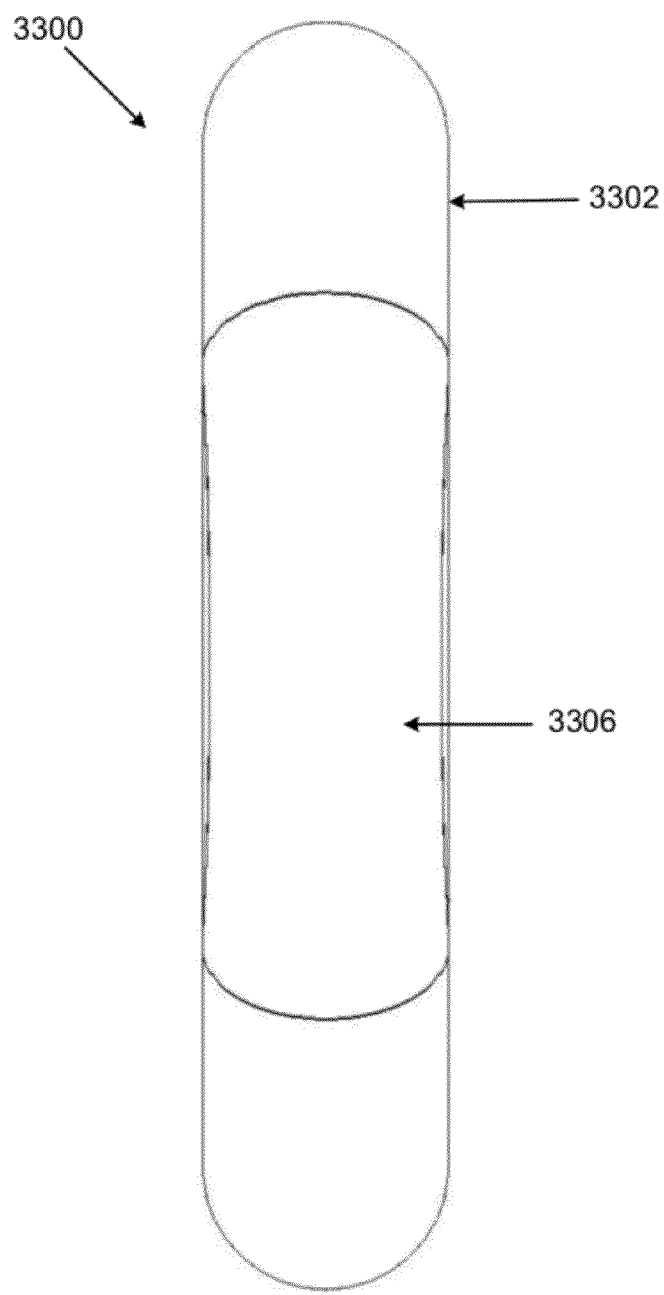
FIG. 33E is a line-drawing front view of the orthopedic joint device in FIG. 33A.
Figure 33F:
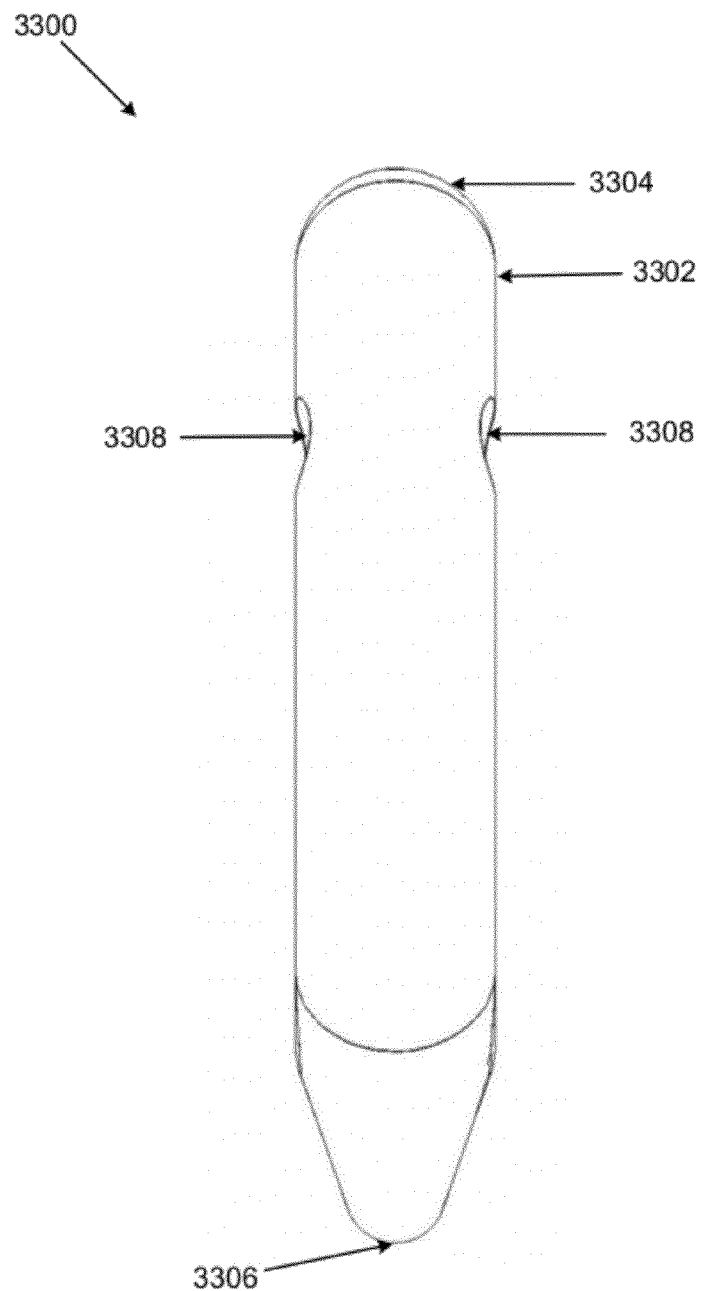
FIG. 33F is a line-drawing side view of the orthopedic joint device in FIG. 33A.
Figure 33G:
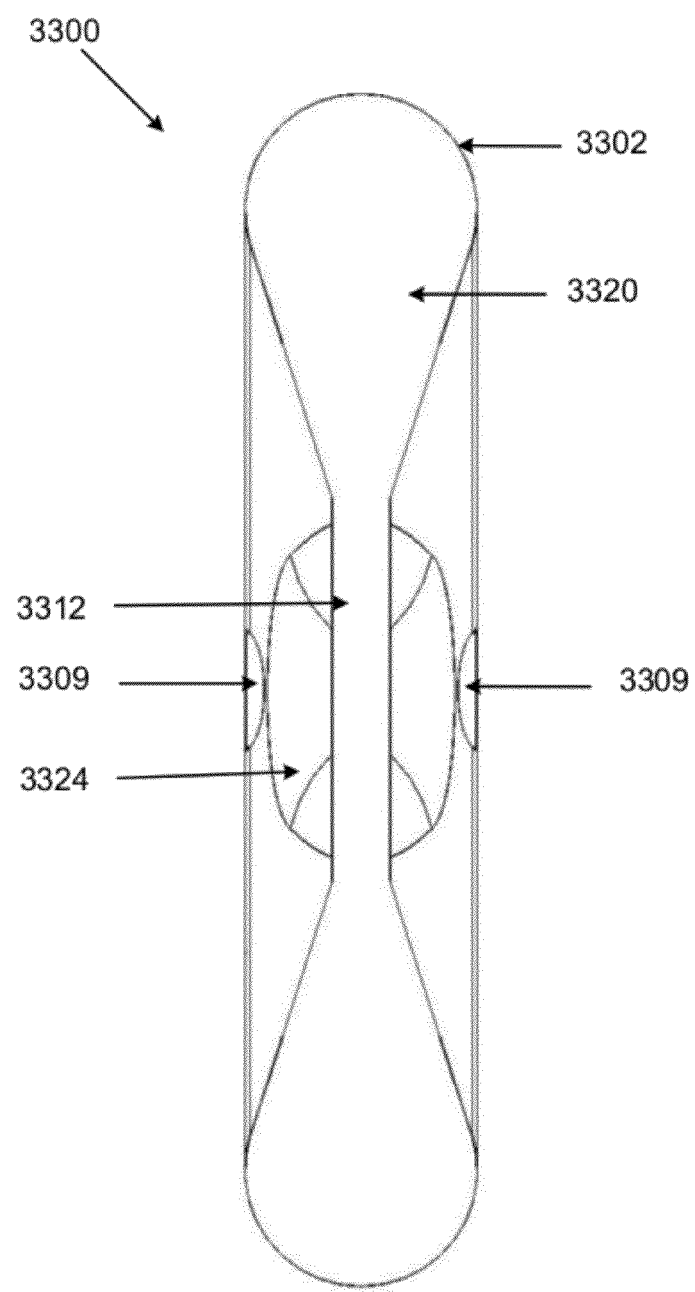
FIG. 33G is a line-drawing cross-sectional view of the orthopedic joint device in FIG. 33A, taken through a plane at the mid-point of the device, looking toward the distal end of the device.

FIG. 33B depicts a line-drawing isometric view of orthopedic joint device 3300. FIG. 33C depicts a line-drawing superior view of orthopedic joint device 3300). FIG. 33D depicts a line-drawing rear view of orthopedic joint device 3300. FIG. 33E depicts a line-drawing front view of orthopedic joint device 3300. FIG. 33F depicts a line-drawing side view of orthopedic joint device 3300. FIG. 33G depicts a line-drawing cross-sectional view of orthopedic joint device 3300, taken through a plane at the mid-point of the device, looking toward the distal end of the device.

FIGS. 34A-34G depict another embodiment of an orthopedic joint device 3400 configured to reduce profile in a direction orthogonal to a direction of insertion of the device into an incision. When taking an arcuate shape, the main body of orthopedic joint device 3400 may include leg tips at its proximal region. The orthopedic joint device 3400 may also include one or more optional holes, that may or may not be used to provide attachment points with which to control deformation of the device during delivery. One or more of the optional holes may comprise a distal edge configured to limit the freedom of movement of a suture threaded through the hole when the orthopedic joint device 3300 is being inserted into an incision, thus preventing device slippage. Orthopedic joint device 3400 may also include a lead surface configured to ease insertion of the orthopedic joint device into an incision. Orthopedic joint device 3400 includes transition regions configured to provide a gradual reduction of height from the main body to an interior region, which may facilitate minimal puckering of orthopedic joint device 3400 when in the deformed configuration. Orthopedic joint device 3400 may also comprise proximal transition regions which may be configured to reduce puckering, promote overlapping of the ends, or both, near the proximal region of the orthopedic device 3400. The interior region 3400 of orthopedic joint device 3400 comprises a central opening, which may reduce the puckering of the device in the deformed configuration. A span member is added in the region of the leg tips to prevent splaying of the device in the deformed configuration, and the span member comprises an inward edge at its proximal region which is configured to reduce puckering in that region.

Figure 34A:
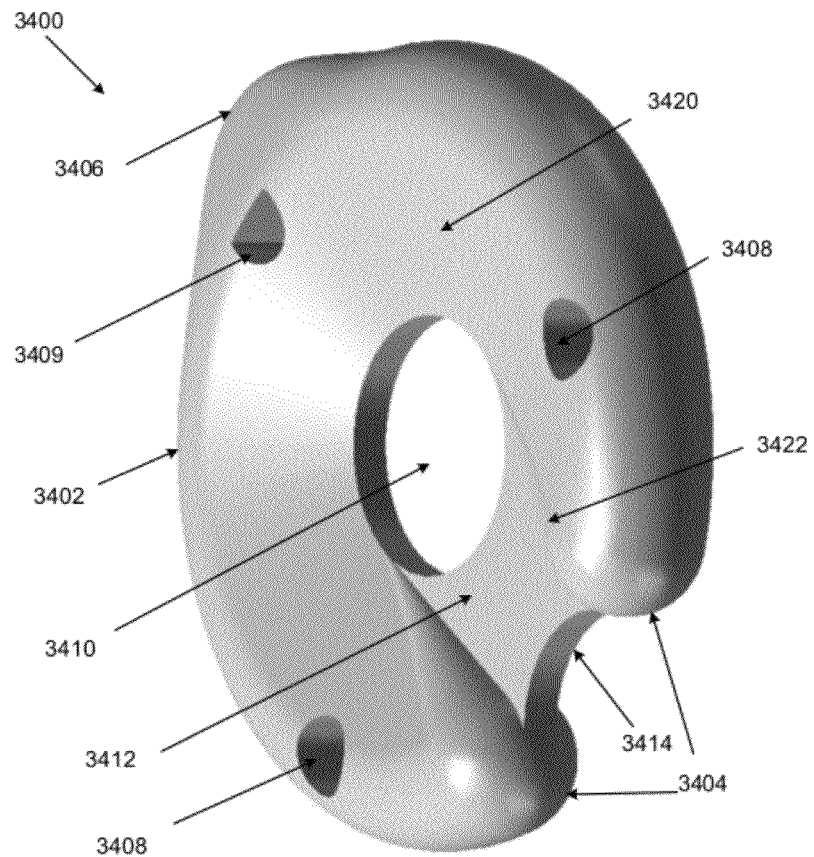
FIG. 34A is a solid isometric view of an embodiment of an orthopedic joint device comprising a transition region, a central cutout, and a distal aperture configured to limit the freedom of movement of a suture coupled to the device.
Figure 34B:
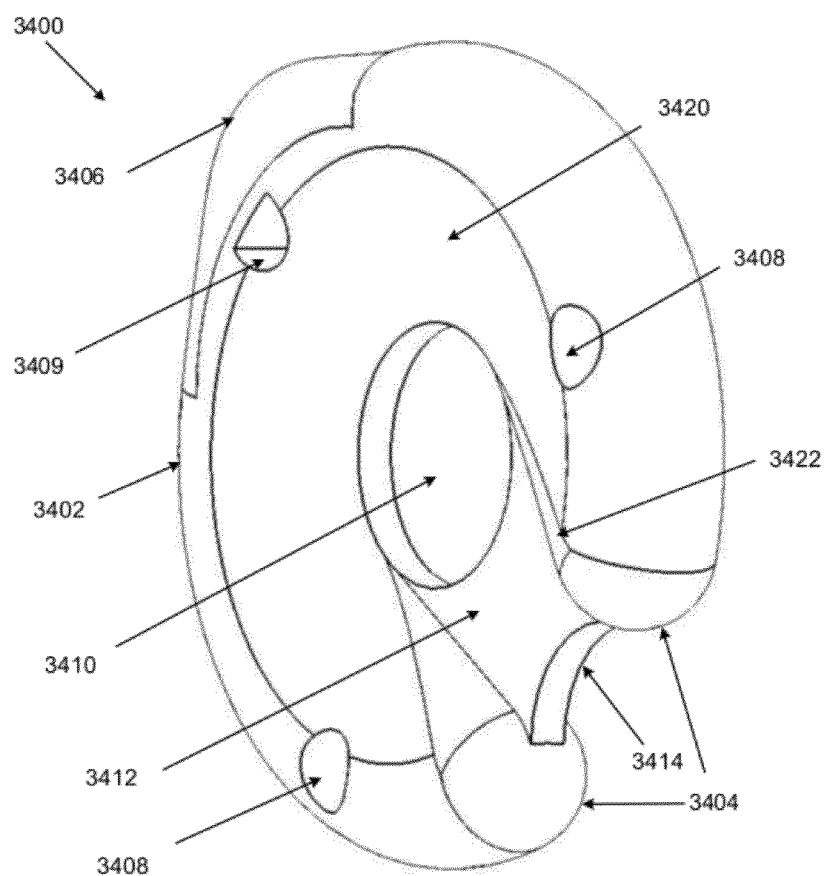
FIG. 34B is a line-drawing isometric view of the orthopedic joint device in FIG. 34A.
Figure 34C:
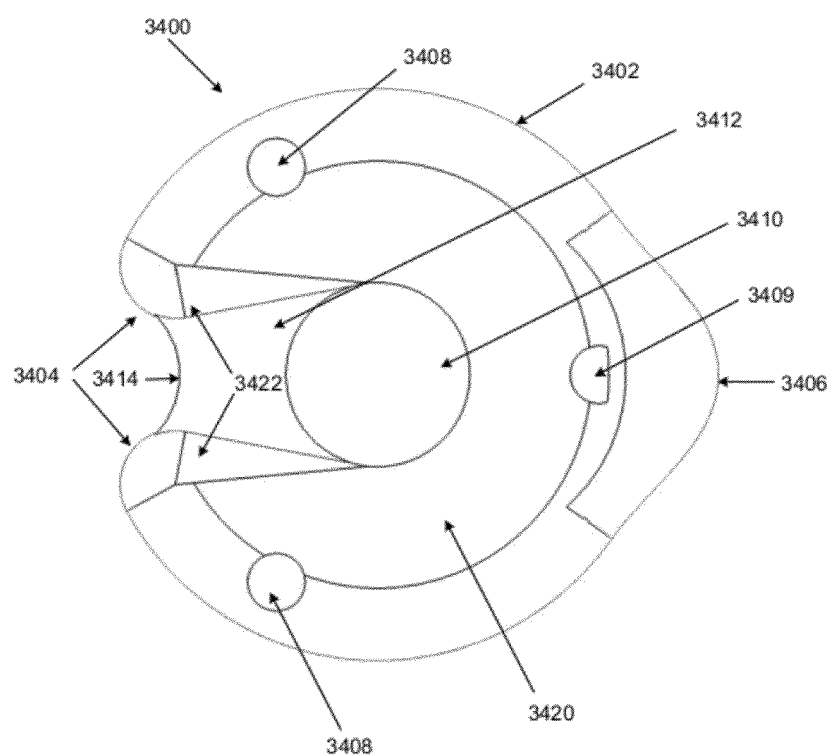
FIG. 34C is a line-drawing superior view of the orthopedic joint device in FIG. 34A.
Figure 34D:
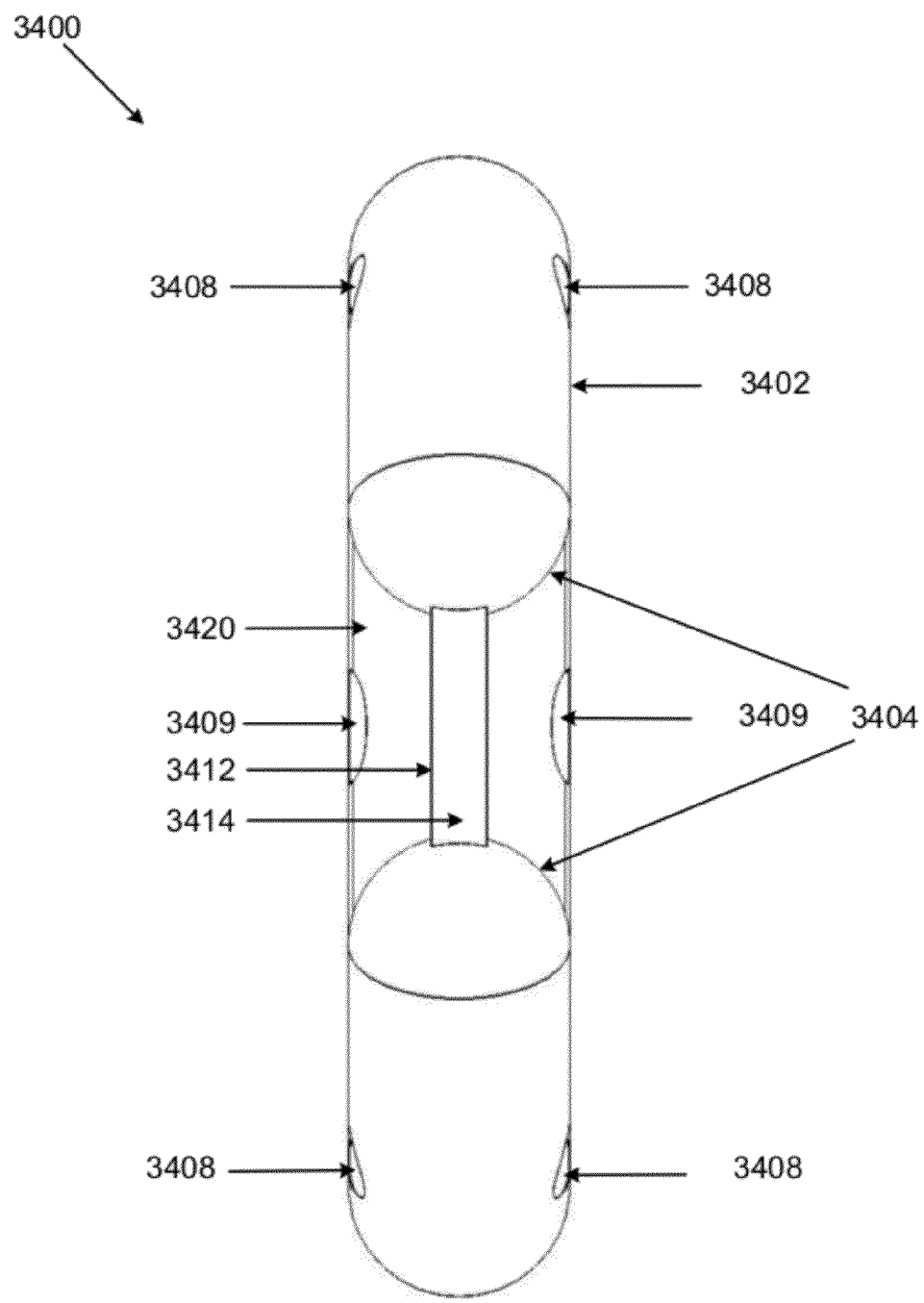
FIG. 34D is a line-drawing rear view of the orthopedic joint device in FIG. 34A.
Figure 34E:
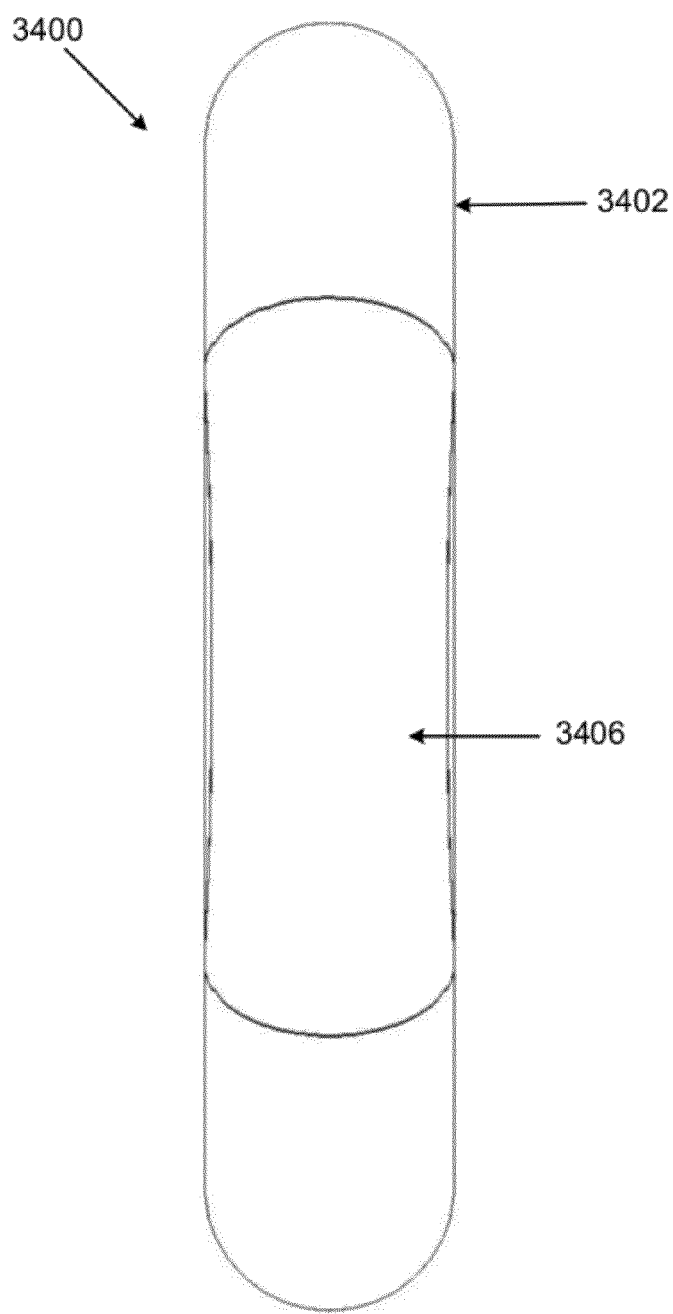
FIG. 34E is a line-drawing front view of the orthopedic joint device in FIG. 34A.
Figure 34F:
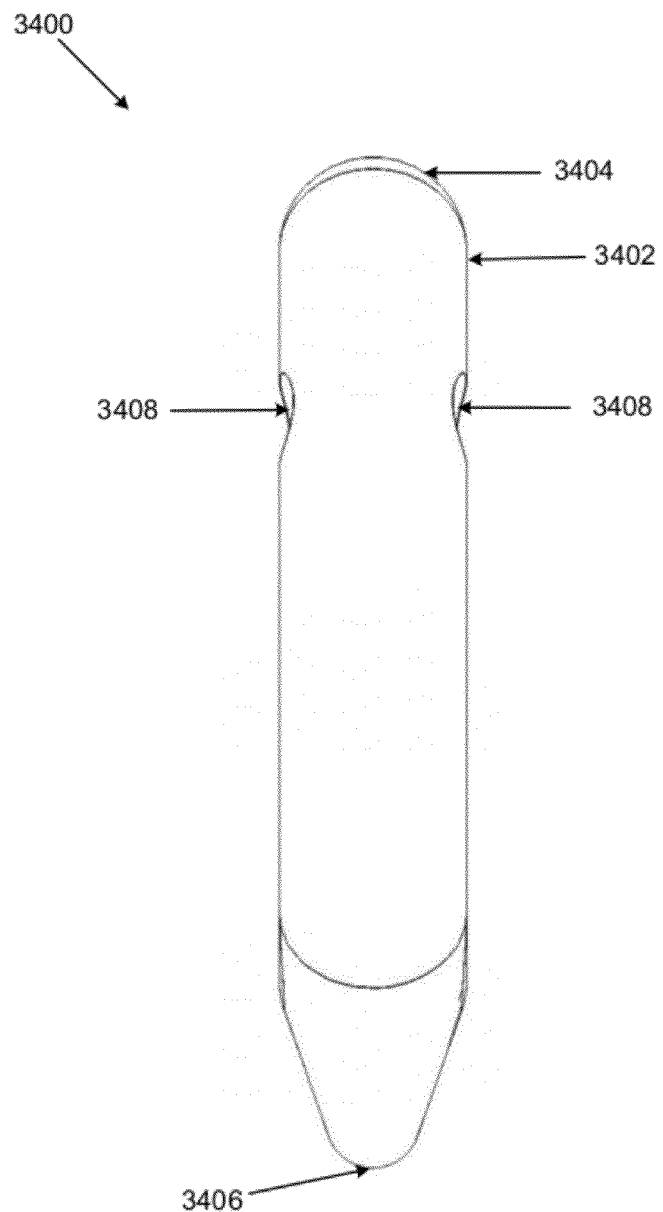
FIG. 34F is a line-drawing side view of the orthopedic joint device in FIG. 34A.
Figure 34G:
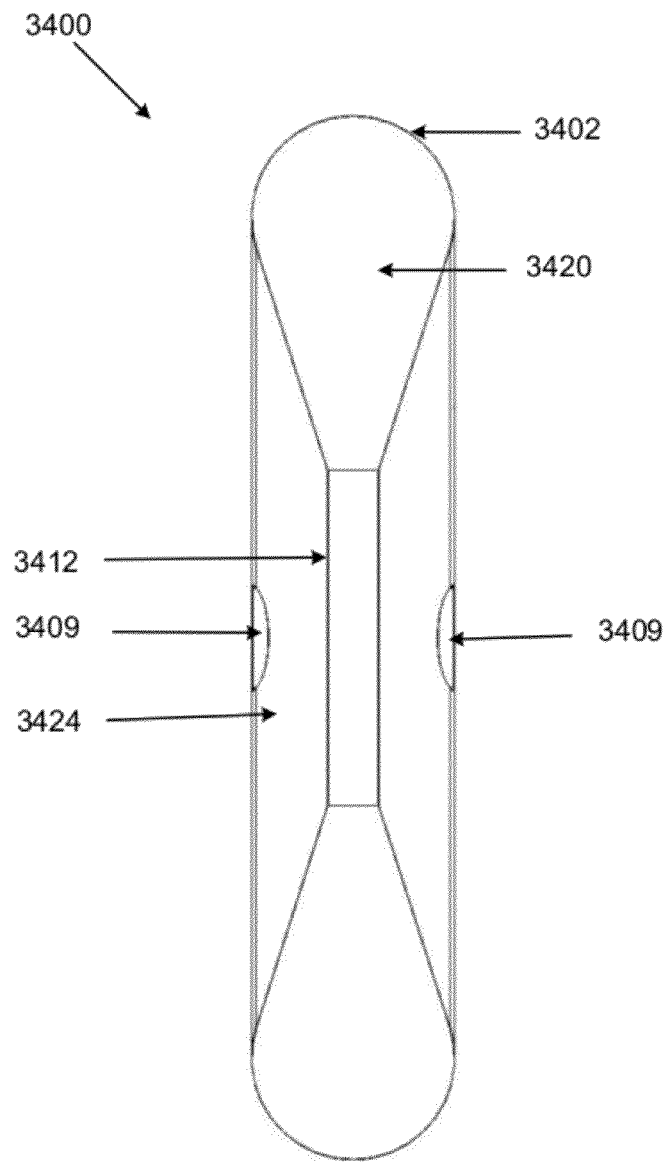
FIG. 34G is a line-drawing cross-sectional view of the orthopedic joint device in FIG. 34A, taken through a plane at the mid-point of the device, looking toward the distal end of the device.

FIG. 34A depicts a solid isometric view of orthopedic joint device 3400. As depicted therein, the orthopedic joint device 3400 may comprise a main body 3402, transition region 3420, and an interior region 3410. FIG. 34B depicts a line-drawing isometric view of orthopedic joint device 3400. FIG. 34C depicts a line-drawing superior view of orthopedic joint device 3400. FIG. 34D depicts a line-drawing rear view of orthopedic joint device 3400. FIG. 34E depicts a line-drawing front view of orthopedic joint device 3400. FIG. 34F depicts a line-drawing side view of orthopedic joint device 3400. FIG. 34G depicts a line-drawing cross-sectional view of orthopedic joint device 3400, taken through a plane at the mid-point of the device, looking toward the distal end of the device.

FIGS. 35A-G depict another embodiment of an orthopedic joint device 3500 configured to reduce profile in a direction orthogonal to a direction of insertion of the device into an incision. When taking an arcuate shape, the main body of orthopedic joint device 3500 may include leg tips at its proximal region. The orthopedic joint device 3500 may also include on or more optional holes that may provide attachment points with which to control deformation of the device during delivery. One or more of the holes may comprise a distal edge configured to limit the freedom of movement of a suture threaded through the hole when the orthopedic joint device 3300 is being inserted into an incision, thus preventing device slippage. Orthopedic joint device 3500 may also include a lead surface configured to ease insertion of the orthopedic joint device into an incision. Orthopedic joint device 3500 includes transition regions configured to provide a gradual reduction of height from the main body to an interior region, which may facilitate minimal puckering of orthopedic joint device 3500 when in the deformed configuration. Orthopedic joint device 3500 may also comprise proximal transition regions which may be configured to reduce puckering, promote overlapping of the ends, or both, near the proximal region of the orthopedic device 3500. The interior region of orthopedic joint device 3500 may comprise one or more span members covering the central region of the device. At least one span member may comprise an inward edge at its proximal region which is configured to reduce puckering in that region.

Figure 35A:
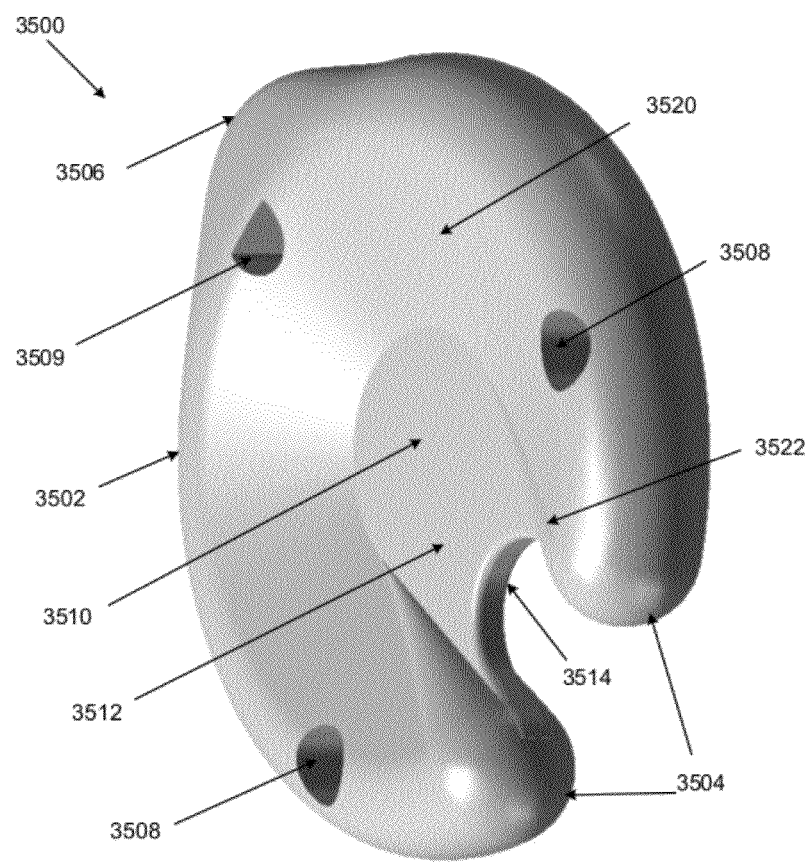
FIG. 35A is a solid isometric view of another embodiment of an orthopedic joint device comprising a transition region, a span member covering a central region, and a distal aperture configured to limit the freedom of movement of a suture coupled to the device.
Figure 35B:
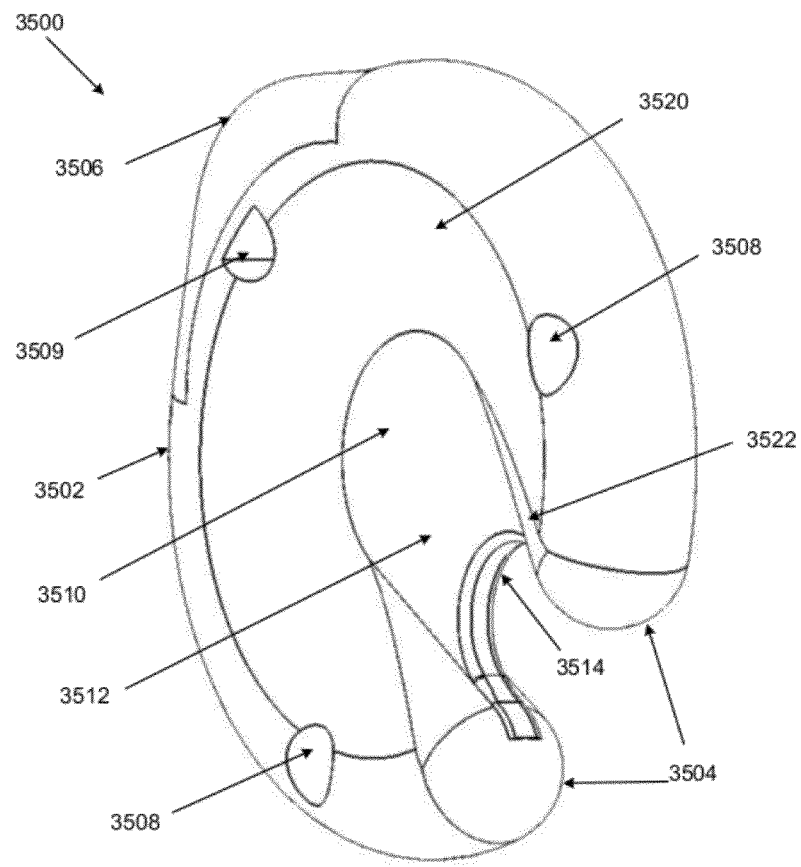
FIG. 35B is a line-drawing isometric view of the orthopedic joint device in FIG. 35A.
Figure 35C:
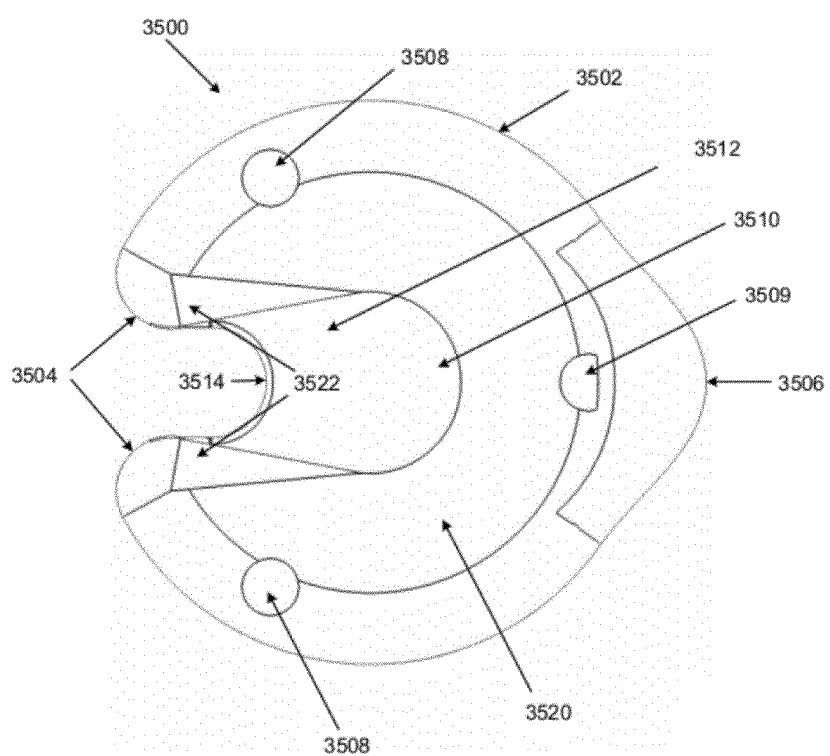
FIG. 35C is a line-drawing superior view of the orthopedic joint device in FIG. 35A.
Figure 35D:
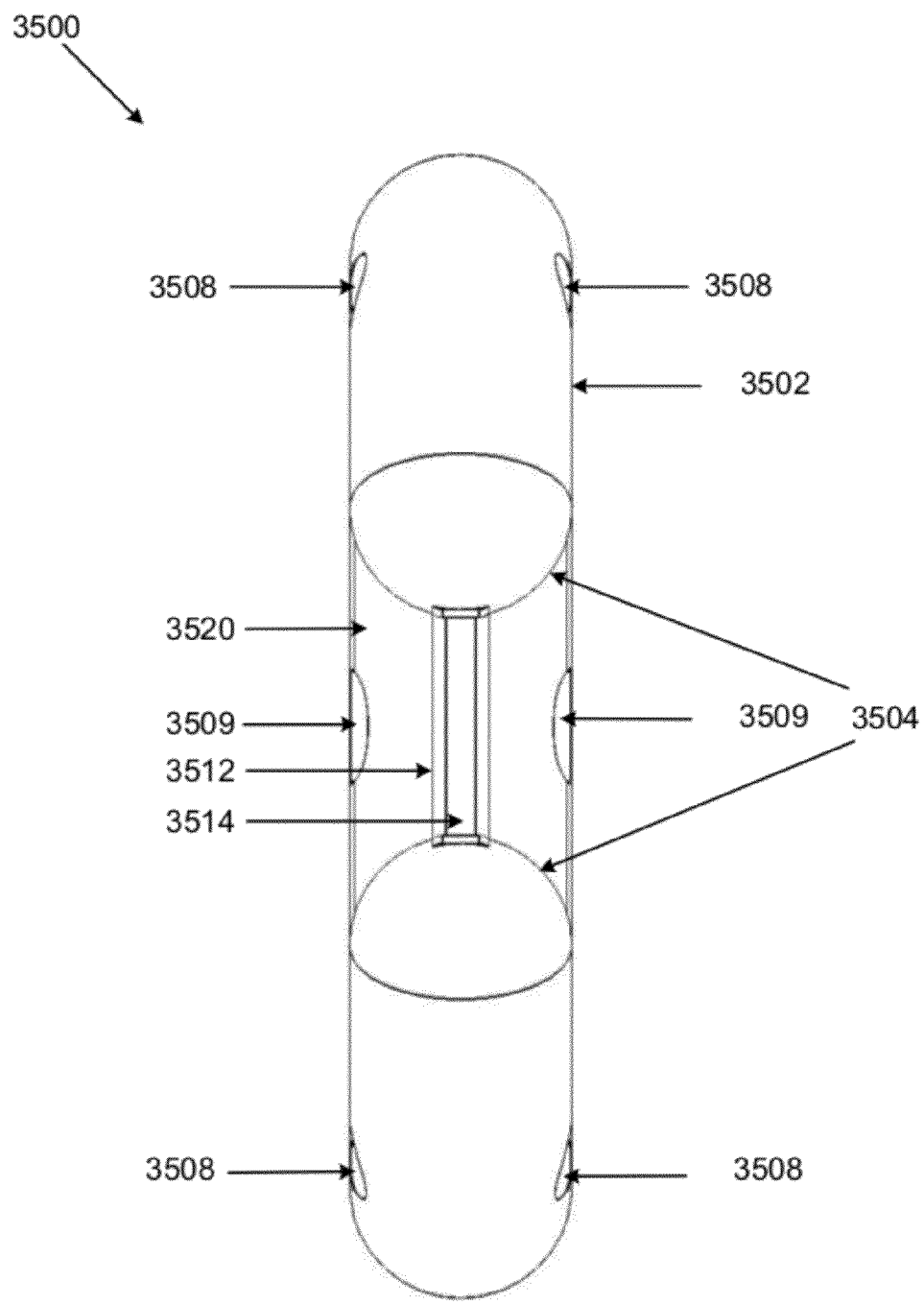
FIG. 35D is a line-drawing rear view of the orthopedic joint device in FIG. 35A.
Figure 35E:
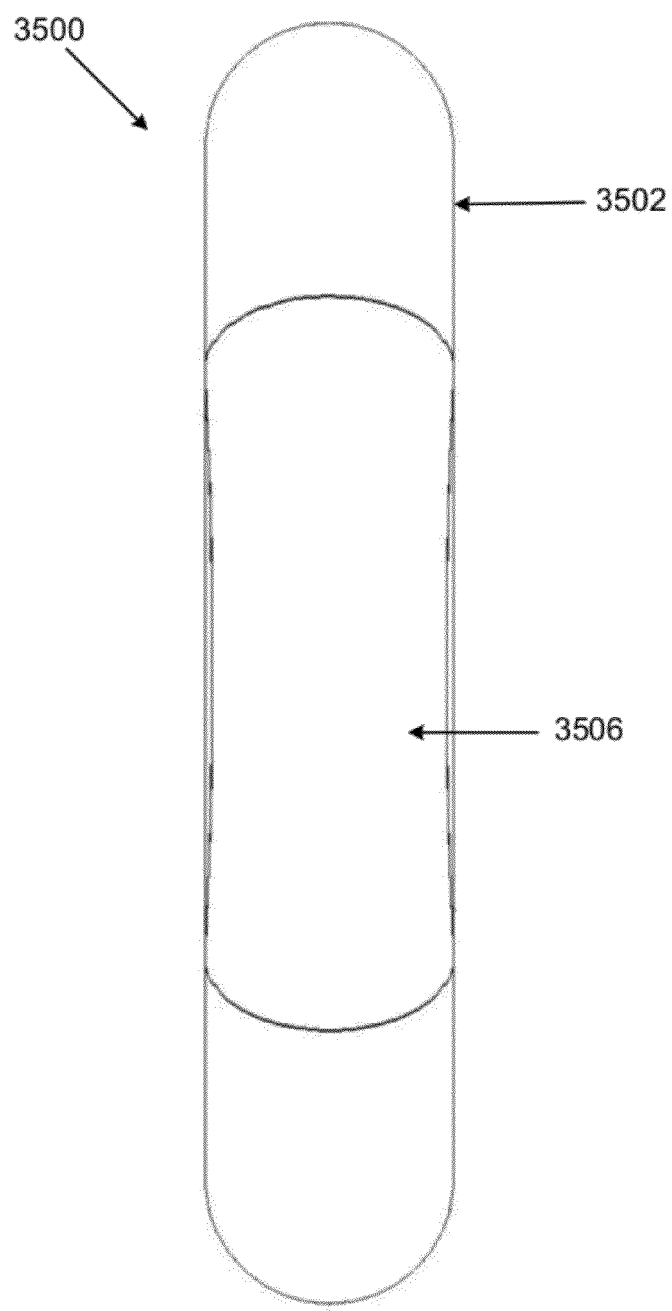
FIG. 35E is a line-drawing front view of the orthopedic joint device in FIG. 35A.
Figure 35F:
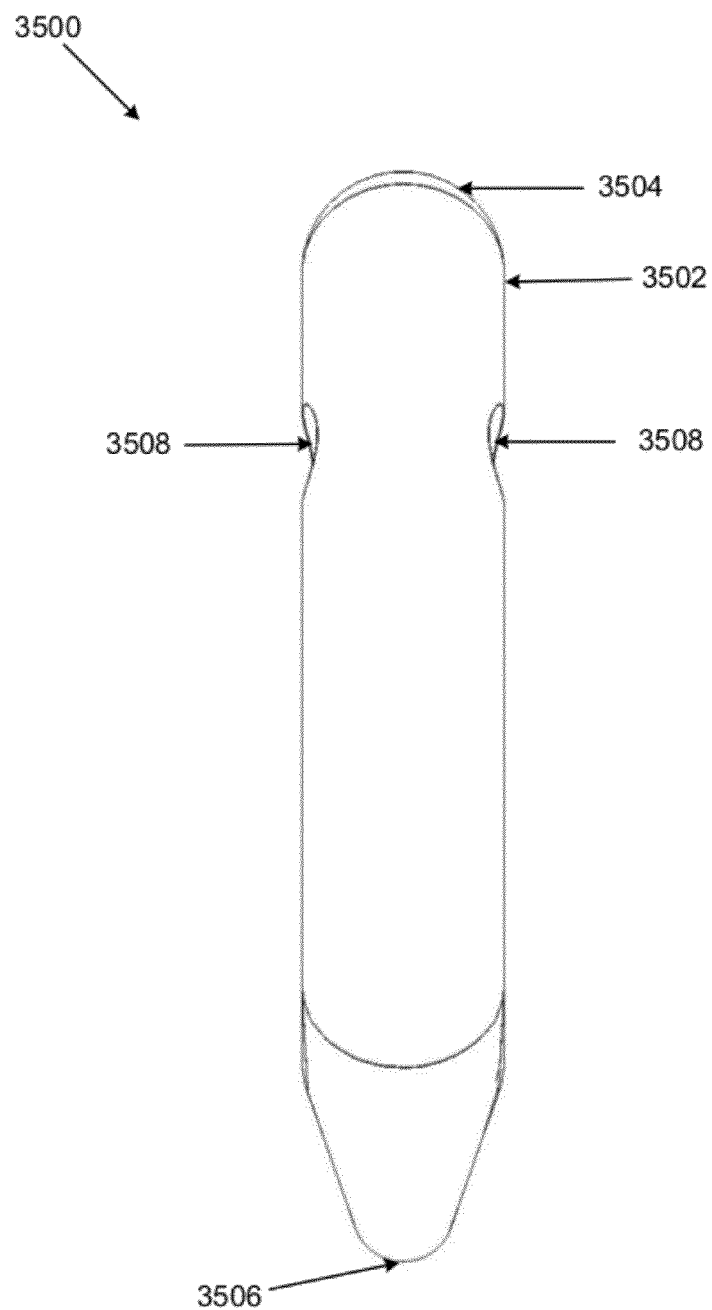
FIG. 35F is a line-drawing side view of the orthopedic joint device in FIG. 35A.

FIG. 35A depicts a solid isometric view of orthopedic joint device 3500. As depicted therein, the orthopedic joint device 3500 may comprise a main body 3502, transition region 3520, and an interior region 3510. FIG. 35B depicts a line-drawing isometric view of orthopedic joint device 3500. FIG. 35C depicts a line-drawing superior view of orthopedic joint device 3500. FIG. 35D depicts a line-drawing rear view of orthopedic joint device 3500. FIG. 35E depicts a line-drawing front view of orthopedic joint device 3500. FIG. 35F depicts a line-drawing side view of orthopedic joint device 3500.

Figure 35G:
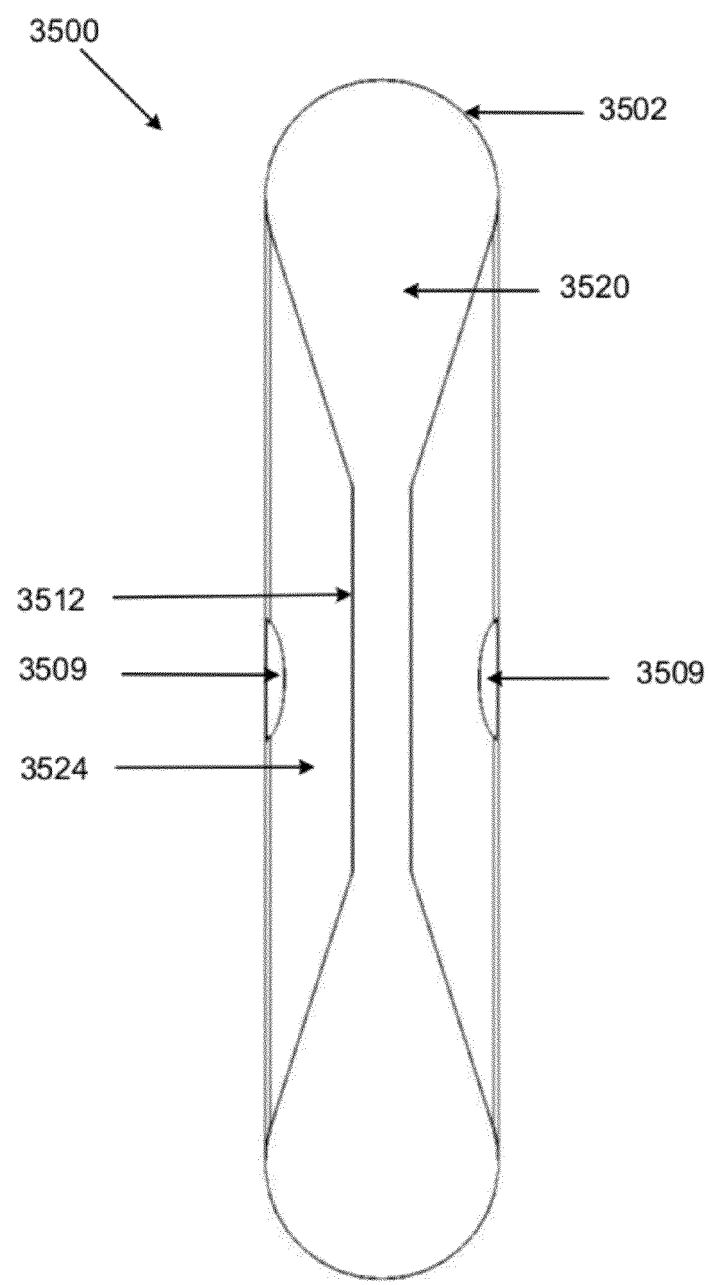
FIG. 35G is a line-drawing cross-sectional view of the orthopedic joint device in FIG. 35A, taken through a plane at the mid-point of the device, looking toward the distal end of the device.

FIG. 35G depicts a line-drawing cross-sectional view of orthopedic joint device 3500, taken through a plane at the mid-point of the device, looking toward the distal end of the device.

Figure 36A:
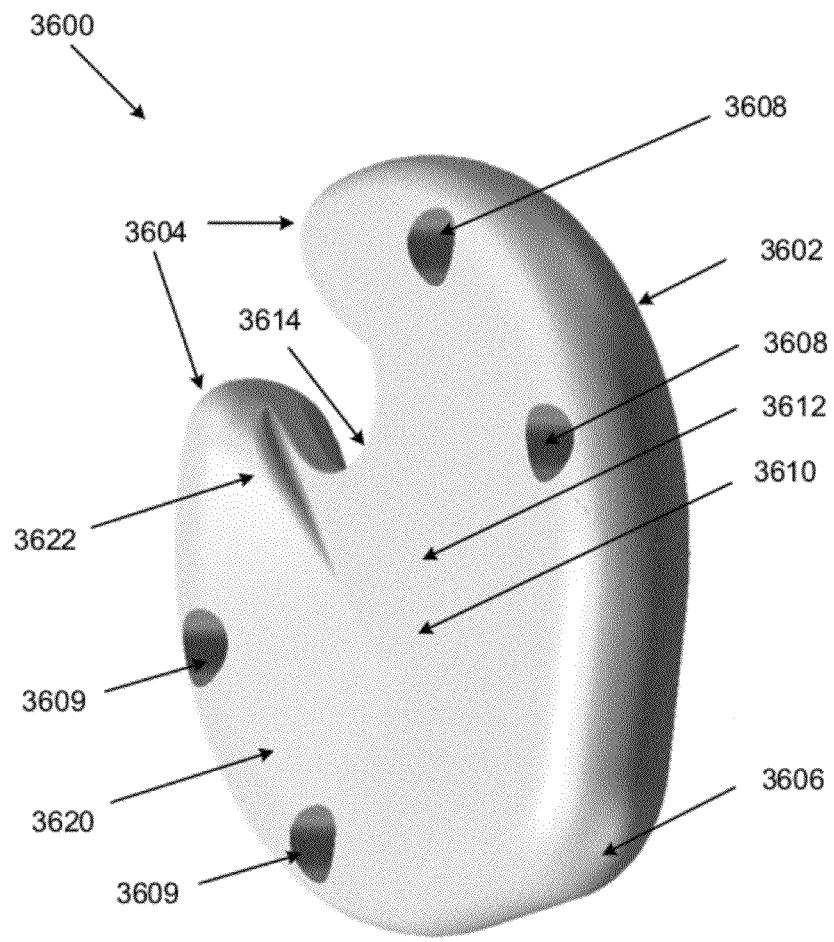
FIG. 36A is a solid isometric view of an embodiment of an orthopedic joint device comprising a transition region, a span member covering a central region, and two inner cores.

FIGS. 36A-36H depict another embodiment of an orthopedic joint device 3600. FIG. 36A depicts a solid isometric view of orthopedic joint device 3600. As depicted therein, the orthopedic joint device 3600 may comprise a main body 3602, transition region 3620, and an interior region 3610. Main body 3602 may comprise leg tips 3604, lead surface 3606, optional holes 3608 and/or 3609, and inner cores 3630 and 3635. Transition region 3620 may comprise proximal transition regions 3622. Interior region 3610 may comprise span member 3612 and an inward proximal edge 3614 on span member 3612.

Figure 36B:
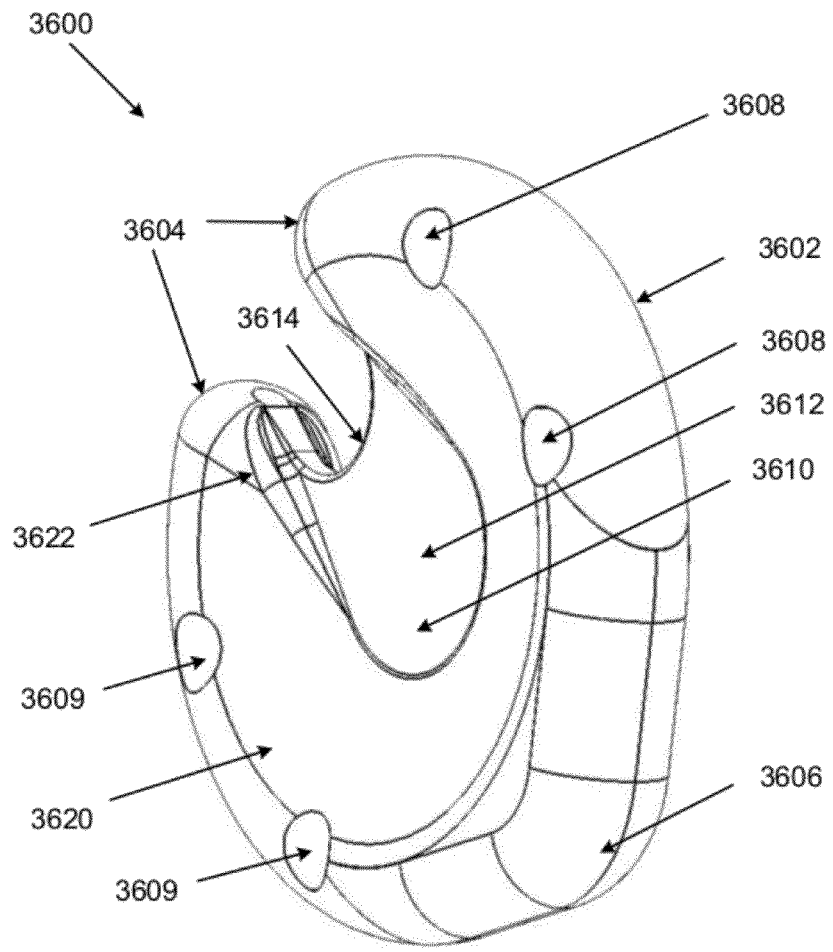
FIG. 36B is a line-drawing isometric view of the orthopedic joint device in FIG. 36A.
Figure 36C:
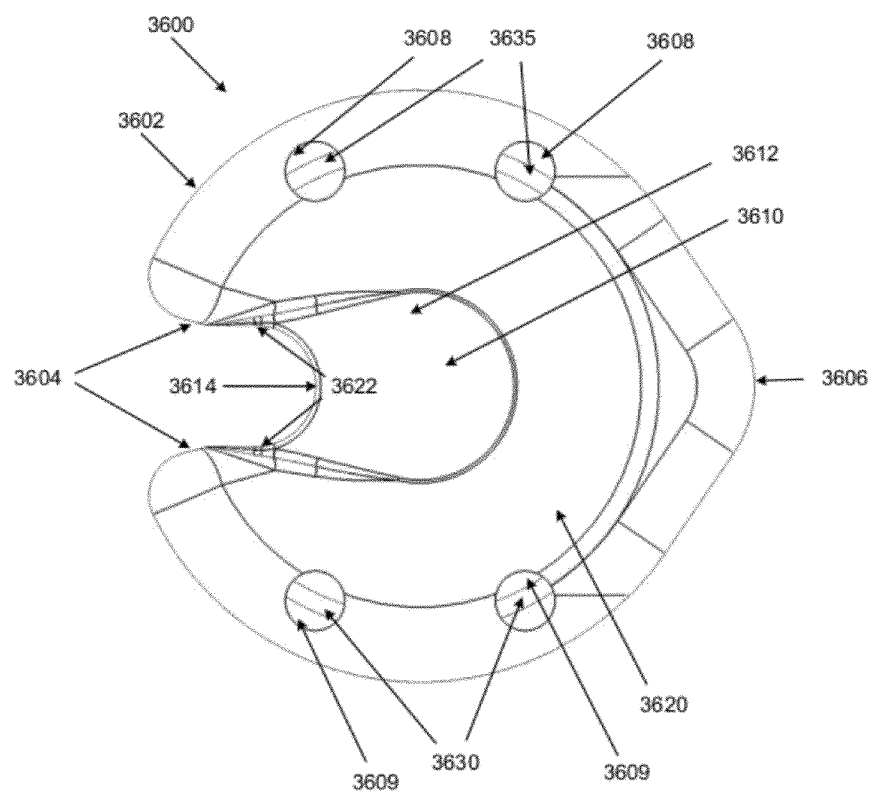
FIG. 36C is a line-drawing superior view of the orthopedic joint device in FIG. 36A.
Figure 36D:
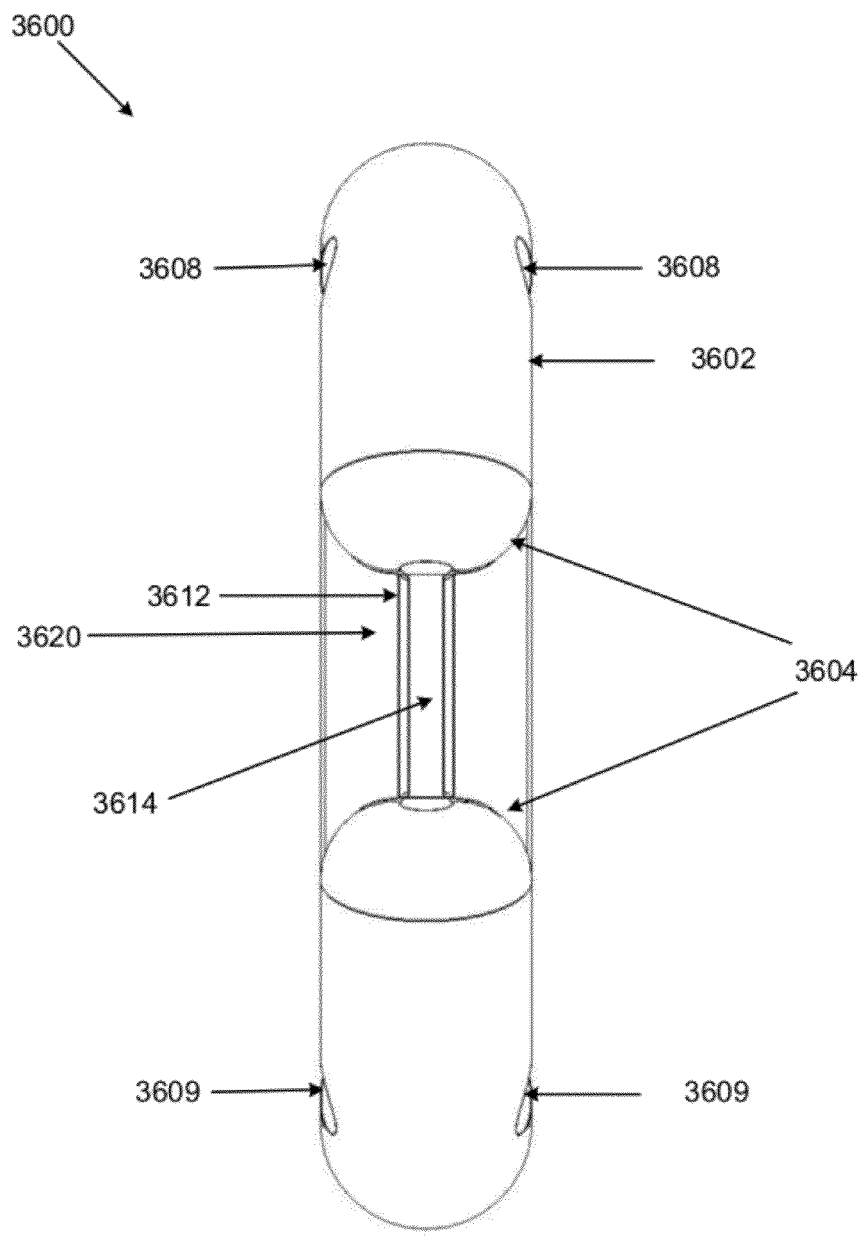
FIG. 36D is a line-drawing rear view of the orthopedic joint device in FIG. 36A.
Figure 36E:
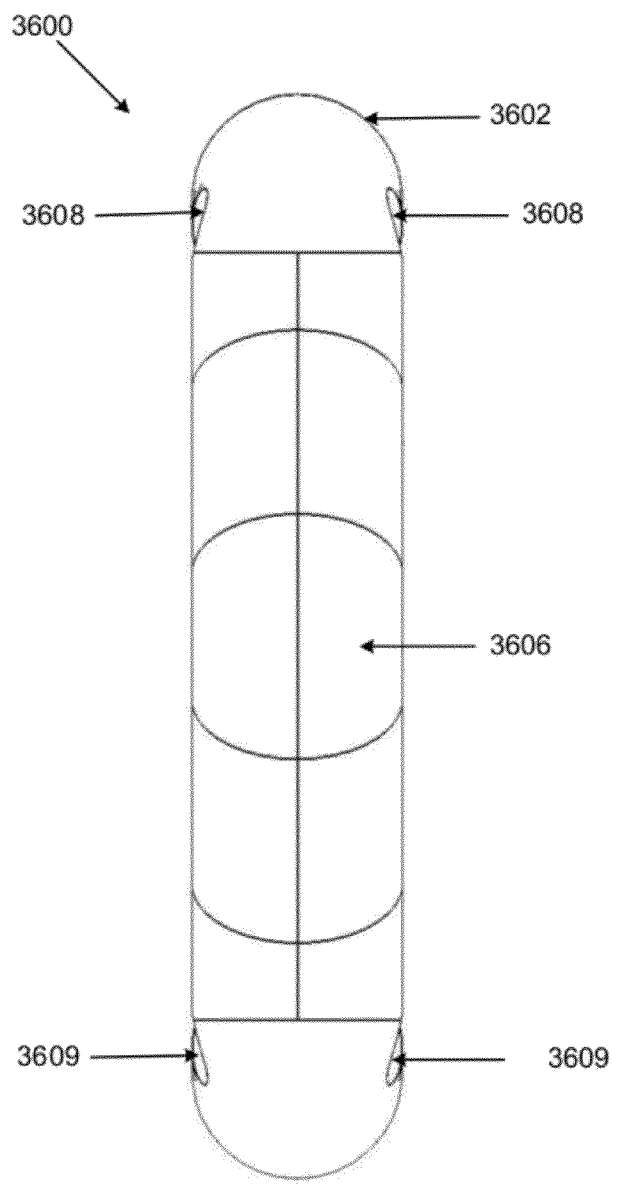
FIG. 36E is a line-drawing front view of the orthopedic joint device in FIG. 36A.
Figure 36F:
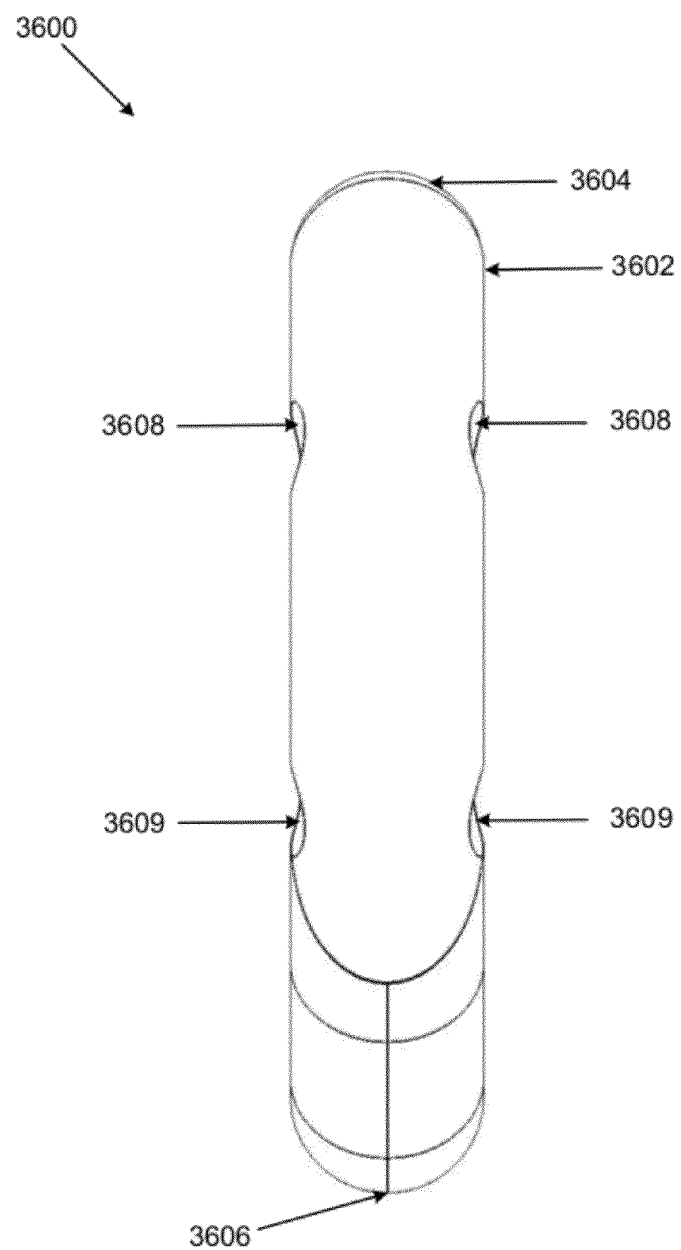
FIG. 36F is a line-drawing side view of the orthopedic joint device in FIG. 36A.
Figure 36G:
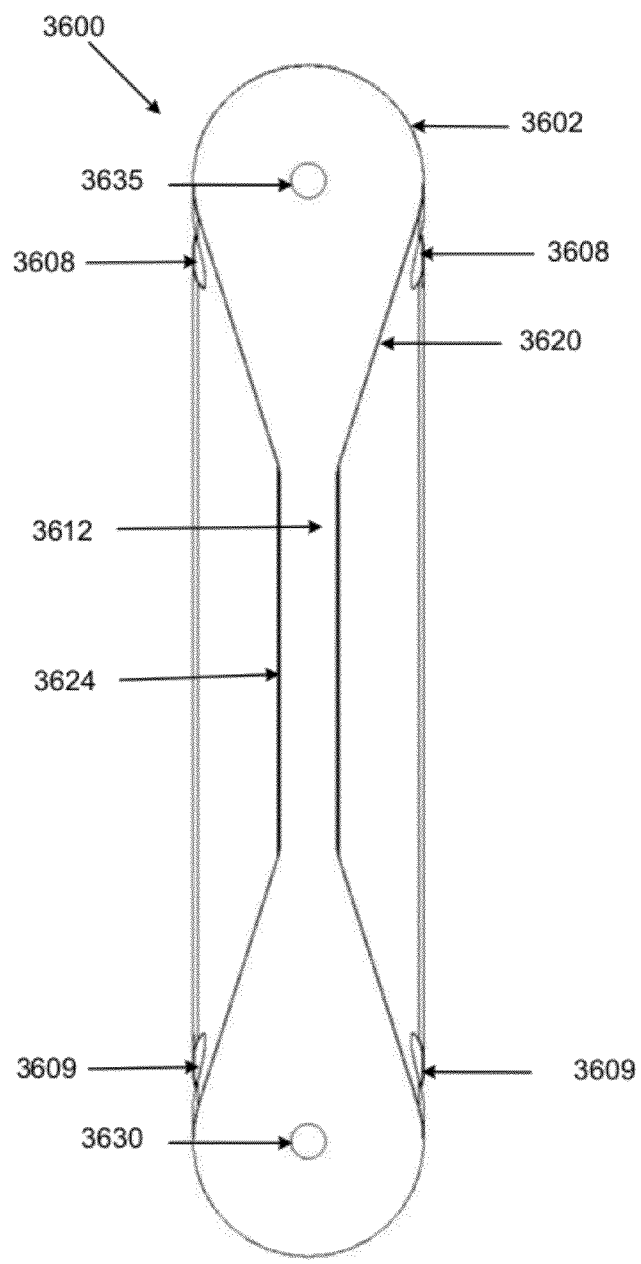
FIG. 36G is a line-drawing cross-sectional view of the orthopedic joint device in FIG. 36A, taken through a plane at the mid-point of the device, looking toward the distal end of the device.
Figure 36H:
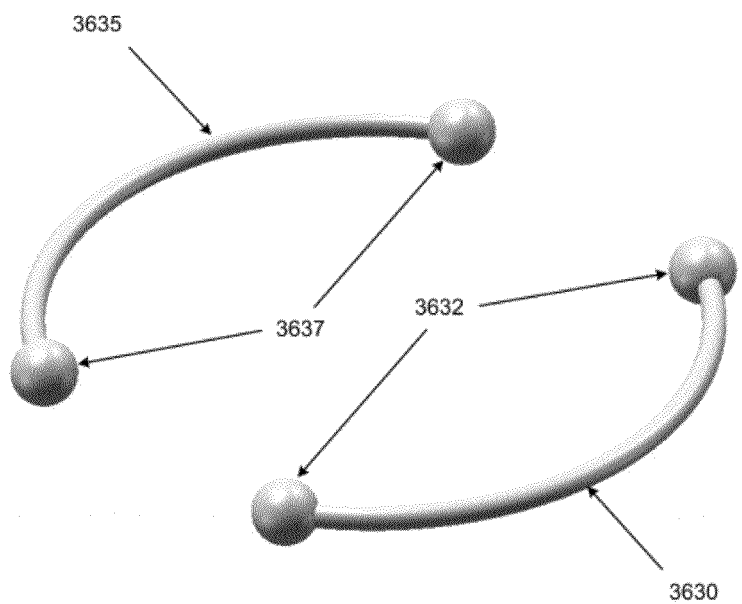
FIG. 36H is a solid isometric view of the orthopedic joint device in FIG. 36A with only the two cores visible.

FIG. 36B depicts a line-drawing isometric view of orthopedic joint device 3600. FIG. 36C depicts a line-drawing superior view of orthopedic joint device 3600. Optional holes 3608 and 3609 may be located along inner cores 3630 and 3635 respectively. The holes may result from a manufacturing process and may be the points at which the cores are secured as the outer body is added. In some embodiments, the holes may provide attachment points with which to control deformation of the device during delivery. FIG. 36D depicts a line-drawing rear view of orthopedic joint device 3600. FIG. 36E depicts a line-drawing front view of orthopedic joint device 3600. FIG. 36F depicts a line-drawing side view of orthopedic joint device 3600. FIG. 36G depicts a line-drawing cross-sectional view of orthopedic joint device 3600, taken through a plane at the mid-point of the device, looking toward the distal end of the device. FIG. 36H depicts a solid isometric view of the orthopedic joint device 3600 with the main body 3602, transition regions 3620, and interior region 3610 removed so that the location and structural features of inner cores 3630 and 3635 can be appreciated. Inner cores 3630 and 3635 may comprise radiopaque materials, as described in more detail above. Inner cores 3630 and 3635 may comprise ends 3635 and 3637, respectively, for securing the inner cores in position, which may prevent motion of the inner cores relative to the outer body. Inner cores 3630 and 3635 comprise arcs with a radius similar to that of the main body. In some embodiments, the inner core comprises an arc with a radius different to that of the main body, wherein the radius is configured to achieve a desired property, such as deformability of the orthopedic joint device, for example. In some embodiments, the inner cores do not comprise an arc and instead comprise a line, a combination of lines, or a combination of lines and curves.

Figure 37A:
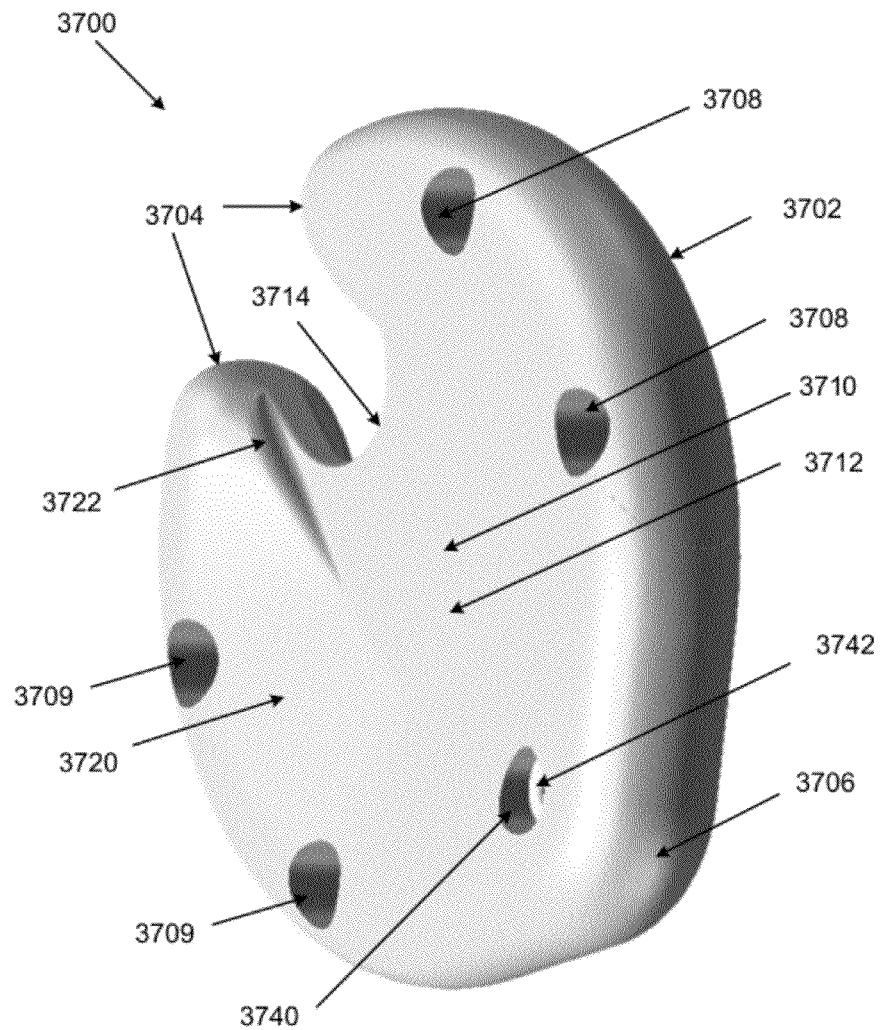
FIG. 37A is a solid isometric view of an embodiment of an orthopedic joint device comprising a transition region, a span member covering a central region, two inner cores, and a grommet.

FIGS. 37A-37I depict another embodiment of an orthopedic joint device 3700. FIG. 37A depicts a solid isometric view of orthopedic joint device 3700. As depicted therein, the orthopedic joint device 3700 may comprise a main body 3702, transition region 3720, and an interior region 3710. Main body 3702 may comprise leg tips 3704, lead surface 3706, optional lateral holes 3708 and 3709, inner cores 3730 and 3735, and optional distal hole 3740. Distal hole 3740 may further comprise grommet 3742 and a flange 3744 coupled to the grommet and configured to prevent motion of the grommet relative to the main body. Transition region 3720 may comprise proximal transition regions 3722. Interior region 3710 may comprise span member 3712 and an inward proximal edge 3714 on span member 3712.

Figure 37B:
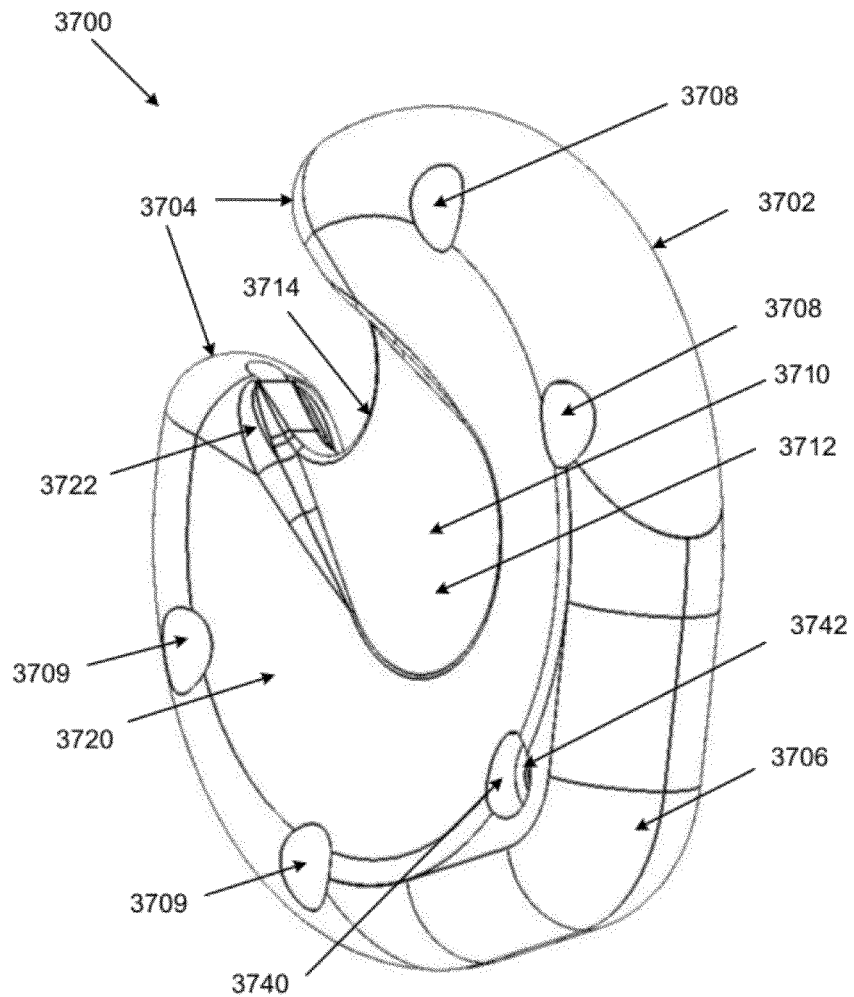
FIG. 37B is a line-drawing isometric view of the orthopedic joint device in FIG. 37A.
Figure 37C:
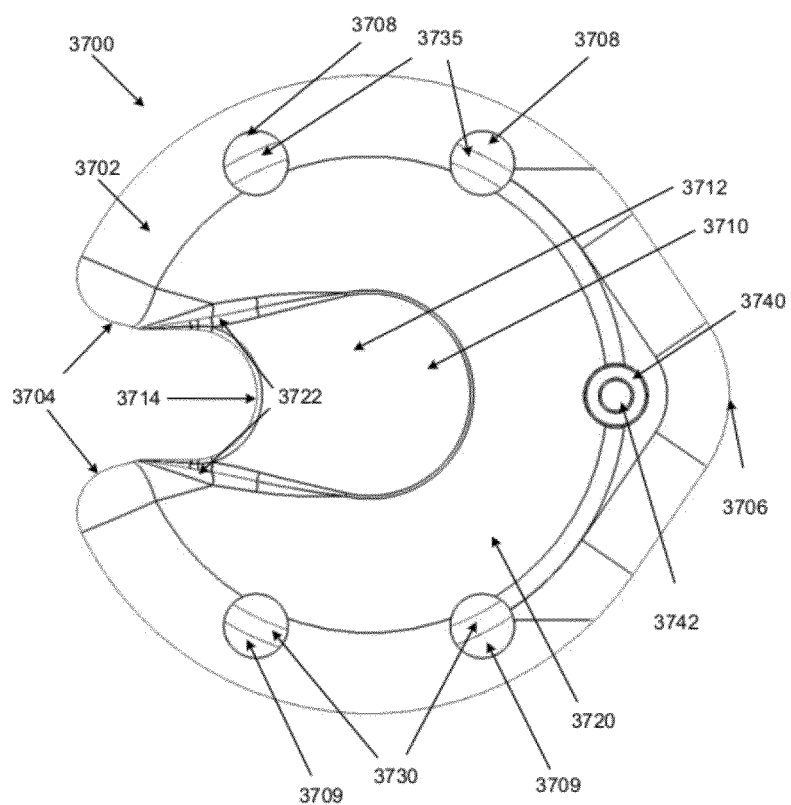
FIG. 37C is a line-drawing superior view of the orthopedic joint device in FIG. 37A.
Figure 37D:
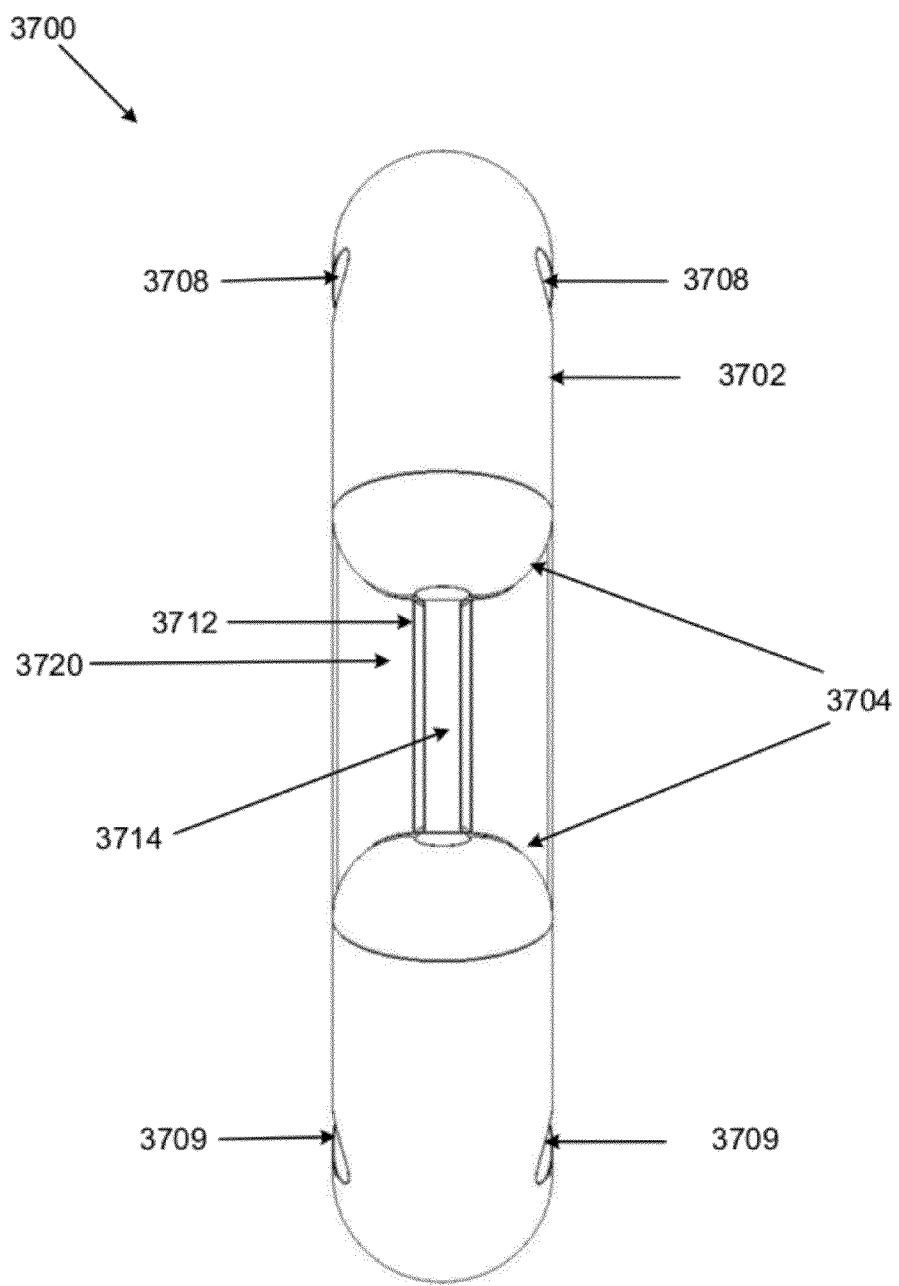
FIG. 37D is a line-drawing rear view of the orthopedic joint device in FIG. 37A.
Figure 37E:
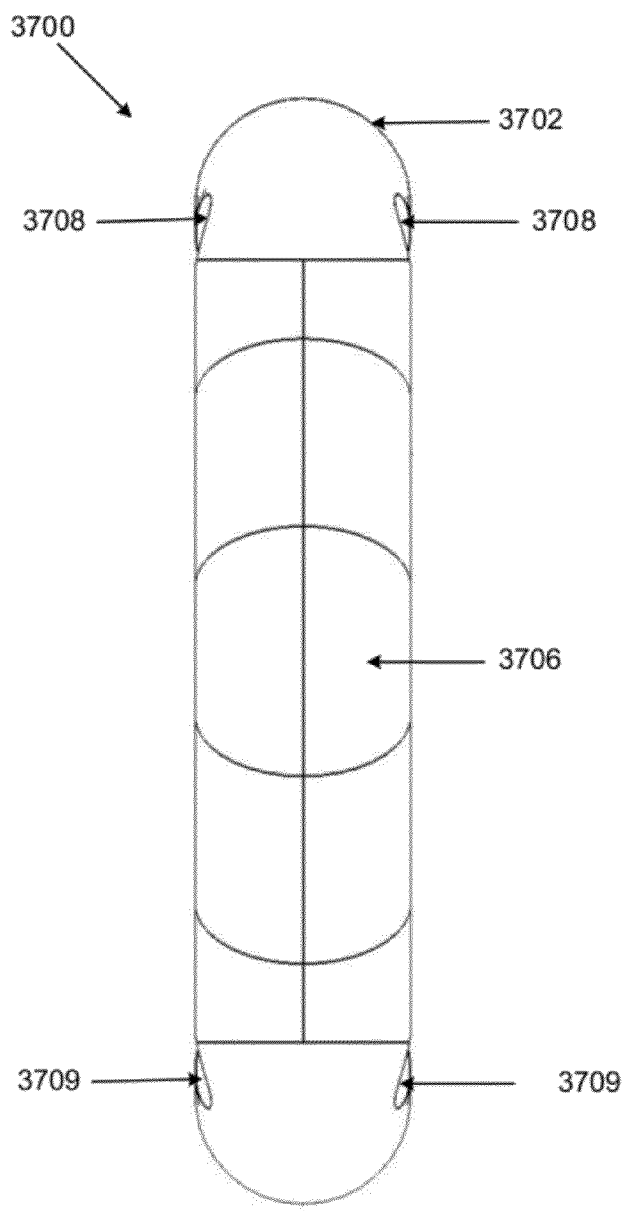
FIG. 37E is a line-drawing front view of the orthopedic joint device in FIG. 37A.
Figure 37F:
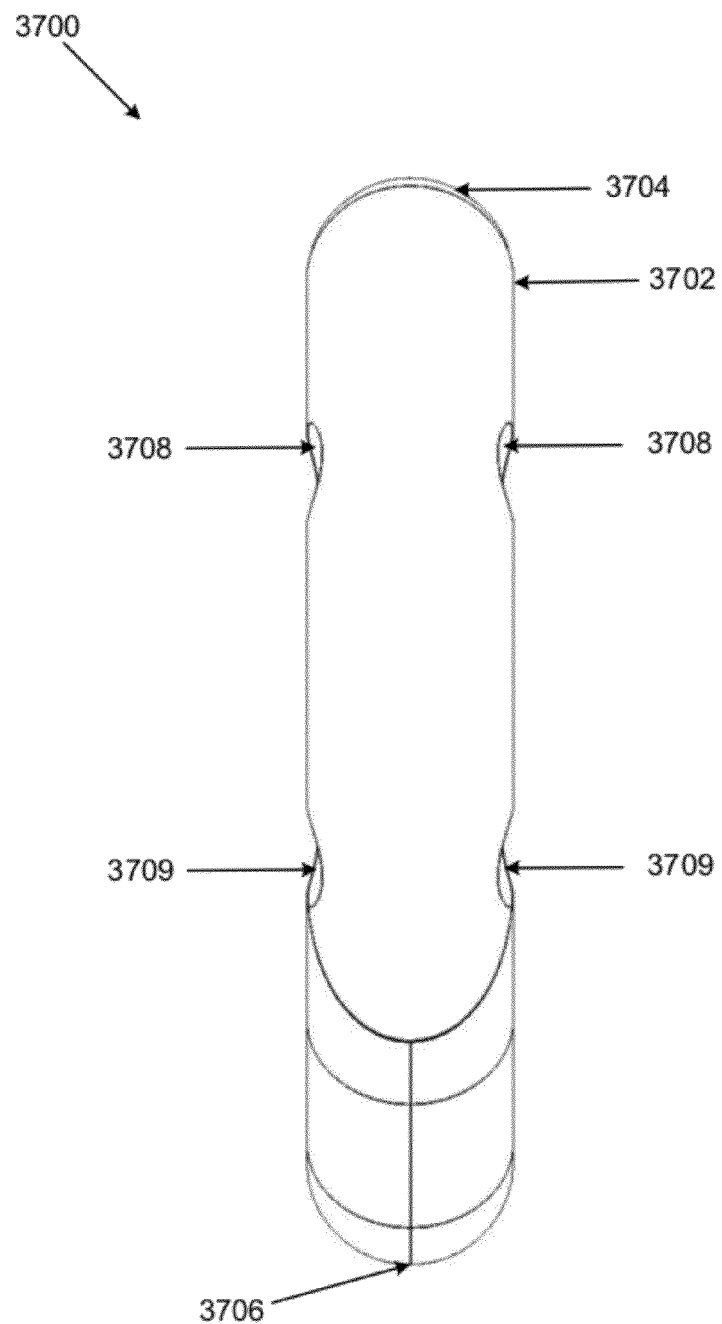
FIG. 37F is a line-drawing side view of the orthopedic joint device in FIG. 37A.
Figure 37G:
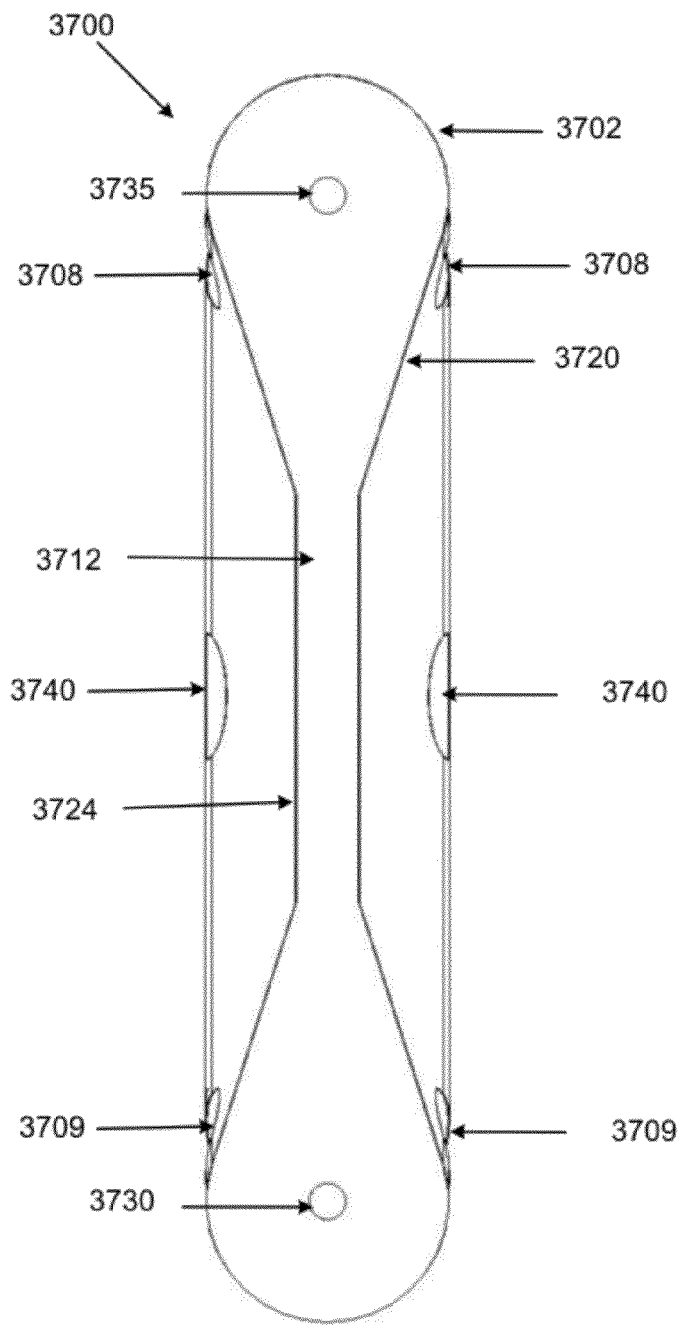
FIG. 37G is a line-drawing cross-sectional view of the orthopedic joint device in FIG. 37A, taken through a plane at the mid-point of the device, looking toward the distal end of the device.
Figure 37H:
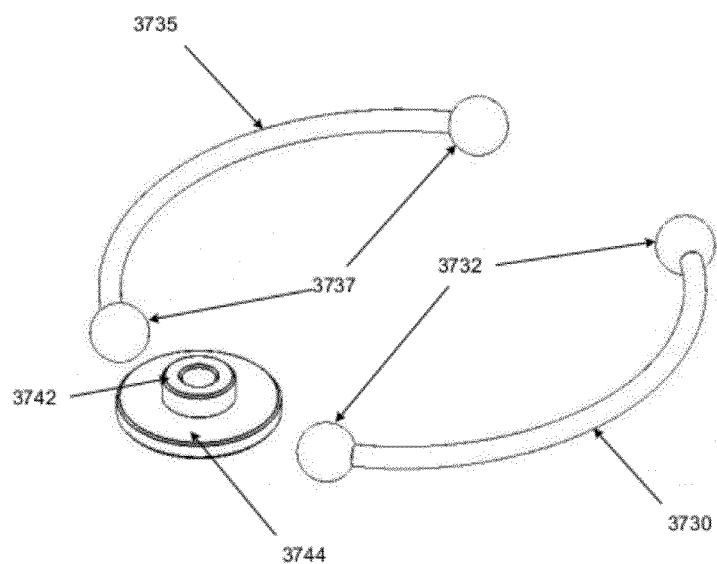
FIG. 37H is a solid isometric view of the orthopedic joint device in FIG. 37A with only the grommet and cores visible.
Figure 37I:
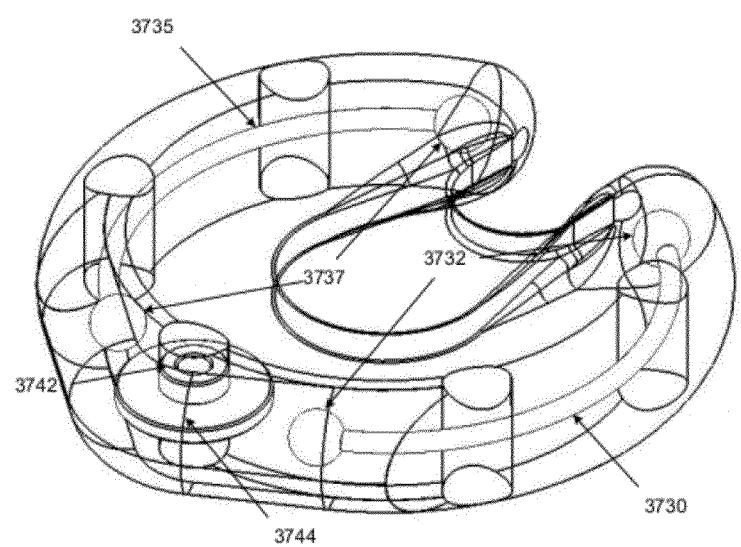
FIG. 37I is a line-drawing isometric view of the orthopedic joint device in FIG. 37H with all parts transparent except the grommet and two cores.

FIG. 37B depicts a line-drawing isometric view of orthopedic joint device 3700. FIG. 37C depicts a line-drawing superior view of orthopedic joint device 3700. Grommet 3742 may be inserted in distal hole 3740 to resist acute fracture and/or rupture of the orthopedic joint device during delivery. The grommet need not be limited to the distal hole and other embodiments may include grommets in some or all of the other holes. FIG. 37D depicts a line-drawing rear view of orthopedic joint device 3700. FIG. 37E depicts a line-drawing front view of orthopedic joint device 3700. FIG. 37F depicts a line-drawing side view of orthopedic joint device 3700. FIG. 37G depicts a line-drawing cross-sectional view of orthopedic joint device 3700, taken through a plane at the mid-point of the device, looking toward the distal end of the device. FIG. 37H depicts a line-drawing isometric view of the orthopedic joint device 3700 with the main body 3702, transition regions 3720, and interior region 3710 removed so that the location and structural features of inner cores 3730 and 3735 and grommet 3740 can be appreciated. Inner cores 3730 and 3675 may comprise radiopaque materials, as described in more detail above. Grommet 3742 includes a flange 3744 to securely fix grommet 3742 in the distal hole 3740. The flange 3744 serves to prevent movement of the grommet relative to the main body 3702. Some embodiments are configured with one inner core and a grommet component integrally formed in the core. Flange 3744 is depicted in FIG. 37H as a toroid, but any configuration that prevents relative movement of the grommet could be used without deviating from the scope of the invention. Such configurations may include, for example, a protrusion from the grommet that fits in a recess of the main body. FIG. 37I depicts a line-drawing isometric view of the orthopedic joint device 3700 with the main body 3702, transition regions 3720, and interior region 3710 transparent so that the location of inner cores 3730 and 3735 and grommet 3740 can be better appreciated.

Figure 38A:
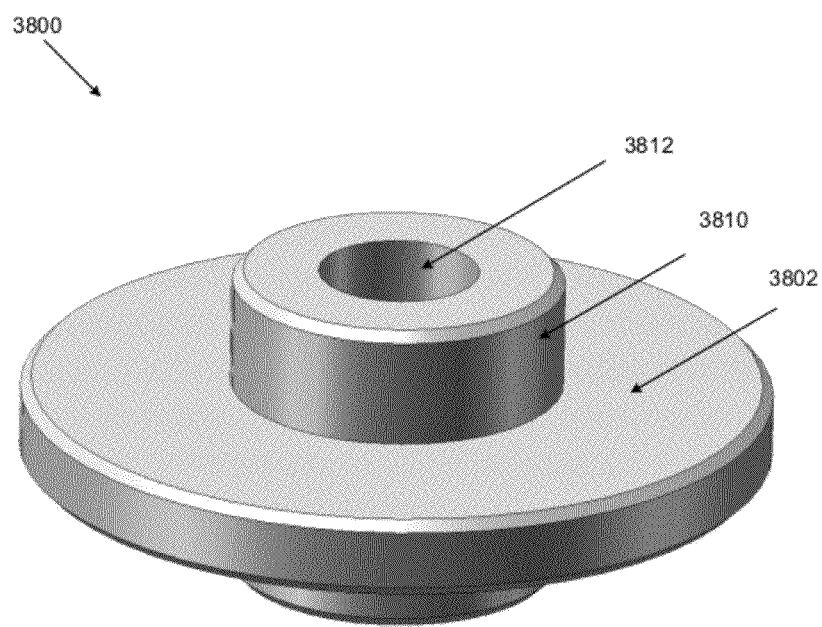
FIG. 38A is a solid isometric view of an embodiment of a grommet.
Figure 38B:
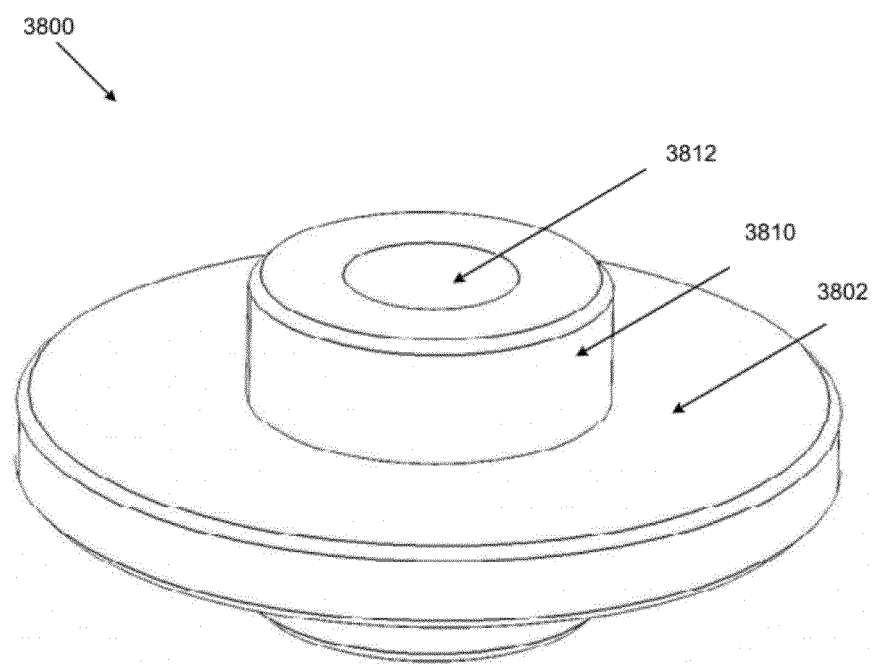
FIG. 38B is a line-drawing isometric view of the grommet of FIG. 38A.
Figure 38C:
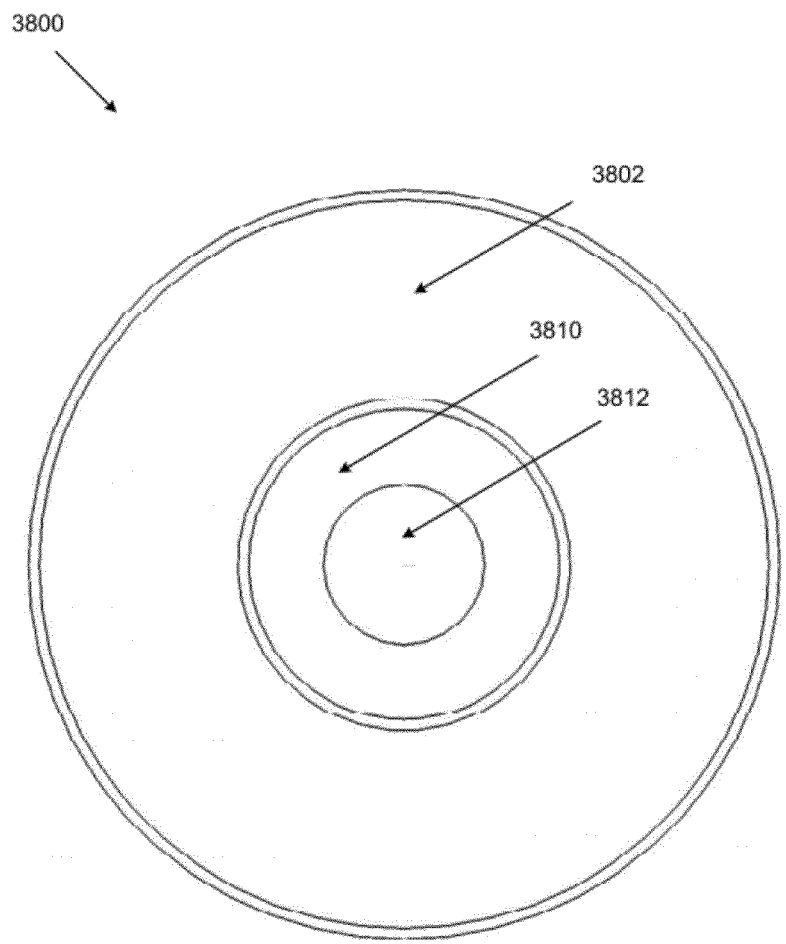
FIG. 38C is a line-drawing superior view of the grommet of FIG. 38A.
Figure 38D:
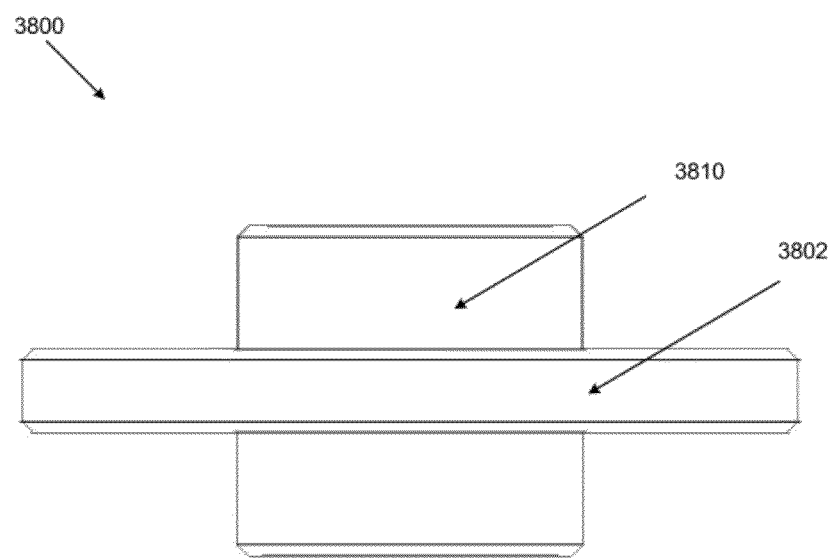
FIG. 38D is a line-drawing side view of the grommet of FIG. 38A.
Figure 38E:
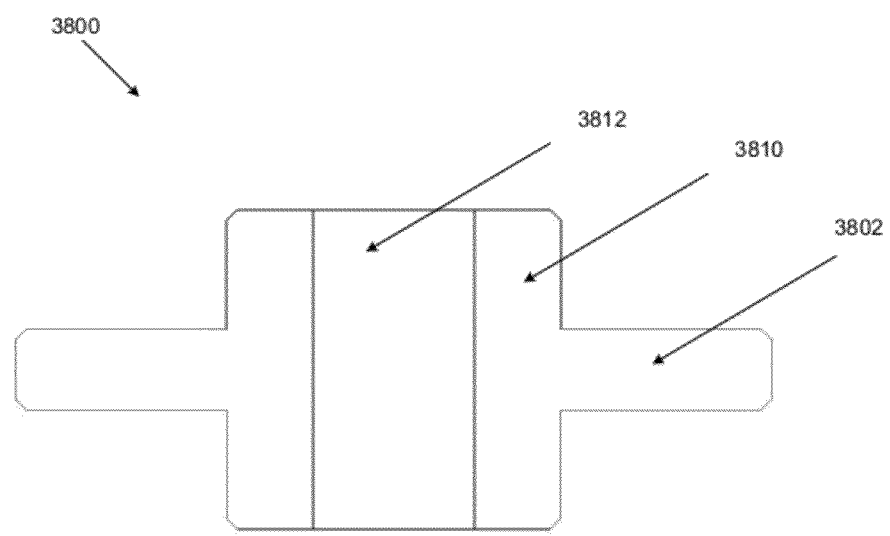
FIG. 38E is a line-drawing cross-sectional view of the grommet of FIG. 38A, taken through a plane at the mid-point of the device, looking toward the distal end of the device.

FIGS. 38A-38E depict an embodiment of grommet 3800 wherein a main body is coupled to a flange configured to prevent motion of the grommet in a direction along an axis of the grommet. FIG. 38A depicts a solid isometric view of grommet 3800. As depicted therein, the grommet 3800 may comprise a flange 3802, a main body 3810, and an aperture 3812. In some embodiments, the flange may comprise a washer, a series of protrusions, or any mechanism configured to prevent relative motion between the grommet and the main body. These mechanisms for preventing relative motion may comprise a circumferential design, such as flange 3802, or may comprise a series of protrusions, which may are not be symmetrically positioned on the main body. The protrusions could take any shape that is configured to resist relative motion between the grommet and the outer body, including cross-sectional profiles that are polygonal and/or circular, and cross-sectional profiles that vary along a length of the protrusion. In some embodiments, the flange may be configured to be bulbous, or enlarged, at a free end, thereby providing additional resistance to relative motion between the main body and the grommet. Grommet 3800 may represent grommet 3742 described above with respect to orthopedic joint device 3700. FIG. 38B depicts a line-drawing isometric view of grommet 3800. FIG. 38C depicts a line-drawing superior view of grommet 3800. FIG. 38D depicts a line-drawing side view of grommet 3800. FIG. 38E depicts a line-drawing cross-sectional view of grommet 3800, taken through a plane at the mid-point of the device, looking toward the distal end of the device.

Figure 39A:
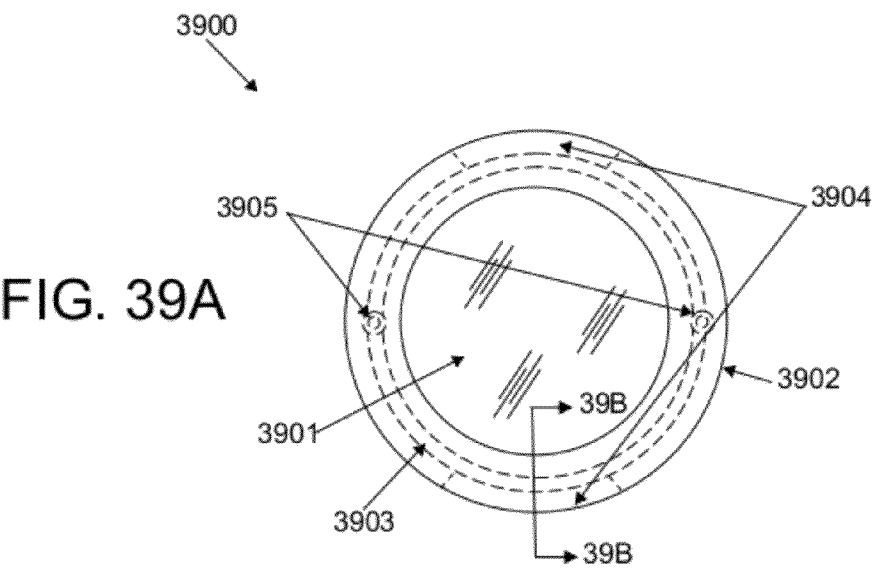
FIG. 39A is a schematic superior view of an embodiment of an orthopedic joint device comprising a core with articulations, an inner membrane, and receiving grooves.
Figure 39B:
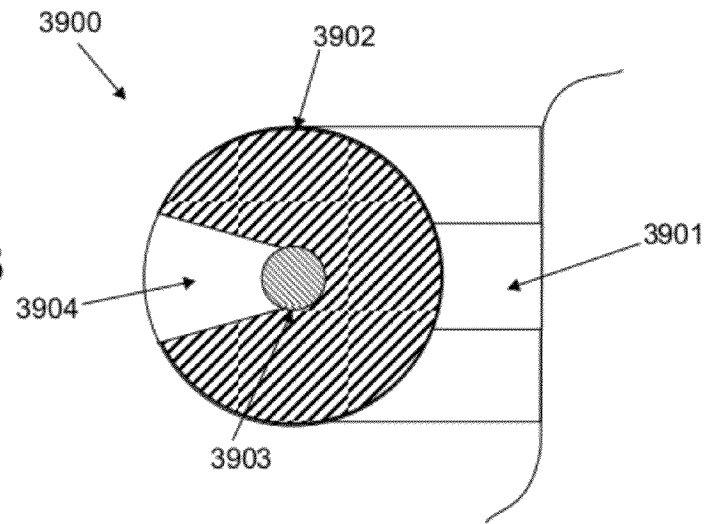
FIG. 39B is a schematic axial cross-sectional view of the orthopedic joint device in FIG. 39A.

FIGS. 39A and 39B depict another embodiment of an orthopedic joint device 3900. Orthopedic joint device 3900 includes receiving grooves 3904 configured to secure a delivery device (not shown) to the orthopedic joint device 3900. The delivery device may comprise opposable members configured to apply a constraining force to the orthopedic joint device 3900 at the receiving grooves 3904. When the constraining force is applied to the receiving grooves 3904, the orthopedic joint device 3900 reduces its profile in a direction orthogonal to the direction of implantation. The delivery device may also be used to insert the orthopedic joint device 3900 into a joint of a patient. When the delivery member is withdrawn and the constraining force thereby removed, the orthopedic joint device may return to its base configuration. Examples of delivery devices with opposable members include, but are not limited to, tweezers and forceps. The receiving grooves 3904 may include end walls to securely hold the opposable members of the delivery device in place during implantation of the orthopedic joint device 3900.

As depicted in FIG. 39A, orthopedic joint device 3900 comprises an inner membrane 3901, an outer body 3902, an inner core 3903, receiving grooves 3904, and articulations 3905. FIG. 39B depicts a cross-section of orthopedic joint device 3900 taken through the plane shown in FIG. 39A. Receiving groove 3904 comprises an aperture in outer body 3902 that takes a "V" shape, but other embodiments may take different configurations, such as a rectangular or arcuate shape, for example. The aperture may be added during processing of the outer body or may be added after the outer body is completed. In the embodiment depicted in FIG. 39B, receiving groove 3904 comprises the region from the edge of the outer body 3902 to the edge of the core 3903, but other embodiments may remove less of the outer body 3902 or some of the core 3903. Receiving grooves 3904 are depicted in FIGS. 39A and B as being located at the point furthest from the articulations 3903, but other embodiments may locate the receiving grooves closer to the articulations.

Figure 40A:
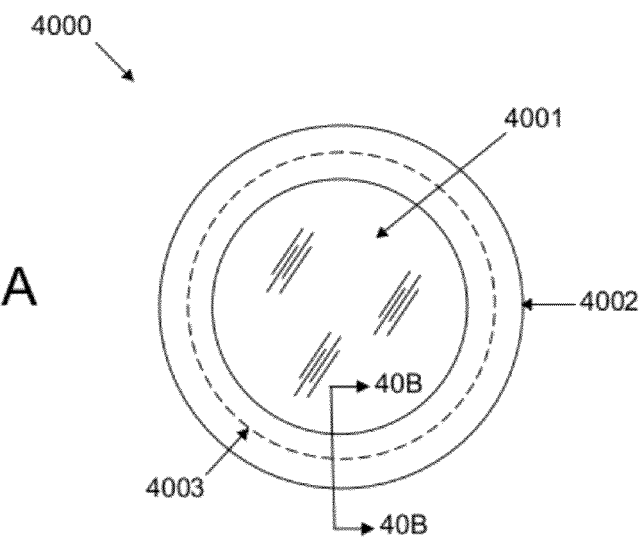
FIG. 40A is a schematic superior view of an embodiment of an orthopedic joint device comprising a core with articulations, an inner membrane, and a recess along a perimeter of the device.
Figure 40B:
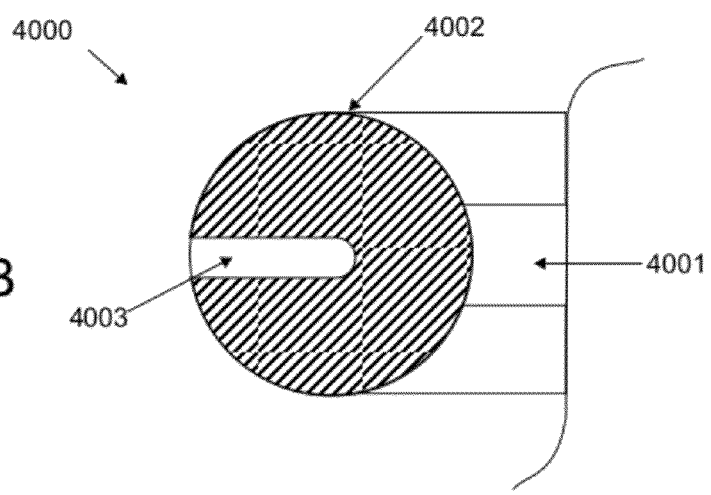
FIG. 40B is a schematic axial cross-sectional view of the orthopedic joint device in FIG. 40A.

FIGS. 40A and B depict another embodiment of an orthopedic joint device 4000 comprising a recess along a perimeter of an outer portion of a main body, wherein the recess is configured to receive a delivery device (not shown), such as a loop of thread. As depicted in FIG. 40A, orthopedic joint device 4000 includes a main body 4002, a central region 4001, and a recess 4003. Recess 4003 encircles the entire perimeter of the main body 4002, but in other embodiments, a recess may comprise only a portion of the perimeter. FIG. 40B depicts a cross-section of orthopedic joint device 4000 taken through the plane shown in FIG. 40A. As depicted in FIG. 40B, recess 4003 is generally rectangular with an arc at the center of the main body. In other embodiments, the recess may take other configurations, such as one or more sloped sides to ease coupling of the delivery member to the orthopedic joint device. In some embodiments, the recess may be more or less than the radius of the main body.

FIG. 41 depicts an orthopedic joint device 4100 comprising a recessed main body and a delivery member. The delivery member may comprise a thread or similar mechanism for securing the main body and pulling the device into a patient's joint. Orthopedic joint device 4100 includes a main body 4102, a central region 4101, a recess 4103, and a delivery member 4110. Main body 4102, central region 4101, and recess 4103 may correspond to orthopedic joint device 4000 described above. When the delivery member is coupled to the main body, a suture may be attached the thread and passed through an incision of a patient, through a joint, and out of the proximal side of the joint, thereby pulling the main body 4100 into the joint. The suture may take any configuration, including one coupled to the device and a resorbable suture, as is known in the art. Once the main body is fully inserted in the joint, the thread may be removed from the main body by detaching the suture and pulling on one end of the thread.

FIGS. 42A and 42B depict an orthopedic joint device 4200 with substantially similar features to orthopedic joint device 4100. Orthopedic joint device is further equipped with a lumen 4211 to gather the excess thread, thereby giving the delivery member a more secure grasp on the main body 4202. In some embodiments, lumen 4211 is configured to receive the implant to further secure the main body 4202 during implantation. In some embodiments, lumen 4211 comprises an aperture or slot at its proximal end that is configured to prevent relative torsional motion between the main body and the lumen during delivery. Although the lumen is depicted in FIGS. 42A and B as comprising a cylindrical tube with circular cross section, a cylinder with any cross-sectional shape can be used without deviating from the scope of the invention. Lumen 4211 may facilitate insertion of the main body 4202 without a suture, which may eliminate the need for a proximal incision. After the main body 4202 and delivery member 4210 are fully coupled, as shown in FIG. 42B, the main body 4202 can be inserted into a patient's joint, with the edge opposite the lumen 4211 acting as the lead surface. Thus, orthopedic joint device 4200 is pushed into a joint of a patient. Once the main body 4202 is fully inserted, the lumen and thread can be removed.

Figure 43A:
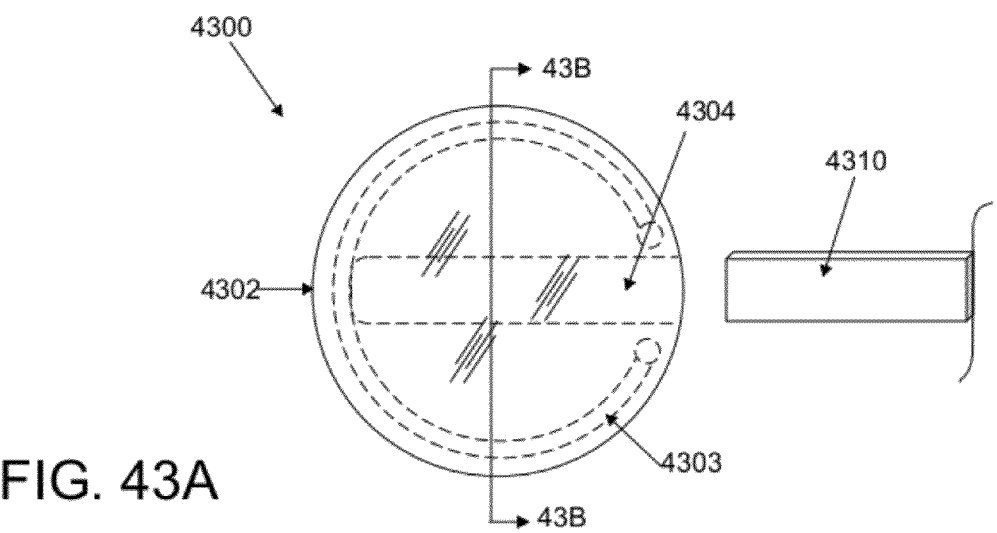
FIG. 43A is a schematic superior view of an orthopedic joint device comprising a channel and a delivery member.
Figure 43B:
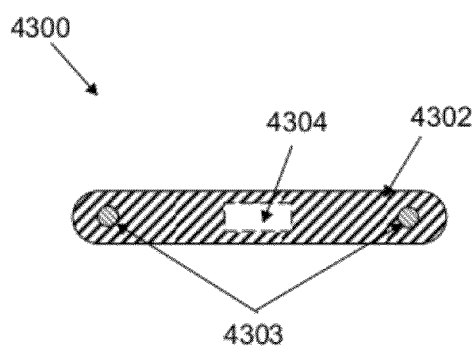
FIG. 43B is a schematic cross-sectional view of the orthopedic joint device in FIG. 43A.

FIGS. 43A and B depict an orthopedic joint device 4300 comprising a main body 4302, an inner core 4303, a channel 4304, and a delivery member 4310. Channel 4304 is configured to receive rigid delivery member 4310. When delivery member 4310 is inserted into channel 4304, the orthopedic joint device 4300 can be delivered into a patient's joint. After the main body 4302 is fully inserted in the patient's joint, the delivery member can be withdrawn from the channel. Although delivery member 4310 and channel 4303 are shown as having rectangular cross-sections, any cross-sectional geometry could be used. Such geometries may be selected to prevent rotation of the main body about the delivery member when the two are coupled. FIG. 43B depicts a cross-section of orthopedic joint device 4000 taken through the plane shown in FIG. 43A.

FIG. 44 depicts an orthopedic joint device 4400 comprising a main body 4402, an inner region 4401, an inner core 4403, parallel channels 4404, a flexible core region 4405, and a delivery member 4410. Delivery member 4410 comprises two rigid inserts 4411 configured to be inserted into channels 4404, thereby coupling main body 4402 and delivery member 4410. Because the inner core 4403 may obstruct entry of the delivery member, flexible core region 4405 may be configured to ease entry of the delivery member into the main body. Flexible core region may be contain apertures in the core, or may comprise a material which allows the delivery member to pass through, but still provides a resistance to deformation during use. After main body 4402 is inserted into a patient's joint, the delivery member 4410 can be removed. Delivery member further comprises a back stop 4412 and handle 4413.

FIG. 45 depicts another embodiment of an orthopedic joint device 4500 which is substantially similar to orthopedic joint device 4400. Unlike channels 4404, channels 4504 of orthopedic joint device 4500 are not parallel. After a delivery member or delivery members are coupled to main body 4502, orthopedic joint device 4500 may be deformed by re-orienting the channels to be closer to parallel. This deformed configuration may ease insertion of the orthopedic joint device 4500 through an incision.

It is noted that various features of an orthopedic joint device, such as articulations 901, 1000, 1010, 1020, 1101, 1201, 1501, 1601, 1701, and 3905, bodies 902, 1102, 1202, 1402, 1502, 1602, 1702, 1802, 2102, 2702, 2802, 2902, 3002, 3102, 3202, 3302, 3402, 3502, 3602, 3702, 3902, 4002, 4102, 4302, 4402, and 4502, cores 903, 1001, 1011, 1021, 1103, 1203, 1403, 1503, 1603, 1703, 1803, 2103, 3630, 3650, 3730, 3750, 3903, 4303, and 4403, membranes/span members 1404, 1504, 1604, 1704, 1804, 1900, 2000, 2104, 2712, 2812, 2912, 3012, 3112, 3212, 3312, 3412, 3512, 3612, 3712, and 3901, transition regions 2720, 2820, 2920, 3020, 3120, 3220, 3320, 3420, 3520, 3620, and 3720, and interior regions 2710, 2810, 2910, 3010, 3110, 3210 3310, 3410, 3510, 3610, and 3710 have been discussed throughout this specification. In any embodiment, they may be present individually or in any combination with any of the other aspects of the device, such as the configuration of the outer body, the configuration of the grommets, the configuration of holes, and/or the delivery mechanism, for example.

It will be understood that the foregoing is only illustrative of the principles of the invention, and that various modifications, alterations, and combinations can be made by those skilled in the art without departing from the scope and spirit of the invention. Any of the embodiments of the various orthopedic joint devices disclosed herein can include features described by any other orthopedic joint devices or combination of orthopedic joint devices herein. Furthermore, any of the embodiment of the various orthopedic joint device delivery and/or retrieval systems can be used with any of the orthopedic joint devices disclosed, and can include features described by any other orthopedic joint device delivery and/or retrieval systems or combination of orthopedic joint device delivery and/or retrieval systems herein. Accordingly, it is not intended that the invention be limited, except as by the appended claims. For all of the embodiments described above, the steps of the methods need not be performed sequentially.

It will be understood that the foregoing is only illustrative of the principles of the invention, and that various modifications, alterations, and combinations can be made by those skilled in the art without departing from the scope and spirit of the invention. Any of the embodiments of the various orthopedic devices disclosed herein can include features described by any other orthopedic devices or combination of orthopedic devices herein. Furthermore, any of the embodiment of the various orthopedic device delivery and/or retrieval systems can be used with any of the orthopedic devices disclosed, and can include features described by any other orthopedic device delivery and/or retrieval systems or combination of orthopedic device delivery and/or retrieval systems herein. Accordingly, it is not intended that the invention be limited, except as by the appended claims. For all of the embodiments described above, the steps of the methods need not be performed sequentially.

What is claimed is:

1. An orthopedic implant configured to be inserted into a patient's joint, the implant comprising:
    a main body with a generally planar configuration, wherein the main body has a distal edge configured to be first inserted into the patient's joint;
    a first dimension orthogonal to the planar configuration;
    a second coplanar dimension orthogonal to the direction of insertion of the implant, wherein the implant is configured to resiliently decrease in size in the second dimension;
    an inner region at least partially surrounded by the main body, the inner region comprising a span member at least partially spanning the inner region, the span member comprising an inward proximal edge, wherein the inward proximal edge comprises at least one region that is closer to the distal edge of the main body than a widest point of the main body in the second dimension; and
    at least one transition region configured to gradually reduce the height of the main body in the first dimension to the height of the inner region in the first dimension, wherein the transition region comprises a slope selected from the group consisting of: a constant and a linear function of the distance of the transition region from a perimeter of the main body.

2. The orthopedic implant of claim 1, wherein the inward proximal edge comprises an arc of radius between 5-25% of the width of the orthopedic implant in the second dimension.

3. The orthopedic implant of claim 1, wherein the inner region further comprises a central opening, and wherein the central opening comprises an inward distal edge of the span member, wherein an inward distal edge comprises at least one region that is further from the distal edge of the main body than the widest point of the main body in the second dimension.

4. The orthopedic implant of claim 3, wherein the central opening comprises a diameter in the second dimension between 30-50% of the width of the orthopedic implant in the second dimension.

5. The orthopedic implant of claim 1, wherein the height of the inner region in the first dimension is between 15-35% of the height of the orthopedic implant in the first dimension.

6. The orthopedic implant of claim 1, wherein the transition region further comprises a proximal transition region configured to ease overlapping of the main body.

7. The orthopedic implant of claim 6, wherein the proximal region transition region further comprises an acute angle.

8. The orthopedic implant of claim 1, wherein the inner region further comprises a distal outward edge, and wherein the transition region further comprises a distal transition region configured to gradually reduce the distal height of the main body in the first dimension to the height of the inner region in the first dimension.

9. The orthopedic implant of claim 1, wherein the distal edge further comprises a lead surface configured to ease insertion of the orthopedic implant through an incision, wherein the lead surface comprises:
    at least one of an arc with a radius different from the radius of the main body and an arc eccentric to the main body; and
    a tapered region joining the distal edge to the main body.

10. The orthopedic implant of claim 9, wherein the tapered region comprises a surface with a slope that is a linear function of distance from the distal edge.

11. The orthopedic implant of claim 1, further comprising a distal edge transition region which linearly increases the height of the distal edge to the height of the main body.

12. The orthopedic implant of claim 1, wherein the main body further comprises at least one resilient core configured to resist deformation.

13. The orthopedic implant of claim 12, wherein the main body further comprises two resilient cores.

14. The orthopedic implant of claim 1, wherein the main body further comprises at least one radiopaque core.

15. The orthopedic implant of claim 14, wherein the at least one hole comprises at least one angle configured to reduce slippage of the delivery member.

16. The orthopedic implant of claim 1, wherein the main body further comprises at least one hole configured for releasably coupling to a delivery member.

17. The orthopedic implant of claim 1, wherein the inner region height in the first dimension is between 2-12% of the width of the orthopedic implant in the second dimension.

18. The orthopedic implant of claim 1, wherein the main body comprises two leg tips.

19. The orthopedic implant of claim 18, wherein the leg tips are separated by a width in the second dimension between 10-30% of the width of the orthopedic implant in the second dimension.

20. The orthopedic implant of claim 1, wherein the perimeter comprises an arcuate shape.

21. The orthopedic implant of claim 20, wherein the height of the orthopedic implant in the first dimension is between 15-35% of the width of the orthopedic implant in the second dimension.

22. The orthopedic implant of claim 20, wherein the inner region further comprises a central opening with a diameter in the second dimension between 30-50% of the orthopedic implant in the second dimension.

23. The orthopedic implant of claim 20, wherein the inner region height in the first dimension is between 2-12% of the width of the orthopedic implant in the second dimension.

24. The orthopedic implant of claim 20, wherein the main body further comprises two leg tips separated by a width in the second dimension between 10-30% of the width of the orthopedic implant in the second dimension.

25. The orthopedic implant of claim 1, wherein the width of the orthopedic implant in the second dimension is sized to fit in a patient's carpometacarpal joint.

* * * * *